United States Patent
Sonnet et al.

(10) Patent No.: US 11,220,482 B2
(45) Date of Patent: Jan. 11, 2022

(54) AMINOPYRIDINEMETHANOL COMPOUNDS AND THEIR USE

(71) Applicants: UNIVERSITE AMIENS PICARDIE JULES VERNE, Amiens (FR); CENTRE HOSPITALIER UNIVERSITAIRE D'AMIENS, Amiens (FR); CENTRE NATIONAL DE LA RECHERCHE SCIENTIFIQUE—CNRS—, Paris (FR)

(72) Inventors: Pascal Sonnet, Pont de Metz (FR); Alexandra Dassonville-Klimpt, Amiens (FR); Guillaume Bentzinger, Amiens (FR); Catherine Mullie-Demailly, Cagny (FR); Patrice Agnamey, Amiens (FR)

(73) Assignees: UNIVERSITE AMIENS PICARDIE JULES VERNE, Amiens (FR); CENTRE HOSPITALIER UNIVERSITAIRE D'AMIENS, Amiens (FR); CENTRE NATIONAL DE LA RECHERCHE SCIENTIFIQUE-CNRS-, Paris (FR)

( * ) Notice: Subject to any disclaimer, the term of this patent is extended or adjusted under 35 U.S.C. 154(b) by 0 days.

(21) Appl. No.: 16/760,766

(22) PCT Filed: Nov. 2, 2018

(86) PCT No.: PCT/EP2018/080026
§ 371 (c)(1),
(2) Date: Apr. 30, 2020

(87) PCT Pub. No.: WO2019/086614
PCT Pub. Date: May 9, 2019

(65) Prior Publication Data
US 2020/0255379 A1    Aug. 13, 2020

(30) Foreign Application Priority Data

Nov. 3, 2017  (EP) .................................. 17306526

(51) Int. Cl.
*C07D 213/38* (2006.01)
*A61P 33/06* (2006.01)
*C07D 401/12* (2006.01)
*C07D 401/14* (2006.01)
*C07F 17/02* (2006.01)

(52) U.S. Cl.
CPC ............ *C07D 213/38* (2013.01); *A61P 33/06* (2018.01); *C07D 401/12* (2013.01); *C07D 401/14* (2013.01); *C07F 17/02* (2013.01)

(58) Field of Classification Search
CPC .. C07D 213/38; C07D 401/12; C07D 401/14; C07F 17/02; A61P 33/06
See application file for complete search history.

(56) References Cited

U.S. PATENT DOCUMENTS

| | | | | |
|---|---|---|---|---|
| 3,886,167 A | * | 5/1975 | Ash ......................... | C07C 59/88 |
| | | | | 546/185 |
| 3,940,404 A | * | 2/1976 | Ash ....................... | C07D 213/30 |
| | | | | 546/334 |
| 3,953,463 A | * | 4/1976 | Ash ....................... | C07D 213/30 |
| | | | | 546/326 |

FOREIGN PATENT DOCUMENTS

WO         0196320 A1    12/2001

OTHER PUBLICATIONS

LaMontagne J Med Chem, VOl 16(0), 1973, 1040-1041. (Year: 1973).*
Kim, J Med Chem, vol. 22(4), 366-391, 1979. (Year: 1979).*
Schmidt, Antimicrobial Agents and Chemotherapy, Sep. 1978, VOl 14(3), 420-435. (Year: 1978).*
The International Search Report and Written Opinion, dated Jan. 4, 2019, in the corresponding PCT Appl. No. PCT/EP2018/080026.
M. P. Lamontagne et al.: "Antimalarials. 5. 2-Aryl-6-trifluoromethy-1-4-pyridinemethanols", Journal of Medicinal Chemistry, vol. 16, No. 9, Sep. 1, 1973 (Sep. 1, 1973), pp. 1040-1041, XP055464285.
LK Basco et al.: "In vitro activity of the enantiomers of mefloquine, halofantrine and enpiroline against Plasmodium falciparum ", British Journal of Clinical Pharmacology., vol. 33, No. 5, May 1, 1992 (May 1, 1992), pp. 517-520, XP055464284.

* cited by examiner

*Primary Examiner* — D Margaret M Seaman

(57) ABSTRACT

The present invention is directed to novel compounds of Formula (I): pharmaceutically acceptable salts or solvates thereof, and their use, in particular in the treatment or prevention of malaria.

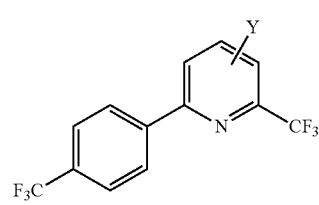

(I)

17 Claims, No Drawings

AMINOPYRIDINEMETHANOL COMPOUNDS AND THEIR USE

CROSS-REFERENCE TO RELATED APPLICATIONS

This application is a National Stage Application of PCT/EP2018/080026 filed Nov. 2, 2018, which claims priority from European Patent Application No. 17306526.9, filed on Nov. 3, 2017. The priority of said PCT and European Patent Application are claimed. Each of the prior mentioned applications is hereby incorporated by reference herein in its entirety.

The present invention relates to novel aminopyridinemethanol compounds including their pharmaceutically acceptable salts and solvates, as well as the synthesis methods and the use of such compounds, particularly in the treatment of malaria.

BACKGROUND OF THE INVENTION

Malaria is a neglected tropical disease that remains a leading cause of morbidity and mortality among the world's poorest populations. The 2015 global malaria report published by the World Health Organization (WHO) estimated that there were 214 million cases of malaria (range: 149-303 million) leading to 438000 deaths (range: 236000-635000) in 2015. More than 100 tropical and sub-tropical countries are endemic for this infectious disease. Pregnant women and children under the age of five are the most sensitive to this infection. Malaria has also a severe socioeconomic impact in countries where it is endemic because of the persistent and disabling symptoms of the disease. In Africa the economic burden is estimated at $12 billion annually.

Among the six species of *Plasmodium* responsible for human malaria, *P. falciparum* and *P. knowlesi* are species inducing severe forms of the disease. Regarding *P. falciparum*, the phenomenon of multidrug resistance is widespread causing an excess burden. Several strategies are currently being deployed in parallel to control this disease: (i) use of vaccines (Seder R. A. et al., Science, 2014, 344, 871-877), (ii) novel drugs, and (iii) vector control methods. Currently, the most advanced malaria vaccine, RTS,S/AS01, is in clinical development. Results from a phase III clinical trial have shown that RTS,S/AS01 is able to prevent malaria cases, particularly among children in high impact areas (Agnandji S T et al., PloS Med., 2014, 11, e1001685). Strategies to control mosquitoes (insecticide-treated nets and indoor residual spraying) have been very effective in the past but are currently at risk due to increased resistance to the insecticides used (mainly pyrethroids) (N'Guessan R. et al., Emerging Infect. Dis., 2007, 13, 199-206).

The currently available antimalarial agents can be classified according to their biological activity and chemical structure:

Blood Schizontocides: These drugs act on the blood forms of the parasite. They are important to control the symptoms of the disease and the associated mortality. Most of the antimalarial agents target this stage: quinoline (chloroquine, amodiaquine, quinine, mefloquine), artemisinin derivatives (artesunate, dihydroartemisinin, artemether . . . ) and nucleic acid synthesis inhibitors such as atovaquone and antifolates (sulfalene, sulfadoxine, dapsone, proguanil and pyrimethamine).

Tissue Schizontocides for Causal Prophylaxis: These drugs act on the primary tissue forms of *Plasmodium* which, after growth within the liver, initiate the erythrocytic stage. By blocking this stage, further development of the infection can be prevented. Primaquine and pyrimethamine (to a lesser extent) have activity against this stage. However, since it is impossible to predict the infection before clinical symptoms begin, this mode of therapy is more theoretical than practical.

Tissue Schizontocides for Preventing Relapse: These drugs act on hypnozoites of *P. vivax* and *P. ovale* in the liver which cause relapse of symptoms on reactivation. Primaquine is the only drug approved for this stage. Atovaquone/proguanil is usually preferred because it is well tolerated, but is expensive.

Gametocytocides: These drugs destroy the sexual forms of the parasite in the blood, and prevent transmission of the infection to the mosquito. Chloroquine and quinine have gametocytocidal activity against *P. vivax* and *P. malariae*, but not against *P. falciparum*. However, primaquine has gametocytocidal activity against all human malarial parasite species including *P. falciparum* (Dondorp A. M., Clin. Infect. Dis., 2012, 56, 694-696).

Sporontocides: These drugs prevent the development of oocysts in the mosquito and thus ablate the transmission. Primaquine and chloroguanidine are known to be active on sporozoites.

The two important concepts in the treatment of malaria include suppressive and radical treatment of the infection. Since 2006, Artemisinin-based Combination Therapies (ACTs) have been recommended by WHO and currently remain the first-line treatment. Five ACTs are commercially available; artemether-lumefantrine, artesunate-amodiaquine, artesunate-mefloquine, artesunate sulfadoxine-pyrimethamine, and dihydroartemisinin-piperaquine.

However, *P. falciparum* has become resistant to all commercially available antimalarials such as amodiaquine, chloroquine, mefloquine, quinine and sulfadoxine-pyrimethamine. Recent reports even described artemisinin resistant strains of *P. falciparum* emerging in some malaria endemic areas leading to an alarming situation (Cheeseman I. H. et al., Science, 2012, 336, 79-8; Dondorp A. M. et al., N. Engl. J. Med., 2009, 361, 455-467; Fairhurst R. M. et al., Am. J. Trop. Med. Hyg., 2012, 87, 231-241; Lubell Y. et al., Malar. J., 2014, 13, 452).

Most of the treatments with antimalarial compounds are associated with undesirable side effects and toxicity. For example, administration of quinine (base and salts) involves a whole range of symptoms, known as "cinchonism", like, in its benign form, acouphenes, cephalgias, nauseas, vertigo and dysphoria with sometimes eye troubles (Genton B. et al., PLoS Medicine, 2008, 5:e136). More serious side effects are vomiting, abdominal pains, diarrheas and intense vertigo. Among chloroquine side effects, there are cephalgias, rashes, and gastrointestinal disorders such as nauseas, vomiting or diarrheas. Less often, central nervous system side effects such as convulsions and mental disorders can be observed. A long time use of chloroquine (five years and over) can involve eye troubles like keratoplasty or retinopathy.

Thus, the long term efficacy of ACTs seems compromised and undesirable side effects induced by antimalarial therapy have increased the urgency to discover and develop new drugs against this disease.

New, innovative drugs should also be (i) fast acting, (ii) safe for children and pregnant women, and (iii) ideally amenable to a single-dose administration. They must be obtained with reduced costs and efficient synthesis.

The evolution of *Plasmodium*-resistant strains has been accelerated due to the fact that very few new classes of antimalarials have emerged over the last decade. Moreover, antimalarial treatment is often associated to side effects which can be serious as central nervous system side effects.

This is why new aminoarylmethanols compounds with a strong antimalarial activity and less undesirable effects to fight the resistance phenomenon are being developed.

The four major groups of antimalarial arylmethanols described below are: 4-quinolinemethanols (quinine, mefloquine), 9-phenanthrenemethanols (halofantrine), 9-fluorenemethanols (lumefantrine) and 4-pyridinemethanols (enpiroline).

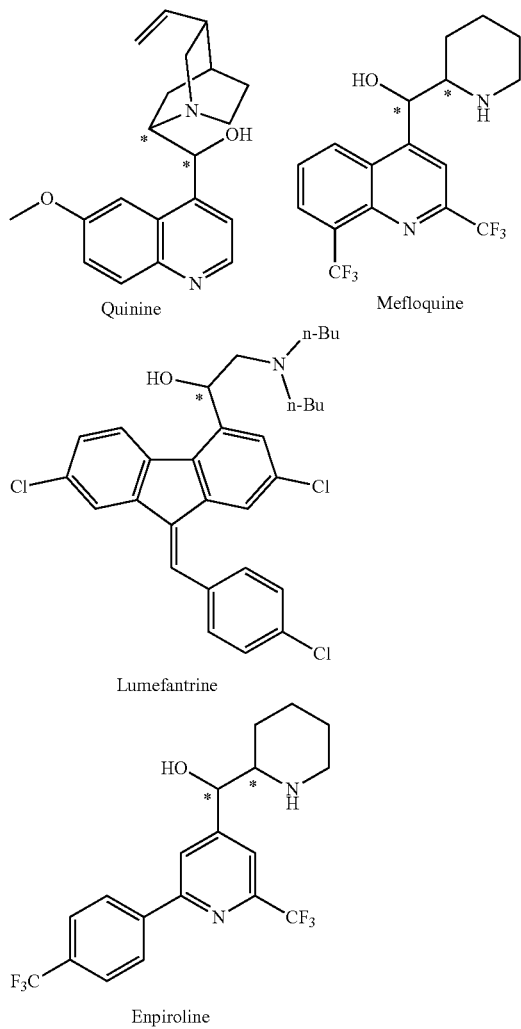

Because of their interesting pharmacokinetics parameters, lumefantrine and mefloquine are good candidates in ACTs. Artemisinin and its derivatives have a fast onset of action but are cleared rapidly (human $t_{1/2}$=1 h) (Morris C. A. et al., Malar. J., 2011, 10, 263), and are therefore combined with slow-clearing drugs to kill residual parasites. Typical partner drugs include lumefantrine (human $t_{1/2}$=3-4 days) (Djimde A. et al., Malar. J., 2009, 8, S4) and mefloquine (human $t_{1/2}$=2-4 weeks). Enpiroline can also be a good candidate because its mean half-life was estimated to be 6 days (Cosgriff T. M. et al., Am. J. Trop. Med. Hyg., 1984, 33, 767-771).

Mefloquine was proposed, for a long time, as the drug of choice for chloroquine-resistant malaria and artesunate-mefloquine combination was the most prescribed ACT in high mefloquine resistance areas. This antimalarial drug possesses good pharmacokinetic properties such as a longer half-life, compared to other antimalarial drugs, which permits weekly administration and facilitates a better observance for prophylactic treatment (Karbwang J. et al., Clin. Pharmacokinet., 1990, 19, 264-279). Mefloquine is the only registered drug effective in a single dose. Mefloquine is relatively safe during pregnancy and can be given to children of more than three years (Nosten F. et al., J. Infect. Dis., 1994, 169, 595-603). However, emergence of resistance to mefloquine and its associated neuropsychiatric side effects have limited its use. Mefloquine is commercially available as a racemate (Lariam®), although both enantiomers have shown differences in biological activities. On the one hand, the antimalarial activities of the two isomers are close but (+)-mefloquine is more active by a factor of 1.6-1.8 on *P. falciparum* D6, W2 and 3D7 strains (Karle J. M. et al., Exp. Parasitol., 1993, 76, 345-351; Dassonville-Klimpt A. et al., ChemPlusChem, 2013, 78, 642-646). On the other hand, the neuropsychiatric side effects correspond with a greater accumulation of (−)-mefloquine compared to (+)-mefloquine in the central nervous system due to a stereoselective cerebral transport of mefloquine (Pham Y. T. et al., Biochim. Biophys. Acta, 2000, 1524, 212-219; Barraud de Lagerie S. et al., Br. J. Pharmacol., 2004, 141, 1214-1222; Gimenez F. et al., J. Pharm. Sci., 1994, 6, 824-827). Moreover, (−)-mefloquine is 100 to 400-fold more potent than (+)-mefloquine as an adenosine receptor agonist (WO 98/39003).

Among several approaches to lower the mefloquine neurotoxicity and to improve its resistance profiles (Dow G. S., Antimicrob. Agents Chemother., 2004, 48, 2624-2632; Milner E. et al., Malaria J., 2010, 9, 51-60; Milner E. et al., Bioorg. Med. Chem. Lett., 2010, 10, 1347-1351; WO 2010/144101), modulation of the mefloquine core as a pure enantiomer is an attractive strategy.

The inventors recently reported the asymmetric synthesis and the biological activity of (R)- and (S)-4-aminoquinolinemethanols as mefloquine analogues (WO 2012/107532). Several compounds showed a promising antimalarial activity, in the range of nanomolar, against *P. falciparum* W2 and 3D7 strains.

Prior investigations have demonstrated that certain 2-aryl-6-trifluoromethyl-4-pyridinyl-carbinolamines, and particularly 2-(butylamino)-1-(2-(trifluoromethyl)-6-(4-(trifluoromethyl)phenyl)pyridin-4-yl)ethanol, 2-(pentan-3-ylamino)-1-(2-(trifluoromethyl)-6-(4-(trifluoromethyl)phenyl)pyridin-4-yl)ethanol and 2-(heptan-4-ylamino)-1-(2-(trifluoromethyl)-6-(4-(trifluoromethyl)phenyl)pyridin-4-yl)ethanol, have antimalarial activity (LaMontagne M. P. et al., J. Med. Chem., 1973, 16, 1040-1041; U.S. Pat. Nos. 3,886,167; 3,940,404; 3,953,463; Schmidt et al., Antimicrob. Agents Chemother., 1978, 17, 420-435). These compounds are described as racemates.

A series of 2-chloropyridin-3-ylmethanol was described as antimalarial agents (WO2007/032016). These pyridines displayed a weak antimalarial activity with $IC_{50}$ values close to the micromolar against chloroquine sensitive and resistant *P. falciparum* strains.

(±)-Threo-alpha-(2-piperidyl)-2-trifluoromethyl-6-(4-trifluoromethylphenyl)-4-pyridinemethanol or enpiroline, an aminoalcohol as mefloquine and quinine, has shown blood schizontocidal activity against *P. falciparum* and *P. vivax* with weak toxicity (Basco L. K. et al., Br. J. Clin. Pharmacol., 1992, 33, 517-520). Enpiroline has also shown a good antimalarial activity in vivo against *Plasmodium berghei* in mice (LaMontagne M. P. et al., J. Med. Chem., 1974, 17, 519).

Toxicological and pharmacokinetic studies with enpiroline in human volunteers have shown good tolerability, absorption and distribution. Enpiroline was curative in human volunteers with induced infection with the multidrug resistant Vietnam Smith *P. falciparum* isolate.

Moreover, enpiroline, as mefloquine, possesses also excellent in vivo antischistosomal properties (Ingram K. et al., Antimicrob. Agents Chemother., 2012, 56, 3207-3215).

There is however still a need for new compounds that may be of therapeutic value in the treatment of malaria.

SUMMARY OF THE INVENTION

The invention thus relates to compounds of general Formula I, their pharmaceutically acceptable salts and solvates as well as methods of use of such compounds or compositions comprising such compounds as antimalarial agents.

In a general aspect, the invention provides compounds of general Formula I:

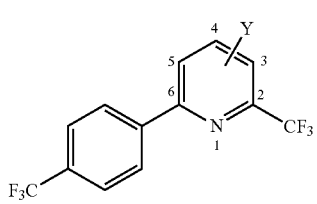

and pharmaceutically acceptable salts or solvates thereof, in which Y is selected from formulae i or ii:

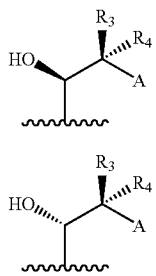

wherein
A is $NR^1R^2$ wherein
$R^1$ and $R^2$ are independently selected from the group consisting of:
a hydrogen atom;
a straight or branched C1-C9 alkyl or haloalkyl group;
a straight or branched C1-C9 heteroalkyl group containing one or two heteroatoms, said group being optionally substituted by one or two groups selected from aryl, heteroaryl, cycloalkyl or metallocene;
a group of following formula:

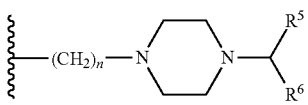

wherein n is an integer from 1 to 6 and $R^5$ and $R^6$ are aryl or heteroaryl groups,
a substituted or unsubstituted C3-C7 cycloalkyl group; or
an aryl group;
with the proviso that $R^1$ and $R^2$ are not both a hydrogen atom;
$R^3$ and $R^4$ are independently selected from the group consisting of a hydrogen atom, or a C1-C9 alkyl group optionally containing a heteroatom, said group being optionally substituted by an aryl group or a cycloalkyl group; and
wherein the symbol

means that Y may be located at any free position of the pyridine ring.

In one embodiment, the compound of Formula I is not one, more or all of the following:
2-(butylamino)-1-(2-(trifluoromethyl)-6-(4-(trifluoromethyl)phenyl)pyridin-4-yl)ethan-1-ol;
2-(dibutylamino)-1-(2-(trifluoromethyl)-6-(4-(trifluoromethyl)phenyl)pyridin-4-yl)ethan-1-ol;
2-(pentan-3-ylamino)-1-(2-(trifluoromethyl)-6-(4-(trifluoromethyl)phenyl)pyridin-4-yl)ethan-1-ol;
2-(di(pentan-3-yl)amino)-1-(2-(trifluoromethyl)-6-(4-(trifluoromethyl)phenyl)pyridin-4-yl)ethan-1-ol; and
2-(heptan-4-ylamino)-1-(2-(trifluoromethyl)-6-(4-(trifluoromethyl)phenyl)pyridin-4-yl)ethan-1-ol.

The present invention further relates to a process for providing the compound of Formula I.

In another aspect, the present invention provides a pharmaceutical composition comprising at least one compound according to the invention or a pharmaceutically acceptable salt or solvate thereof.

The invention also relates to the use of the above compounds or their pharmaceutically acceptable salts and solvates in treating and/or preventing malaria.

DETAILED DESCRIPTION OF THE INVENTION

As noted above, the invention relates to compounds of Formula I, as well as their pharmaceutically acceptable salts and solvates.

Preferred compounds of Formula I and pharmaceutically acceptable salts and solvates thereof are those wherein one or more of Y, A and $R^1$-$R^4$ are defined as follows:
A is $NR^1R^2$ wherein
$R^1$ and $R^2$ are independently selected from the group consisting of:
a hydrogen atom;
a straight or branched C1-C9 alkyl or haloalkyl group;
a straight or branched C1-C9 heteroalkyl group containing one or two heteroatoms, said group being optionally substituted by one or two groups selected from aryl, heteroaryl, cycloalkyl or metallocene;
a group of following formula:

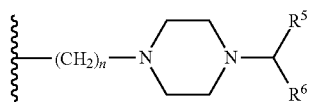

wherein n is an integer from 1 to 6 and $R^5$ and $R^6$ are aryl or heteroaryl groups,
a substituted or unsubstituted C3-C7 cycloalkyl group; or
an aryl group;
with the proviso that $R^1$ and $R^2$ are not both a hydrogen atom.

Preferably, $R^1$ and $R^2$ are independently selected from the group consisting of:
a hydrogen atom;
a straight or branched C4-C7 alkyl or haloalkyl group;
a straight or branched C1-C9 heteroalkyl group containing one or two heteroatoms, said group being optionally substituted by one or two groups selected from aryl, heteroaryl, cycloalkyl or metallocene; or
a group of following formula:

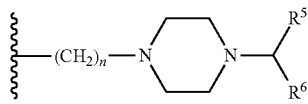

herein n is an integer from 2 to 5 and $R^5$ and $R^6$ are aryl or heteroaryl groups,
with the proviso that $R^1$ and $R^2$ are not both a hydrogen atom.

More preferably, $R^1$ and $R^2$ are independently selected from the group consisting of:
a hydrogen atom;
a straight C4-C7 alkyl or haloalkyl, preferably fluoroalkyl, group;
a straight or branched C1-C9 heteroalkyl group containing one heteroatom, said group being substituted by one or two groups selected from phenyl, pyridyl, cyclopropyl or ferrocene; or
a group of following formula:

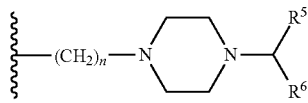

wherein n is an integer from 2 to 4 and $R^5$ and $R^6$ are phenyl or pyridyl,
with the proviso that $R^1$ and $R^2$ are not both a hydrogen atom.

More preferably, $R^1$ and $R^2$ are independently selected from the group consisting of:
a hydrogen atom;
a straight C4-C7 alkyl group;
a straight or branched C1-C9 heteroalkyl group containing an oxygen atom or a nitrogen atom, said group being substituted by one or two groups selected from phenyl or ferrocene; or
a group of following formula:

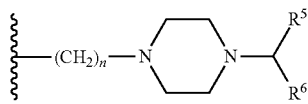

wherein n is an integer from 2 to 3 and $R^5$ and $R^6$ are phenyl,
with the proviso that $R^1$ and $R^2$ are not both a hydrogen atom.

Still more preferably, $R^1$ is selected from the group consisting of C4-C7 alkyl, C4-C7 haloalkyl, (arylalkylamino)alkyl, (heteroarylalkylamino)alkyl, alkoxyarylalkyl, (metallocenylalkylamino)alkyl, (arylalkylpiperazinyl)alkyl, (heteroarylalkylpiperazinyl)alkyl, or (cycloalkylalkoxy)arylalkyl and $R^2$ is a hydrogen atom.

Still more preferably, $R^1$ is selected from the group consisting of C4-C7 alkyl, (arylalkylamino)alkyl, alkoxyarylalkyl, (metallocenylalkylamino)alkyl, or (arylalkylpiperazinyl)alkyl and $R^2$ is a hydrogen atom.

Even more preferably, $R^1$ is selected from n-butyl, n-pentyl, n-hexyl, n-heptyl, 4,4,4-trifluoro-n-butyl, 5,5,5-trifluoro-n-pentyl, 5,5-difluoro-n-pentyl, 5-fluoro-n-pentyl, 4,4-difluoro-n-pentyl, 6-fluoro-n-hexyl, 2-(benzhydrylamino)ethyl, 2-((di(pyridin-2-yl)methyl)amino)ethyl, (S)-1-methoxy-3-phenylpropan-2-yl, 2-(ferrocenylmethylamino)ethyl, 3-(4-benzhydrylpiperazin-1-yl)propyl, or (S)-1-(cyclopropylmethoxy)-3-phenylpropan-2-yl and $R^2$ is a hydrogen atom. For example, $R^1$ is selected from n-butyl, n-pentyl, n-hexyl, n-heptyl, 4,4,4-trifluoro-n-butyl, 5,5,5-trifluoro-n-pentyl, 5,5-difluoro-n-pentyl, 5-fluoro-n-pentyl, 4,4-difluoro-n-pentyl, 2-(benzhydrylamino)ethyl, (S)-1-methoxy-3-phenylpropan-2-yl, 2-(ferrocenylmethylamino)ethyl, 3-(4-benzhydrylpiperazin-1-yl)propyl, or (S)-1-(cyclopropylmethoxy)-3-phenylpropan-2-yl and $R^2$ is a hydrogen atom.

Even more preferably, $R^1$ is selected from n-butyl, n-pentyl, n-hexyl, n-heptyl, 4,4,4-trifluoro-n-butyl, 6-fluoro-n-hexyl, 2-(benzhydrylamino)ethyl, 2-((di(pyridin-2-yl)methyl)amino)ethyl, (S)-1-methoxy-3-phenylpropan-2-yl, (S)-1-(cyclopropylmethoxy)-3-phenylpropan-2-yl, 2-(ferrocenylmethylamino)ethyl, or 3-(4-benzhydrylpiperazin-1-yl)propyl and $R^2$ is a hydrogen atom. For example, $R^1$ is selected from n-butyl, n-pentyl, n-hexyl, n-heptyl, 2-(benzhydrylamino)ethyl, (S)-1-methoxy-3-phenylpropan-2-yl, 2-(ferrocenylmethylamino)ethyl, or 3-(4-benzhydrylpiperazin-1-yl)propyl and $R^2$ is a hydrogen atom.

$R^3$ and $R^4$ are independently selected from the group consisting of a hydrogen atom, or a C1-C9 alkyl group optionally containing a heteroatom, said group being optionally substituted by an aryl group or a cycloalkyl group. Preferably, $R^3$ and $R^4$ are independently a hydrogen atom or a C1-C9 alkyl group. More preferably, $R^3$ and $R^4$ are hydrogen atoms; and Y is located at any free position of the pyridine ring. Preferably, Y is located at position 3 or 4 of the pyridine ring.

In one embodiment, compounds of Formula I are enantiomerically pure.

In one embodiment, $R^3$ and $R^4$ are hydrogen atoms.

In one embodiment, $R^2$ is a hydrogen atom.

Preferred compounds of Formula I and pharmaceutically acceptable salts and solvates thereof are those wherein A is $NR^1R^2$ wherein $R^1$ and $R^2$ are selected from:
a hydrogen atom;
a straight C1-C9 alkyl group, preferably a straight C4-C7 alkyl group;
a straight C1-C9 haloalkyl group, preferably a straight C4-C7 haloalkyl group, containing 1 to 3 halogen atoms, preferably fluorine;

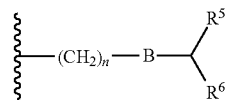

wherein n is an integer from 1 to 6, preferably from 2 to 4, more preferably from 2 to 3, B is NH or

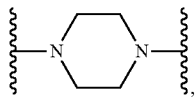

and $R^5$ and $R^6$ are aryl, preferably phenyl, or heteroaryl, preferably pyridyl;

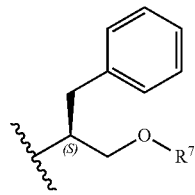

wherein $R^7$ is C1-C4 alkyl, preferably C1-C2 alkyl, more preferably methyl, or cycloalkylalkyl, preferably cyclopropylalkyl, more preferably cyclopropylmethyl; or

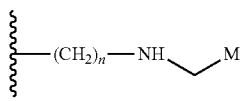

wherein M is a metallocene group, preferably ferrocene;

with the proviso that $R^1$ and $R^2$ are not both a hydrogen atom.

More preferred compounds of Formula I and pharmaceutically acceptable salts and solvates thereof are those wherein A is $NHR^1$ wherein $R^1$ is selected from:

a straight C1-C9 alkyl group, preferably C4-C7;

a straight C1-C9 haloalkyl group, preferably a straight C4-C7 haloalkyl group, containing 1 to 3 halogen atoms, preferably fluorine;

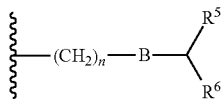

wherein n is an integer from 1 to 6, preferably from 2 to 4, more preferably from 2 to 3, B is NH or

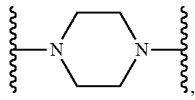

and $R^5$ and $R^6$ are aryl, preferably phenyl, or heteroaryl, preferably pyridyl;

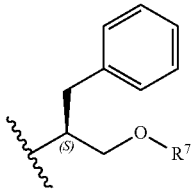

wherein $R^7$ is C1-C4 alkyl, preferably C1-C2 alkyl, more preferably methyl, or cycloalkylalkyl, preferably cyclopropylalkyl, more preferably cyclopropylmethyl; or

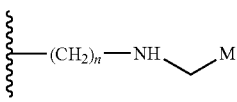

wherein M is a metallocene group, preferably ferrocene.

Still more preferred compounds of Formula I and pharmaceutically acceptable salts and solvates thereof are those wherein A is $NR^1R^2$ wherein $R^1$ and $R^2$ are selected from:

a hydrogen atom;

a straight C1-C9 haloalkyl group, preferably a straight C4-C7 haloalkyl group, containing 1 to 3 halogen atoms, preferably fluorine;

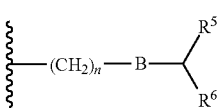

wherein n is an integer from 1 to 6, preferably from 2 to 4, more preferably from 2 to 3, B is NH or

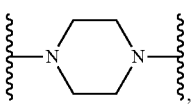

and $R^5$ and $R^6$ are aryl, preferably phenyl, or heteroaryl, preferably pyridyl;

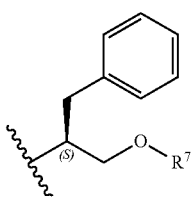

wherein $R^7$ is C1-C4 alkyl, preferably C1-C2 alkyl, more preferably methyl, or cycloalkylalkyl, preferably cyclopropylalkyl, more preferably cyclopropylmethyl; or

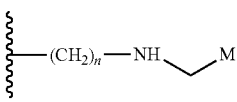

wherein M is a metallocene group, preferably ferrocene;
with the proviso that $R^1$ and $R^2$ are not both a hydrogen atom.

Even more preferred compounds of Formula I and pharmaceutically acceptable salts and solvates thereof are those wherein A is $NHR^1$ wherein $R^1$ is selected from:
a straight C1-C9 haloalkyl group, preferably a straight C4-C7 haloalkyl group, containing 1 to 3 halogen atoms, preferably fluorine;

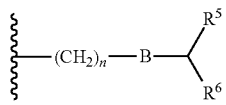

wherein n is an integer from 1 to 6, preferably from 2 to 4, more preferably from 2 to 3, B is NH or

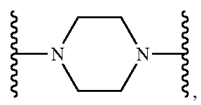

and $R^5$ and $R^6$ are aryl, preferably phenyl, or heteroaryl, preferably pyridyl;

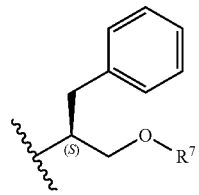

wherein $R^7$ is C1-C4 alkyl, preferably C1-C2 alkyl, more preferably methyl, or cycloalkylalkyl, preferably cyclopropylalkyl, more preferably cyclopropylmethyl; or

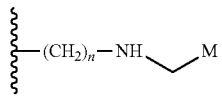

wherein M is a metallocene group, preferably ferrocene.

In one embodiment, A is $NR^1R^2$ wherein
$R^1$ and $R^2$ are independently selected from the group consisting of:
a hydrogen atom;
a straight or branched haloalkyl group;
a straight or branched C1-C9 heteroalkyl group containing one or two heteroatoms, said group being optionally substituted by one or two groups selected from aryl, heteroaryl, cycloalkyl and metallocene;
a group of following formula:

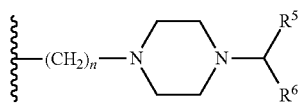

wherein n is an integer from 1 to 6 and $R^5$ and $R^6$ are aryl or heteroaryl groups,
a substituted or unsubstituted C3-C7 cycloalkyl group; and
an aryl group;
with the proviso that $R^1$ and $R^2$ are not both a hydrogen atom.

Preferably, $R^1$ and $R^2$ are independently selected from the group consisting of:
a hydrogen atom;
a straight or branched haloalkyl group;
a straight or branched C1-C9 heteroalkyl group containing one or two heteroatoms, said group being optionally substituted by one or two groups selected from aryl, heteroaryl, cycloalkyl and metallocene; and
a group of following formula:

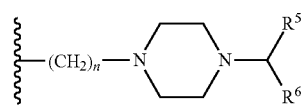

wherein n is an integer from 2 to 5 and $R^5$ and $R^6$ are aryl or heteroaryl groups,
with the proviso that $R^1$ and $R^2$ are not both a hydrogen atom.

More preferably, $R^1$ and $R^2$ are independently selected from the group consisting of:
a hydrogen atom;
a straight haloalkyl, preferably fluoroalkyl, group;
a straight or branched C1-C9 heteroalkyl group containing one heteroatom, said group being substituted by one or two groups selected from phenyl, pyridyl, cyclopropyl and ferrocene; and
a group of following formula:

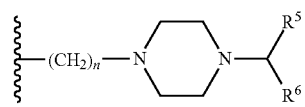

wherein n is an integer from 2 to 4 and $R^5$ and $R^6$ are phenyl or pyridyl,
with the proviso that $R^1$ and $R^2$ are not both a hydrogen atom.

Still more preferably, $R^1$ is selected from the group consisting of C4-C7-haloalkyl, (arylalkylamino)alkyl, (heteroarylalkylamino)alkyl, alkoxyarylalkyl, (metallocenylalkylamino)alkyl, (arylalkylpiperazinyl)alkyl, (heteroarylalkylpiperazinyl)alkyl and (cycloalkylalkoxy)arylalkyl, and $R^2$ is a hydrogen atom.

Still more preferably, $R^1$ is selected from the group consisting of C4-C7 haloalkyl, (arylalkylamino)alkyl, alkoxyarylalkyl, (metallocenylalkylamino)alkyl, (arylalkylpiperazinyl)alkyl and (cycloalkylalkoxy)arylalkyl, and $R^2$ is a hydrogen atom.

Even more preferably, $R^1$ is selected from 4,4,4-trifluoro-n-butyl, 5,5,5-trifluoro-n-pentyl, 5,5-difluoro-n-pentyl, 5-fluoro-n-pentyl, 4,4-difluoro-n-pentyl, 6-fluoro-n-hexyl, 2-(benzhydrylamino)ethyl, 2-((di(pyridin-2-yl)methyl)amino)ethyl, (S)-1-methoxy-3-phenylpropan-2-yl, 2-(ferrocenylmethylamino)ethyl, 3-(4-benzhydrylpiperazin-1-yl)propyl and (S)-1-(cyclopropylmethoxy)-3-phenylpropan-2-yl, and $R^2$ is a hydrogen atom. For example, $R^1$ is selected from n-butyl, n-pentyl, n-hexyl, n-heptyl, 4,4,4-trifluoro-n-butyl, 5,5,5-trifluoro-n-pentyl, 5,5-difluoro-n-pentyl, 5-fluoro-n-pentyl, 4,4-difluoro-n-pentyl, 2-(benzhydrylamino)ethyl, (S)-1-methoxy-3-phenylpropan-2-yl, 2-(ferrocenylmethylamino)ethyl, 3-(4-benzhydrylpiperazin-1-yl)propyl, or (S)-1-(cyclopropylmethoxy)-3-phenylpropan-2-yl and $R^2$ is a hydrogen atom.

Even more preferably, $R^1$ is selected from 4,4,4-trifluoro-n-butyl, 6-fluoro-n-hexyl, 2-(benzhydrylamino)ethyl, 2-((di(pyridin-2-yl)methyl)amino)ethyl, (S)-1-methoxy-3-phenylpropan-2-yl, 2-(ferrocenylmethylamino)ethyl, or 3-(4-benzhydrylpiperazin-1-yl)propyl and (S)-1-(cyclopropylmethoxy)-3-phenylpropan-2-yl, and $R^2$ is a hydrogen atom. For example, $R^1$ is selected from n-butyl, n-pentyl, n-hexyl, n-heptyl, 2-(benzhydrylamino)ethyl, (S)-1-methoxy-3-phenylpropan-2-yl, 2-(ferrocenylmethylamino)ethyl, or 3-(4-benzhydrylpiperazin-1-yl)propyl, and $R^2$ is a hydrogen atom.

In one embodiment, preferred compounds of Formula I are those of Formula II:

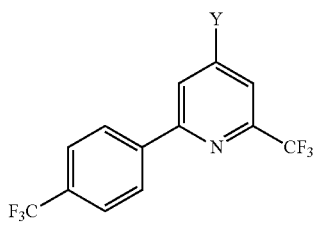

II and pharmaceutically acceptable salts and solvates thereof,
wherein
Y is as defined above with respect to Formula I and any of its embodiments.

In one embodiment, preferred compounds of Formula II are those of Formula IIa:

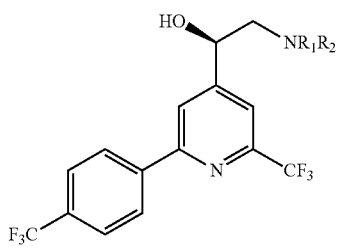

IIa and pharmaceutically acceptable salts and solvates thereof,
wherein
$R^1$ and $R^2$ are as defined above with respect to Formula I and any of its embodiments.

Preferred compounds of formula IIa are those wherein $R^1$ is selected from the group consisting of C5-C7 alkyl, C5-C7 haloalkyl, (arylalkylamino)alkyl, (heteroarylalkylamino)alkyl, alkoxyarylalkyl, (metallocenylalkylamino)alkyl, (arylalkylpiperazinyl)alkyl, (heteroarylalkylpiperazinyl)alkyl or (cycloalkylalkoxy)arylalkyl and $R^2$ is a hydrogen atom. More preferred compounds of formula IIa are those wherein $R^1$ is selected from n-pentyl, n-hexyl, n-heptyl, 4,4,4-trifluoro-n-butyl, 5,5,5-trifluoro-n-pentyl, 5,5-difluoro-n-pentyl, 5-fluoro-n-pentyl, 4,4-difluoro-n-pentyl, 6-fluoro-n-hexyl, 2-(benzhydrylamino)ethyl, 2-((di(pyridin-2-yl)methyl)amino)ethyl, (S)-1-methoxy-3-phenylpropan-2-yl, 2-(ferrocenylmethylamino)ethyl, 3-(4-benzhydrylpiperazin-1-yl)propyl, or (S)-1-(cyclopropylmethoxy)-3-phenylpropan-2-yl and $R^2$ is a hydrogen atom. For example, $R^1$ is selected from n-pentyl, n-hexyl, n-heptyl, 4,4,4-trifluoro-n-butyl, 5,5,5-trifluoro-n-pentyl, 5,5-difluoro-n-pentyl, 5-fluoro-n-pentyl, 4,4-difluoro-n-pentyl, 2-(benzhydrylamino)ethyl, (S)-1-methoxy-3-phenylpropan-2-yl, 2-(ferrocenylmethylamino)ethyl, 3-(4-benzhydrylpiperazin-1-yl)propyl, or (S)-1-(cyclopropylmethoxy)-3-phenylpropan-2-yl and $R^2$ is a hydrogen atom. Even more preferred compounds of formula IIa are those wherein $R^1$ is selected from n-pentyl, n-hexyl, n-heptyl, 2-(benzhydrylamino)ethyl, (S)-1-methoxy-3-phenylpropan-2-yl, 2-(ferrocenylmethylamino)ethyl, or 3-(4-benzhydrylpiperazin-1-yl)propyl, and $R^2$ is a hydrogen atom. Still more preferred compounds of formula IIa are those wherein $R^1$ is selected from n-pentyl, n-hexyl, n-heptyl, (S)-1-methoxy-3-phenylpropan-2-yl, and $R^2$ is a hydrogen atom. Still more preferred compounds of formula IIa are those wherein $R^1$ is selected from 2-(benzhydrylamino)ethyl or (S)-1-methoxy-3-phenylpropan-2-yl and $R^2$ is a hydrogen atom.

In one embodiment, preferred compounds of formula IIa are those wherein $R^1$ is selected from the group consisting of C4-C7-haloalkyl, (arylalkylamino)alkyl, (heteroarylalkylamino)alkyl, alkoxyarylalkyl, (metallocenylalkylamino)alkyl, (arylalkylpiperazinyl)alkyl, (heteroarylalkylpiperazinyl)alkyl and (cycloalkylalkoxy)arylalkyl, and $R^2$ is a hydrogen atom. More preferred compounds of formula IIa are those wherein $R^1$ is selected from 4,4,4-trifluoro-n-butyl, 5,5,5-trifluoro-n-pentyl, 5,5-difluoro-n-pentyl, 5-fluoro-n-pentyl, 4,4-difluoro-n-pentyl, 6-fluoro-n-hexyl, 2-(benzhydrylamino)ethyl, 2-((di(pyridin-2-yl)methyl)amino)ethyl, (S)-1-methoxy-3-phenylpropan-2-yl, 2-(ferrocenylmethylamino)ethyl, 3-(4-benzhydrylpiperazin-1-yl)propyl and (S)-1-(cyclopropylmethoxy)-3-phenylpropan-2-yl, and $R^2$ is a hydrogen atom. Even more preferred compounds of formula IIa are those wherein $R^1$ is selected from 4,4,4-trifluoro-n-butyl, 6-fluoro-n-hexyl, 2-(benzhydrylamino)ethyl, 2-((di(pyridin-2-yl)methyl)amino)ethyl, (S)-1-methoxy-3-phenylpropan-2-yl, 2-(ferrocenylmethylamino)ethyl, 3-(4-benzhydrylpiperazin-1-yl)propyl and (S)-1-(cyclopropylmethoxy)-3-phenylpropan-2-yl, and $R^2$ is a hydrogen atom. Still more preferred compounds of formula IIa are those wherein $R^1$ is selected from 2-(benzhydrylamino)ethyl, (S)-1-methoxy-3-phenylpropan-2-yl, 4,4,4-trifluoro-n-butyl, 6-fluoro-n-hexyl and (S)-1-(cyclopropylmethoxy)-3-phenylpropan-2-yl, and $R^2$ is a hydrogen atom.

In one embodiment, preferred compounds of Formula II are those of Formula IIb:

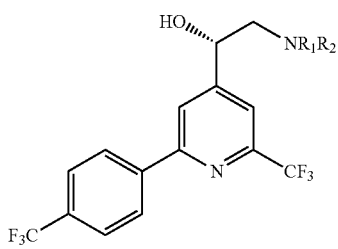

IIb and pharmaceutically acceptable salts and solvates thereof,
wherein
R¹ and R² are as defined above with respect to Formula I and any of its embodiments.

Preferred compounds of formula IIb are those wherein R¹ is selected from the group consisting of C5-C7 alkyl, C5-C7 haloalkyl, (arylalkylamino)alkyl, (arylalkylpiperazinyl)alkyl, alkoxyarylalkyl, (metallocenylalkylamino)alkyl, (arylalkylpiperazinyl)alkyl, (heteroarylalkylpiperazinyl)alkyl or (cycloalkylalkoxy)arylalkyl and R² is a hydrogen atom. More preferred compounds of formula IIb are those wherein R¹ is selected from n-pentyl, n-hexyl, n-heptyl, 4,4,4-trifluoro-n-butyl, 5,5,5-trifluoro-n-pentyl, 5,5-difluoro-n-pentyl, 5-fluoro-n-pentyl, 4,4-difluoro-n-pentyl, 6-fluoro-n-hexyl, 2-(benzhydrylamino)ethyl, 2-((di(pyridin-2-yl)methyl)amino)ethyl, (S)-1-methoxy-3-phenylpropan-2-yl, 2-(ferrocenylmethylamino)ethyl, 3-(4-benzhydrylpiperazin-1-yl)propyl, or (S)-1-(cyclopropylmethoxy)-3-phenylpropan-2-yl and R² is a hydrogen atom. For example, R¹ is selected from n-pentyl, n-hexyl, n-heptyl, 4,4,4-trifluoro-n-butyl, 5,5,5-trifluoro-n-pentyl, 5,5-difluoro-n-pentyl, 5-fluoro-n-pentyl, 4,4-difluoro-n-pentyl, 2-(benzhydrylamino)ethyl, (S)-1-methoxy-3-phenylpropan-2-yl, 2-(ferrocenylmethylamino)ethyl, 3-(4-benzhydrylpiperazin-1-yl)propyl, or (S)-1-(cyclopropylmethoxy)-3-phenylpropan-2-yl and R² is a hydrogen atom. Even more preferred compounds of formula IIb are those wherein R¹ is selected from n-pentyl, n-hexyl, n-heptyl, 2-(benzhydrylamino)ethyl, (S)-1-methoxy-3-phenylpropan-2-yl, 2-(ferrocenylmethylamino)ethyl, or 3-(4-benzhydrylpiperazin-1-yl)propyl, and R² is a hydrogen atom. Still more preferred compounds of formula IIa are those wherein R¹ is selected from n-pentyl, n-hexyl, n-heptyl, 2-(benzhydrylamino)ethyl, (S)-1-methoxy-3-phenylpropan-2-yl, and R² is a hydrogen atom. Still more preferred compounds of formula IIa are those wherein R¹ is selected from 2-(benzhydrylamino)ethyl or (S)-1-methoxy-3-phenylpropan-2-yl, and R² is a hydrogen atom.

In one embodiment, preferred compounds of formula IIb are those wherein R¹ is selected from the group consisting of C4-C7 haloalkyl, (arylalkylamino)alkyl, (heteroarylalkylamino)alkyl, alkoxyarylalkyl, (metallocenylalkylamino)alkyl, (arylalkylpiperazinyl)alkyl, (heteroarylalkylpiperazinyl)alkyl and (cycloalkylalkoxy)arylalkyl, and R² is a hydrogen atom. More preferred compounds of formula IIa are those wherein R¹ is selected from 4,4,4-trifluoro-n-butyl, 5,5,5-trifluoro-n-pentyl, 5,5-difluoro-n-pentyl, 5-fluoro-n-pentyl, 4,4-difluoro-n-pentyl, 6-fluoro-n-hexyl, 2-(benzhydrylamino)ethyl, 2-((di(pyridin-2-yl)methyl)amino)ethyl, (S)-1-methoxy-3-phenylpropan-2-yl, 2-(ferrocenylmethylamino)ethyl, 3-(4-benzhydrylpiperazin-1-yl)propyl and (S)-1-(cyclopropylmethoxy)-3-phenylpropan-2-yl, and R² is a hydrogen atom. Even more preferred compounds of formula IIa are those wherein R¹ is selected from 4,4,4-trifluoro-n-butyl, 6-fluoro-n-hexyl, 2-(benzhydrylamino)ethyl, 2-((di(pyridin-2-yl)methyl)amino)ethyl, (S)-1-methoxy-3-phenylpropan-2-yl, 2-(ferrocenylmethylamino)ethyl, 3-(4-benzhydrylpiperazin-1-yl)propyl and (S)-1-(cyclopropylmethoxy)-3-phenylpropan-2-yl, and R² is a hydrogen atom. Still more preferred compounds of formula IIa are those wherein R¹ is selected from 2-(benzhydrylamino)ethyl, (S)-1-methoxy-3-phenylpropan-2-yl, 4,4,4-trifluoro-n-butyl, 6-fluoro-n-hexyl and (S)-1-(cyclopropylmethoxy)-3-phenylpropan-2-yl, and R² is a hydrogen atom.

In one embodiment, preferred compounds of Formula I are those of Formula III:

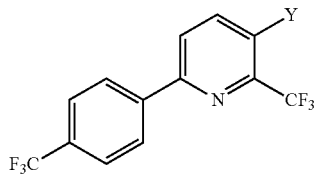

and pharmaceutically acceptable salts and solvates thereof,
wherein
Y is as defined above with respect to Formula I and any of its embodiments.

In one embodiment, preferred compounds of Formula III are those of Formula IIIa:

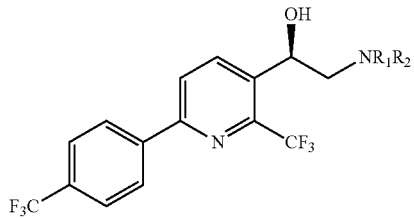

and pharmaceutically acceptable salts and solvates thereof,
wherein
R¹ and R² are as defined above with respect to Formula I and any of its embodiments.

Preferred compounds of formula IIIa are those wherein R¹ is selected from the group consisting of C4-C7 alkyl, C4-C7 haloalkyl, (arylalkylamino)alkyl, (arylalkylpiperazinyl)alkyl, alkoxyarylalkyl, (metallocenylalkylamino)alkyl, (arylalkylpiperazinyl)alkyl, (heteroarylalkylpiperazinyl)alkyl or (cycloalkylalkoxy)arylalkyl and R² is a hydrogen atom. More preferred compounds of formula IIIa are those wherein R¹ is selected from n-butyl, n-pentyl, n-hexyl, n-heptyl, 4,4,4-trifluoro-n-butyl, 5,5,5-trifluoro-n-pentyl, 5,5-difluoro-n-pentyl, 5-fluoro-n-pentyl, 6-fluoro-n-hexyl, 4,4-difluoro-n-pentyl, 2-(benzhydrylamino)ethyl, (S)-1-methoxy-3-phenylpropan-2-yl, 2-(ferrocenylmethylamino)ethyl, 3-(4-benzhydrylpiperazin-1-yl)propyl, or (S)-1-(cyclopropylmethoxy)-3-phenylpropan-2-yl and R² is a hydrogen atom. For example, R¹ is selected from n-butyl, n-pentyl, n-hexyl, n-heptyl, 4,4,4-trifluoro-n-butyl, 5,5,5-trifluoro-n-pentyl, 5,5-difluoro-n-pentyl, 5-fluoro-n-pentyl, 4,4-difluoro-n-pentyl, 2-(benzhydrylamino)ethyl, (S)-1-methoxy-3-phenylpropan-2-yl, 2-(ferrocenylmethylamino)ethyl, 3-(4-benzhydrylpiperazin-1-yl)propyl, or (S)-1-(cyclopropylmethoxy)-3-phenylpropan-2-yl and R² is a hydrogen atom. Even more preferred compounds of formula IIIa are those wherein R¹ is selected from n-butyl, n-pentyl, n-hexyl, n-heptyl, 6-fluoro-n-hexyl, 2-(benzhydrylamino)ethyl, (S)-1-methoxy-3-phenylpropan-2-yl, 2-(ferrocenylmethylamino)ethyl, or 3-(4-benzhydrylpiperazin-1-yl)propyl and R² is a hydrogen atom. For example, R¹ is selected from n-butyl, n-pentyl, n-hexyl, n-heptyl, 2-(benzhydrylamino)ethyl, (S)-1-methoxy-3-phenylpropan-2-yl, 2-(ferrocenylmethylamino)ethyl, or 3-(4-benzhydrylpiperazin-1-yl)propyl and R² is a hydrogen atom In one embodiment, preferred compounds of Formula III are those of Formula IIIb:

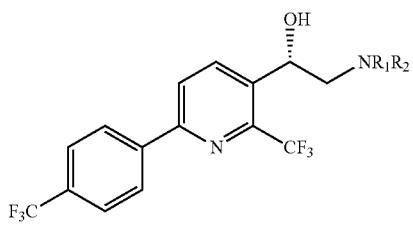

and pharmaceutically acceptable salts and solvates thereof,
wherein
$R^1$ and $R^2$ are as defined above with respect to Formula I and any of its embodiments.

Preferred compounds of formula IIIb are those wherein $R^1$ is selected from the group consisting of C4-C7 alkyl, C4-C7 haloalkyl, (arylalkylamino)alkyl, (arylalkylpiperazinyl)alkyl, alkoxyarylalkyl, (metallocenylalkylamino)alkyl, (arylalkylpiperazinyl)alkyl, (heteroarylalkylpiperazinyl)alkyl or (cycloalkylalkoxy)arylalkyl and $R^2$ is a hydrogen atom. More preferred compounds of formula IIIb are those wherein $R^1$ is selected from n-butyl, n-pentyl, n-hexyl, n-heptyl, 4,4,4-trifluoro-n-butyl, 5,5,5-trifluoro-n-pentyl, 5,5-difluoro-n-pentyl, 5-fluoro-n-pentyl, 4,4-difluoro-n-pentyl, 6-fluoro-n-hexyl, 2-(benzhydrylamino)ethyl, (S)-1-methoxy-3-phenylpropan-2-yl, 2-(ferrocenylmethylamino) ethyl, 3-(4-benzhydrylpiperazin-1-yl)propyl, or (S)-1-(cyclopropylmethoxy)-3-phenylpropan-2-yl and $R^2$ is a hydrogen atom. For example, $R^1$ is selected from n-butyl, n-pentyl, n-hexyl, n-heptyl, 4,4,4-trifluoro-n-butyl, 5,5,5-trifluoro-n-pentyl, 5,5-difluoro-n-pentyl, 5-fluoro-n-pentyl, 4,4-difluoro-n-pentyl, 2-(benzhydrylamino)ethyl, (S)-1-methoxy-3-phenylpropan-2-yl, 2-(ferrocenylmethylamino) ethyl, 3-(4-benzhydrylpiperazin-1-yl)propyl, or (S)-1-(cyclopropylmethoxy)-3-phenylpropan-2-yl and $R^2$ is a hydrogen atom. Even more preferred compounds of formula IIIb are those wherein $R^1$ is selected from n-butyl, n-pentyl, n-hexyl, n-heptyl, 6-fluoro-n-hexyl, 2-(benzhydrylamino) ethyl, (S)-1-methoxy-3-phenylpropan-2-yl, 2-(ferrocenylmethylamino)ethyl, or 3-(4-benzhydrylpiperazin-1-yl)propyl and $R^2$ is a hydrogen atom. For example, $R^1$ is selected from n-butyl, n-pentyl, n-hexyl, n-heptyl, 2-(benzhydrylamino) ethyl, (S)-1-methoxy-3-phenylpropan-2-yl, 2-(ferrocenylmethylamino)ethyl, or 3-(4-benzhydrylpiperazin-1-yl)propyl and $R^2$ is a hydrogen atom. Still more preferred compounds of formula IIIb are those wherein $R^1$ is selected from n-pentyl, n-hexyl, or n-heptyl and $R^2$ is a hydrogen atom.

Particularly, preferred compounds of the invention are those listed in Table 1 hereafter:

TABLE 1

| Number | Structure | Name |
|---|---|---|
| 1a | 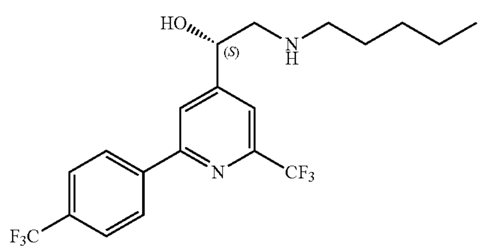 | (S)-2-(n-pentylamino)-1-(2-(trifluoromethyl)-6-(4-(trifluoromethyl)phenyl)pyridin-4-yl)ethanol |
| 1b | 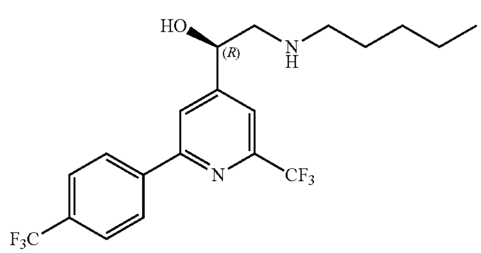 | (R)-2-(n-pentylamino)-1-(2-(trifluoromethyl)-6-(4-(trifluoromethyl)phenyl)pyridin-4-yl)ethanol |
| 1c | 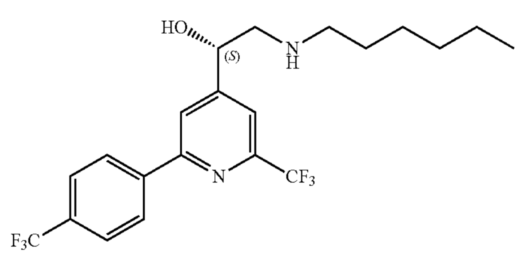 | (S)-2-(n-hexylamino)-1-(2-(trifluoromethyl)-6-(4-(trifluoromethyl)phenyl)pyridin-4-yl)ethanol |

TABLE 1-continued

| Number | Structure | Name |
|---|---|---|
| 1d | 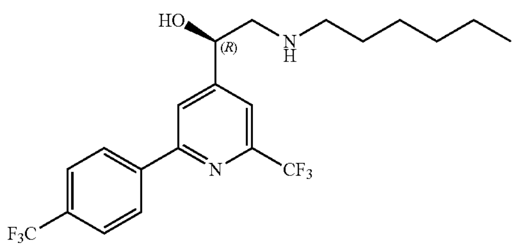 | (R)-2-(n-hexylamino)-1-(2-(trifluoromethyl)-6-(4-(trifluoromethyl)phenyl)pyridin-4-yl)ethanol |
| 1e | 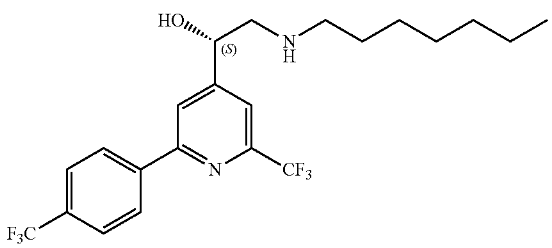 | (S)-2-(n-heptylamino)-1-(2-(trifluoromethyl)-6-(4-(trifluoromethyl)phenyl)pyridin-4-yl)ethanol |
| 1f | 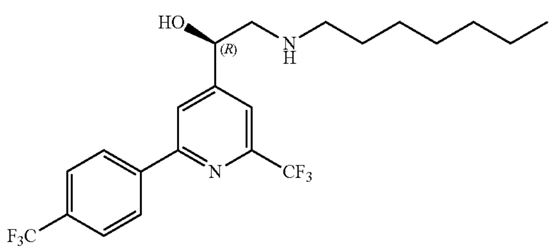 | (R)-2-(n-heptylamino)-1-(2-(trifluoromethyl)-6-(4-(trifluoromethyl)phenyl)pyridin-4-yl)ethanol |
| 1g | 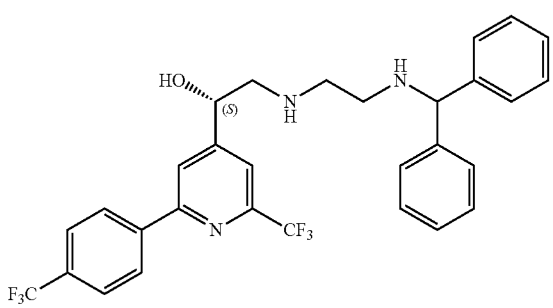 | (S)-2-((2-(benzhydrylamino)ethyl)amino)-1-(2-(trifluoromethyl)-6-(4-(trifluoromethyl)phenyl)pyridin-4-yl)ethanol |
| 1h | 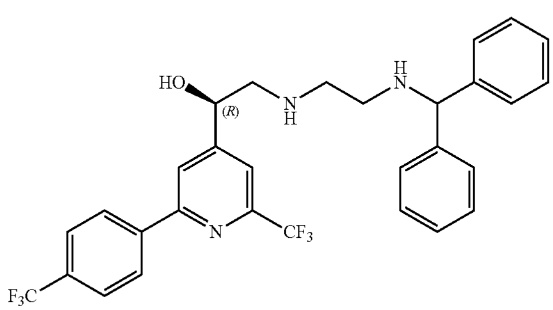 | (R)-2-((2-(benzhydrylamino)ethyl)amino)-1-(2-(trifluoromethyl)-6-(4-(trifluoromethyl)phenyl)pyridin-4-yl)ethanol |

TABLE 1-continued

| Number | Structure | Name |
|---|---|---|
| 1i | 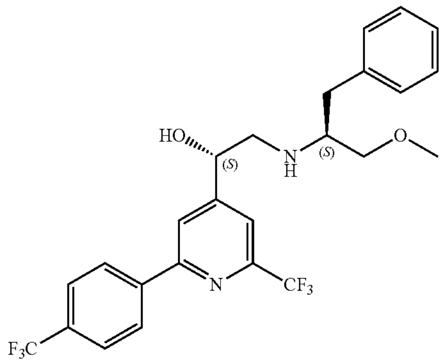 | (S)-2-(((S)-1-methoxy-3-phenylpropan-2-yl)amino)-1-(2-(trifluoromethyl)-6-(4-(trifluoromethyl)phenyl)pyridin-4-yl)ethanol |
| 1j | 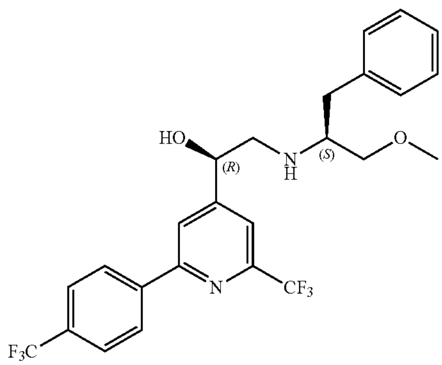 | (R)-2-(((S)-1-methoxy-3-phenylpropan-2-yl)amino)-1-(2-(trifluoromethyl)-6-(4-(trifluoromethyl)phenyl)pyridin-4-yl)ethanol |
| 1k | 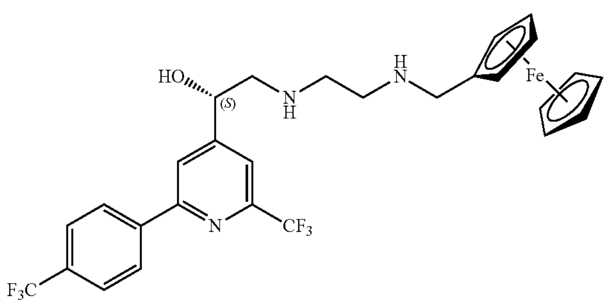 | (S)-2-((2-(ferrocenylmethylamino)ethyl)amino)-1-(2-(trifluoromethyl)-6-(4-(trifluoromethyl)phenyl)pyridin-4-yl)ethanol |
| 1l | 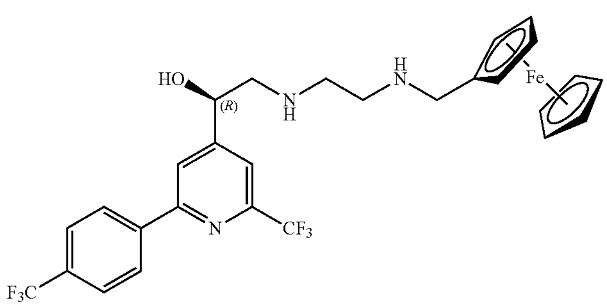 | (R)-2-((2-(ferrocenylmethylamino)ethyl)amino)-1-(2-(trifluoromethyl)-6-(4-(trifluoromethyl)phenyl)pyridin-4-yl)ethanol |
| 1m | 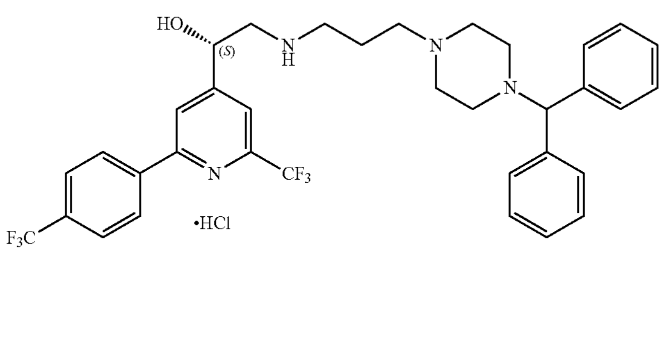 | (S)-2-((3-(4-benzhydrylpiperazin-1-yl)propyl)amino)-1-(2-(trifluoromethyl)-6-(4-(trifluoromethyl)phenyl)pyridin-4-yl)ethanol |

TABLE 1-continued

| Number | Structure | Name |
|---|---|---|
| 1n | 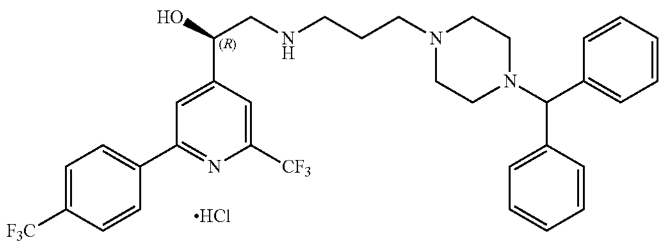 | (R)-2-((3-(4-benzhydrylpiperazin-1-yl)propyl)amino)-1-(2-(trifluoromethyl)-6-(4-(trifluoromethyl)phenyl)pyridin-4-yl)ethanol |
| 1o | 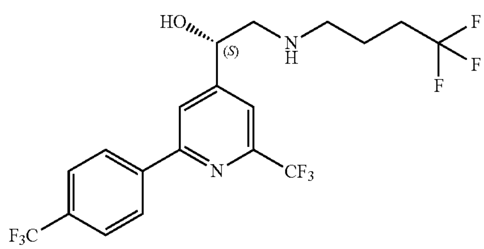 | (S)-2-((4,4,4-trifluorobutyl)amino)-1-(2-(trifluoromethyl)-6-(4-(trifluoromethyl)phenyl)pyridin-4-yl)ethan-1-ol |
| 1p | 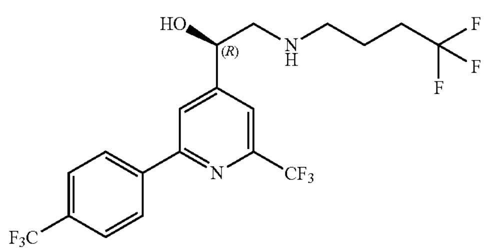 | (R)-2-((4,4,4-trifluorobutyl)amino)-1-(2-(trifluoromethyl)-6-(4-(trifluoromethyl)phenyl)pyridin-4-yl)ethan-1-ol |
| 1q | 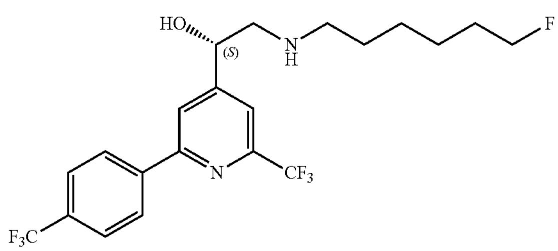 | (S)2-((6-fluorohexyl)amino)-1-(2-(trifluoromethyl)-6-(4-(trifluoromethyl)phenyl)pyridine-4-yl)ethan-1-ol |
| 1r | 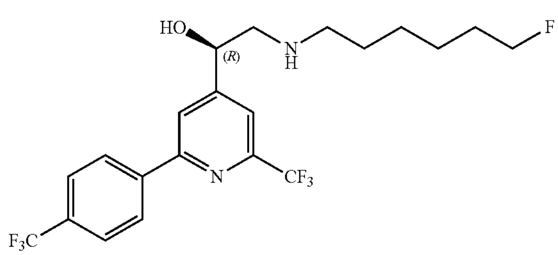 | (R)-2-((6-fluorohexyl)amino)-1-(2-(trifluoromethyl)-6-(4-(trifluoromethyl)phenyl)pyridine-4-yl)ethan-1-ol |
| 1s | 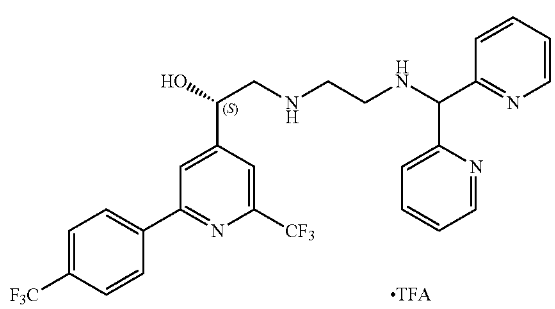 | (S)-2-((2-((di(pyridine-2-yl)methyl)amino)ethyl)amino)-1-(2-(trifluoromethyl)-6-(4-(trifluoromethyl)phenyl)pyridin-4-yl)ethan-1-ol trifluoroacetic acid salt |

TABLE 1-continued

| Number | Structure | Name |
|---|---|---|
| 1t | 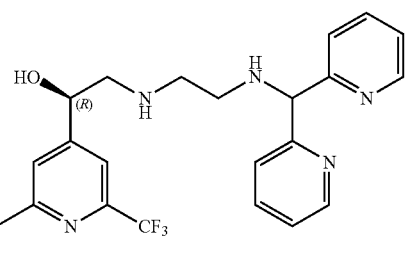 ·TFA | (R)-2-((2-((di(pyridine-2-yl)methyl)amino)ethyl)amino)-1-(2-(trifluoromethyl)-6-(4-(trifluoromethyl)phenyl)pyridin-4-yl)ethan-1-ol trifluoroacetic acid salt |
| 1u | 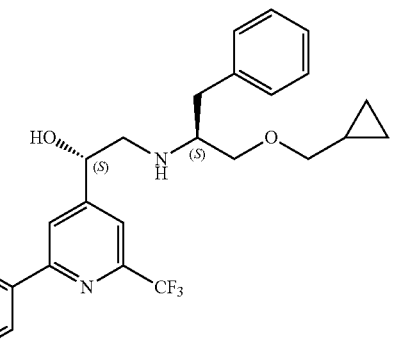 | (S)-2-(((S)-1-(cyclopropylmethoxy)-3-phenylpropan-2-yl)amino)-1-(2-(trifluoromethyl)-6-(4-(trifluoromethyl)phenyl)pyridin-4-yl)ethan-1-ol |
| 1v | 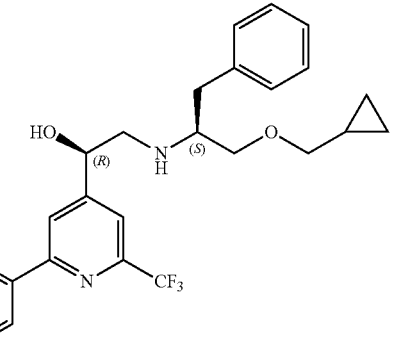 | (R)-2-(((S)-1-(cyclopropylmethoxy)-3-phenylpropan-2-yl)amino)-1-(2-(trifluoromethyl)-6-(4-(trifluoromethyl)phenyl)pyridin-4-yl)ethan-1-ol |
| 30a | 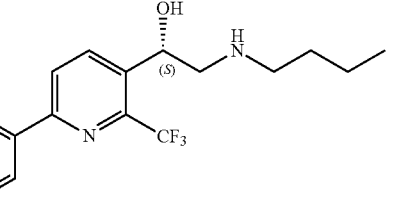 | (S)-2-n-butylamino)-1-(2-(trifluoromethyl)-6-(4-(trifluoromethyl)phenyl)pyridin-3-yl)ethanol |
| 30b | 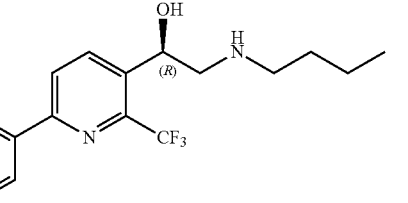 | (R)-2-(n-butylamino)-1-(2-(trifluoromethyl)-6-(4-(trifluoromethyl)phenyl)pyridin-3-yl)ethanol |

TABLE 1-continued

| Number | Structure | Name |
|---|---|---|
| 30c | 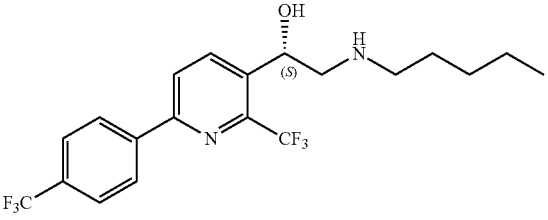 | (S)-2-(n-pentylamino)-1-(2-(trifluoromethyl)-6-(4-(trifluoromethyl)phenyl)pyridin-3-yl)ethanol |
| 30d | 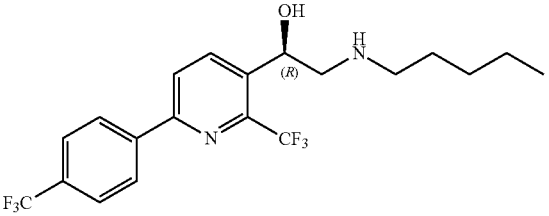 | (R)-2-n-pentylamino)-1-(2-(trifluoromethyl)-6-(4-(trifluoromethyl)phenyl)pyridin-3-yl)ethanol |
| 30e | 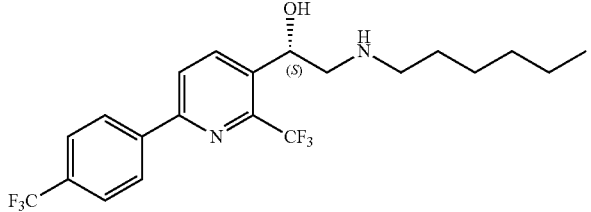 | (S)2-(n-hexylamino)-1-(2-(trifluoromethyl)-6-(4-(trifluoromethyl)phenyl)pyridin-3-yl)ethanol |
| 30f | 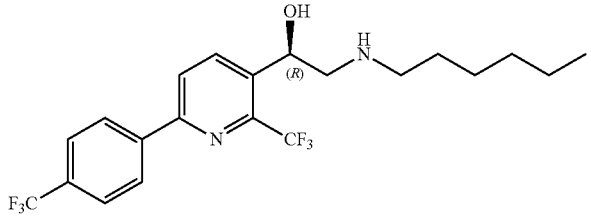 | (R)-2-(n-hexylamino)-1-(2-(trifluoromethyl)-6-(4-(trifluoromethyl)phenyl)pyridin-3-yl)ethanol |
| 30g | 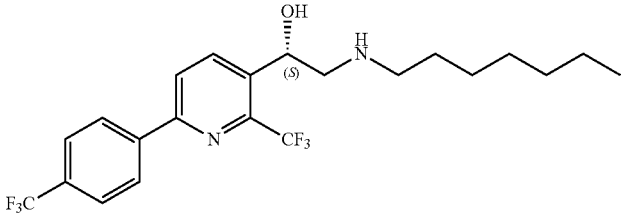 | (S)-2-(n-heptylamino)-1-(2-(trifluoromethyl)-6-(4-(trifluoromethyl)phenyl)pyridin-3-yl)ethanol |
| 30h | 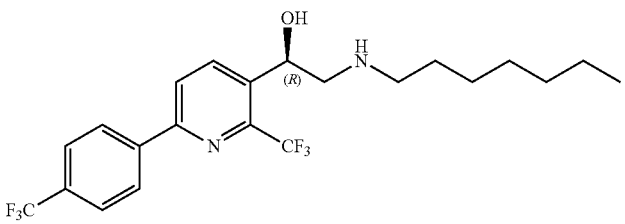 | (R)-2-(n-heptylamino)-1-(2-(trifluoromethyl)-6-(4-(trifluoromethyl)phenyl)pyridin-3-yl)ethanol |

TABLE 1-continued

| Number | Structure | Name |
|---|---|---|
| 30i | 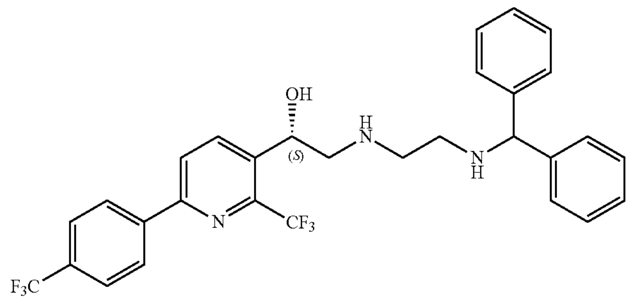 | (S)-2-((2-(benzhydrylamino)ethyl)amino)-1-(2-(trifluoromethyl)-6-(4-(trifluoromethyl)phenyl)pyridin-3-yl)ethanol |
| 30j | 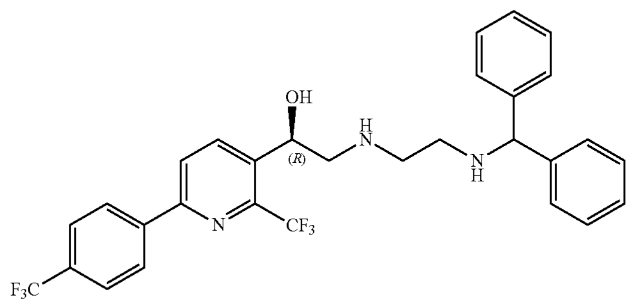 | (R)-2-((2-(benzhydrylamino)ethyl)amino)-1-(2-(trifluoromethyl)-6-(4-(trifluoromethyl)phenyl)pyridin-3-yl)ethanol |
| 30k | 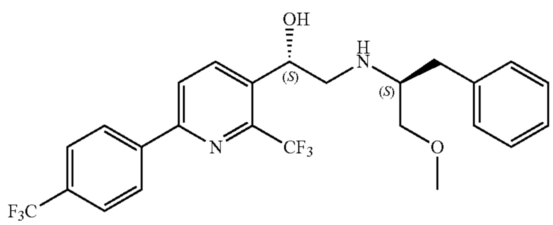 | (S)-2-(((S)-1-methoxy-3-phenylpropan-2-yl)amino)-1-(2-(trifluoromethyl)-6-(4-(trifluoromethyl)phenyl)pyridin-3-yl)ethanol |
| 30l | 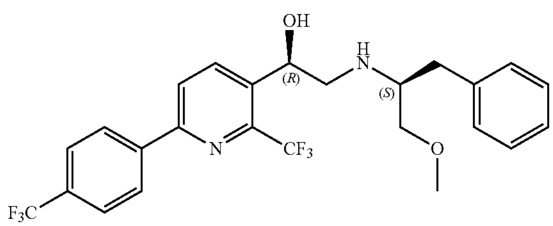 | (R)-2-(((S)-1-methoxy-3-phenylpropan-2-yl)amino)-1-(2-(trifluoromethyl)-6-(4-(trifluoromethyl)phenyl)pyridin-3-yl)ethanol |
| 30m | 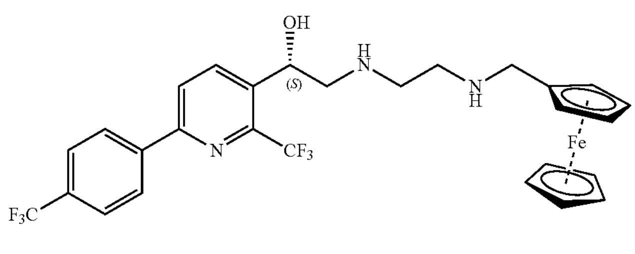 | (S)-2-((2-(ferrocenylmethylamino)ethyl)amino)-1-(2-(trifluoromethyl)-6-(4(trifluoromethyl) phenyl)pyridin-3-yl)ethanol |
| 30n | 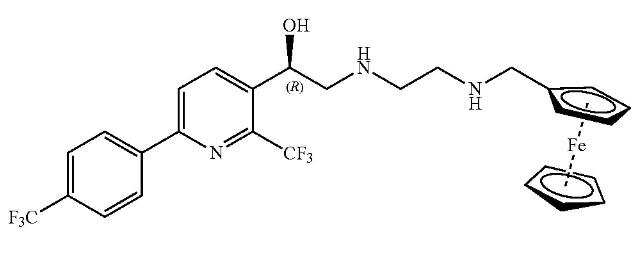 | (R)-2-((2-(ferrocenylmethylamino)ethyl)amino)-1-(2-(trifluoromethyl)-6-(4(trifluoromethyl) phenyl)pyridin-3-yl)ethanol |

TABLE 1-continued

| Number | Structure | Name |
|---|---|---|
| 30o | 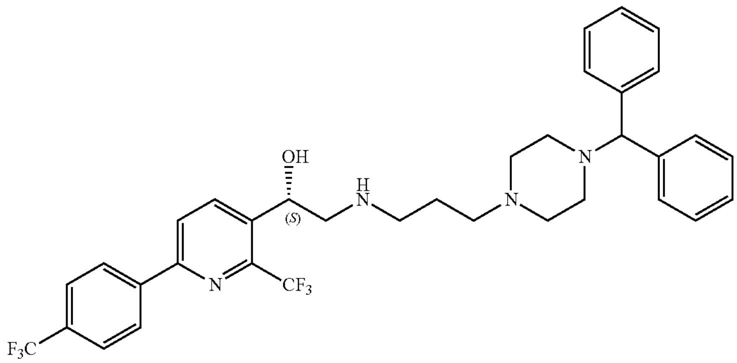 | (S)-2-((3-(4-benzhydrylpiperazin-1-yl)propyl)amino)-1-(2-(trifluoromethyl)-6-(4-(trifluoromethyl)phenyl)pyridin-3-yl)ethanol |
| 30p | 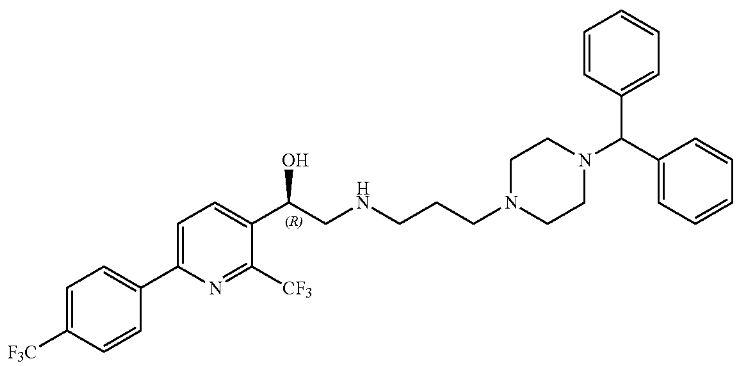 | (R)-2-((3-(4-benzhydrylpiperazin-1-yl)propyl)amino)-1-(2-(trifluoromethyl)-6-(4-(trifluoromethyl)phenyl)pyridin-3-yl)ethanol |
| 30q | 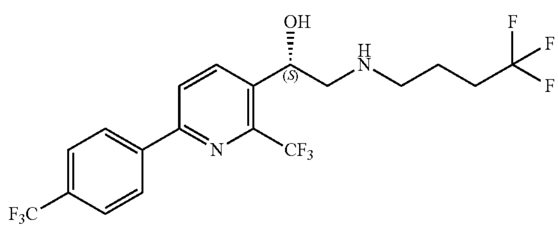 | (S)2-((4,4,4-trifluorobutyl)amino)-1-(2-(trifluoromethyl)-6-(4-(trifluoromethyl)phenyl)pyridin-3-yl)ethan-1-ol |
| 30r | 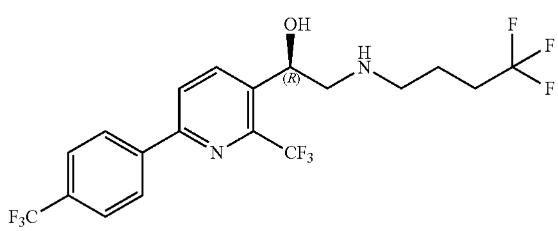 | (R)-2-((4,4,4-trifluorobutyl)amino)-1-(2-(trifluoromethyl)-6-(4-(trifluoromethyl)phenyl)pyridin-3-yl)ethan-1-ol |
| 30s | 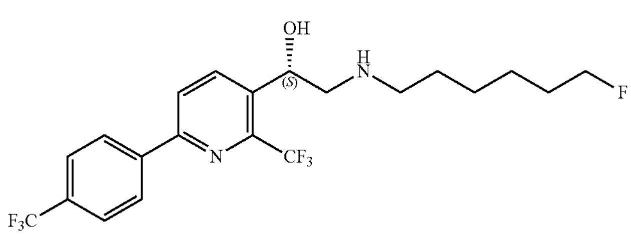 | (S)-2-((6-fluorohexyl)amino)-1-(2-(trifluoromethyl)-6-(4-(trifluoromethyl)phenyl)pyridine-3-yl)ethan-1-ol |

TABLE 1-continued

| Number | Structure | Name |
|---|---|---|
| 30t | 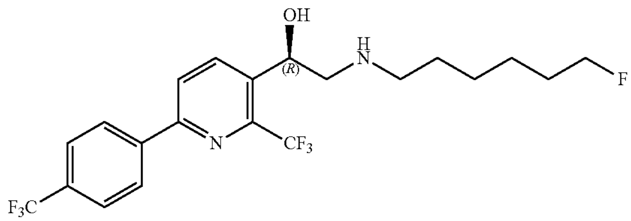 | (R)-2-((6-fluorohexyl)amino)-1-(2-(trifluoromethyl)-6-(4-(trifluoromethyl)phenyl)pyridine-3-yl)ethan-1-ol |
| 30u | 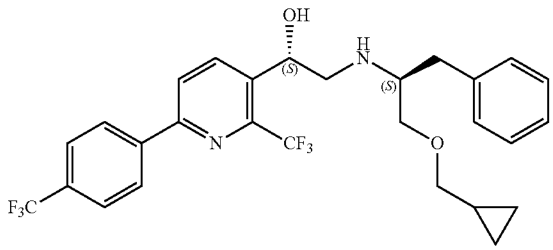 | (S)-2-(((S)-1-(cyclopropylmethoxy)-3-phenylpropan-2-yl)amino)-1-(2-(trifluoromethyl)-6-(4-(trifluoromethyl)phenyl)pyridin-3-yl)ethan-1-ol |
| 30v | 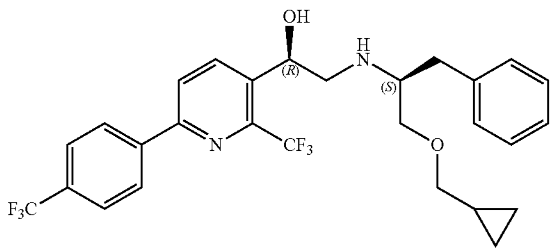 | (R)-2-(((S)-1-(cyclopropylmethoxy)-3-phenylpropan-2-yl)amino)-1-(2-(trifluoromethyl)-6-(4-(trifluoromethyl)phenyl)pyridin-3-yl)ethan-1-ol |

The compounds of the invention can be prepared by different ways with reactions known by the person skilled in the art. Reaction schemes as described in the example section illustrate by way of example different possible approaches.

The present invention further relates to a process for providing a compound of formula I as defined above. The process comprises the following steps in the following order:

preparation of 2-(trifluoromethyl)-6-(4-(trifluoromethyl)phenyl)-vinylpyridine, preferably 2-(trifluoromethyl)-6-(4-(trifluoromethyl)phenyl)-4-vinylpyridine or 2-(trifluoromethyl)-6-(4-(trifluoromethyl)phenyl)-3-vinylpyridine;

addition of an asymmetric dihydroxylation catalyst to said 2-(trifluoromethyl)-6-(4-(trifluoromethyl)phenyl)-vinylpyridine to obtain (R)- or (S)-1-(2-(trifluoromethyl)-6-(4-(trifluoromethyl)phenyl)pyridinyl) ethane-1,2-diol, preferably (R)- or (S)-1-(2-(trifluoromethyl)-6-(4-(trifluoromethyl)phenyl)pyridin-4-yl) ethane-1,2-diol or (R)- or (S)-1-(2-(trifluoromethyl)-6-(4-(trifluoromethyl)phenyl)pyridin-3-yl)ethane-1,2-diol respectively;

preparation of (R)- or (S)-(oxiran-2-yl)-2-(trifluoromethyl)-6-(4-(trifluoromethyl)phenyl)pyridine, preferably (R)- or (S)-4-(oxiran-2-yl)-2-(trifluoromethyl)-6-(4-(trifluoromethyl)phenyl)pyridine or (R)- or (S)-3-(oxiran-2-yl)-2-(trifluoromethyl)-6-(4-(trifluoromethyl)phenyl)pyridine, starting from said (R)- or (S)-1-(2-(trifluoromethyl)-6-(4-(trifluoromethyl)phenyl)pyridinyl) ethane-1,2-diol respectively; and addition of an amine to said (R)- or (S)-(oxiran-2-yl)-2-(trifluoromethyl)-6-(4-(trifluoromethyl)phenyl)pyridine. Preferred amines include n-butylamine, n-pentylamine, n-hexylamine, n-heptylamine, N-benzhydrylethane-1,2-diamine, (S)-1-methoxy-3-phenylpropan-2-amine, ethylenediamine, and 3-(4-benzhydrylpiperazin-1-yl)propan-1-amine.

The 2-(trifluoromethyl)-6-(4-(trifluoromethyl)phenyl)-vinylpyridine is prepared with reactions known by the person skilled in the art. Preferably, said 2-(trifluoromethyl)-6-(4-(trifluoromethyl)phenyl)-4-vinylpyridine is prepared by reacting a 4-bromo-2-(trifluoromethyl)-6-(4-(trifluoromethyl)phenyl)pyridine with potassium vinyltrifluoroborate using the $Pd(PPh_3)_4$ as catalyst while 2-(trifluoromethyl)-6-(4-(trifluoromethyl)phenyl)-3-vinylpyridine is prepared by reacting a 2-(trifluoromethyl)-6-(4-(trifluoromethyl)phenyl)pyridin-3-yltrifluoromethanesulfonate with tributyl(vinyl)stannane using the $Pd(PPh_3)_4$ as catalyst.

Preferably yet, the asymmetric dihydroxylation catalysts is one of AD-mix α and AD-mix β. Also, (R)-1-(2-(trifluoromethyl)-6-(4-(trifluoromethyl)phenyl)pyridin-4-yl)ethane-1,2-diol and (S)-1-(2-(trifluoromethyl)-6-(4-(trifluoromethyl)phenyl)pyridin-4-yl)ethane-1,2-diol are prepared by reacting said 2-(trifluoromethyl)-6-(4-(trifluoromethyl)phenyl)-4-vinylpyridine with respectively AD-mix β and AD-mix α in a solution of t-BuOH/$H_2O$ at 0° C. And, (R)-1-(2-(trifluoromethyl)-6-(4-(trifluoromethyl)phenyl)pyridin-3-yl)ethane-1,2-diol and (S)-1-(2-(trifluoromethyl)-6-(4-(trifluoromethyl)phenyl)pyridin-3-yl)ethane-1,2-diol are prepared by reacting said 2-(trifluoromethyl)-6-(4-(trifluoromethyl)phenyl)-3-vinylpyridine with respectively AD-mix β and AD-mix α in a solution of t-BuOH/$H_2O$ at 0° C. It is preferable that $K_2OsO_2(OH)_4$ is further added to prepare said (R)- or (S)-1-(2-(trifluoromethyl)-6-(4-(trifluoromethyl)phenyl)pyridinyl) ethane-1,2-diol, preferably (R)-1-(2-(trifluoromethyl)-6-(4-(trifluoromethyl)phenyl)pyridin-4-yl)ethane-1,2-diol, (S)-1-(2-(trifluoromethyl)-6-(4-(trifluoromethyl)phenyl)pyridin-4-yl)ethane-1,2-diol, (R)-1-(2-(trifluoromethyl)-6-(4-(trifluoromethyl)phenyl)pyridin-3-yl)ethane-1,2-diol and (S)-1-(2-(trifluoromethyl)-6-(4-(trifluoromethyl)phenyl)pyridin-3-yl)ethane-1,2-diol.

Preferably still, starting from respectively (R)-1-(2-(trifluoromethyl)-6-(4-(trifluoromethyl)phenyl)pyridin-4-yl) ethane-1,2-diol, (S)-1-(2-(trifluoromethyl)-6-(4-(trifluoromethyl)phenyl)pyridin-4-yl)ethane-1,2-diol, (R)-1-(2-(trifluoromethyl)-6-(4-(trifluoromethyl)phenyl)pyridin-3-yl)ethane-1,2-diol or (S)-1-(2-(trifluoromethyl)-6-(4-(trifluoromethyl)phenyl)pyridin-3-yl)ethane-1,2-diol, said respectively (R)-4-(oxiran-2-yl)-2-(trifluoromethyl)-6-(4-(trifluoromethyl)phenyl)pyridine, (S)-4-(oxiran-2-yl)-2-(trifluoromethyl)-6-(4-(trifluoromethyl)phenyl)pyridine, (R)-3-(oxiran-2-yl)-2-(trifluoromethyl)-6-(4-(trifluoromethyl) phenyl)pyridine and (S)-3-(oxiran-2-yl)-2-(trifluoromethyl)-6-(4-(trifluoromethyl)phenyl)pyridine are prepared by a process comprising the steps of:
- formation of the cyclic orthoester by acid catalyzed transesterification;
- generation of halohydrins ester via regioselective opening of acetoxonium ion by addition of trimethylsilyl chloride or bromide; and
- cyclization to epoxide by base mediated saponification in methanol.

The process according to the present invention enables to provide an enantiopure, synthetic, and straightforward route to prepare 3- or 4-aminopyridine derivatives through the enantiopure 3- or 4-oxirane synthesis. The preparation of (R)- or (S)-1-(2-(trifluoromethyl)-6-(4-(trifluoromethyl) phenyl)pyridin-4-yl)ethane-1,2-diol or (R)- or (S)-1-(2-(trifluoromethyl)-6-(4-(trifluoromethyl)phenyl)pyridin-3-yl) ethane-1,2-diol is carried out from corresponding 4-vinylpyridine or 3-vinylpyridine compound respectively in two steps via a Sharpless asymmetric dihydroxylation with retention of configuration. The key-intermediate enantiopure 3- or 4-(oxiran-2-yl)-2-(trifluoromethyl)-6-(4-(trifluoromethyl)phenyl)pyridine has been easily diversified, on position 3 or 4, through a regioselective $S_N2$ ring opening mechanism with various amines, to provide the corresponding enantiopure 3- or 4-aminopyridinemethanols (R) or (S) of formula II and III with excellent yields. Consequently, the fabrication cost of the antimalarial drugs can be drastically reduced.

Applications

The compounds of the invention display an antimalarial activity on *Plasmodium falciparum* strains W2 and 3D7. The 3D7 strain is susceptible to chloroquine but displays a decreased susceptibility to mefloquine while W2 strain is resistant to chloroquine and sensitive to mefloquine. The compounds of the invention, particularly (R)-4-aminopyridinemethanols, (S)-4-aminopyridinemethanols and (S)-3-aminopyridinemethanols, more particularly (R)-4-aminopyridinemethanols and (S)-4-aminopyridinemethanols, are more active than chloroquine and mefloquine whatever the strain. No cross-resistance was observed neither with mefloquine nor with chloroquine. In addition, compounds of the invention are devoid of clastogenic and/or aneugenic activities and devoid of mutagenic activity.

The compounds of the invention are therefore useful in the prevention and/or treatment of malaria. The invention thus also relates to a compound of the invention or a pharmaceutically acceptable salt or solvate thereof for use in treating and/or preventing malaria. Or in other terms, the invention also relates to a method of treating and/or preventing malaria, comprising the administration of a therapeutically effective amount of a compound or pharmaceutically acceptable salt or solvate of the invention, to a patient in need thereof. Preferably the patient is a warm-blooded animal, more preferably a human.

The invention further provides the use of a compound of the invention or a pharmaceutically acceptable salt or solvate thereof for the manufacture of a medicament for use in treating and/or preventing malaria.

According to a further feature of the present invention, there is provided the use of a compound of the invention or a pharmaceutically acceptable salt or solvate thereof for treating and/or preventing malaria, in a patient, in need of such treatment, comprising administering to said patient an effective amount of a compound of the present invention, or a pharmaceutically acceptable salt or solvate thereof. In other terms, the invention also provides a method for treating and/or preventing malaria, in a patient, in need of such treatment, which comprises administering to said patient an effective amount of a compound of the present invention, or a pharmaceutically acceptable salt or solvate thereof. Preferably, the patient is a warm blooded animal, and even more preferably a human.

According to one embodiment, the compounds of the invention, their pharmaceutical acceptable salts or solvates may be administered as part of a combination therapy. Thus, are included within the scope of the present invention embodiments comprising coadministration of, and compositions and medicaments which contain, in addition to a compound of the present invention, a pharmaceutically acceptable salt or solvate thereof as active ingredient, additional therapeutic agents and/or active ingredients. Such multiple drug regimens, often referred to as combination therapy, may be used in the treatment and/or prevention of malaria.

Thus, the methods of treatment and pharmaceutical compositions of the present invention may employ the compounds of the invention or their pharmaceutical acceptable salts or solvates thereof in the form of monotherapy, but said methods and compositions may also be used in the form of combination therapy in which one or more compounds of the invention or their pharmaceutically acceptable salts or solvates are coadministered in combination with one or more other therapeutic agents. Such additional therapeutic agents include, but are not limited to, amodiaquine, artemisinin and derivatives, chloroquine, enpiroline, lumefrantrine, mefloquine, quinine and sulfadoxine-pyrimethamine. Preferred additional therapeutic agents are artemisinin and derivatives.

The invention also provides pharmaceutical compositions comprising a compound of the invention or a pharmaceutically acceptable salt or solvate thereof and at least one pharmaceutically acceptable carrier, diluent, excipient and/or adjuvant. As indicated above, the invention also covers pharmaceutical compositions which contain, in addition to a compound of the present invention, a pharmaceutically acceptable salt or solvate thereof as active ingredient, additional therapeutic agents and/or active ingredients.

Another object of this invention is a medicament comprising at least one compound of the invention, or a pharmaceutically acceptable salt or solvate thereof, as active ingredient.

Generally, for pharmaceutical use, the compounds of the inventions may be formulated as a pharmaceutical preparation comprising at least one compound of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Definitions

The definitions and explanations below are for the terms as used throughout the entire application, including both the specification and the claims.

Unless otherwise stated, any reference to compounds of the invention herein means the compounds as such as well as their pharmaceutically acceptable salts and solvates.

When describing the compounds of the invention, the terms used are to be construed in accordance with the following definitions, unless indicated otherwise.

The term "halo" or "halogen" means fluoro, chloro, bromo, or iodo. Preferred halo groups are fluoro and chloro, fluoro being particularly preferred.

The term "alkyl" by itself or as part of another substituent refers to a hydrocarbyl radical of Formula $C_nH_{2n+1}$ wherein n is a number greater than or equal to 1.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, I-bromoethyl, fluoromethyl, difluoromethyl, trifluoromethyl, 1,1,1-trifluoroethyl, trifluorobutyl, fluropentyl, difluoropentyl, trifluoropentyl, and the like. A preferred haloalkyl radical is trifluoromethyl.

The term "cycloalkyl" or "cyclic alkyl" as used herein is a monovalent, saturated, or unsaturated monocyclic or bicyclic hydrocarbyl group. Cycloalkyl groups may comprise 3 or more carbon atoms in the ring and generally, according to this invention comprise from 3 to 10, more preferably from 3 to 8 carbon atoms, still more preferably from 3 to 6 carbon atoms. Examples of cycloalkyl groups include but are not limited to cyclopropyl, cyclobutyl, cyclopentyl, and cyclohexyl.

The term "heteroatom" as used herein refers to any atom that is not carbon or hydrogen. Non-limiting examples of such heteroatoms include nitrogen, oxygen, sulfur, and phosphorus. Preferred heteroatoms are nitrogen and oxygen.

The term "heteroalkyl" as used herein by itself or as part of another group, refers to an alkyl radical having the meaning as defined above wherein one or more carbons are replaced with a heteroatom as defined above. Preferred heteroatoms are nitrogen and oxygen.

The terms "heterocyclyl", "heterocycloalkyl" or "heterocyclo" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. Examples of heterocyclyl groups include but are not limited to aziridinyl, oxiranyl, thiiranyl, azetidinyl, oxetanyl, thietanyl, pyrrolidinyl, oxolanyl, thiolanyl, piperidinyl, oxanyl, thianyl, azepanyl, oxepanyl, thiepanyl, piperazinyl, morpholinyl, thiomorpholinyl, dioxanyl, and dithianyl. Preferred heterocyclyl group is piperazinyl.

The term "aryl" as used herein refers to a polyunsaturated, aromatic hydrocarbyl group having a single ring (i.e. phenyl) or multiple aromatic rings fused together (e.g. naphtyl), typically containing 5 to 14 atoms; preferably 6 to 10, wherein at least one ring is aromatic. Examples of aryl groups include but are not limited to phenyl, naphtyl, anthracyl. Preferred aryl group is phenyl.

The term "heteroaryl" as used herein by itself or as part of another group refers but is not limited to 5 to 12 carbon-atom aromatic rings or ring systems containing 1 to 2 rings which are fused together, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Examples of heteroaryl groups include but are not limited to pyridyl, pyrazinyl, pyrimidinyl, pyridazinyl, triazinyl, quinolinyl, quinoxalinyl, quinazolinyl, furanyl, benzofuranyl, pyrrolyl, indolyl, thiophenyl, benzothiophenyl, imidazolyl, benzimidazolyl, pyrazolyl, indazolyl, oxazolyl, benzoxazolyl, isoxazolyl, benzisoxazolyl, thiazolyl, and benzothiazolyl. Preferred heteroaryl group is pyridyl.

The term "metallocene" as used herein refers to a group consisting of two cyclopentadienyl anions ($C_5H_5^-$) bound to a metal centre (M) in the oxidation state II, with the resulting general formula $(C_5H_5)_2M$. Non-limiting examples of such metal centres include iron, cobalt, chromium, nickel, and vanadium. Preferred metal is iron.

The compounds of the invention containing a basic functional group may be in the form of pharmaceutically acceptable salts. Pharmaceutically acceptable salts of the compounds of the invention containing one or more basic functional groups include in particular the acid addition salts thereof. Suitable acid addition salts are formed from acids which form non-toxic salts. Examples include the acetate, adipate, ascorbate, aspartate, benzoate, besylate, bicarbonate/carbonate, bisulphate/sulphate, borate, camsylate, cinnamate, citrate, cyclamate, edisylate, embonate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Pharmaceutically acceptable salts of compounds of Formulae I and subformulae may for example be prepared as follows:

(i) reacting the compound of Formula I or any of its subformulae with the desired acid; or (ii) converting one salt of the compound of Formula I or any of its subformulae to another by reaction with an appropriate acid or by means of a suitable ion exchange column.

All these reactions are typically carried out in solution. The salt, may precipitate from solution and be collected by filtration or may be recovered by evaporation of the solvent.

The degree of ionization in the salt may vary from completely ionized to almost non-ionized.

The term "solvate" is used herein to describe a molecular complex comprising the compound of the invention and one or more pharmaceutically acceptable solvent molecules, for example, ethanol. The term 'hydrate' is employed when said solvent is water.

All references to compounds of Formula I include references to salts and solvates thereof.

The compounds of the invention include compounds of the invention as hereinbefore defined, including all polymorphs and crystal habits thereof, prodrugs and isomers thereof (including optical, geometric and tautomeric isomers) and isotopically-labeled compounds of the invention.

In addition, although generally, with respect to the salts of the compounds of the invention, pharmaceutically acceptable salts are preferred, it should be noted that the invention in its broadest sense also includes non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of the invention.

The term "patient" refers to a warm-blooded animal, more preferably a human, who/which is awaiting or receiving medical care or is or will be the object of a medical procedure.

The term "human" refers to subjects of both genders and at any stage of development (i.e. neonate, infant, juvenile, adolescent, adult). In one embodiment, the human is an adolescent or adult, preferably an adult.

The terms "treat", "treating" and "treatment, as used herein, are meant to include alleviating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient which is sufficient to achieve the desired therapeutic or prophylactic effect in the individual to which it is administered.

The term "administration", or a variant thereof (e.g., "administering"), means providing the active agent or active ingredient, alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.

The present invention will be better understood with reference to the following examples and figures. These examples are intended to be representative of specific embodiments of the invention, and are not intended as limiting the scope of the invention.

EXAMPLES

Chemistry Examples

Example 1. Synthesis of Compounds of Formula II

The 4-aminopyridinemethanols derivatives 1 can be obtained from the corresponding vinyl derivative 3. The enantiopure epoxide 2 can be diversified on position 4, through a regioselective $S_N 2$ ring opening mechanism using the desired amine. The 4-oxirane 2 was synthesized from the 4-vinylpyridine 3 in two steps via an enantioselective Sharpless dihydroxylation. The 4-vinylpyridine was prepared using a Suzuki coupling from the 4-bromopyridine 4, which can be obtained in five steps from the 2-bromo-6-iodopyridine derivative 5. Finally, the 2-bromo-6-iodopyridine 5 was obtained in three steps from the 2,6-dibromopyridine 6.

Scheme 1. Retrosynthetic scheme of the 4-aminopyridinemethanols 1 (formula II).

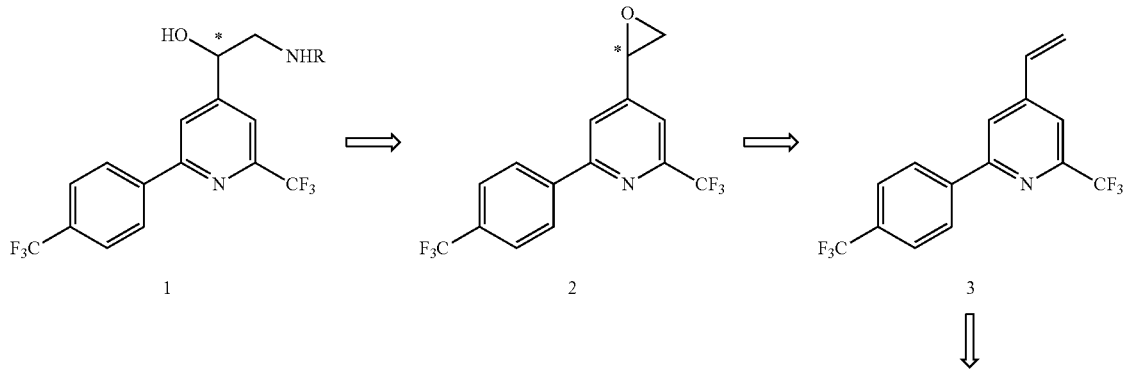

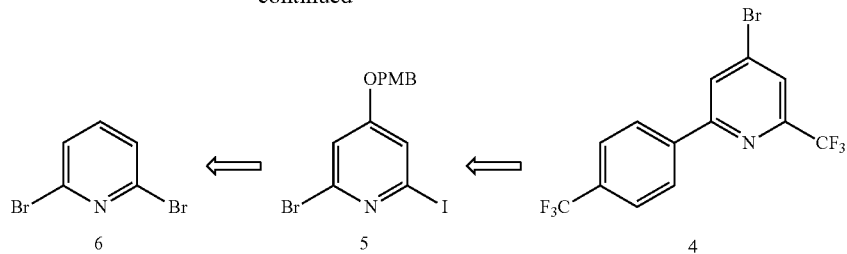

The 2,6-dibromopyridin-4-ol 6 was converted into a borane derivative using pinacolborane, [IrCl(cod)]$_2$ as catalyst and ethylenebis(diphenylphosphine) (dppe) as ligand at 130° C. (scheme 2) (Waki M. et al., Chem. Eur. J., 2006, 12, 7839-7847). The borane derivative obtained was oxidized with a solution of oxone at 25° C. to afford the 2,6-dibromopyridin-4-ol 7 in 78% yield. The hydroxyl group was then protected in DMF in presence of p-methoxybenzylchloride (PMBCl) and K$_2$CO$_3$, heated at reflux for 24 h to afford 8 in 93% yield.

Scheme 2. Preparation of 8.

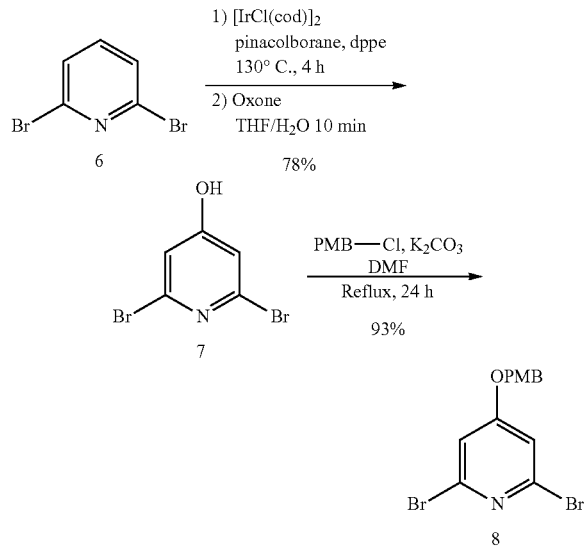

To obtain 5, a first assay was realized using 4 eq. of iPrMgCl and 4 eq. of iodine (entry 1, table 2) (Trécourt F. et al., Tetrahedron, 2000, 56, 1349-1360). Unfortunately, the 2-bromo-6-iodo-4-((4-methoxybenzyl)oxy)pyridine 5 has been obtained in only 56% yield. In order to limit the use of Grignard reagent and to improve the yield "Turbo Grignard" reagent, iPrMgCl stabilized with LiCl, was used. First, the same conditions used with iPrMgCl were used with "Turbo Grignard" reagent (entry 2, table 2). In these conditions, the monoiodated compound 5 was formed but the presence of the diiodide compound 9 was also observed. Unfortunately, both compounds were not separable and were present in 83:17 (5/9) determined by GC-MS. Thus, the number of equivalent of iPrMgCl.LiCl and I$_2$ were changed in order to find the best conditions to avoid the formation of 9. It has been observed that less than 2 eq. of iPrMgCl.LiCl and I$_2$ were required (entries 3-5). From 1.6 and 1.7 eq. of iPrMgCl.LiCl and I$_2$, the conversion of 8 was not complete anymore (entries 6 and 7). In this case 1% of 8 and only 2% of 9 were observed. However, with 1.6 eq. (entry 7) the yield in 5 was largely better than those in entry 5. Under 1.5 eq. and 1.1 eq. of iPrMgCl.LiCl and I$_2$ (entries 7 and 8), there was no formation of 9 but the proportion in 8 were bigger (from 8% to 15%). Consequently, the best conditions to perform this reaction in order to have the best conversion of 8, the best yield in 5 and to limit the formation of 9 were in entry 7, using only 1.6 eq. of iPrMgCl.LiCl and I$_2$.

TABLE 2

Preparation of 5.

| Entry | Grignard reagent (eq.) | I$_2$ (eq.) | 5 (%)$^a$ | 9 (%)$^a$ | 8 (%)$^a$ | 5 (%)$^b$ |
|---|---|---|---|---|---|---|
| 1 | i-PrMgCl (4) | 4 | / | / | 0 | 56 |
| 1 | i-PrMgCl·LiCl (4) | 4 | 83 | 17 | 0 | N.D. |
| 2 | i-PrMgCl·LiCl (3) | 3 | 87 | 13 | 0 | N.D. |
| 3 | i-PrMgCl·LiCl (2) | 2 | 96 | 4 | 0 | N.D. |

TABLE 2-continued

Preparation of 5.

| Entry | Grignard reagent (eq.) | $I_2$ (eq.) | 5 (%)[a] | 9 (%)[a] | 8 (%)[a] | 5 (%)[b] |
|---|---|---|---|---|---|---|
| 4 | i-PrMgCl·LiCl (1.8) | 1.8 | 95 | 5 | 0 | 66 |
| 5 | i-PrMgCl·LiCl (1.7) | 1.7 | 97 | 2 | 1 | 61 |
| 6 | i-PrMgCl·LiCl (1.6) | 1.6 | 97 | 2 | 1 | 85 |
| 7 | i-PrMgCl·LiCl (1.5) | 1.5 | 92 | 0 | 8 | 75 |
| 8 | i-PrMgCl·LiCl (1.1) | 1.1 | 85 | 0 | 15 | N.D. |

[a] Proportion determined by GC-MS analysis;
[b] Yield obtained of isolated compound after purification by flash chromatography.

The next step consisted in a Suzuki coupling to introduce the trifluoromethylphenyl group (scheme 3). In order to form the compound 10, the 4-(trifluoromethyl)phenyl)boronic acid was used in the presence of $Na_2CO_3$ as base and $Pd(PPh_3)_4$ as catalyst in a mixture of toluene/EtOH/$H_2O$ (6:1:1) (Doebelin C. et al., J. Org. Chem., 2014, 79, 908-918). The reaction was heated at 110° C. for 15 h to afford 10 in 95% yield after purification. Then, the bromide was exchanged with an iodide using CuI as catalyst, NaI as source of iodine, N,N'-dimethylethylenediamine as ligand in anhydrous 1,4-dioxane and heated at 110° C. to afford 11 in 88% yield.

Scheme 3. Synthesis of 11 from 5.

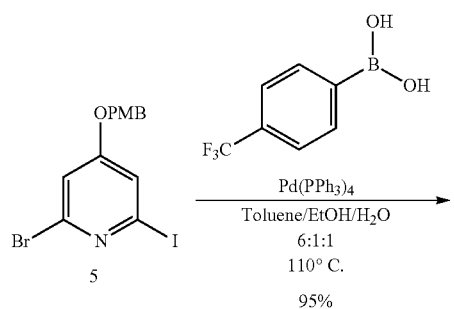

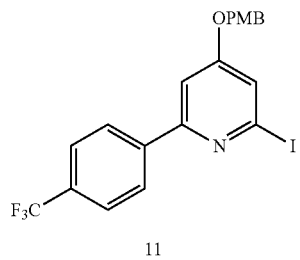

11

Compound 11 was converted into the trifluoromethyl derivative 12 using the reaction conditions described by Gonda et al. (scheme 4)(Gonda Z. et al., Org. Lett., 2014, 16, 4268-4271). The iodo derivative 11 was reacted with $TMSCF_3$, KF, $B(OMe)_3$ as Lewis acid, CuI as catalyst and 1,10-phenantroline as ligand in DMSO at 60° C. The trifluoromethyl 12 was obtained in 89% yield. Then, the p-methoxybenzyl was deprotected. First, a hydrogenation using classical conditions, Pd/C in methanol, were attempted. Unfortunately no conversion was observed. Then, as the advantage of the PMB group is its lability in acidic conditions, the deprotection was performed in DCM with 2% of trifluoroacetic acid (TFA)(2% v/v TFA/DCM). The work up was carried out to recover the pyridine 13 and not its salt.

Scheme 4. Formation of 13.

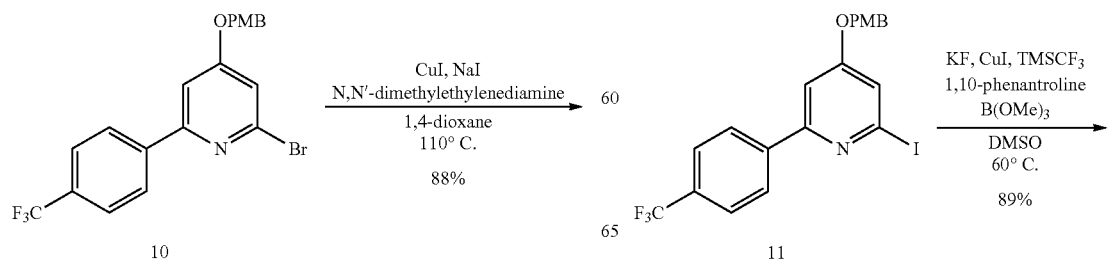

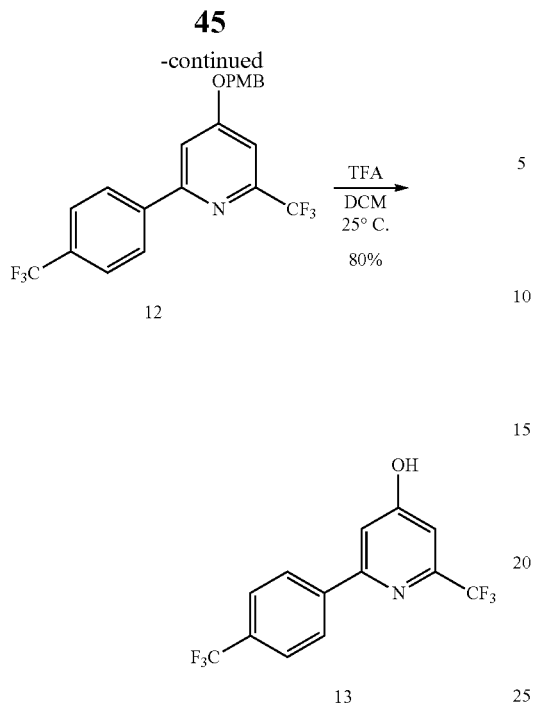

A Suzuki coupling was then performed with potassium vinyltrifluoroborate to obtain 3 in 86% yield (scheme 5).

Scheme 5. Preparation of 3.

Once the deprotection performed, the hydroxyl moiety was substituted with a bromine group (Table 3).

First, the phosphorus oxybromide was heated at 90° C., 13 was added before heating the reaction mixture at 170° C. (m.p. of 13) without solvent for 4 h. After purification, 32% of the brominated compound was obtained (entry 1). Then, conditions described by R. Upadhayaya et al. were used (entry 2)(Upadhayaya R. et al., Bioorg. Chem. Lett., 2013, 23, 2750-2758). A mixture of phosphorus tribromide and 13 was placed into DMF and stirred at 150° C. for 20 h. The conversion was still not complete and only 5% of 4 were obtained. The use of 4 eq. of phosphorus oxybromide in place of phosphorus tribromide in DMF at 110° C. led to 4 in 81% yield (entry 3).

In order to introduce the stereogenic center, enantioselective Sharpless dihydroxylation was used (scheme 6). The (S)-diol 14a was prepared from AD-mix α in the presence of 1 mol % of $K_2OsO_2(OH)_4$, in a mixture of solvent tBuOH/$H_2O$ 1:1. 14a was obtained in 95% yield and with 99% ee ($[\alpha]_D^{20}$: +29.1° (c=0.1, MeOH)). The (R)-diol 14b was prepared in the same conditions from AD-mix β. 14b was obtained in 82% yield and 99% ee ($[\alpha]_D^{20}$: −29.3° (c=0.1, MeOH)).

TABLE 3

Preparation of 4.

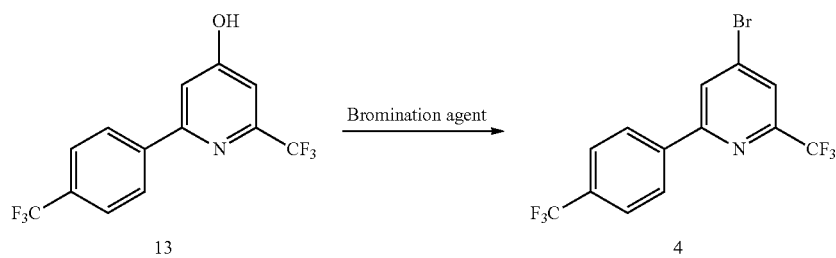 [SMILES: Oc1cc(-c2ccc(C(F)(F)F)cc2)nc(C(F)(F)F)c1 ; FC(F)(F)c1ccc(-c2cc(Br)cc(C(F)(F)F)n2)cc1]

| Entry | Bromination agent (eq.) | Solvent | Temperature (° C.) | Time (h) | 4 (%) |
|---|---|---|---|---|---|
| 1 | POBr₃ (1) | / | 170 | 4 | 32 |
| 2 | PBr₃ (4) | DMF | 150 | 20 | 5 |
| 3 | POBr₃ (4) | DMF | 110 | 15 | 81 |

Scheme 6. Preparation of 14a and 14b.

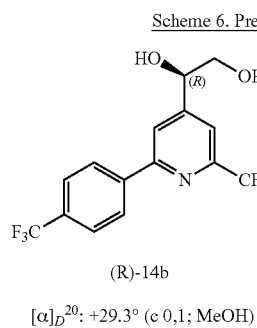

(R)-14b $[\alpha]_D^{20}$: +29.3° (c 0,1; MeOH)

(S)-14a $[\alpha]_D^{20}$: +29.1° (c 0,1; MeOH)

Epoxide 2a and 2b were prepared by a "one-pot" method via Sharpless acetoxonium ion (scheme 7). Three operations were carried out in one reaction vessel without isolation of any intermediates but each step was followed and validated by GC-MS. Thus, the slightly modified Sharpless conditions (TMSBr vs TMSCl) applied to the conversion of diols 14a and 14b give the corresponding oxiranes 2a and 2b with retention of configuration according to optical rotation of each compound.

Scheme 7. Preparation of 2a and 2b.

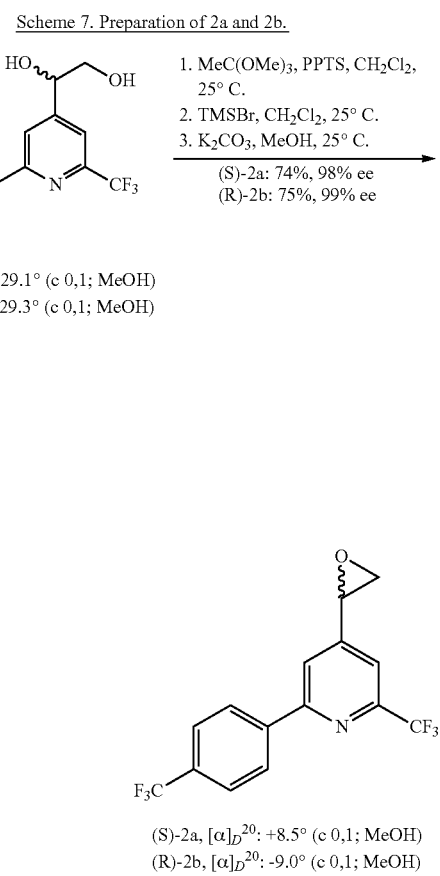

This "one-pot" conversion involves three successive steps (scheme 8) (Kolb C. et al., Tetrahedron, 1992, 48, 10515-10530):

(i) formation of the cyclic orthoester by acid catalyzed transesterification;

(ii) generation of halohydrins ester via regioselective opening of acetoxonium ion by addition of tributyldimethylsilyl chloride; and (iii) cyclization to epoxide by base mediated saponification in methanol.

This conversion of the diol 14a to the oxirane 2a was accomplished with global retention of configuration because this process involves two successive inversions at the same stereocenter: (i) inversion at the halide receiving stereocenter at the time of halohydrins ester formation and (ii) second inversion at the halide center while cyclization to epoxide (as indicated below).

Scheme 8. Formation of the epoxide 2a using a "one-pot" reaction.

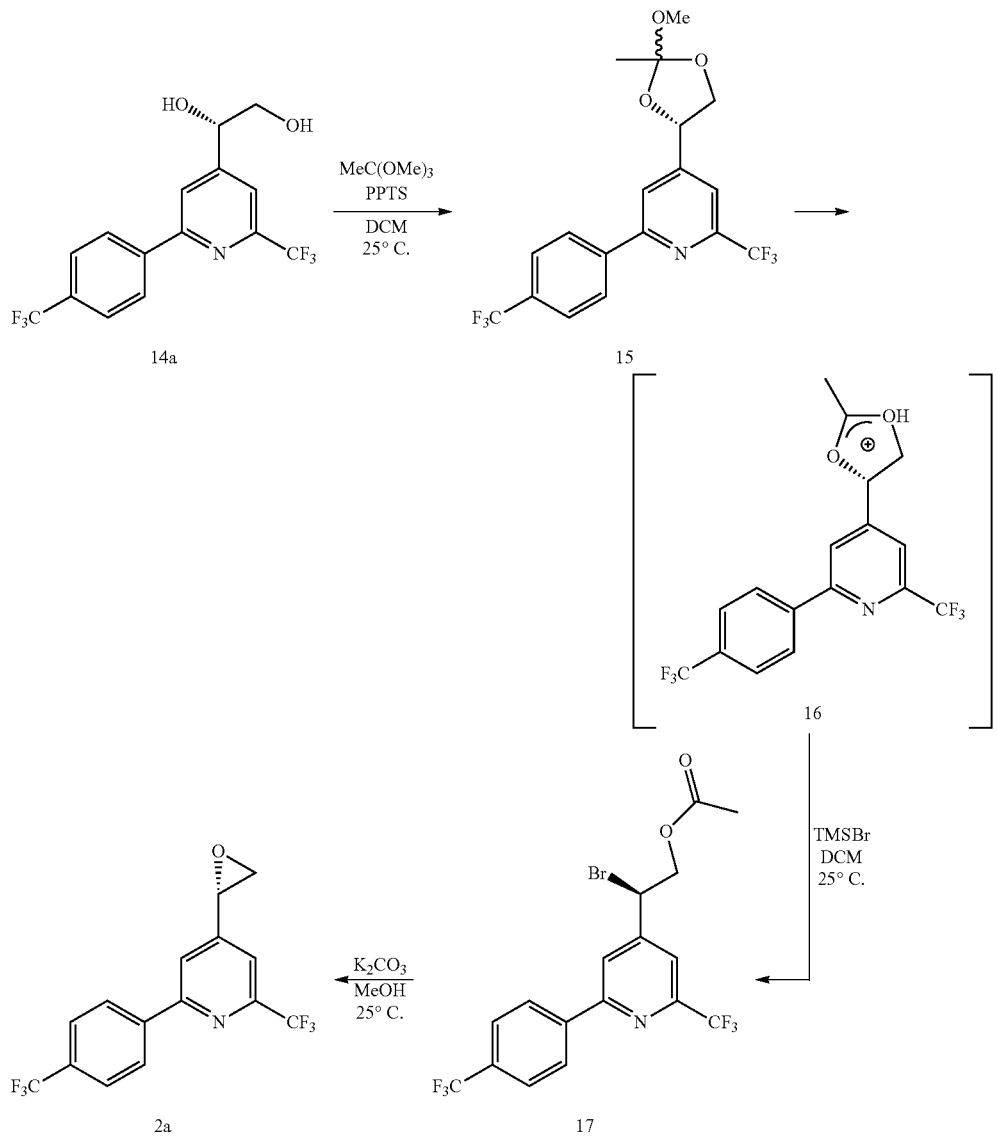

Finally the epoxides 2a and 2b were opened, using a regioselective $S_N2$ ring opening mechanism with diverse amines and microwave irradiations scheme 9).

Scheme 9. Preparation of 4-aminopyridinemethanols of formula II 1a-1f.

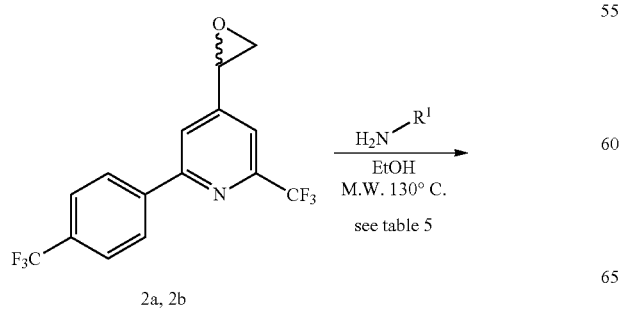

-continued

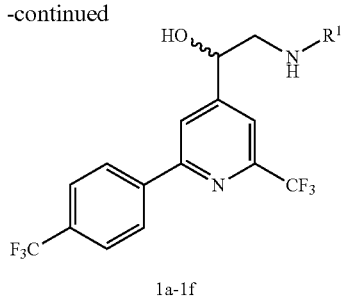

First, the (R)- and (S)-4-aminopyridinemethanol bearing an alkyl chain were synthesized (table 4, entries 1-6). Compounds 1a-1f were obtained in good yields (between 60-85%) and excellent enantiomeric excess (between 98-99%). In order to synthesize 1g and 1b (table 4, entries 7 and 8), the $N^1$-benzhydrylethane-1,2-diamine 19 was previously prepared in a single step. Chlorodiphenylmethane 18 and ethylenediamine were heated at reflux in acetonitrile and in the presence of KI for 20 h (scheme 10). The amine 19 was obtained in 90% yield. The reaction between the epoxides 2a, 2b and the amine 19 has afforded respectively to 1g in 65% yield, 99% ee and 1h in 80% yield, 98% ee.

Scheme 10. Preparation of 19.

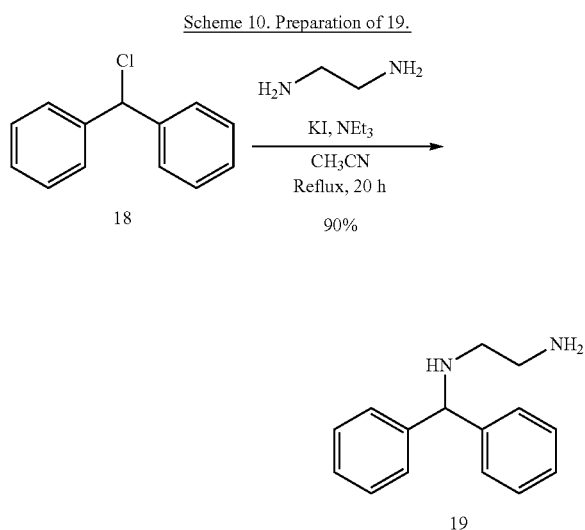

In order to obtain 1i and 1j (table 4, entries 9 and 10), the amine 23 (S)-1-methoxy-3-phenylpropan-2-amine was obtained in three steps from (S)-2-amino-3-phenylpropan-1-ol 20 (scheme 11). The amine 20 was protected using Boc₂O in DCM at 25° C. to afford 21 in 95% yield. Then, the alcohol group was methylated in the presence of silver oxide and iodomethane in DCM. The suspension was stirred at 25° C. for six days to afford 22 in 88% yield. Finally, the amine group was deprotected with TFA in DCM at 25° C. and stirred for 12 h. This step has afforded the (S)-1-methoxy-3-phenylpropan-2-amine 23 in 91% yield. As for the others compounds 1, the epoxides 2a and 2b were reacted with the amine 23 to afford respectively 1i in 80% yield and 99% de and 1j in 71% yield and 98% de (table 4, entries 9 and 10).

Scheme 11. Preparation of the (S)-1-methoxy-3-phenylpropan-2-amine 23.

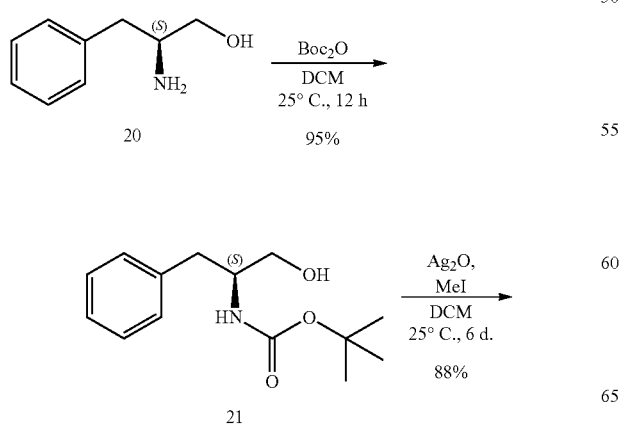

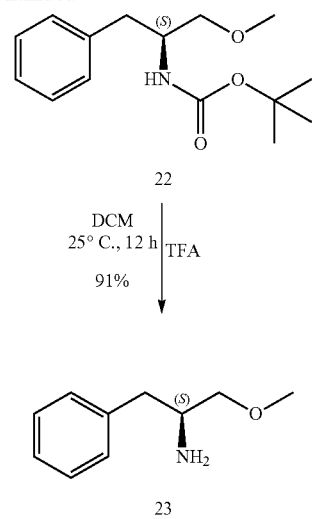

In order to obtain the 4-aminopyridinemethanols in entries 11 and 12 (table 4), the epoxides 2 were opened with ethylenediamine. Then the amine obtained was reacted with ferrocenecarboxaldehyde in a reductive amination reaction to afford 1k in 30% yield, 98% ee and 1l in 17% yield, 98% ee (scheme 12, table 4).

Scheme 12. Synthesis of the ferrocene derivative 1m and 1n.

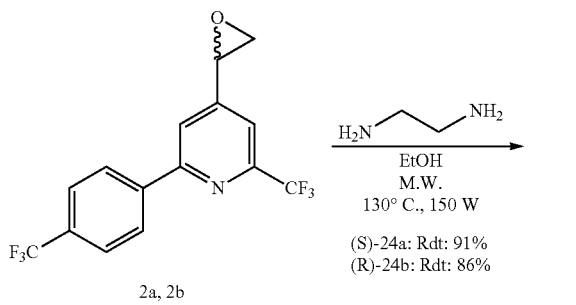

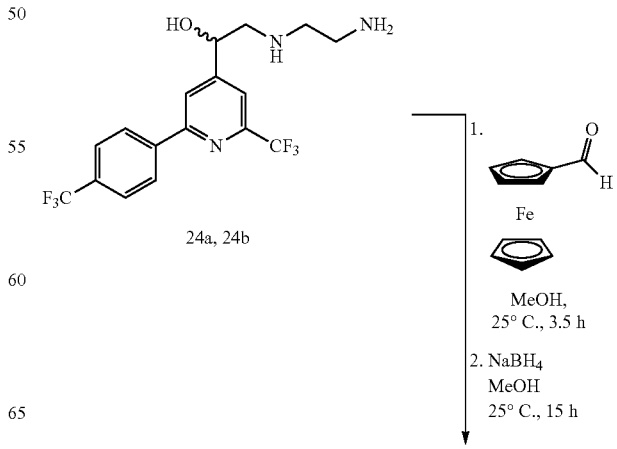

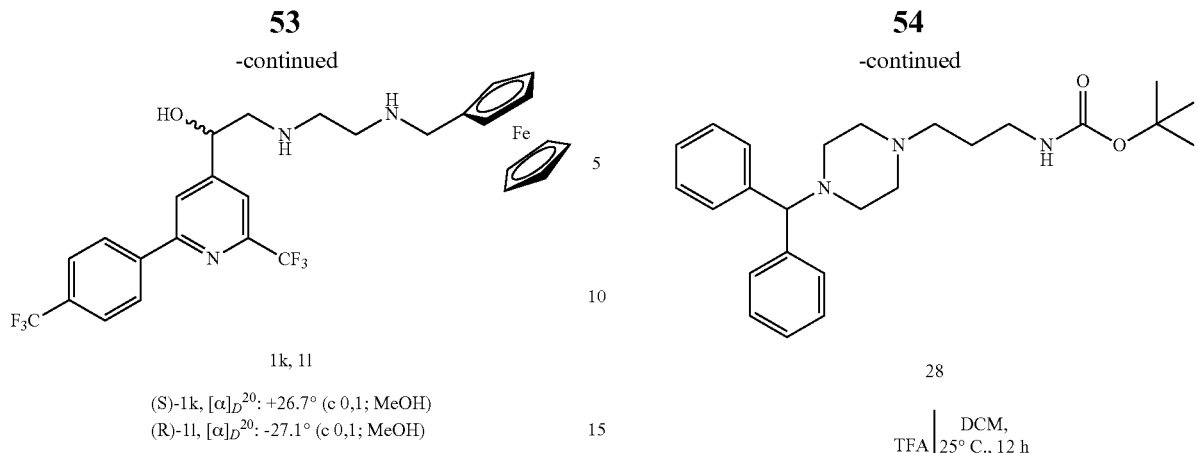

1k, 1l (S)-1k, [α]$_D^{20}$: +26.7° (c 0,1; MeOH)
(R)-1l, [α]$_D^{20}$: -27.1° (c 0,1; MeOH)

To obtain 1m and 1n (entries 13 and 14, table 4), the amine 28 was previously synthesized (scheme 13). The 3-bromopropanamine was protected with (Boc)$_2$O in the presence of triethylamine in MeOH at 25° C. to obtain 26 in 74% yield. The bromine group of 26 was substituted by 1-benzhydrylpiperazine 27 in MeCN, using triethylamine as base and KI as catalyst. The reaction was heated at reflux for 12 h to afford 28 in 73% yield. Finally, the amine group was deprotected with TFA in DCM to obtain 29 in quantitative yield.

Scheme 13. Synthesis of 3-(4-benzhydrylpiperazin-1-yl)propan-1-amine 29.

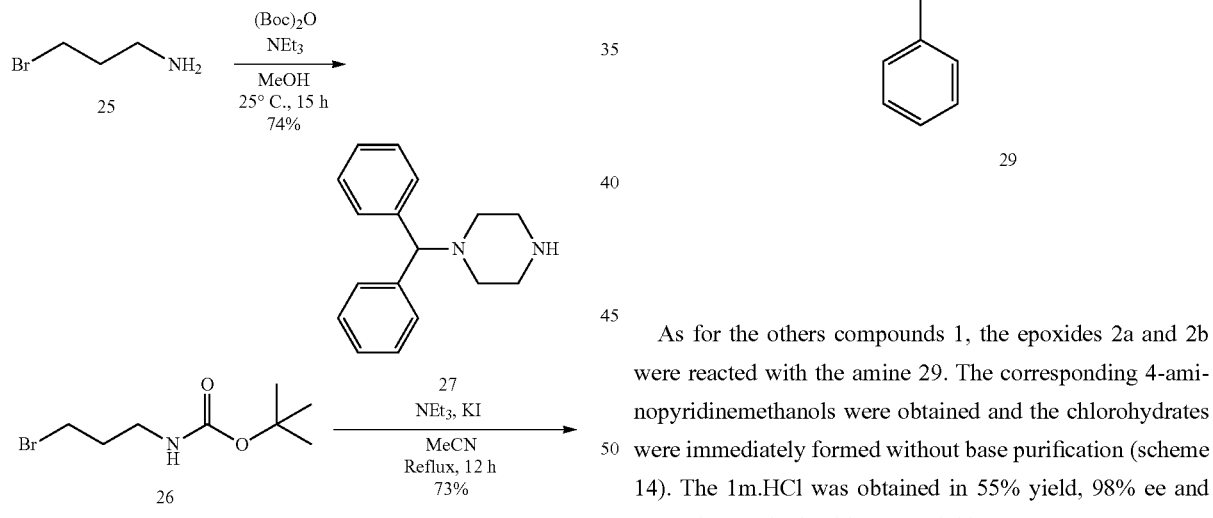

As for the others compounds 1, the epoxides 2a and 2b were reacted with the amine 29. The corresponding 4-aminopyridinemethanols were obtained and the chlorohydrates were immediately formed without base purification (scheme 14). The 1m.HCl was obtained in 55% yield, 98% ee and 1n.HCl was obtained in 65% yield, 96% ee.

Scheme 14. Formation of the chlorhydrate 1m.HCl and 1n.HCl.

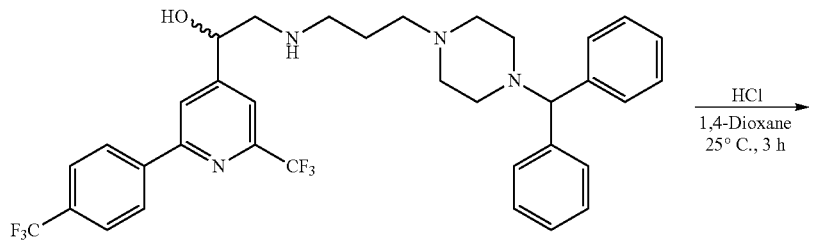

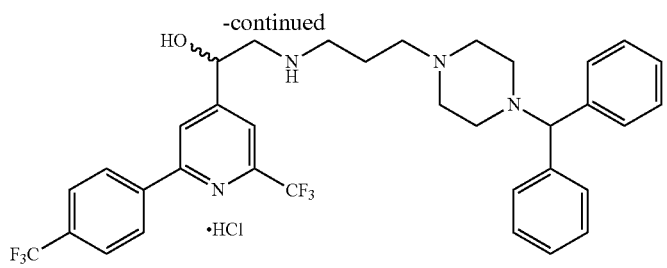

In order to obtain compounds 1o and 1p (entries 15 and 16, table 4), epoxides 2a and 2b were reacted with 4,4,4-trifluorobutylamine.

In order to obtain compounds 1q and 1r (entries 17 and 18, table 4), epoxides 2a and 2b were reacted with amine C.

To obtain amine C, the hydroxyl group of tert-butyl(6-hydroxyhexyl)carbamate D was mesylated and replaced with a fluorine atom in a 77% yield. Amine E, was deprotected with HCl and after evaporation, amine C was quantitatively obtained as the hydrochloride salt (Scheme A).

Scheme A

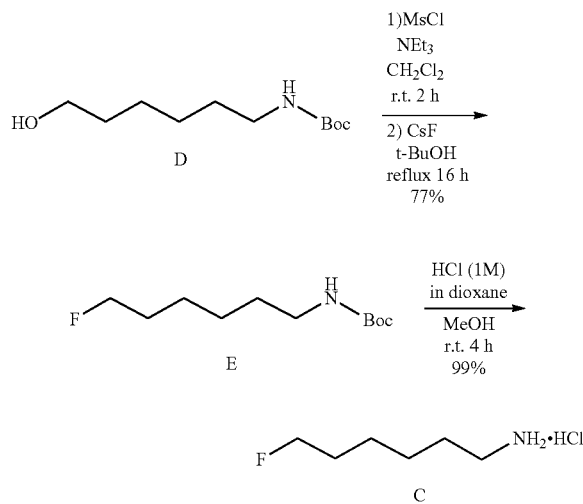

Reaction of epoxides 2a and 2b with amine C hydrochloride salt was conducted in presence of N,N-diisopropylethylamine. The crude mixture was extracted at neutral pH to yield compounds 1q and 1r as free amines in 47% and 51% yield respectively.

In order to obtain compounds 1s and 1t (entries 19 and 20, table 4), epoxides 2a and 2b were reacted with amine B.

Amine B was obtained in two steps. First ethylenediamine and bis(2-pyridyl)ketone were refluxed in MeOH with acetic acid for 20 hours. The reaction mixture was then cooled to 0° C. and sodium borohydride was added. After stirring at room temperature for 5 days, the mixture was hydrolyzed and extracted with DCM to afford B in 97% yield after chromatography (Scheme B).

Scheme B

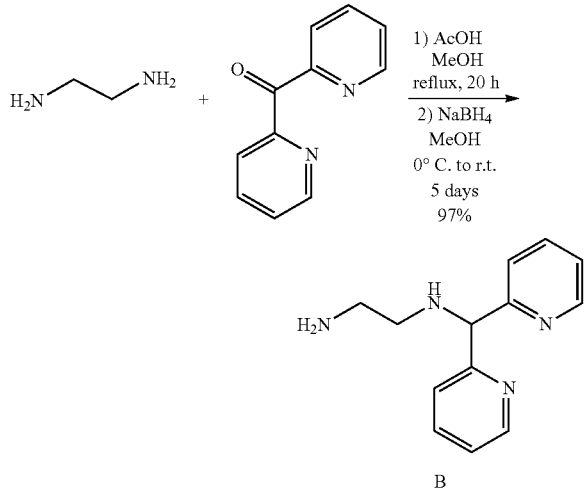

Compound 1s and 1t were obtained from the reaction of epoxides 2a and 2b with amine B and isolated as trifluoroacetic acid salts after semi-preparative HPLC purification in 32% and 59% yield respectively.

In order to obtain compounds 1u and 1v (entries 21 and 22, table 4), epoxides 2a and 2b were reacted with amine A.

Amine A was obtained from intermediate 21. The alcohol group was alkylated in presence of sodium hydride and iodomethylcyclopropane in DMF. The amine group was then deprotected with TFA in DCM and after chromatography, amine A was obtained in 40% yield (Scheme C).

Scheme C

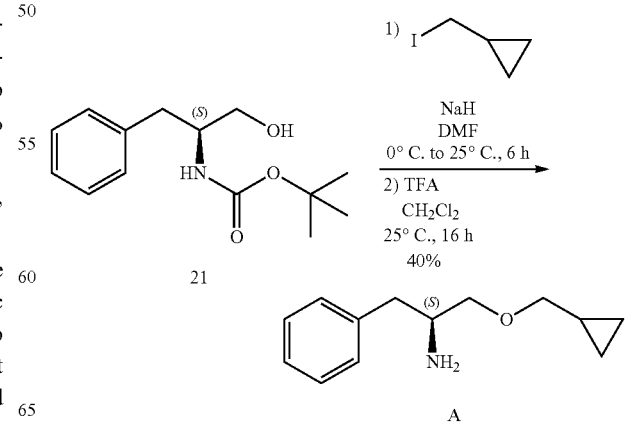

Compound 1u and 1v were obtained from the reaction of epoxides 2a and 2b with amine A and isolated in 65% and 80% yield respectively.

TABLE 4

Summary of the compounds of formula II synthesized.

| Entry | Compound | Amine | Structure | Yield | % ee/ % de[a] |
|---|---|---|---|---|---|
| 1 | 1a (S) | pentylamine | | 78% | 99 |
| 2 | 1b (R) | | | 67% | 99 |
| 3 | 1c (S) | hexylamine | | 67% | 99 |
| 4 | 1d (R) | | | 65% | 98 |
| 5 | 1e (S) | heptylamine | | 60% | 99 |
| 6 | 1f (R) | | | 85% | 99 |
| 7 | 1g (S) | N-benzhydryl ethylenediamine | | 65% | 99 |
| 8 | 1h (R) | | | 80% | 98 |
| 9 | 1i (S,S) | (S)-2-amino-3-phenyl-1-methoxypropane | | 80% | 99 |
| 10 | 1j (R,S) | | | 71% | 98 |

TABLE 4-continued

Summary of the compounds of formula II synthesized.

| Entry | Compound | Amine | Structure | Yield | % ee/% de[a] |
|---|---|---|---|---|---|
| 11 | 1k (S) | | | 30% | 98 |
| 12 | 1l (R) | | | 17% | 98 |
| 13 | 1m·HCl (S) | | | 55% | 98 |
| 14 | 1n·HCl (R) | | | 65% | 96 |
| 15 | 1o (S) | | | 77% | 99 |
| 16 | 1p (R) | | | 60% | 98 |
| 17 | 1q (S) | | | 47% | 98 |
| 18 | 1r (R) | | | 51% | 98 |
| 19 | 1s·TFA (S) | | | 32% | 98 |
| 20 | 1t·TFA (R) | | | 59% | 98 |
| 21 | 1u (S,S) | | | 65% | 99 |
| 22 | 1v (R,S) | | | 80% | 99 |

[a] determined by chiral HPLC.

Example 2. Synthesis of Compounds of Formula III

The 3-aminopyridinemethanols 30 of Formula III can be obtained thanks to the 4-aminopyridinemethanols 1a-p from the corresponding vinyl 32 (scheme 15). The enantiopure epoxide 31 can be diversified in position 3, through a regioselective $S_N2$ ring opening mechanism using the desired amine. The 3-oxirane 31 was obtained from the 3-vinylpyridine 32 in two steps via an enantioselective Sharpless dihydroxylation. The vinyl 32 was formed through a Stille coupling from the triflate derivative 33 obtained in three steps. The 2-bromo-6-iodo derivative 34 was obtained from 2-bromo-pyridin-3-ol 35 in two steps.

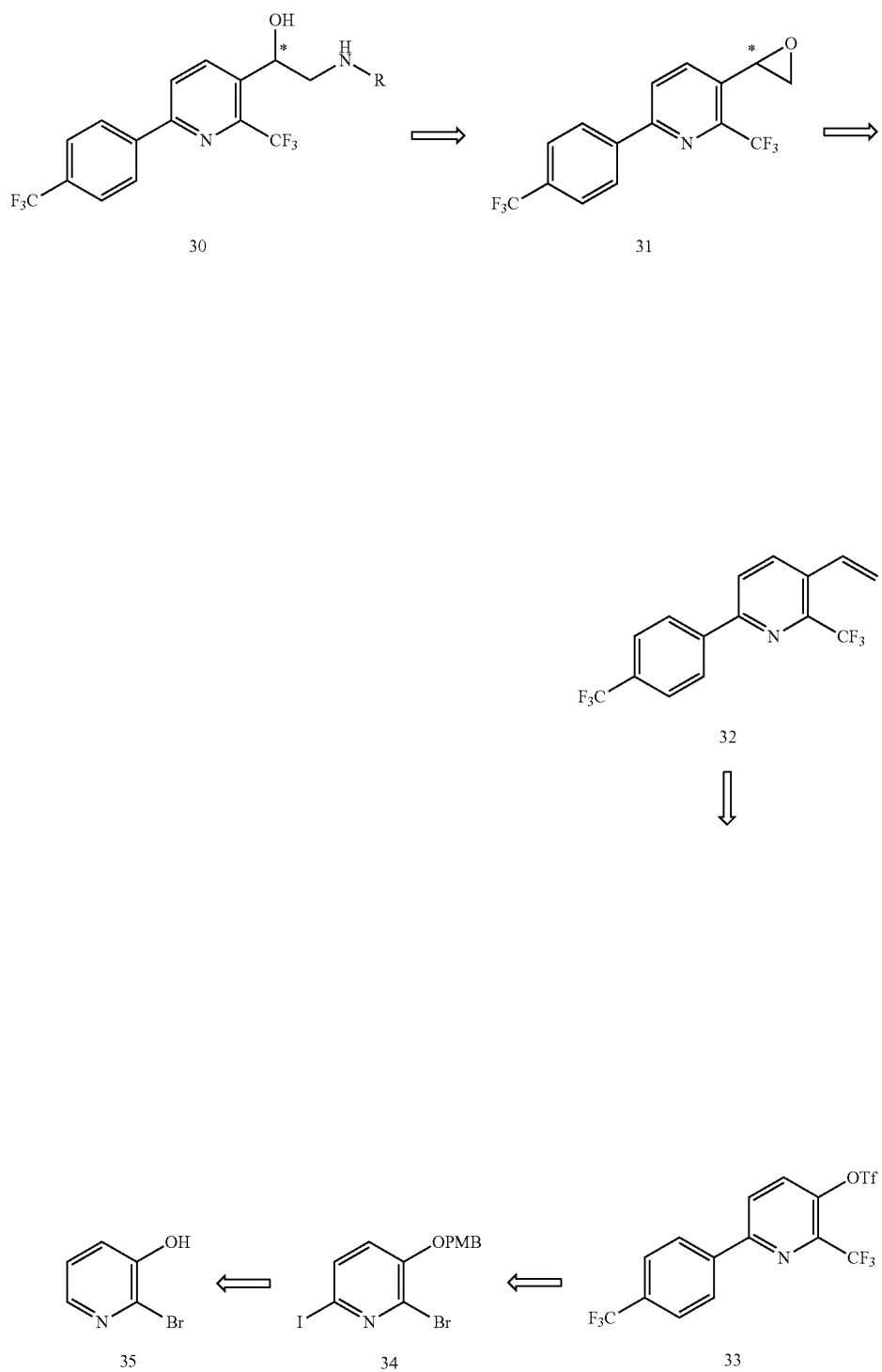

Scheme 15. Retrosynthetic scheme of the 3-aminopyridinemethanols 30 of Formula III.

The commercialized 2-bromopyridin-3-ol 35 was converted into the 2-bromo-6-iodopyridin-3-ol 36 according to the procedure described by Wolkenberg (WO 2011/109261). 36 was obtained in 87% yield. Then the hydroxyl was protected using the p-methoxylbenzyl protecting group. The hydroxyl 36 was reacted with p-methoxylbenzylchloride and $K_2CO_3$ in DMF at 110° C. After 8 h, the p-methoxylbenzyl derivative 34 was obtained in 82% yield (scheme 16).

Scheme 16. Preparation of 34.

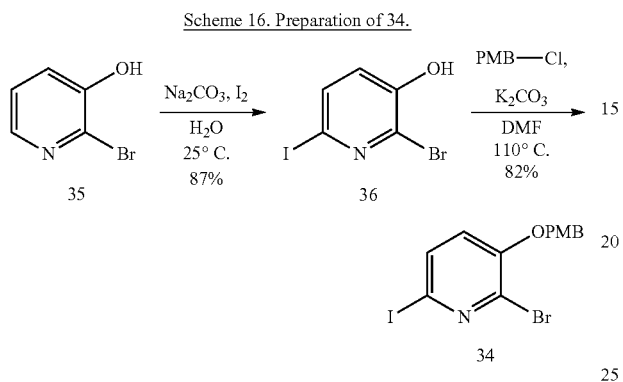

This latter was converted into the derivative 39 through a Suzuki coupling using the conditions described by Doebelin (Doebelin C. et al, J. Org. Chem., 2014, 79, 908-918). In order to carry out this reaction, two boronic derivatives were used: the potassium trifluoroborate derivative 37 and the boronic acid 38 (scheme 17). In both conditions, 39 was obtained in high yields: 85% with 37 and 93% with 38.

Scheme 17. Preparation of 39.

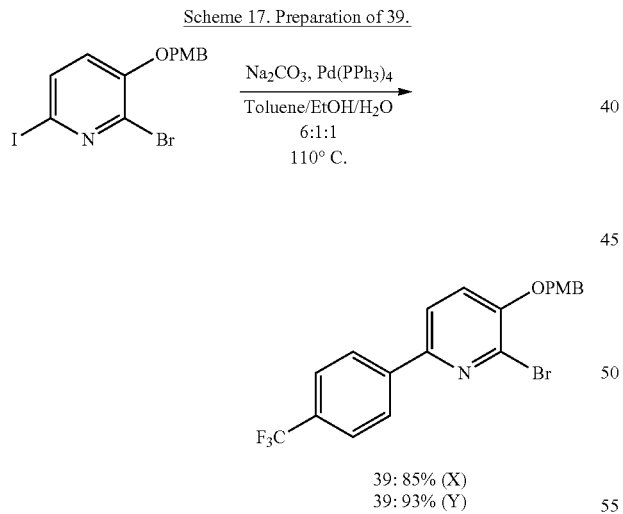

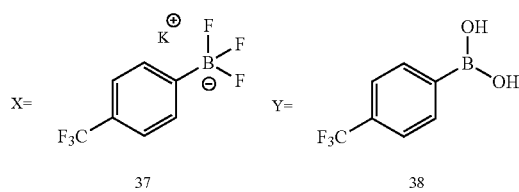

The bromide moiety was then converted into iodide using a Finkelstein reaction in aromatic series described by Meyer-Eppler (Meyer-Eppler G. et al, Synthesis, 2014, 46, 1085-1090). The bromo derivative 39 was reacted with NaI as nucleophile, CuI as catalyst, N,N'-dimethylethylenediamine as ligand in 1,4-dioxane as solvent. The suspension was heated at 110° C. for 15 h. After treatment and purification the iodide derivative 40 was obtained in 82% yield (scheme 18).

Scheme 18. Preparation of 40.

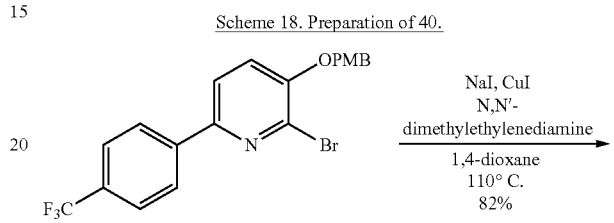

Then, a trifluoromethylation was carried out according to the method described in the literature by Gonda et al. (Gonda Z. et al., Org. Lett., 2014, 4268-4271). The trifluoromethyl derivative 41 was obtained in 88% yield. The p-methoxylbenzyl protecting group was then cleaved by means of a hydrogenation with Pd/C under $H_2$ atmosphere. The hydroxyl compound 42 was obtained in 95% yield (scheme 19).

Scheme 19. Preparation of 42.

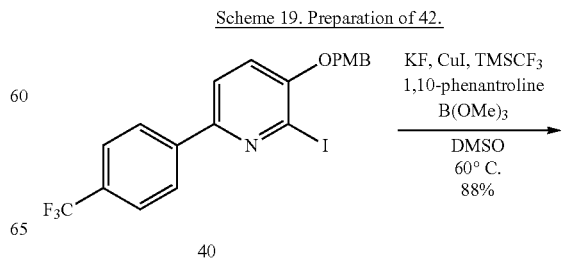

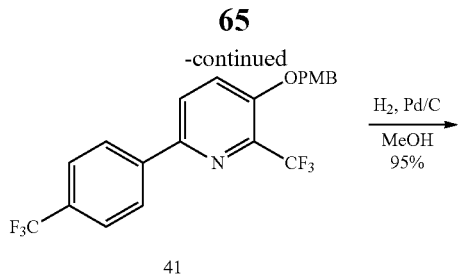

41

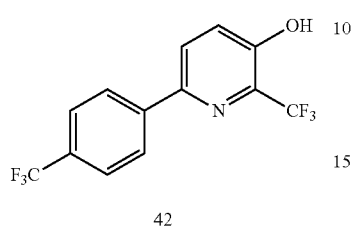

42

The next step consisted in the conversion of the hydroxyl moiety into a suitable leaving group to perform a coupling reaction (scheme 20). A substitution of the hydroxyl by a bromine group was attempted. First, the phosphorus oxybromide was reacted with 42. POBr$_3$ was heated at 90° C., the hydroxyl 42 was added before heating the mixture at 150° C. without solvent for 6 h. Unfortunately this method has not afford the bromine derivative 43 but only products of degradation. Then, a method using a solvent was attempted. The hydroxyl derivative 42 was dissolved in DMF in presence of PBr$_3$ as bromination agent. The solution was heated at 155° C. for 22 h but the substitution has not occurred and the raw material was isolated. As the substitution of the hydroxyl group by a bromine group was unsuccessful, the hydroxyl was converted to the triflate 33. The conditions described in the literature by Seganish et al. were used (Seganish W. et al., J. Org. Chem., 2004, 69, 1137-1143). The hydroxyl 42 was dissolved in pyridine and cooled to 0° C. Then trifluoromethanesulfonic anhydride was added dropwise. The mixture was stirred for 20 min at 0° C. and 15 h at 25° C. After treatment and purification, the triflate derivative 33 was obtained in 91% yield.

Then a Stille coupling was performed in order to introduce the vinyl group and to obtain 32 (scheme 21). The conditions described in the literature by G. Bridger et al. were used (US 2004/0209921). The vinyl compound 32 was obtained in 90% yield.

Scheme 21. Preparation of 32.

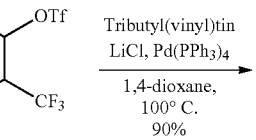

33

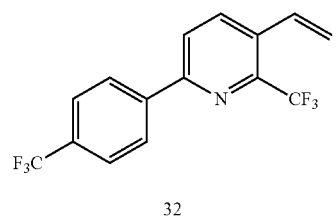

32

Once the vinyl derivative 32 was obtained, the three last steps consisted exactly as for the 4-APMs: i) enantioselective Sharpless dihydroxylation, ii) epoxide formation, iii) epoxide opening. The Sharpless dihydroxylation afforded the (S)- and (R)-diols (S)-44a and (R)-44b in good yields (73% and 71% respectively) and very high enantiomeric excesses (99%) (scheme 22).

Scheme 20. Substitution of the hydroxyl derivative 42.

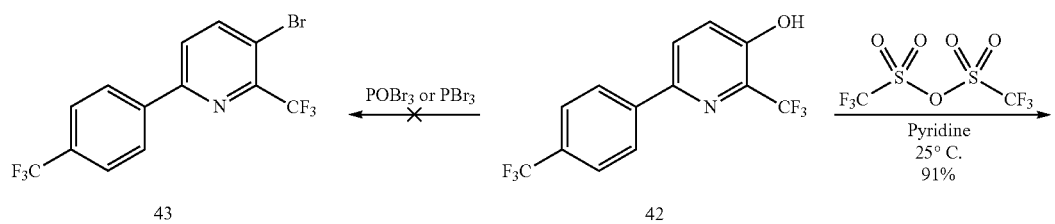

43    42

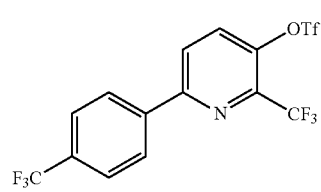

33

Scheme 22. Preparation of 44.

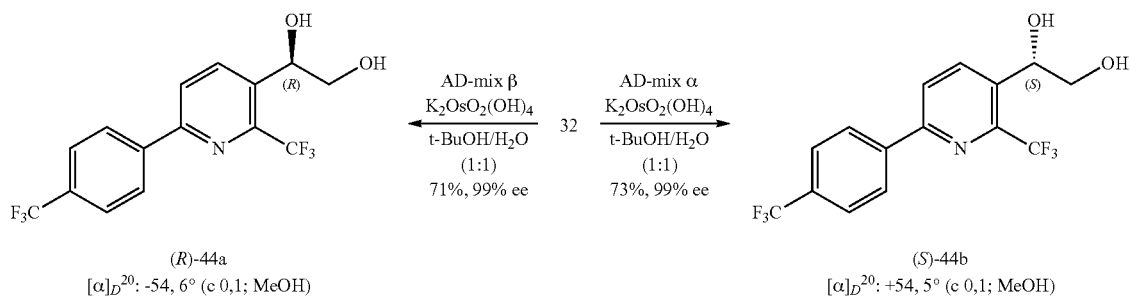

(R)-44a
[α]$_D^{20}$: -54, 6° (c 0,1; MeOH)

(S)-44b
[α]$_D^{20}$: +54, 5° (c 0,1; MeOH)

The ring closure to afford the epoxide has afforded the (S)-oxirane 31a in 92% yield and 98% ee, the (R)-oxirane 31b in 77% yield and 98% ee (scheme 23).

Finally the epoxides 31a, 31b were opened, using a regioselective $S_N^2$ ring opening mechanism, with diverse amines commercially available or previously described scheme 10-13 and microwave irradiations (scheme 24, table 5).

Scheme 23. Preparation of 31.

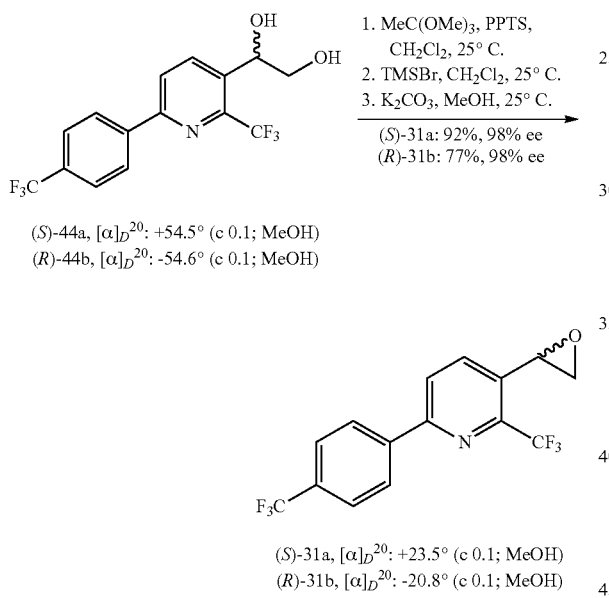

(S)-44a, [α]$_D^{20}$: +54.5° (c 0.1; MeOH)
(R)-44b, [α]$_D^{20}$: -54.6° (c 0.1; MeOH)

(S)-31a: 92%, 98% ee
(R)-31b: 77%, 98% ee

Scheme 24. Preparation of 30.

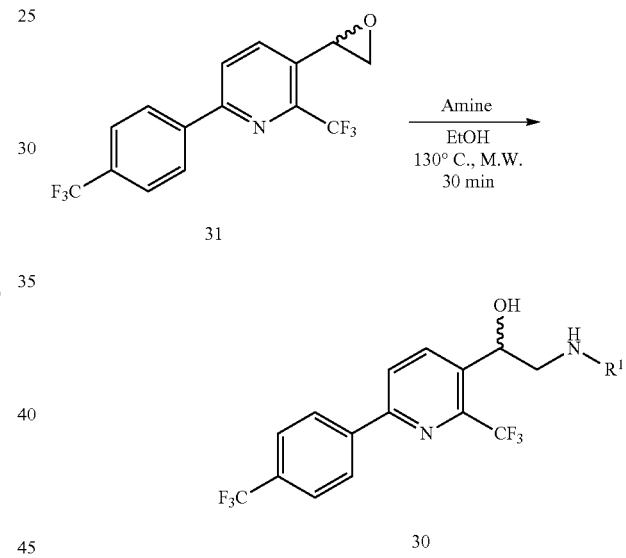

(S)-31a, [α]$_D^{20}$: +23.5° (c 0.1; MeOH)
(R)-31b, [α]$_D^{20}$: -20.8° (c 0.1; MeOH)

TABLE 5

Summary of the compound of formulae IIIa and IIIb synthesized.

| Entry | Compound | Amine | Structure | Yield | % ee/% ed[a] |
|---|---|---|---|---|---|
| 1 | 30a (S) | ~~~NH₂ (butylamine) | | 84% | 96 |
| 2 | 30b (R) | | | 92% | 99 |

TABLE 5-continued

Summary of the compound of formulae IIIa and IIIb synthesized.

| Entry | Compound | Amine | Structure | Yield | % ee/% ed[a] |
|---|---|---|---|---|---|
| 3 | 30c (S) | | | 67% | 99 |
| 4 | 30d (R) | pentylamine | pyridine-CH(OH)-CH2-NH-pentyl with 4-CF3-phenyl and CF3 substituents | 81% | 96 |
| 5 | 30e (S) | | | 80% | 99 |
| 6 | 30f (R) | hexylamine | pyridine-CH(OH)-CH2-NH-hexyl with 4-CF3-phenyl and CF3 substituents | 80% | 96 |
| 7 | 30g (S) | | | 82% | 99 |
| 8 | 30h (R) | heptylamine | pyridine-CH(OH)-CH2-NH-heptyl with 4-CF3-phenyl and CF3 substituents | 90% | 99 |
| 9 | 30i (S) | | | 80% | 99 |
| 10 | 30j (R) | H2N-CH2CH2-NH-CH(Ph)2 | pyridine-CH(OH)-CH2-NH-CH2CH2-NH-CH(Ph)2 | 87% | 99 |
| 11 | 30k (S,S) | | | 69% | 99 |
| 12 | 30l (R,S) | (S)-H2N-CH(CH2Ph)-CH2-OMe | pyridine-CH(OH)-CH2-NH-(S)-CH(CH2Ph)-CH2-OMe | 80% | 98 |
| 13 | 30m (S) | | | 35% | 82 |
| 14 | 30n (R) | HO-CH(pyridyl)-CH2-NH-CH2CH2-NH2 | pyridine-CH(OH)-CH2-NH-CH2CH2-NH-CH2-ferrocenyl | 26% | 96 |
| 15 | 30o (S) | | | 48% | 99 |
| 16 | 30p (R) | H2N-CH2CH2CH2-N(piperazine)-CH(Ph)2 | pyridine-CH(OH)-CH2-NH-CH2CH2CH2-N(piperazine)-CH(Ph)2 | 67% | 98 |

TABLE 5-continued

Summary of the compound of formulae IIIa and IIIb synthesized.

| Entry | Compound | Amine | Structure | Yield | % ee/ % ed[a] |
|---|---|---|---|---|---|
| 17 | 30q (S) | | 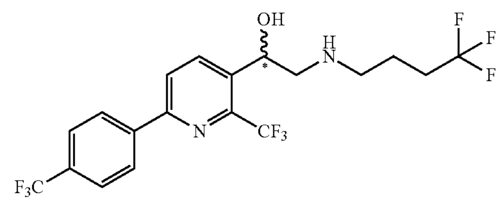 [SMILES: OC(CNCCCC(F)(F)F)c1ccc(-c2ccc(C(F)(F)F)cc2)nc1C(F)(F)F] | 78% | 98 |
| 18 | 30r (R) | | | 77% | 98 |
| 19 | 30s (S) | | 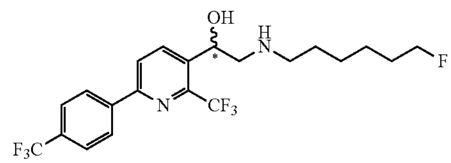 [SMILES: OC(CNCCCCCCF)c1ccc(-c2ccc(C(F)(F)F)cc2)nc1C(F)(F)F] | 65% | 98 |
| 20 | 30t (R) | | | 42% | 99 |
| 21 | 30u (S,S) | | 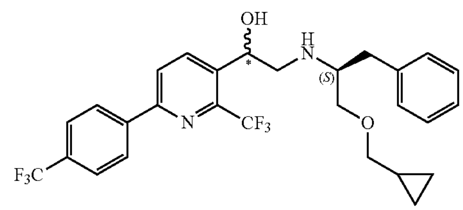 | 97% | 98 |
| 22 | 30v (R,S) | | | 94% | 98 |

[a] determined by chiral HPLC.

Example 3. Chemistry

3.1. Generalities

Solvents and Reagents purification: Tert-butanol, N,N-dimethylformamide, anhydrous 1,4-dioxane, pyridine, toluene, chloroform purchased from Acros; ethanol, acetonitrile, diethyl ether, ethyl acetate, cyclohexane purchased from VWR Chemicals; anhydrous DMSO purchased from Sigma-Aldrich were all used without any purification. Anhydrous tetrahydrofuran, methanol, acetonitrile, N,N-dimethylformamide, dichloromethane were dried using a solvent dryer Pure Solv-Innovative Technology PS-MD-5 purchased from Serlabo Technologies. The different reagents were purchased from Acros, Sigma-Aldrich and VWR Chemicals and used without any purification.

Chromatography: All the reactions were monitored by thin layer chromatography (TLC) on silica gel on aluminium plates 60F$_{254}$ purchased from Merck. The TLC plates were observed by ultra-violet (UV) with a wavelength of 254 nm, before being revealed chemically by phosphomolybdic acid in ethanol followed by a heating to obtain a maximal coloration.

Compounds were purified using flash chromatography on silica gel Kieselgel 60 (40-63 µm) purchased from Merck.

Enantiomeric excesses (ee) and diastereomeric excesses (de) were determined by High Pressure Liquid Chromatography (HPLC) Shimadzu LC-20AD equipped with an UV detector and with two injection pumps SPD-10AS. Several kinds of chiral columns were used: Chiralpak IA, IB, IC or IG.

Monitoring of metallo-catalysed reactions were performed using Gas Chromatography (GC) coupled to Mass Spectrometry (MS) Shimadzu CGSM-QP2010S equipped with SLB-5 ms column.

High Resolution Mass Spectrometry (HRMS) have been carried out using Micromass Q-TOF Ultima with positive electrospray ionization mode.

Mass Spectrometry (MS) analyses were carried out using a Shimadzu LCMS-2020 spectrometer.

Nuclear Magnetic Resonance (NMR): NMR analyses were performed on NMR Brucker 300 MHz (NMR $^1$H at 300 MHz and NMR $^{13}$C at 75 MHz), NMR Brucker 400-cryosonde (NMR $^1$H at 400 MHz and NMR $^{13}$C at 100 MHz) devices. NMR $^1$H and $^{13}$C Chemical shifts (δ) were in parts per million (ppm) according to the reference solvent used. NMR spectra analyses was carried out specifying chemical shifts, multiplicity (s=singlet, d=doublet,t=triplet, q=quartet, m=multiplet, dd=doublet of doublet) and coupling constants (J).

Infrared (IR): Infrared spectrometry analyses were performed using FT/IR-4200 Jasco spectrometer equipped with ATR-Golden gate system permitting us to analyze solid and liquid compounds.

Melting Point (m.p.): Melting points were determined using Stuart SMP3 device.

Rotatory Power ([α]$_D^{20}$): Rotatory power were measured using a Jasco P-1010 polarimeter.

3.2. General Method for Preparation of Intermediate Compounds

3.2.1. General Procedures

General procedure for the alcohol protection with 4-methoxybenzyl chloride: To a solution of the alcohol in anhydrous DMF (0.20 M) were added the 4-methoxybenzyl chloride (1 eq.) and K$_2$CO$_3$ (1.3 eq.). The suspension was heated at 110° C. for 4 h before being filtered through a celite pad. The filtrate was concentrated invacuo. The residue was placed in ethyl acetate before being treated with a 0.5 M sodium hydroxide aqueous solution.

The aqueous layer was extracted with ethyl acetate. The organic layers were dried over Na$_2$SO$_4$, filtered and concentrated in vacuo. The residue was purified by flash chromatography to afford the protected alcohol.

General Procedure for Diol Preparation:

To a suspension of AD-mix (α for (S) enantiomer and β for (R) enantiomer) in a solvent mixture of tBuOH/H$_2$O (1:1, 1.40 g d'AD-mix for 1 mmol of vinylpyridine and 5 mL of solvent) was added K$_2$OsO$_2$(OH)$_4$ (0.01 eq.). The reactional mixture was cooled to 0° C. and then a solution of vinylpyridine in the same solvent system (0.20 M) was added. The suspension was stirred at 0° C. for 5 min and then at 25° C. for 15 h before being treated by the addition of Na$_2$SO$_3$ at 0° C. (776 mg of Na$_2$SO$_3$ per grams of AD-mix). The mixture was stirred for 10 min at 0° C. and then 10 min at 25° C. before being extracted with ethyl acetate. The organic layers were dried over Na$_2$SO$_4$, filtered and concentrated in vacuo. The residue was precipitated in cyclohexane before to filter the resulting solid.

General Procedure for a Suzuki Reaction:

To a solution, under argon, of the iodo compound in a mixture of toluene/EtOH/H$_2$O (6:1:1) as solvent (0.06 M) were added the boronic reagent (0.9 eq.), Na$_2$CO$_3$ (2 eq.) and Pd(PPh$_3$)$_4$ (0.05 eq.). The reaction was heated at 110° C. for 15 h before being cooled to 25° C. and concentrated in vacuo. The residue was directly purified by flash chromatography to afford expected product.

3.2.2. Preparation of 2-(trifluoromethyl)-6-(4-(trifluoromethyl)phenyl)-4-vinylpyridine (3)

2,6-Dibromopyridin-4-ol (7)

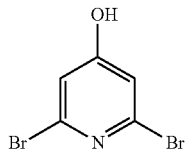

A mixture, under argon, of 500 mg (2.11 mmol, 1 eq.) of 2,6-dibromopyridine 6, 1.53 mL (10.6 mmol, 5 eq.) of pinacolborane, 27.0 mg (0.04 mmol, 0.02 eq.) of [IrCl(cod)]$_2$ and 34.0 mg (0.08 mmol, 0.04 eq.) of 1,2-bis(diphenylphosphino)ethane was heated at 130° C. for 4 h. The solution was cooled to 25° C. and concentrated in vacuo. The residue was dissolved in 8 mL of THF and then was added a solution of 713 mg (2.32 mmol, 1.1 eq.) of oxone monopersulfate in 7 mL of water. The reaction mixture was stirred at 25° C. for 10 min, treated by 4 mL of a 1 M sodium hydrogenosulfite solution and then extracted with diethyl ether. The organic layers were washed with brine, dried over Na$_2$SO$_4$, filtered and concentrated in vacuo. The residue was purified by flash chromatography (cyclohexane/AcOEt 5:1) to afford 417 mg of 7 as a white solid. Yield: 78%; m.p. 207° C.; NMR $^1$H (400 MHz, CD$_3$OD): δ 6.97 (s, 2H) ppm; NMR 13C (100 MHz, CD$_3$OD): δ 116.0, 141.8, 168.6 ppm; IR $\vee_{max}$: 2838, 1540, 1147, 769 cm$^{-1}$; HRMS calcd. for C$_5$H$_3$NOBr$_2$Na (M+Na)$^+$ 273.8479, found 273.8467.

2,6-Dibromo-4-((4-methoxybenzyl)oxy)pyridine (8)

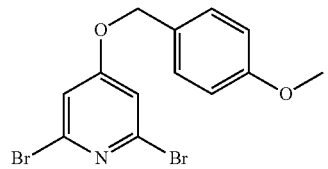 [SMILES: COc1ccc(COc2cc(Br)nc(Br)c2)cc1]

The compound 8 was obtained with 7 (386 mg, 1.53 mmol, 1 eq.) according to the general procedure for the alcohol protection with 4-methoxybenzyl chloride. The residue was purified by flash chromatography (cyclohexane/AcOEt 5:1) to afford 513 mg of 8 as a white solid. Yield: 90%; m.p. 69° C.; NMR $^1$H (400 MHz, CDCl$_3$): δ 3.83 (s, 3H), 5.00 (s, 2H), 6.94 (d, J=8.7 Hz, 2H), 7.04 (s, 2H), 7.31 (d, J=8.7 Hz, 2H) ppm; NMR $^{13}$C (100 MHz, CDCl$_3$): δ 55.3, 70.8, 114.0, 114.2, 126.3, 129.5, 141.1, 160.0, 166.7 ppm; IR $\vee_{max}$: 2925, 1572, 1514, 982, 826 cm$^{-1}$; HRMScalcd. for C$_{13}$H$_{11}$Br$_2$NO$_2$Na (M+Na)$^+$ 393.9054, found 393.9065.

2-Bromo-6-iodo-4-((4-methoxybenzyl)oxy)pyridine (5)

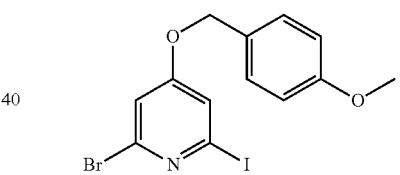

To a solution, under argon, of 4.97 g (13.1 mmol, 1 eq.) of 2,6-dibromo-4-((4-methoxybenzyl)oxy)pyridine 8 in 13 mL of anhydrous THF were added 16.2 mL (21.0 mmol, 1.6 eq.) of iPrMgCl.LiCl (1.3 M in THF). The solution was stirred at 25° C. for 2 h before cooling it to 0° C. and adding, by portions, 5.33 g (21.0 mmol, 1.6 eq.) of iodine. The reaction mixture was stirred at 0° C. for 5 min and for 15 h at 25° C. before being treated by 3×40 mL of a 0.5 M Na$_2$S$_2$O$_3$ solution. The mixture was extracted with ethyl acetate. The organic layers were washed with brine, dried over Na$_2$SO$_4$, filtered and concentrated in vacuo. The residue was purified by flash chromatography (cyclohexane/AcOEt 10:1) to afford 4.68 g of 5 as a white solid. Yield: 85%; m.p. 96° C.; NMR $^1$H (400 MHz, CDCl$_3$): δ 3.83 (s, 3H), 4.99 (s, 2H), 6.93 (d, J=8.7 Hz, 2H), 7.04 (d, J=1.9 Hz, 1H), 7.26-7.34 (m, 3H) ppm; NMR $^{13}$C (100 MHz, CDCl$_3$): δ 55.3, 70.6, 114.27, 114.3, 115.5, 121.2, 126.4, 129.5, 141.0, 160.0, 165.6 ppm; IR $\vee_{max}$: 2928, 1563, 1516, 1251, 983, 826 cm$^{-1}$; HRMScalcd. for C$_{13}$H$_{12}$BrINO$_2$ (M+H)$^+$ 419.9096, found 419.9097.

2-Bromo-4-((4-methoxybenzyl)oxy)-6-(4-(trifluoromethyl)phenyl)pyridine (10)

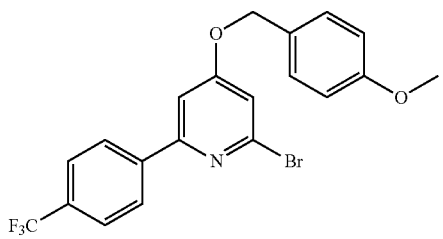 [SMILES: COc1ccc(COc2cc(Br)nc(-c3ccc(C(F)(F)F)cc3)c2)cc1]

The compound 10 was obtained from 5 (2.74 g, 6.52 mmol, 1 eq.) and (4-(trifluoromethyl)phenyl)boronic acid (1.12 g, 5.87 mmol, 0.9 eq.) according to the general procedure for a Suzuki reaction. The residue was directly purified by flash chromatography (cyclohexane/AcOEt 8:1) to afford 2.73 g of 10 as a yellow oil. Yield: 95%; NMR $^1$H (400 MHz, CDCl$_3$): δ 3.83 (s, 3H), 5.08 (s, 2H), 6.95 (d, J=8.6 Hz, 2H), 7.07 (d, J=2.0 Hz, 1H), 7.27 (d, J=2.0 Hz, 1H), 7.36 (d, J=8.6 Hz, 2H), 7.70 (d, J=8.2 Hz, 2H), 8.04 (d, J=8.2 Hz, 2H) ppm; NMR $^{13}$C (100 MHz, CDCl$_3$): δ 55.3, 70.5, 108.1, 112.7, 114.3, 124.0 (q, J=272.2 Hz), 125.6 (q, J=3.8 Hz), 126.8, 127.2, 129.5, 131.3 (q, J=32.6 Hz), 141.0, 143.1, 157.4, 160.0, 166.6 ppm; IR ν$_{max}$: 2935, 1580, 1321 cm$^{-1}$; MS (ESI$^+$) m/z: 439 (M+H)$^+$.

2-Iodo-4-((4-methoxybenzyl)oxy)-6-(4-(trifluoromethyl)phenyl)pyridine (11)

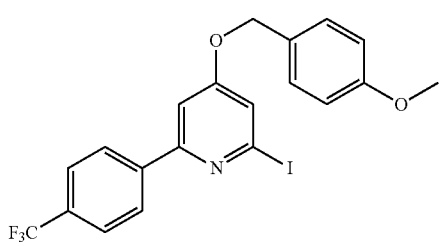

To a solution, under argon, of 2-bromo-4-((4-methoxybenzyl)oxy)-6-(4-(trifluoromethyl)phenyl)pyridine 10 (453 mg, 1.03 mmol, 1 eq.), CuI (10 mg, 0.05 mmol, 0.05 eq.), NaI (309 mg, 2.06 mmol, 2 eq.) in 1.3 mL of 1,4-dioxane were added 11.0 µL (0.10 mmol, 0.1 eq.) of N,N'-dimethylethylenediamine. The solution was heated at 110° C. for 28 h, treated with 10 mL of NH$_3$ (~28%) and diluted with water. The mixture was extracted with CH$_2$Cl$_2$. The organic layers were washed with brine, dried over Na$_2$SO$_4$, filtered and concentrated in vacuo. The residue was purified by flash chromatography (cyclohexane/AcOEt 8:1) to afford 442 mg of 11 as a colorless oil. Yield: 88%; NMR $^1$H (400 MHz, CDCl$_3$): δ 3.74 (s, 3H), 4.96 (s, 2H), 6.86 (d, J=8.6 Hz, 2H), 7.17 (d, J=2.0 Hz, 1H), 7.21 (d, J=2.0 Hz, 1H), 7.26 (d, J=8.6 Hz, 2H), 7.59 (d, J=8.2 Hz, 2H), 7.93 (d, J=8.2 Hz, 2H) ppm; NMR $^{13}$C (100 MHz, CDCl$_3$): δ55.3, 70.3, 108.4, 114.2, 118.8, 119.7, 124.0 (q, J=272.3 Hz), 125.6 (q, J=3.7 Hz), 126.9, 127.2, 129.5, 131.2 (q, J=32.5 Hz), 141.0, 157.9, 160.0, 165.5 ppm; IR ν$_{max}$: 2935, 1575, 1319, 1110, 993, 827 cm$^{-1}$; HRMS calcd. for C$_{20}$H$_{16}$F$_3$INO$_2$ (M+H)$^+$ 486.0178, found 486.0190.

4-((4-Methoxybenzyl)oxy)-2-(trifluoromethyl)-6-(4-(trifluoromethyl)phenyl)pyridine (12)

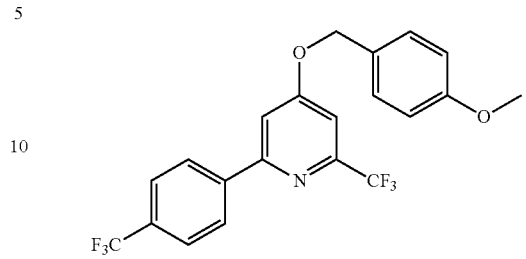

A mixture, under argon, of 2-iodo-4-((4-methoxybenzyl)oxy)-6-(4-(trifluoromethyl)phenyl)pyridine 11 (2.28 g, 4.70 mmol, 1 eq.), KF (1.64 g, 28.2 mmol, 6 eq.), CuI (0.36 g, 1.88 mmol, 0.4 eq.), 1,10-phenantroline (0.34 g, 1.88 mmol, 0.4 eq.), B(OMe)$_3$ (3.14 mL, 28.2 mmol, 6 eq.), TMSCF$_3$ (14.1 mL, 28.2 mmol, 6 eq.) (2 M in THF) in 68 mL of anhydrous DMSO was heated at 60° C. for 24 h. The solution was treated with 20 mL of an aqueous solution of NH$_3$ (~28%) and extracted with diethyl ether. The organic layers were washed with brine, dried over Na$_2$SO$_4$, filtered and concentrated in vacuo. The residue was purified by flash chromatography (cyclohexane/AcOEt 4:1) to afford 1.78 g of 12 as a yellow oil. Yield: 89%; NMR $^1$H (400 MHz, CDCl$_3$): δ 3.75 (s, 3H), 5.07 (s, 2H), 6.88 (d, J=8.7 Hz, 2H), 7.17 (d, J=2.0 Hz, 1H), 7.30 (d, J=8.7 Hz, 2H), 7.35 (d, J=2.0 Hz, 1H), 7.63 (d, J=8.2 Hz, 2H), 8.02 (d, J=8.2 Hz, 2H) ppm; NMR $^{13}$C (100 MHz, CDCl$_3$): δ 55.3, 70.5, 106.6 (q, J=2.8 Hz), 109.7, 114.3, 121.4 (q, J=274.6 Hz), 124.0 (q, J=272.2 Hz), 125.7 (q, J=3.8 Hz), 126.7, 127.4, 129.5, 131.5 (q, J=32.6 Hz), 141.2, 150.0 (q, J=34.5 Hz), 157.9, 160.0, 166.7 ppm; IR ν$_{max}$: 2935, 1604, 1324, 1126 cm$^{-1}$; MS (ESI$^+$) m/z: 428 (M+H)$^+$.

2-(Trifluoromethyl)-6-(4-(trifluoromethyl)phenyl)pyridin-4-ol (13)

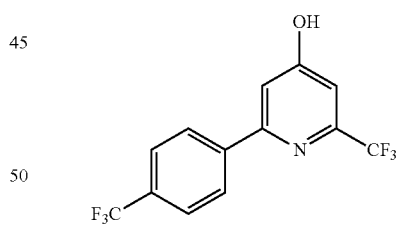

To a solution, under argon, of 4-((4-methoxybenzyl)oxy)-2-(trifluoromethyl)-6-(4-(trifluoromethyl)phenyl)pyridine 12 (1.78 g, 4.17 mmol, 1 eq.) in 42 mL of CH$_2$Cl$_2$ was added 1.68 mL of TFA (2% v/v TFA/CH$_2$Cl$_2$). The mixture was stirred at 25° C. for 7 h before being treated with 3×20 mL of a 1 M NaOH solution. The aqueous layer was neutralized to pH=7 with a 1M HCl solution and then concentrated in vacuo. The residue was washed with MeOH and filtered. The filtrate was concentrated in vacuo. The residue was purified by flash chromatography (cyclohexane/AcOEt 1:1) to afford 1.03 g of 13 as a white solid. Yield: 80%; m.p. 170° C.; NMR $^1$H (400 MHz, CD$_3$OD): δ×7.14 (d, J=2.0 Hz, 1H), 7.48 (d, J=2.0 Hz, 1H), 7.77 (d, J=8.2 Hz, 2H), 8.20 (d, J=8.2 Hz, 2H) ppm; NMR $^{13}$C (100 MHz, CD$_3$OD): δ 108.8 (q, J=2.8 Hz), 111.7, 123.0 (q, J=273.5 Hz), 125.7 (q, J=271.3 Hz), 126.7 (q, J=3.8 Hz), 128.7, 132.4 (q, J=32.2 Hz), 143.0, 150.8 (q, J=34.2 Hz), 159.2, 168.1 ppm; IR $v_{max}$: 3097, 1611, 1582, 1323, 1108, 1061, 849 cm$^{-1}$; HRMS calcd. for $C_{13}H_8F_6NO$ (M+H)$^+$ 308.0510, found 308.0523.

4-Bromo-2-(trifluoromethyl)-6-(4-(trifluoromethyl)phenyl)pyridine (4)

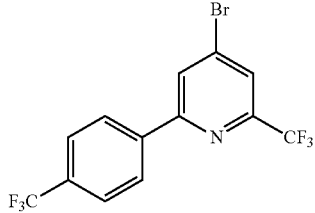

A mixture, under argon, of 2-(trifluoromethyl)-6-(4-(trifluoromethyl)phenyl)pyridin-4-ol 13 (0.75 g, 2.45 mmol, 1 eq.), phosphorous oxybromide (2.81 g, 9.80 mmol, 4 eq.) in 15 mL of anhydrous DMF was heated at 110° C. for 15 h. The reaction mixture was treated with water before being extracted with ethyl acetate. The organic layers were washed with brine, dried over Na$_2$SO$_4$, filtered and concentrated in vacuo. The residue was purified by flash chromatography (cyclohexane/AcOEt 10:1) to afford 0.73 g of 4 as a white solid. Yield: 81%; m.p. 59° C.; NMR $^1$H (400 MHz, CDCl$_3$): δ 7.76 (d, J=8.2 Hz, 2H), 7.83 (s, 1H), 8.12 (s, 1H), 8.16 (d, J=8.2 Hz, 2H) ppm; NMR $^{13}$C (100 MHz, CDCl$_3$): δ 120.7 (q, J=275.1 Hz), 122.9 (q, J=2.8 Hz), 123.9 (q, J=272.4 Hz), 126.0 (q, J=3.8 Hz), 126.4, 127.6, 132.2 (q, J=32.7 Hz), 134.9, 139.7, 149.3 (q, J=35.4 Hz), 157.5 ppm; IR $v_{max}$: 1573, 1320, 1119, 1057, 843 cm$^{-1}$.

2-(Trifluoromethyl)-6-(4-(trifluoromethyl)phenyl)-4-vinylpyridine (3)

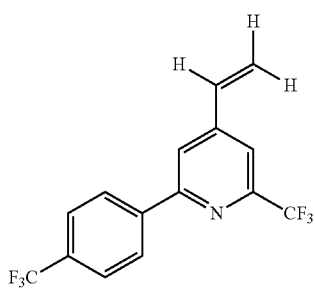 [SMILES: C=Cc1cc(-c2ccc(C(F)(F)F)cc2)nc(C(F)(F)F)c1]

The compound 3 was obtained from 4 (963 mg, 2.60 mmol, 1 eq.) and potassium vinyltrifluoroborate (383 mg, 2.86 mmol, 1.1 eq.) according to the general procedure for a Suzuki reaction. The residue was directly purified by flash chromatography (cyclohexane/AcOEt 10:1) to afford 711 mg of 3 as an oil, solidifying himself in a light yellow solid. Yield: 86%; m.p. 37° C.; NMR $^1$H (400 MHz, CDCl$_3$): δ 5.66 (d, J=10.9 Hz, 1H), 6.15 (d, J=17.6 Hz, 1H), 6.78 (dd, J=17.6, 10.9 Hz, 1H), 7.65 (s, 1H), 7.72 (d, J=8.2 Hz, 2H), 7.83 (s, 1H), 8.15 (d, J=8.2 Hz, 2H) ppm; NMR $^{13}$C (100 MHz, CDCl$_3$): δ 116.2 (q, J=2.7 Hz), 120.3, 120.7, 121.3 (q, J=272.2 Hz), 123.9 (q, J=272.2 Hz), 125.7 (q, J=3.4 Hz), 127.4, 10131.5 (q, J=32.5 Hz), 133.7, 141.0, 147.7, 148.9 (q, J=34.5 Hz), 156.7 ppm IR $v_{max}$: 1321, 1108 cm$^{-1}$; HMRS calcd. for $C_{15}H_{10}F_6N$ (M+H)$^+$ 318.0717, found 318.0725.

3.2.3. Preparation of Diols (14a) and (14b)

(S)-1-(2-(Trifluoromethyl)-6-(4-(trifluoromethyl)phenyl)pyridin-4-yl)ethane-1,2-diol

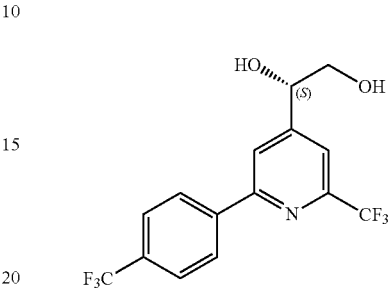

The compound 14a was obtained from 3 (260 mg, 0.81 mmol, 1 eq.), AD-mix α (1.13 g for 8 mL of solvent tBuOH/H$_2$O 1:1), K$_2$OsO$_2$(OH)$_4$ (4.00 mg, 0.8 mol %, 0.01 eq.) according to the general procedure for diol formation. 270 mg of 14a as a white solid were obtained. Yield: 95%; m.p. 101° C.; NMR $^1$H (400 MHz, CD$_3$OD): δ 3.77 [AB (ABX), J=11.4 Hz, J=5.6 Hz, J=5.1 Hz, 2H], 4.89 [X(ABX), J=5.6 Hz, J=5.1 Hz, 1H, H$_{14}$], 7.76 (d, J=8.3 Hz, 2H), 7.84 (s, 1H), 8.20 (s, 1H), 8.29 (d, J=8.3 Hz, 2H) ppm; NMR $^{13}$C (100 MHz, CD$_3$OD): δ 67.8, 74.2, 118.7 (q, J=2.8 Hz), 122.5, 123.2 (q, J=273.6 Hz), 125.6 (q, J=271.3 Hz), 126.8 (q, J=3.8 Hz), 128.7, 132.5 (q, J=32.3 Hz), 142.7, 149.2 (q, J=34.3 Hz), 157.0, 157.2 ppm; IR $v_{max}$: 3293, 1323, 1097 cm$^{-1}$; HRMS calcd. for $C_{15}H_{11}F_6NO_2Na$ (M+Na)$^+$ 374.0578, found 374.0583; $[α]_D^{20}$: +29.1° (c 0.1; MeOH); Chiral HPLC 99% ee, Chiralpak IB column, heptane/i-PrOH, 90:10, flow 1 mL/min, tr(R)=11.1 min, tr(S)=12.7 min.

(R)-1-(2-(Trifluoromethyl)-6-(4-(trifluoromethyl)phenyl)pyridin-4-yl)ethane-1,2-diol (14)

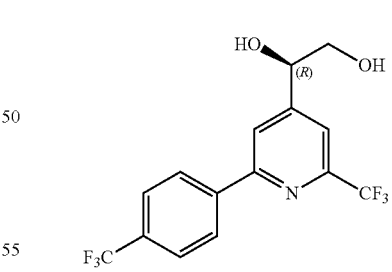

The compound 14b was obtained from 3 (278 mg, 0.88 mmol, 1 eq.), AD-mix β (1.23 g for 8 mL of solvent tBuOH/H$_2$O 1:1), K$_2$OsO$_2$(OH)$_4$ (4.00 mg, 0.8 mol %, 0.01 eq.) according to the general procedure for diol formation. 254 mg of 14b as a white solid were obtained. Yield: 82%; The NMR ($^1$H and $^{13}$C), IR spectra, HRMS and m.p. were identical to those of 14a; $[α]_D^{20}$: −29.3° (c 0.1; MeOH); Chiral HPLC 99% ee, Chiralpak IB column, heptane/i-PrOH, 90:10, flow 1 mL/min, tr(R)=11.1 min, tr(S)=12.7 min.

3.2.4. Preparation of Epoxides (2a) and (2b)

(S)-4-(Oxiran-2-yl)-2-(trifluoromethyl)-6-(4-(trifluoromethyl)phenyl)pyridine (2a)

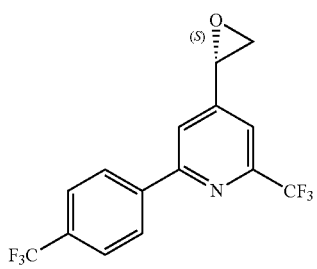

To a solution, under argon, of 288 mg (0.82 mmol, 1 eq.) of (S)-1-(2-(trifluoromethyl)-6-(4-(trifluoromethyl)phenyl)pyridin-4-yl)ethane-1,2-diol 14a in 8 mL of anhydrous $CH_2Cl_2$ were added 0.31 mL (2.46 mmol, 3 eq.) of trimethylorthoacetate and 7.00 mg (0.04 mmol, 0.05 eq.) of pTsOH. The reactional mixture was stirred for 7 h at 25° C. before being concentrated invacuo. The residue, under argon, was placed in 8 mL of anhydrous $CH_2Cl_2$, cooled to 0° C. and then 0.32 mL (2.46 mmol, 3 eq.) of TMSBr were added. The solution was stirred for 5 min at 0° C. and 15 h at 25° C. The mixture was concentrated in vacuo and the residue placed, under argon, in 8 mL of anhydrous MeOH before adding 567 mg (4.10 mmol, 5 eq.) of dried $K_2CO_3$. The suspension was stirred for 4 h at 25° C., treated by the addition of a saturated $NH_4Cl$ solution. The mixture was extracted with $CH_2Cl_2$. The organic layers were dried over $Na_2SO_4$, filtered and concentrated in vacuo. The residue was purified by flash chromatography (cyclohexane/AcOEt 4:1) to afford 203 mg of 2a as a white solid. Yield: 74%; m.p. 70° C.; NMR $^1H$ (400 MHz, $CDCl_3$): δ 3.06 [AB(ABX), J=5.5 Hz, J=4.2 Hz, J=2.4 Hz, 2H], 4.02 [X(ABX), J=4.2 Hz, J=2.4 Hz, 1H], 7.59 (s, 1H), 7.75 (d, J=8.2 Hz, 2H), 7.86 (s, 1H), 8.18 (d, J=8.2 Hz, 2H) ppm; NMR $^{13}C$ (100 MHz, $CDCl_3$): δ 50.9, 51.5, 116.3 (q, J=2.7 Hz), 119.6, 123.97 (q, J=272.2 Hz), 124.03 (q, J=274.4 Hz), 125.8 (q, J=3.8 Hz), 127.5, 131.8 (q, J=32.6 Hz), 140.7, 148.8 (q, J=34.9 Hz), 150.4, 156.7 ppm; IR $v_{max}$: 3251, 1323, 1095 $cm^{-1}$; HRMS calcd. for $C_{15}H_{10}F_6NO$ $(M+H)^+$ 334.0667, found 334.0679; [α]L: +8.5° (c 0.1; MeOH); Chiral HPLC 98% ee, Chiralpak IB column, heptane/i-PrOH, 95:5, flow 1 mL/min, tr(R)=8.1 min, tr(S)=8.6 min.

(R)-4-(Oxiran-2-yl)-2-(trifluoromethyl)-6-(4-(trifluoromethyl)phenyl)pyridine (2b)

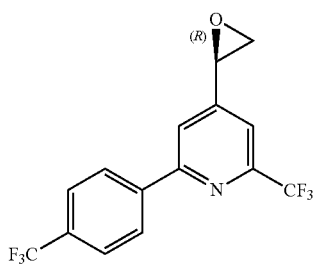

The compound 2b was obtained from 14b (100 mg, 0.28 mmol) according to the same procedure as 2a to afford 70 mg of 2b as a white solid. Yield: 75%; The NMR ($^1H$ and $^{13}C$), IR spectra, HRMS and m.p. were identical to those of 2a; $[α]_D^{20}$: −9.0° (c 0.1; MeOH); Chiral HPLC 99% ee, Chiralpak IC column, heptane/i-PrOH, 99:1, flow 1 mL/min, tr(R)=4.9 min, tr(S)=9.0 min.

3.2.5. Preparation of 2-(trifluoromethyl)-6-(4-(trifluoromethyl)phenyl)-3-vinylpyridine (32)

2-Bromo-6-iodopyridin-3-ol (36)

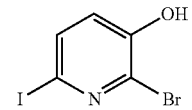

To a suspension of 25.0 g (0.14 mol, 1 eq.) of 2-bromopyridin-3-ol 35 in 500 mL of water were added 30.4 g (0.29 mol, 2 eq.) of $Na_2CO_3$ and 36.5 g (0.14 mmol, 1 eq.) of iodine. The solution was stirred at 25° C. for 24 h and then neutralized to pH ~6 with a 1 M HCl solution. The solid was filtered and dried under vacuum to afford 37.6 g of 36 as a beige solid. Yield: 87%; m.p. 157° C.; NMR $^1H$ (400 MHz, $CD_3OD$): δ 6.94 (d, J=8.2 Hz, 1H), 7.56 (d, J=8.2 Hz, 1H) ppm; NMR $^{11}C$ (100 MHz, $CD_3OD$): δ 101.1, 126.5, 131.1, 136.0, 153.4 ppm; IR $v_{max}$: 2734, 1388, 1282, 1222 $cm^{-1}$.

2-Bromo-6-Iodo-3-((4-methoxybenzyl)oxy)pyridine (34)

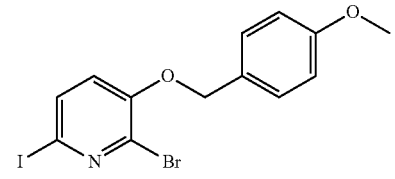 [SMILES: COc1ccc(COc2ccc(I)nc2Br)cc1]

The compound 34 was obtained from 36 (10.0 g, 33.3 mmol, 1 eq.) according to the general procedure for the alcohol protection with 4-methoxybenzyl chloride. The residue was purified by flash chromatography (cyclohexane/AcOEt 2:1) to afford 11.3 g of 34 as a light yellow solid. Yield: 82%; m.p. 106° C.; NMR $^1H$ (400 MHz, $CDCl_3$) δ 3.81 (s, 3H), 5.08 (s, 2H), 6.85 (d, J=8.3 Hz, 1H), 6.91 (d, J=8.7 Hz, 2H), 7.34 (d, J=8.7 Hz, 2H), 7.52 (d, J=8.3 Hz, 1H) ppm; NMR $^{13}C$ (100 MHz, $CDCl_3$): δ 55.3, 71.1, 102.5, 114.1, 122.6, 126.9, 128.8, 132.6, 134.1, 152.4, 159.7 ppm; IR $v_{max}$: 2924, 1512, 1410, 1230, 1068, 1019 $cm^{-1}$; HRMS calcd. for $C_{13}H_{11}BrINO_2Na$ $(M+Na)^+$ 441.8916, found 441.8901.

2-Bromo-3-((4-methoxybenzyl)oxy)-6-(4-(trifluoromethyl)phenyl)pyridine (39)

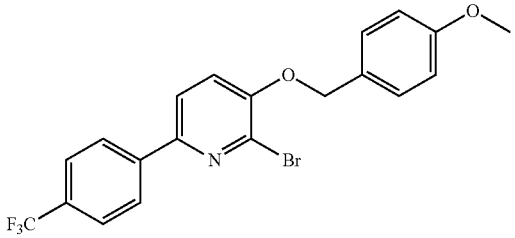

The compound 39 was obtained from 34 (4.37 g, 10.4 mmol, 1 eq.) and (4-(trifluoromethyl)phenyl)boronic acid (1.78 g, 9.36 mmol, 0.9 eq.) according to the general procedure for a Suzuki reaction. The residue was directly purified by flash chromatography (cyclohexane/AcOEt 4:1) to afford 4.26 g of 39 as a white solid. Yield: 93%; m.p. 125° C.; NMR $^1$H (400 MHz, CDCl$_3$): δ 3.82 (s, 3H), 5.15 (s, 2H), 6.94 (d, J=8.6 Hz, 2H), 7.23 (d, J=8.4 Hz, 1H), 7.39 (d, J=8.6 Hz, 2H), 7.62 (d, J=8.4 Hz, 1H), 7.67 (d, J=8.3 Hz, 2H), 8.03 (d, J=8.3 Hz, 2H) ppm; NMR $^{13}$C (100 MHz, CDCl$_3$): δ 55.3, 71.0, 114.1, 120.1, 121.0, 124.1 (q, J=272.1 Hz), 125.6 (q, J=3.8 Hz), 126.6, 127.3, 128.8, 130.4 (q, J=32.4 Hz), 140.7, 148.2, 151.6, 159.7 ppm; IR $\nu_{max}$: 2964, 1443, 1323, 1105 cm$^{-1}$; HRMS calcd. for $C_{20}H_{15}BrF_3NO_2Na$ (M+Na)$^+$ 460.0136, found 460.0116.

2-Iodo-3-((4-methoxybenzyl)oxy)-6-(4-(trifluoromethyl)phenyl)pyridine (40)

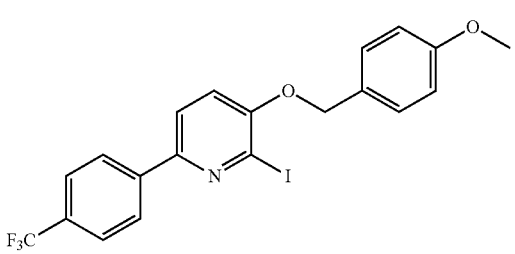 [SMILES: COc1ccc(COc2ccc(-c3ccc(C(F)(F)F)cc3)nc2I)cc1]

A solution, under argon, of 5.35 g (12.2 mmol, 1 eq.) of 2-bromo-3-((4-methoxybenzyl)oxy)-6-(4-(trifluoromethyl)phenyl)pyridine 39, 116 mg (0.61 mmol, 0.05 eq.) of CuI, 3.66 g (24.4 mmol, 2 eq.) of NaI, 0.13 mL (1.22 mmol, 0.1 eq.) of N,N'-dimethylethylenediamine in 15 mL of anhydrous 1,4-dioxane was heated at 110° C. for 28 h. The mixture was then cooled to 25° C. before being treated with an aqueous solution of NH$_3$ (~28%), diluted with water and extracted with CH$_2$Cl$_2$. The organic layers were dried over Na$_2$SO$_4$, filtered and concentrated in vacuo. The residue was purified by flash chromatography (cyclohexane/AcOEt 4:1) to afford 4.84 g of 40 as a white solid. Yield: 82%; m.p.: 110° C.; NMR $^1$H (400 MHz, CDCl$_3$): δ 3.82 (s, 3H), 5.14 (s, 2H), 6.94 (d, J=8.7 Hz, 2H), 7.07 (d, J=8.4 Hz, 1H), 7.41 (d, J=8.7 Hz, 2H), 7.59 (d, J=8.4 Hz, 1H), 7.67 (d, J=8.3 Hz, 2H), 8.02 (d, J=8.3 Hz, 2H) ppm; NMR $^{13}$C (100 MHz, CDCl$_3$): δ 55.3, 71.0, 112.8, 114.1, 119.1, 120.2, 124.1 (q, J=272.0 Hz), 125.6 (q, J=3.8 Hz), 126.5, 127.3, 128.8, 130.3 (q, J=32.4 Hz), 140.8, 149.5, 153.9, 159.6 ppm; IR $\nu_{max}$: 2932, 1513, 1437, 1321, 1111 cm$^{-1}$; HRMS calcd. for $C_{20}H_{15}IF_3NO_2Na$ (M+Na)$^+$ 507.9997, found 507.9976.

3-((4-Methoxybenzyl)oxy)-2-(trifluoromethyl)-6-(4-(trifluoromethyl)phenyl)pyridine (41)

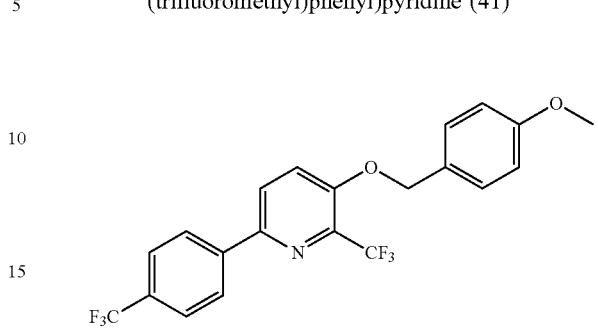

To a solution, under argon, of 789 mg (1.63 mmol, 1 eq.) of 2-iodo-3-((4-methoxybenzyl)oxy)-6-(4-(trifluoromethyl)phenyl)pyridine 40, 284 mg (4.89 mmol, 3 eq.) of KF, 63 mg (0.33 mmol, 0.2 eq.) of CuI, 59 mg (0.33 mmol, 0.2 eq.) of 1,10-phenantroline in 18 mL of anhydrous DMSO were added 0.55 mL (4.89 mmol, 3 eq.) of trimethyl borate and 2.45 mL (4.89 mmol, 3 eq.) of a solution of trifluoromethyltrimethylsilane (2 M in THF). The mixture was heated at 60° C. for 27 h, cooled to 25° C., diluted with diethyl ether. The solution was treated with 20 mL of an aqueous solution of NH$_3$ (~28%) and stirred at 25° C. until the end of the gas emission. The mixture was then extracted with diethyl ether. The organic layers were washed with brine, dried over Na$_2$SO$_4$, filtered and concentrated in vacuo. The residue was purified by flash chromatography (cyclohexane/AcOEt 4:1) to afford 611 mg of 41 as a light yellow solid. Yield: 88%; m.p. 94° C.; NMR $^1$H (400 MHz, CDCl$_3$): δ 3.82 (s, 3H), 5.20 (s, 2H), 6.93 (d, J=8.7 Hz, 2H), 7.37 (d, J=8.7 Hz, 2H), 7.48 (d, J=8.8 Hz, 1H), 7.70 (d, J=8.3 Hz, 2H), 7.87 (d, J=8.8 Hz, 1H), 8.09 (d, J=8.3 Hz, 2H) ppm; NMR $^{13}$C (100 MHz, CDCl$_3$): δ 55.3, 70.6, 114.2, 121.5 (q, J=274.9 Hz), 122.4, 124.08, 124.12 (q, J=272.1 Hz), 125.7 (q, J=3.8 Hz), 126.6, 127.2, 128.7, 130.1 (q, J=32.4 Hz), 136.9 (q, J=33.9 Hz), 140.9, 146.6, 152.7, 159.7 ppm; IR $\nu_{max}$: 2920, 1462, 1325, 1108 cm$^{-1}$; HRMS calcd. for $C_{21}H_{15}F_6NO_2Na$ (M+Na)$^+$ 450.0905, found 450.0920.

2-(Trifluoromethyl)-6-(4-(trifluoromethyl)phenyl)pyridin-3-ol (42)

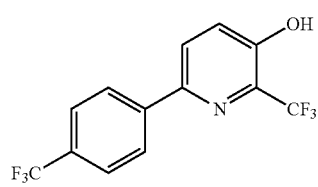

To a suspension, under argon, of 600 mg (1.40 mmol, 1 eq.) of 3-((4-methoxybenzyl)oxy)-2-(trifluoromethyl)-6-(4-(trifluoromethyl)phenyl)pyridine 41 in 14 mL of anhydrous MeOH were added 60 mg (10% w/w) of Pd/C. The suspension was placed under H$_2$ atm. and stirred for 15 h at 25° C. The palladium was then filtered on a celite pad. The filtrate was concentrated in vacuo and the residue purified by flash chromatography (cyclohexane/AcOEt 4:1) to afford 409 mg of 42 as a white solid. Yield: 95%; m.p. 155° C.; NMR $^1$H (400 MHz, CDCl$_3$): δ 7.46 (d, J=8.7 Hz, 1H), 7.72 (d, J=8.3 Hz, 2H), 8.00 (d, J=8.7 Hz, 1H), 8.17 (d, J=8.3 Hz, 2H) ppm; NMR $^{13}$C (100 MHz, CDCl$_3$): δ 123.4 (q, J=273.6 Hz), 125.8 (q, J=271.1 Hz), 126.0, 126.6 (q, J=3.8 Hz), 127.1, 127.7, 131.2 (q, J=32.3 Hz), 135.4 (q, J=33.6 Hz), 142.9, 146.7, 153.8 ppm; IR ν$_{max}$: 2988, 1323, 1188, 1110 cm$^{-1}$; HRMS calcd. for C$_{13}$H$_8$F$_6$NO (M+H)$^+$ 308.0510, found 308.0522.

2-(Trifluoromethyl-6-(4-(trifluoromethyl)phenyl) pyridin-3-yl trifluoromethanesulfonate (33)

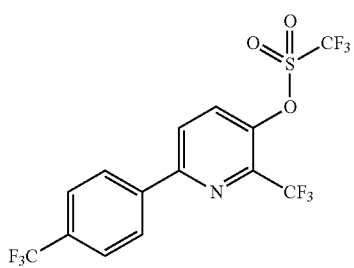 [SMILES: O=S(=O)(Oc1ccc(-c2ccc(C(F)(F)F)cc2)nc1C(F)(F)F)C(F)(F)F]

A solution, under argon, of 816 mg (2.66 mmol, 1 eq.) of 2-(trifluoromethyl)-6-(4-(trifluoromethyl)phenyl)pyridin-3-ol 42 in 3 mL of pyridine was cooled to 0° C. Then 0.49 mL (2.93 mmol, 1.1 eq.) of trifluoromethanesulfonic anhydride were added dropwise. The solution was stirred for 20 min at 0° C. and 15 h at 25° C. The mixture was diluted with ethyl ether and treated with 2×10 mL of a 1M CuSO$_4$ solution. The aqueous layers were extracted with diethyl ether. The organic layers were washed with brine, dried over Na$_2$SO$_4$, filtered and concentrated in vacuo. The residue was purified by flash chromatography (cyclohexane/AcOEt 5:1) to afford 1.06 g of 33 as a white solid. Yield: 91%; m.p. 64° C.; NMR $^1$H (400 MHz, CDCl$_3$): δ 7.78 (d, J=8.3 Hz, 2H), 7.98 (d, J=8.8 Hz, 1H), 8.08 (d, J=8.8 Hz, 1H), 8.17 (d, J=8.3 Hz, 2H) ppm; NMR $^{13}$C (100 MHz, CDCl$_3$): δ 118.6 (q, J=320.6 Hz), 120.4 (q, J=275.5 Hz), 124.0 (q, J=272.3 Hz), 124.8, 126.3 (q, J=3.8 Hz), 127.7, 132.1, 132.5 (q, J=32.8 Hz), 139.3, 140.0 (q, J=35.8 Hz), 143.3, 154.8 ppm; IR ν$_{max}$: 2969, 1428, 1323, 1208, 1125 cm$^{-1}$.

2-(Trifluoromethyl-6-(4-(trifluoromethyl)phenyl)-3-vinylpyridine (32)

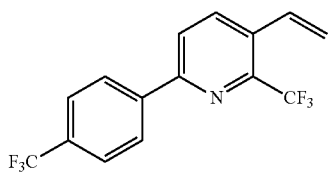 [SMILES: C=Cc1ccc(-c2ccc(C(F)(F)F)cc2)nc1C(F)(F)F]

To a solution, under argon, of 1.04 g (2.37 mmol, 1 eq.) of 2-(trifluoromethyl)-6-(4-(trifluoromethyl)phenyl)pyridin-3-yl trifluoromethanesulfonate 33 in 6 mL of anhydrous 1,4-dioxane were added 0.30 g (7.11 mmol, 3 eq.) of LiCl, 0.76 mL (2.61 mmol, 1.1 eq.) of tributyl(vinyl)tin, 0.11 g (0.09 mmol, 0.04 eq.) of Pd(PPh$_3$)$_4$. The suspension was heated at 100° C. and stirred for 15 h. The reactional mixture was concentrated in vacuo. The residue was directly purified by flash chromatography (cyclohexane/AcOEt 10:1) to afford 680 mg of 32 as a colorless oil. Yield: 90%; NMR $^1$H (400 MHz, CDCl$_3$): δ 5.58 (d, J=11.0 Hz, 1H), 5.86 (d, J=17.3 Hz, 1H), 7.14 (dd, J=11.0, 17.3 Hz, 1H), 7.74 (d, J=8.2 Hz, 2H), 7.93 (d, J=8.3 Hz, 1H), 8.09 (d, J=8.3 Hz, 1H), 8.19 (d, J=8.2 Hz, 2H) ppm; NMR $^{13}$C (100 MHz, CDCl$_3$): δ 120.0, 122.0 (q, J=276.0 Hz), 124.0 (q, J=272.2 Hz), 122.9, 125.8 (q, J=3.8 Hz), 127.2, 130.3 (q, J=2.7 Hz), 131.4 (q, J=32.6 Hz), 131.5, 136.3, 140.7, 144.4 (q, J=33.2 Hz), 153.7 ppm; IR ν$_{max}$: 2926, 1320, 1109 cm$^{-1}$; MS (ESI$^+$) m/z: 318 (M+H).

3.2.6. Preparation of Diols (44a) and (44b)

(S)-1-(2-(Trifluoromethyl)-6-(4-(trifluoromethyl) phenyl)pyridin-3-yl)ethane-1,2-diol (44a)

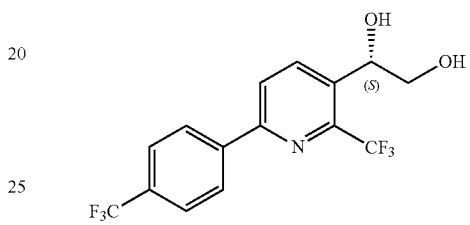

The compound 44a was obtained from 32 (680 mg, 2.14 mmol, 1 eq.), AD-mix α (3.00 g for 52 mL of solvent tBuOH/H$_2$O 1:1), K$_2$OsO$_2$(OH)$_4$ (4.00 mg, 1.00 mol %, 0.01 eq.) according to the general procedure for diol formation. 529 mg of 44a as a white solid were obtained. Yield: 73%; m.p. 120° C.; NMR $^1$H (400 MHz, CD$_3$OD): δ 3.68 [AB (ABX), J=11.5 Hz, J=7.0 Hz, J=3.5 Hz, 2H], 5.14-5.26 (m, 1H), 7.80 (d, J=8.3 Hz, 2H), 8.23 (d, J=8.3 Hz, 1H), 8.32 (d, J=8.3 Hz, 2H), 8.36 (d, J=8.3 Hz, 1H) ppm; NMR $^{13}$C (100 MHz, CD$_3$OD): δ68.1, 70.0, 123.7 (q, J=275.1 Hz), 125.7 (q, J=271.3 Hz), 126.8 (q, J=3.8 Hz), 128.6, 132.4 (q, J=32.3 Hz), 137.9, 140.3, 142.5, 145.2 (q, J=33.2 Hz), 155.1 ppm; IR ν$_{max}$: 3328, 2952, 1322, 1120, 1067, 1041 cm$^{-1}$; MS (ESI$^+$) m/z: 352 (M+H)$^+$; [α]$_D^{20}$: +54.5° (c 0.1; MeOH); Chiral HPLC 99% ee, Chiralpak IB column, heptane/i-PrOH/EDA, 95:5:0.1, flow 1 mL/min, tr(R)=43.7 min, tr(S) =46.9 min.

(R)-1-(2-(Trifluoromethyl)-6-(4-(trifluoromethyl) phenyl)pyridin-3-yl)ethane-1,2-diol

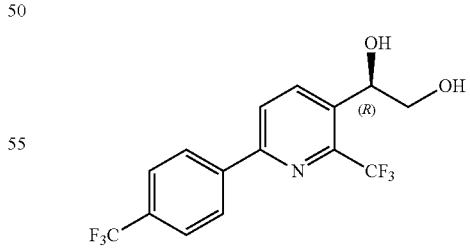

The compound 44b was obtained from 32 (1.21 g, 3.81 mmol, 1 eq.), AD-mix β (5.35 g for 96 mL of solvent tBuOH/H$_2$O 1:1), K$_2$OsO$_2$(OH)$_4$ (0.02 g, 4.00 mol %, 0.01 eq.) according to the general procedure for diol formation. 951 mg of 44b as a white solid were obtained. Yield: 71%; The NMR ($^1$H and $^{13}$C), IR spectra, MS and m.p. were identical to those of 44a. [α]$_D^{20}$: −54.6° (c 0.1; MeOH);

Chiral HPLC 99% ee, Chiralpak IB column, heptane/i-PrOH/EDA, 95:5:0.1, flow 1 mL/min, tr(R)=43.7 min, tr(S)=46.9 min.

3.2.7. Preparation of Epoxides (31a) and (31b)

(S)-3-(Oxiran-2-yl)-2-(trifluoromethyl)-6-(4-(trifluoromethyl)phenyl)pyridine (31a)

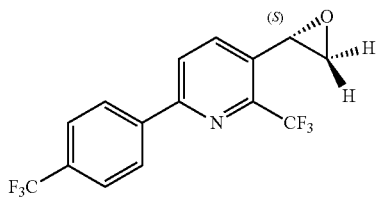

To a solution, under argon, of 100 mg (0.28 mmol, 1 eq.) of (S)-1-(2-(trifluoromethyl)-6-(4-(trifluoromethyl)phenyl)pyridin-3-yl)ethane-1,2-diol 44a in 3 mL of anhydrous $CH_2Cl_2$ were added 0.11 mL (0.85 mmol, 3 eq.) of trimethylorthoacetate and 3.00 mg (0.02 mmol, 0.05 eq.) of pTsOH. The solution was stirred for 1 h at 25° C. before being concentrated in vacuo. The residue was placed under argon and dissolved in 3 mL of anhydrous $CH_2Cl_2$. The solution was cooled to 0° C. before adding 0.11 mL (0.85 mmol, 3 eq.) of TMSBr, stirred for 5 min at 0° C. and 1 h at 25° C. The mixture was then concentrated in vacuo. The residue was placed under argon and dissolved in 3 mL of anhydrous MeOH before adding 193 mg (1.40 mmol, 5 eq.) of dried $K_2CO_3$. The suspension was stirred at 25° C. for 1 h, treated with a saturated solution of $NH_4Cl$ and extracted with $CH_2Cl_2$. The organic layers were dried over $Na_2SO_4$, filtered and concentrated in vacuo. The residue was purified by flash chromatography (cyclohexane/AcOEt 4:1) to afford 86 mg of 31a as a white solid. Yield: 92%; m.p. 81° C.; NMR $^1H$ (400 MHz, $CDCl_3$): δ 2.99 [AB(ABX), J=5.4 Hz, J=4.3 Hz, J=2.5 Hz, 2H], 4.28-4.29 (m, 1H), 7.75 (d, J=8.3 Hz, 2H), 7.91-7.98 (m, 2H), 8.18 (d, J=8.3 Hz, 2H) ppm; NMR $^{13}C$ (100 MHz, $CDCl_3$): δ 48.1 (q, J=4.1 Hz), 50.9, 121.9 (q, J=275.6 Hz), 123.1, 124.0 (q, J=272.2 Hz), 125.9 (q, J=3.7 Hz), 127.3, 131.6 (q, J=32.5 Hz), 132.1, 135.5, 140.6, 145.6 (q, J=34.6 Hz), 154.3 ppm; IR $v_{max}$: 2928, 1319, 1105, 1068 $cm^{-1}$; GC-MS m/z: 334 $(M+H)^+$; $[\alpha]_D^{20}$: +23.5° (c 0.1; MeOH); Chiral HPLC 98% ee, Chiralpak IB column, heptane/i-PrOH, 99:1, flow 1 mL/min, tr(R)=9.5 min, tr(S)=10.4 min.

(R)-3-(Oxiran-2-yl)-2-(trifluoromethyl)-6-(4-(trifluoromethyl)phenyl)pyridine (31b)

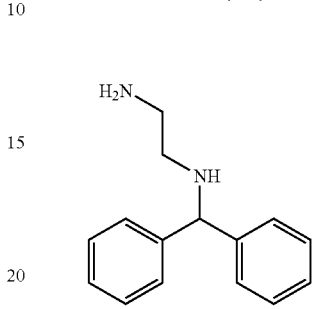

The compound 31b was obtained from 44b (884 mg, 2.52 mmol) according to the same procedure as 31a to afford 653 mg of 31b as a white solid. Yield: 77%; The NMR ($^1H$ and $^{13}C$), IR spectra, MS and m.p. were identical to those of 31a; $[\alpha]_D^{20}$: −20.8° (c 0.1; MeOH); Chiral HPLC 98% ee, Chiralpak IB column, heptane/i-PrOH, 99:1, flow 1 mL/min, tr(R)=9.5 min, tr(S)=10.4 min.

3.2.8. Preparation of Amines

N-benzhydrylethane-1,2-diamine (19)

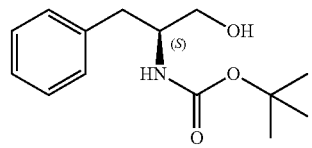

To a solution of 0.88 mL (4.90 mmol, 1 eq.) of chlorodiphenylmethane in 50 mL of acetonitrile were added 1.64 mL (24.5 mmol, 5 eq.) of ethylenediamine, 1.02 mL (7.40 mmol, 1.5 eq.) of triethylamine and 8 mg (0.05 mmol, 0.01 eq.) of KI. The mixture was heated at reflux for 20 h before being concentrated in vacuo. The residue was directly purified by flash chromatography (AcOEt/MeOH/$NH_4OH$ 8:1:1) to afford 1.00 g of 19 as a colorless oil. Yield: 90%; NMR $^1H$ (400 MHz, $CDCl_3$): δ 1.80-1.86 (m, 3H), 2.63-2.67 (m, 2H), 2.80-2.83 (m, 2H), 4.82 (s, 1H), 7.21 (t, J=7.3 Hz, 2H), 7.28 (t, J=7.3 Hz, 4H), 7.39 (d, J=7.3 Hz) ppm; NMR $^{13}C$ (100 MHz, $CDCl_3$): δ 41.9, 50.6, 67.4, 127.0, 127.2, 128.4, 144.1 ppm; IR $v_{max}$: 2910, 1488, 1450 $cm^{-1}$; MS $(ESI^+)$ m/z: 227 $(M+H)^+$.

(S)-1-Methoxy-3-phenylpropan-2-amine (23)

(S)-Tert-butyl-(1-hydroxy-3-phenylpropan-2-yl)carbamate (21)

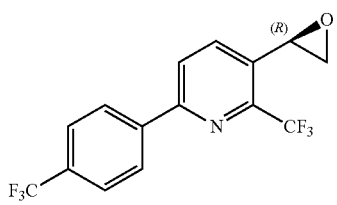

To a solution, under argon and at 0° C., of 2.00 g (13.2 mmol, 1 eq.) of (S)-2-amino-3-phenylpropan-1-ol in 40 mL of anhydrous $CH_2Cl_2$ were added 3.63 mL (3.48 g, 15.8 mmol, 1.2 eq.) of di-tert-butyl dicarbonate. The solution was stirred at 25° C. for 12 h, washed with 50 mL of a 10% aqueous acetic acid solution and with 40 mL of brine. The organic layer was dried over $Na_2SO_4$, filtered and concentrated in vacuo. The residue was purified by flash chromatography (cyclohexane/AcOEt 2:1) to afford 3.15 g of 21 as a white solid were obtained. Yield: 95%; NMR $^1H$ (400 MHz, $CDCl_3$): δ 1.41 (9H, s), 2.78-2.90 (m, 2H), 3.61 [AB(ABX), J=11.0 Hz, J=5.3 Hz, J=3.8 Hz, 2H], 3.87 ($s_{br}$, 1H), 4.77 ($s_{br}$, 1H), 7.20-7.26 (m, 3H), 7.28-7.32 (m, 2H) ppm; NMR $^{13}C$ (100 MHz, $CDCl_3$): δ 28.3, 37.5, 53.8, 64.3, 79.7, 126.5, 128.5, 129.3, 137.8, 156.1 ppm; IR $v_{max}$: 3346, 2934, 1681, 1447, 1314, 1259 cm$^{-1}$; MS (ESI+) m/z: 252 (M+H)$^+$; [α]$_D^{20}$: −15.9° (c 0.1; AcOEt).

(S)-Tert-butyl (1-methoxy-3-phenylpropan-2-yl) carbamate (22)

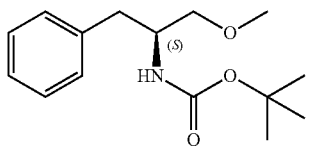

To a solution, under argon and in the dark, of 1.67 g (6.61 mmol, 1 eq.) of 21 in 32 mL of anhydrous CH$_2$Cl$_2$ were added 7.30 g (33.0 mmol, 5 eq.) of silver oxide and 3.90 mL (63.0 mmol, 10 eq.) of iodomethane. The suspension was stirred at 25° C. and in the dark for 6 days. The mixture was filtered through a celite pad. The filtrate was concentrated in vacuo before to purify the residue by flash chromatography (cyclohexane/AcOEt 5:1) to afford 465 mg of 22 as a yellow oil. Yield: 88%; NMR $^1$H (400 MHz, CDCl$_3$): δ 1.42 (s, 9H), 2.85 [AB(ABX), J=13.3 Hz, J=8.2 Hz, J=6.6 Hz, 2H], 3.25-3.34 (m, 2H), 3.34 (s, 3H), 4.82 (s$_{br}$, 1H), 7.20-7.22 (m, 3H), 7.26-7.31 (m, 2H) ppm; NMR $^{13}$C (100 MHz, CDCl$_3$): δ 28.3, 37.7, 51.4, 58.8, 72.4, 79.2, 126.2, 128.3, 129.3, 138.1, 155.3 ppm; IR $v_{max}$: 3350, 2928, 1682, 1451, 1324, 1252 cm$^{-1}$; MS (ESI$^+$) m/z: 266 (M+H)$^+$; [α]$_D^{20}$: −19.6° (c 0.1; AcOEt).

(S)-1-Methoxy-3-phenylpropan-2-amine (23)

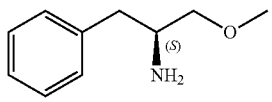

To a solution, under argon, of 378 mg (1.42 mmol, 1 eq.) of 22 in 6 mL of anhydrous CH$_2$Cl$_2$ were added 4 mL of 40% TFA solution in CH$_2$Cl$_2$. The solution was stirred at 25° C. for 12 h. An aqueous solution of NaOH (1 M) was added to pH 14. The aqueous layer was extracted with CH$_2$Cl$_2$. The organic layer was dried over Na$_2$SO$_4$, filtered and concentrated in vacuo. The residue was purified by flash chromatography (AcOEt/MeOH/NH$_4$OH 8:1:1) to afford 214 mg of 23 as a yellow oil. Yield: 91%; NMR $^1$H (400 MHz, CD$_3$OD): δ2.69 [AB(ABX), J=13.5 Hz, J=7.3 Hz, J=6.4 Hz, 2H], 3.12-3.20 (m, 1H), 3.19-3.31 (m, 2H), 3.34 (s, 3H), 7.17-7.26 (m, 3H), 7.28-7.34 (m, 2H) ppm; NMR $^{13}$C (100 MHz, CD$_3$OD): δ 40.7, 53.5, 59.2, 76.9, 127.6, 129.6, 130.4, 139.8 ppm; IR $v_{max}$: 3016, 1591, 1453, 1111, 915, 828, 744, 699 cm$^{-1}$; MS (ESI$^+$) m/z: 166 (M+H)$^+$; [α]$_D^{20}$: −6.3° (c 0.1; AcOEt).

(S)-2-((2-Aminoethyl)amino)-1-(2-(trifluoromethyl)-6-(4-(trifluoromethyl)phenyl)pyridin-4-yl)ethanol (24a)

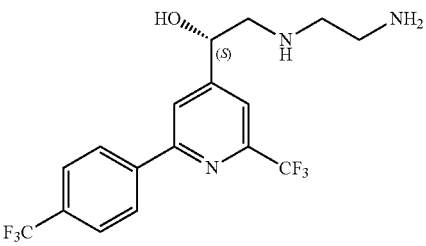

The compound 24a was obtained from 2a (100 mg, 0.30 mmol, 1 eq.) and ethane-1,2-diamine (0.06 mL, 0.90 mmol, 3 eq.) according to the general procedure for aminopyridinemethanols (APMs) preparation. The residue was purified by flash chromatography (AcOEt/MeOH/NH$_4$OH 8:1:1) to afford 118 mg of 24a as a colorless oil. Yield: quant.; NMR $^1$H (400 MHz, CD$_3$OD): δ 2.72-3.07 (m, 6H), 4.99 (dd, J=8.2, J=3.5 Hz, 1H), 7.81 (d, J=8.2 Hz, 2H), 7.85 (s, 1H), 8.22 (s, 1H), 8.31 (d, J=8.1 Hz, 2H) ppm; NMR $^{13}$C (100 MHz, CD$_3$OD): δ 40.9, 57.2, 72.2, 118.3 (q, J=2.7 Hz), 122.1, 125.6 (q, J=271.4 Hz), 125.9 (q, J=273.9 Hz), 126.9 (q, J=3.7 Hz), 128.8, 132.5 (q, J=33.8 Hz), 142.7, 149.3 (q, J=34.4 Hz), 157.4, 158.1 ppm; IR $v_{max}$: 2922, 2853, 1322, 1119 cm$^{-1}$; HRMS calcd. for C$_{17}$H$_{18}$F$_6$N$_3$O (M+H)$^+$ 394.1354, found 394.1336; [α]$_D^{20}$: +24.4° (c 0.1; MeOH).

(R)-2-((2-Aminoethyl)amino)-1-(2-(trifluoromethyl)-6-(4-(trifluoromethyl)phenyl)pyridin-4-yl) ethanol (24b)

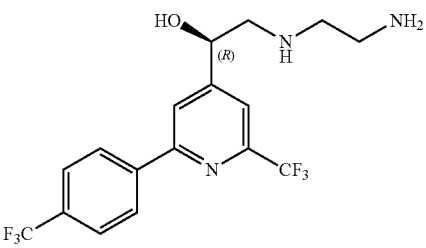

The compound 24b was obtained from 2b (80.0 mg, 0.24 mmol, 1 eq.) and ethane-1,2-diamine (0.06 mL, 0.90 mmol, 3 eq.) according to the general procedure for aminopyridinemethanols (APMs) preparation. The residue was purified by flash chromatography (AcOEt/MeOH/NH$_4$OH 8:1:1) to afford 85.0 mg of 24b as a colorless oil. Yield: 90%; The NMR ($^1$H and $^{13}$C), IR spectra and HRMS were identical to those of 24a. [α]$_D^{20}$: −24.2° (c 0.1; MeOH).

3-(4-benzhydrylpiperazin-1-yl)propran-1-amine (29)

Tert-butyl(3-bromopropyl)carbamate (26)

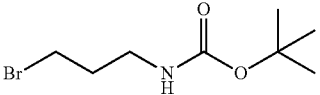

To a solution, under argon and at 0° C., of 5.01 g (36.3 mmol, 1 eq.) of 3-bromopropan-1-amine in 100 mL of anhydrous MeOH were added, dropwise, 11.8 g (54.1 mmol, 1.5 eq.) of di-tert-butyl dicarbonate and 7.60 mL (54.1 mmol, 1.5 eq.) of NEt$_3$. The solution was stirred at 25° C. for 15 h before being concentrated in vacuo. The residue was extracted with AcOEt. The organic layers were dried over Na$_2$SO$_4$, filtered and concentrated in vacuo. The residue was purified by flash chromatography (cyclohexane/AcOEt 5:0.5) to afford 6.40 g of 26 as a colorless oil. Yield: 74%; NMR $^1$H (400 MHz, CDCl$_3$): δ 1.44 (s, 9H), 1.93-2.12 (m, 2H), 3.21-3.34 (m, 2H), 3.37-3.49 (m, 2H), 4.65 (s$_{br}$, 1H) ppm; NMR $^{13}$C (100 MHz, CDCl$_3$): δ 28.4, 30.7, 32.7, 39.0, 79.2, 155.9 ppm; IR $v_{max}$: 3345, 2974, 1689, 1516, 1365, 1251, 1164, 1070, 860, 776 cm$^{-1}$; MS (ESI+) m/z: 239 (M+H)$^+$.

Tert-butyl(3-(4-benzhydrylpiperazin-1-yl)propyl) carbamate (28)

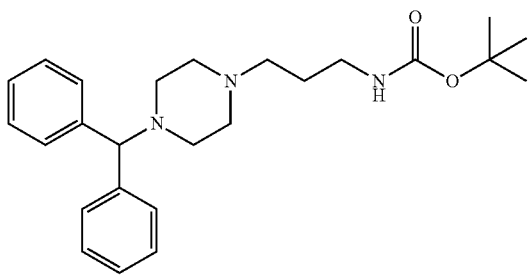 [SMILES: CC(C)(C)OC(=O)NCCCN1CCN(C(c2ccccc2)c2ccccc2)CC1]

To a solution, under argon, of 2.00 g (7.93 mmol, 1 eq.) of 1-benzhydrylpiperazine in 50 mL of anhydrous CH$_3$CN were added 3.80 g (16.0 mmol, 3 eq.) of 26, 2.20 mL (15.8 mmol, 2 eq.) of NEt$_3$ and 13 mg (0.08 mmol, 0.01 eq.) of KI. The mixture was heated at reflux for 15 h before being treated with 100 mL of water and extracted with AcOEt. The organic layers were dried over Na$_2$SO$_4$, filtered and concentrated in vacuo. The residue was purified by flash chromatography (Cyclohexane/AcOEt 4:1) to afford 2.37 g of 28 as a yellow solid. Yield: 73%; NMR $^1$H (400 MHz, CD$_3$OD): δ 1.41 (s, 9H), 1.55-1.73 (m, 2H), 2.32-2.62 (m, 10H), 3.11-3.25 (m, 2H), 4.21 (s, 1H), 7.12-7.18 (m, 2H), 7.21-7.28 (m, 4H), 7.38-7.43 (m, 4H) ppm; NMR $^{13}$C (100 MHz, CD$_3$OD): δ26.4, 28.4, 39.9, 51.9, 53.3, 56.7, 76.2, 126.8, 127.8, 128.4, 142.6, 156.0; IR $v_{max}$: 3290, 2810, 1696, 1524, 1137, 1003 cm$^{-1}$; MS(ESI$^+$) m/z: 410 (M+H)$^+$.

3-(4-benzhydrylpiperazin-1-yl)propan-1-amine (29)

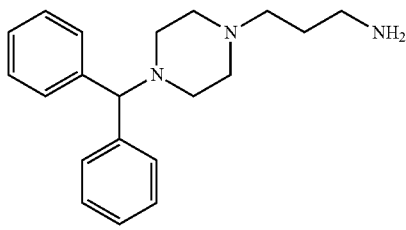 [SMILES: NCCCN1CCN(C(c2ccccc2)c2ccccc2)CC1]

To a solution of 2.65 g (6.47 mmol, 1 eq.) of 28 in 25 mL of anhydrous CH$_2$Cl$_2$ were added 10 mL of TFA. The mixture was stirred at 25° C. for 15 h before being treated with 100 mL of an aqueous solution of NaOH (1 M) and extracted with CH$_2$Cl$_2$. The organic layers were dried over Na$_2$SO$_4$, filtered and concentrated in vacuo. The residue was purified by flash chromatography (AcOEt/MeOH/NH$_4$OH 8:1:1) to afford 2.00 g of 29 as a yellow oil. Yield: quant.; NMR $^1$H (400 MHz, CD$_3$OD): δ 1.64-1.75 (m, 2H), 2.30-2.65 (m, 8H), 2.70-2.77 (m, 2H), 4.26 (s, 1H), 7.14-7.22 (m, 2H), 7.23-7.32 (m, 4H), 7.40-7.48 (m, 4H) ppm; NMR $^{13}$C (100 MHz, CDCl$_3$): δ 29.4, 41.3, 52.9, 54.5, 57.4, 77.5, 128.0, 128.9, 129.5, 144.0 ppm; IR $v_{max}$: 3160, 2943, 2798, 1649, 1297, 1140 cm$^{-1}$; MS (ESI$^+$) m/z: 310 (M+H)$^+$.

(S)-2-((2-aminoethyl)amino)-1-(2-(trifluoromethyl)-6-(4-(trifluoromethyl)phenyl) pyridin-3-yl)ethanol (45a)

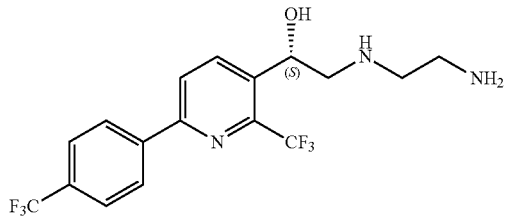

The compound 45a was obtained from 31a (100 mg, 0.30 mmol, 1 eq.) and ethane-1,2-diamine (90 mg, 0.10 mL, 1.50 mmol, 5 eq.) according to the general procedure for aminopyridinemethanols (APMs) preparation. The residue was purified by flash chromatography (AcOEt/MeOH/NH$_4$OH 8:1:1) to afford 107 mg of 45a as a colorless oil. Yield: 91% NMR $^1$H (400 MHz, CD$_3$OD): δ2.67-2.93 (m, 6H), 5.20-5.32 (m, 1H), 7.80 (d, J=8.3 Hz, 2H), 8.25 (d, J=8.3 Hz, 1H), 8.32 (d, J=8.3 Hz, 2H), 8.37 (d, J=8.3 Hz, 1H) ppm; NMR $^{13}$C (100 MHz, CD$_3$OD): δ 41.7, 51.4, 57.7, 67.6, 123.7 (q, J=275.1 Hz), 124.8, 125.7 (q, J=271.3 Hz), 126.9 (q, J=3.9 Hz), 128.6, 132.5 (q, J=32.4 Hz), 139.4, 139.7, 142.4, 144.8 (q, J=33.8 Hz), 155.1 ppm; IR $v_{max}$: 3185, 2921, 1322, 1110 cm$^{-1}$; HRMS calcd. for C$_{17}$H$_{15}$F$_6$N$_3$O (M+H)$^+$ 394.1354, found 394.1360; $[α]_D^2$: +22.4° (c 0.1; MeOH).

(R)-2-((2-aminoethyl)amino)-1-(2-(trifluoromethyl-6-(4-(trifluoromethyl)phenyl)pyridin-3-yl)ethanol (45b)

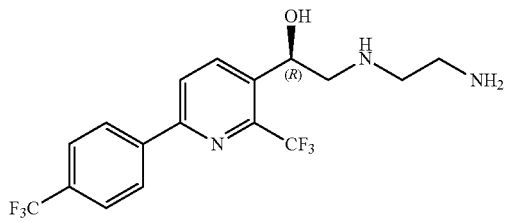

The compound 45b was obtained from 31b (80.0 mg, 0.24 mmol, 1 eq.) and ethane-1,2-diamine (72.0 mg, 0.08 mL, 1.20 mmol, 5 eq.) according to the general procedure for aminopyridinemethanols (APMs) preparation. The residue was purified by flash chromatography (AcOEt/MeOH/NH$_4$OH 8:1:1) to afford 81.0 mg of 45b as a colorless oil.

Yield: 86%; The NMR (¹H and ¹³C), IR spectra and HRMS were identical to those of 45a; $[\alpha]_D^{20}$: −25.7° (c 0.1; MeOH).

(S)-1-(cyclopropylmethoxy)-3-phenylpropan-2-amine (A)

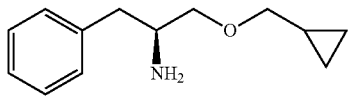 [SMILES: N[C@H](COCC1CC1)Cc1ccccc1]

To a solution, under argon, of 4.00 g (15.92 mmol, 1 eq.) of 21 in 40 mL of anhydrous DMF at 0° C. were added 0.955 g (23.87 mmol, 1.5 eq.) of sodium hydride 60 wt % and 5.80 mL (31.8 mmol, 2.0 eq.) of iodo methylcyclopropane. The suspension was then stirred at 25° C. for 4 hours. Another 0.32 g (7.96 mmol, 0.5 eq.) of sodium hydride 60 wt % were added and the suspension was stirred for 2 hours. The mixture was treated with a saturated solution of ammonium chloride and extracted with dichloromethane. The organic layer was dried over $Na_2SO_4$, filtered and concentrated in vacuo. The residue was filtered on silica gel (cyclohexane/AcOEt 9:1) to afford 5.13 g of a yellow oil. The oil was readily dissolved in dichloromethane (75 mL) and treated with trifluoroacetic acid (13 mL). The mixture was stirred at 25° C. for 16 hours. Aqueous sodium hydroxide (1M) was added carefully until neutral pH was reached. The organic layer was dried over $Na_2SO_4$, filtered and concentrated in vacuo. The residue was purified by flash chromatography (AcOEt+1% of $NH_{3(aq)}$ to AcOEt/MeOH 98/2+1% of $NH_{3(aq)}$) to afford 1.3 g of A as a yellow oil. Yield 40%. NMR ¹H (400 MHz; CDCl₃) $\delta_H$ 7.32-7.28 (2H, m), 7.23-7.20 (3H, m), 3.45 (1H, m), 3.31-3.25 (4H, m), 2.80 (1H, dd, J=13.4, 4.8 Hz), 2.59 (1H, dd, J=13.4, 7.6 Hz), 1.72 (2H, s), 2.80 (1H, dd, J=13.4, 4.8 Hz), 1.06 (1H, m), 0.53 (2H, m), 0.20 (2H, m). NMR ¹³C (100 MHz; CDCl₃) $\delta_C$ 139.0, 128.4, 128.6, 126.5, 76.1, 75.1, 52.6, 40.8, 10.7, 3.16, 3.11. IR $\nu_{max}$ 3081, 3024, 3006, 2923, 2858, 1092, 1024, 830, 743, 701 cm⁻¹. MS (ESI+): calcd for $C_{13}H_{20}NO$ [(M+H)⁺]: 206.2; Found: 206.2.

N¹-(di(pyridin-2-yl)methyl)ethane-1,2-diamine (B)

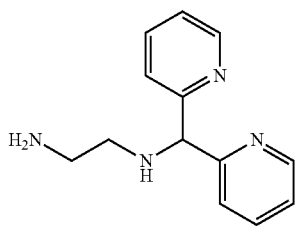 [SMILES: NCCNC(c1ccccn1)c1ccccn1]

To a solution of 1.0 g (5.43 mmol, 1 eq.) of bis(2-pyridyl)ketone and 2.0 mL (29.86 mmol, 5.5 eq.) of ethylenediamine in 100 mL of anhydrous MeOH were added 0.15 mL of acetic acid. The mixture was then stirred under reflux for 20 hours. Half of the reaction mixture was transferred in a new flask and cooled to 0° C. Then, 1.0 g (13.6 mmol, 5.0 eq.) of sodium borohydride was added and the suspension was stirred for 5 days at room temperature. The mixture was hydrolysed with water and extracted with dichloromethane. The organic layer was dried over $Na_2SO_4$, filtered and concentrated in vacuo. The residue was purified by flash chromatography (DCM/MeOH/$NH_{3(aq)}$ 96/2/2 to 90/5/5) to afford 600 mg of B as a yellow oil. Yield 97%. NMR ¹H (400 MHz; CDCl₃) $\delta_H$ 8.55 (2H, m), 7.61 (2H, m), 7.40 (2H, m), 7.13 (2H, m), 5.06 (1H, s), 2.83 (2H, t, J=5.9 Hz), 2.67 (2H, t, J=5.9 Hz). NMR ¹³C (100 MHz; CDCl₃) $\delta_C$ 161.7, 149.3, 136.8, 122.4, 122.3, 69.5, 50.8, 42.2. IR $\nu_{max}$ 3318, 3185, 3056, 2926, 2847, 1666, 1587, 1466, 1429, 1387, 754, 610 cm⁻¹. MS (ESI⁺): calcd for $C_{13}H_{19}N_4$ [(M+H)⁺]: 229.1; Found: 229.1.

Tert-butyl(6-fluorohexyl)carbamate (E)

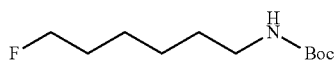

To a solution of 1.0 g (4.6 mmol, 1 eq.) of of tert-butyl (6-hydroxyhexyl)carbamate and 1.15 mL (8.3 mmol, 1.8 eq.) of triethylamine in 18 mL of anhydrous DCM were added 0.53 mL of methanesulfonyl chloride (6.9 mmol, 1.5 eq.). The mixture was stirred at room temperature for 2 hours. The mixture was washed with water and extracted with dichloromethane. The organic layer was dried over $Na_2SO_4$, filtered and concentrated in vacuo. The residue was dissolved in t-BuOH (48 mL) and 3.5 g (23.0 mmol, 5.0 eq) of cesium fluoride were added. The suspension was refluxed for 16 hours. After cooling to room temperature, diethylether was added and the suspension filtered. The filtrate was concentrated in vacuo. The residue was purified by flash chromatography (DCM) to afford 776 mg of E as a colorless oil. Yield 77%. IR $\nu_{max}$ 3354, 2970, 2934, 2866, 1691, 1516, 1364, 1250, 1168, 1045, 984 cm¹. NMR ¹H (400 MHz; CDCl₃) $\delta_H$ 4.43 (2H, dt, J=47.3, 6.1 Hz), 3.11 (2H, q, J=6.7 Hz), 1.68 (2H, ddt, J=25.2, 8.1, 6.2 Hz), 1.53-1.33 (6H, m), 1.44 (9H, s). NMR ¹³C (100 MHz; CDCl₃) $\delta_C$ 156.1, 84.2 (d, J=164 Hz), 79.2, 40.6, 30.5 (d, J=20 Hz), 30.1, 28.6, 26.6, 25.1 (d, J=5.4 Hz). MS (ESI⁺): calcd for $C_{22}H_{45}F_2N_2O_4$ [(2M+H)⁺]: 439.3; Found: 439.3.

6-fluorohexan-1-amine hydrochloride (C)

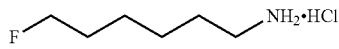

To a solution of 776 mg (3.54 mmol, 1 eq.) of tert-butyl (6-fluorohexyl)carbamate E in 25 mL of anhydrous MeOH were added 7.0 mL of hydrochloric acid in 1,4-dioxane (4M). The mixture was then stirred at room temperature for 4 hours. The solution was concentrated in vacuo. The residue was washed with diethylether and dried in vacuo to afford 550 mg of C as a white solid (lightly hygroscopic). Yield 99%. NMR ¹H (400 MHz; CD₃OD) $\delta_H$ 4.43 (2H, dt, J=47.5, 6.0 Hz), 2.93 (2H, m), 1.78-1.64 (4H, m) 1.52-1.42 (4H, m). NMR ¹³C (100 MHz; CD₃OD) $\delta_C$ 84.7 (d, J=164 Hz), 40.7, 31.3 (d, J=20 Hz), 28.5, 27.1, 26.0 (d, J=5.1 Hz). IR $\nu_{max}$ 2970, 2926, 2858, 1598, 1512, 1393, 1064, 1024, 962, 895, 679, 629 cm¹. MS (ESI⁺): calcd for $C_6H_{15}FN$ [(M+H)⁺]: 120.1; Found: 120.2.

3.3. General Method for Preparation of Compounds 1 and 30 According to the Present Invention General Procedure for Aminopyridinemethanols (APMs) Preparation:

To a solution of epoxide in ethanol (0.05 M) was added the appropriate amine (2.5 to 6 eq.). The reaction mixture was heated at 130° C. using microwave irradiation (P=150 W) for 30 to 180 min. The solution was concentrated in vacuo. The residue was purified by flash chromatography.

Microwave reactor is a microwave Discover SP reactor purchased from CEM.

3.3.1. Compounds 1 of Formulae IIa and IIb (S)-2-(Pentylamino)-1-(2-(trifluoromethyl-6-(4-(trifluoromethyl)phenyl)pyridin-4-yl)ethanol (1a)

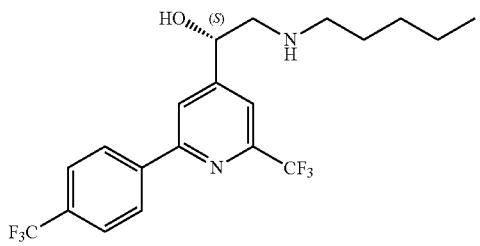

The compound 1a was obtained from 2a (50.0 mg, 0.15 mmol, 1 eq.) and n-pentylamine (0.10 mL, 0.90 mmol, 6 eq.) according to the general procedure for aminopyridinemethanols (APMs) preparation. The residue was purified by flash chromatography (DCM/MeOH 9:1) to afford 49 mg of 1a as a white solid. Yield: 78%; m.p. 112° C.; NMR $^1$H (400 MHz, CDCl$_3$): 50.76-0.99 (m, 3H), 1.18-1.42 (m, 4H), 1.42-1.54 (m, 2H), 2.60-2.81 (m, 3H), 3.07 (dd, J=12.2 Hz, J=3.1 Hz, 1H), 3.24-3.43 (s$_{br}$, 2H), 4.77-4.94 (m, 1H), 7.67 (s, 1H), 7.74 (d, J=8.2 Hz, 2H), 7.99 (s, 1H), 8.17 (d, J=8.2 Hz, 2H) ppm; NMR $^{13}$C (100 MHz, CDCl$_3$): δ 13.9, 22.5, 29.3, 29.6, 49.3, 56.2, 69.7, 116.6 (q, J=2.5 Hz), 120.0, 124.0 (q, J=272.2 Hz), 124.2 (q, J=274.5 Hz), 125.7 (q, J=3.7 Hz), 127.5, 131.5 (q, J=32.5 Hz), 141.1, 148.5 (q, J=34.6 Hz), 155.0, 156.4 ppm; IR ν$_{max}$: 2930, 1327, 1126 cm$^{-1}$; HRMS calcd. for $C_{20}H_{23}F_6N_2O$ (M+H)$^+$ 421.1715, found 421.1720; [α]$_D^{20}$: +23.7° (c 0.1; MeOH); Chiral HPLC 99% ee, Chiralpak IB column, heptane/i-PrOH/EDA, 99:1:0.1, flow 1 mL/min, tr(R)=11.9 min, tr(S)=14.3 min.

(R)-2-(Pentylamino)-1-(2-(trifluoromethyl)-6-(4-(trifluoromethyl)phenyl)pyridin-4-yl)ethanol (1b)

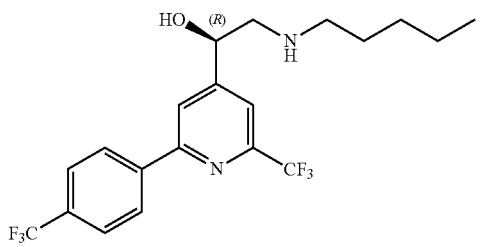

The compound 1b was obtained from 2b (35.0 mg, 0.11 mmol, 1 eq.) and n-pentylamine (0.08 mL, 0.66 mmol, 6 eq.) according to the general procedure for aminopyridinemethanols (APMs) preparation. The residue was purified by flash chromatography (DCM/MeOH 9:1) to afford 31 mg of 1b as a white solid. Yield: 67%; The NMR ($^1$H and $^{13}$C), IR spectra, HRMS and m.p. were identical to those of 1a; [α]$_D^{20}$: −27.9° (c 0.1; MeOH); Chiral HPLC 99% ee, Chiralpak IB column, heptane/i-PrOH/EDA, 99:1:0.1, flow 1 mL/min, tr(R)=11.9 min, tr(S)=14.3 min.

(S)-2-(Hexylamino)-1-(2-(trifluoromethyl)-6-(4-(trifluoromethyl)phenyl)pyridin-4-yl)ethanol (1c

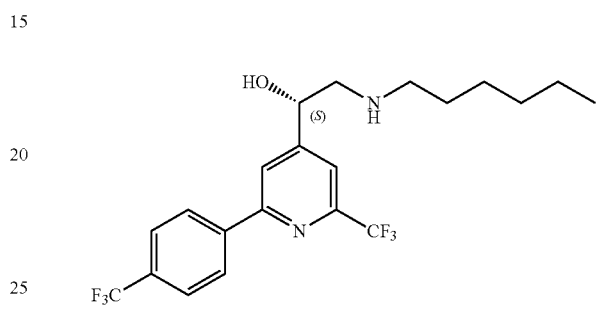

The compound 1c was obtained from 2a (40.0 mg, 0.12 mmol, 1 eq.) and n-hexylamine (0.05 mL, 0.36 mmol, 3 eq.) according to the general procedure for aminopyridinemethanols (APMs) preparation. The residue was purified by flash chromatography (DCM/MeOH 9:1) to afford 35 mg of 1c as a white solid. Yield: 67%; m.p. 84° C.; NMR $^1$H (400 MHz, CDCl$_3$): δ 0.86-0.89 (m, 3H), 1.21-1.37 (m, 6H), 1.50-1.59 (m, 2H), 2.63-2.83 (m, 3H), 3.08 (dd, J=12.4 Hz, J=3.3 Hz, 1H), 3.83 (s$_{br}$, 2H), 4.93 (dd, J=9.3 Hz, J=3.4 Hz, 1H), 7.68 (s, 1H), 7.72 (d, J=8.3 Hz, 2H), 8.00 (s, 1H), 8.17 (d, J=8.1 Hz, 2H) ppm; NMR $^{13}$C (100 MHz, CDCl$_3$): δ 13.9, 22.5, 26.7, 29.4, 31.6, 49.3, 56.0, 69.5, 116.5 (q, J=2.6 Hz), 120.0, 124.0 (q, J=272.2 Hz), 124.2 (q, J=274.6 Hz), 125.7 (q, J=3.8 Hz), 127.5, 131.6 (q, J=32.6 Hz), 141.0, 148.5 (q, J=34.6 Hz), 154.7, 156.4 ppm; IR ν$_{max}$: 2925, 1325, 1112 cm$^{-1}$; HRMS calcd. for $C_{21}H_{25}F_6N_2O$ (M+H)$^+$ 435.1871, found 435.1857; [α]$_D^{20}$: +30.8° (c 0.1; MeOH); Chiral HPLC 99% ee, Chiralpak IB column, heptane/i-PrOH/EDA, 99:1:0.1, flow 1 mL/min, tr(R)=9.7 min, tr(S)=10.8 min.

(R)-2-(Hexylamino)-1-(2-(trifluoromethyl)-6-(4-(trifluoromethyl)phenyl)pyridin-4-yl)ethanol (1d)

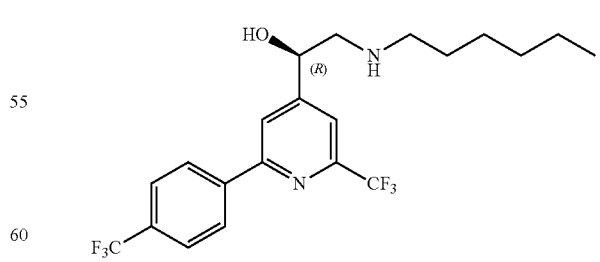

The compound 1d was obtained from 2b (50.0 mg, 0.15 mmol, 1 eq.) and n-hexylamine (0.06 mL, 0.45 mmol, 3 eq.) according to the general procedure for aminopyridinemethanols (APMs) preparation. The residue was purified by flash chromatography (DCM/MeOH 9:1) to afford 42 mg of 1d as a white solid. Yield: 65%; The NMR ($^1$H and $^{13}$C), IR spectra, HRMS and m.p. were identical to those of 1c; $[\alpha]_D^{20}$: −28.6° (c 0.1; MeOH); Chiral HPLC 98% ee, colonne Chiralpak IB, heptane/i-PrOH/EDA, 99:1:0.1, flow 1 mL/min, tr(R)=9.7 min, tr(S)=10.8 min.

(S)-2-(Heptylamino)-1-(2-(trifluoromethyl)-6-(4-(trifluoromethyl)phenyl)pyridin-4-yl)ethanol (1e)

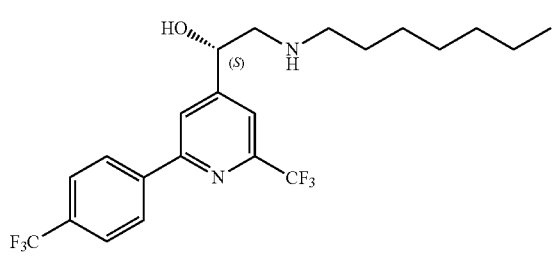

The compound 1e was obtained from 2a (50.0 mg, 0.15 mmol, 1 eq.) and n-heptylamine (0.13 mL, 0.90 mmol, 6 eq.) according to the general procedure for aminopyridinemethanols (APMs) preparation. The residue was purified by flash chromatography (DCM/MeOH 9:1) to afford 40 mg of 1e as a white solid. Yield: 60%; m.p. 76° C.; NMR $^1$H (400 MHz, CDCl$_3$): δ 0.78-0.97 (m, 3H), 1.06-1.43 (m, 8H), 1.45-1.66 (m, 2H), 2.62-2.70 (m, 2H), 2.89 [AB(ABX), J=12.2 Hz, J=8.6 Hz, J=2.7 Hz, 2H], 3.25-3.80 (s$_{br}$, 2H), 4.86 [X(ABX), J=8.6 Hz, J=2.7 Hz, 1H], 7.67 (s, 1H), 7.74 (d, J=7.8 Hz, 2H), 8.00 (s, 1H), 8.19 (d, J=7.8 Hz, 2H) ppm; NMR $^{13}$C (100 MHz, CDCl$_3$): δ 14.0, 22.6, 27.1, 29.1, 29.8, 31.7, 49.3, 56.1, 69.6, 116.6 (q, J=2.6 Hz), 120.0, 124.0 (q, J=272.2 Hz), 124.2 (q, J=274.6 Hz), 125.8 (q, J=3.8 Hz), 127.5, 131.2 (q, J=32.6 Hz), 141.1, 148.5 (q, J=34.7 Hz), 154.9, 156.4 ppm; IR $\sqrt{}_{max}$: 2928, 1324, 1114 cm$^{−1}$; HRMS calcd. for C$_{22}$H$_{27}$F$_6$N$_2$O (M+H)$^+$ 449.2028, found 449.2040; $[\alpha]_D^{20}$: +24.9° (c 0.1; MeOH); Chiral HPLC 99% ee, Chiralpak IB column, heptane/i-PrOH/EDA, 99:1:0.1, flow 1 mL/min, tr(R)=11.7 min, tr(S)=13.5 min.

(R)-2-(Heptylamino)-1-(2-(trifluoromethyl)-6-(4-(trifluoromethyl)phenyl)pyridin-4-yl)ethanol (1f)

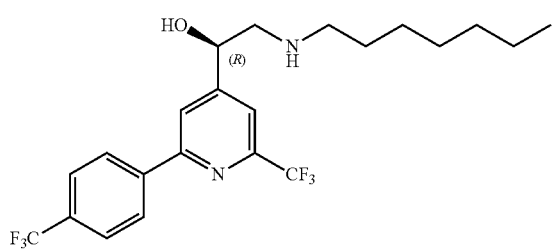

The compound 1f was obtained from 2b (31.0 mg, 0.09 mmol, 1 eq.) and n-heptylamine (0.08 mL, 0.54 mmol, 6 eq.) according to the general procedure for aminopyridinemethanols (APMs) preparation. The residue was purified by flash chromatography (DCM/MeOH 9:1) to afford 34 mg of 1f as a white solid. Yield: 85%; The NMR ($^1$H and $^{13}$C), IR spectra, HRMS and m.p. were identical to those of 1e; Chiral HPLC 99% ee, Chiralpak IB column, heptane/i-PrOH/EDA, 99:1:0.1, flow 1 mL/min, tr(R)=11.7 min, tr(S)=13.5 min; $[\alpha]_D^{20}$: −27.4° (c 0.1; MeOH).

(S)-2-((2-(Benzhydrylamino)ethyl)amino)-1-(2-(trifluoromethyl)-6-(4-(trifluoromethyl) phenyl)pyridin-4-yl)ethanol (1g)

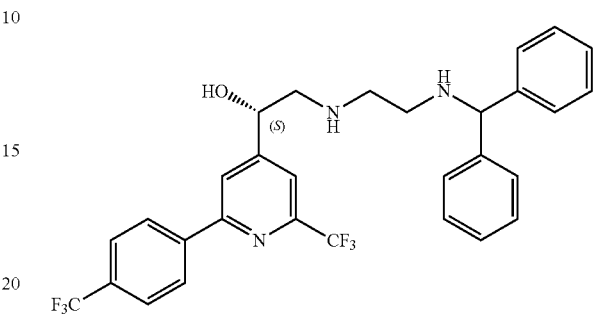

The compound 1g was obtained from 2a (50.0 mg, 0.15 mmol, 1 eq.) and N-benzhydrylethane-1,2-diamine 19 (204 mg, 0.90 mmol, 6 eq.) according to the general procedure for aminopyridinemethanols (APMs) preparation. The residue was purified by flash chromatography (AcOEt/MeOH/NH$_4$OH 8:1:1) to afford 55 mg of 1g as a yellow oil. Yield: 65%; NMR $^1$H (400 MHz, CDCl$_3$): δ 2.64-2.81 (m, 4H), 2.72 [AB(ABX), J=12.4 Hz, J=9.2 Hz, J=3.5 Hz, 2H], 2.93-3.20 (s$_{br}$, 3H), 4.72 (s, 1H), 4.76 [X(ABX), J=9.2 Hz, J=3.5 Hz, 1H], 7.09-7.15 (m, 2H), 7.15-7.24 (m, 4H), 7.24-7.34 (m, 4H), 7.55 (s, 1H), 7.63 (d, J=8.2 Hz), 7.88 (s, 1H), 8.08 (d, J=8.2 Hz, 2H) ppm; NMR $^{13}$C (100 MHz, CDCl$_3$): δ 48.0, 48.8, 56.0, 67.5, 70.1, 116.6 (q, J=2.7 Hz), 120.1, 121.3 (q, J=274.5 Hz), 124.0 (q, J=272.3 Hz), 125.7 (q, J=3.7 Hz), 127.2, 127.5, 128.6, 131.5 (q, J=32.5 Hz), 141.0, 143.5, 148.4 (q, J=34.6 Hz), 154.9, 156.3 ppm; IR $\sqrt{}_{max}$: 2921, 1323, 1121 cm$^{−1}$; HRMS calcd. for C$_{30}$H$_{27}$F$_6$N$_3$ONa$^+$ (M+Na)$^+$ 582.1956, found 582.1984; $[\alpha]_D^{20}$: +15.5° (c 0.1; MeOH); Chiral HPLC 99% ee, Chiralpak IB column, heptane/i-PrOH/EDA, 99:1 0.1; flow: 1 mL/min, tr(R)=40.1 min, tr(S)=37.8 min.

(R)-2-((2-Benzhydrylamino)ethylamino)-1-(2-(trifluoromethyl)-6-(4-(trifluoromethyl) phenyl)pyridin-4-yl)ethanol (1h)

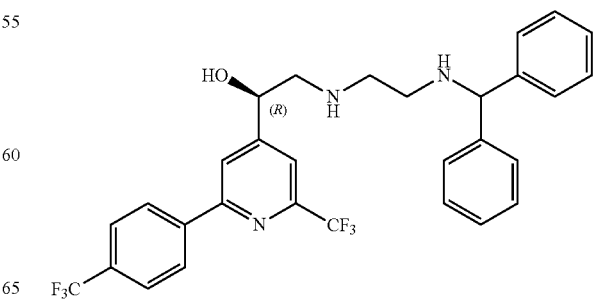

The compound 1b was obtained from 2b (30.0 mg, 0.09 mmol, 1 eq.) and N-benzhydrylethane-1,2-diamine 19 (122 mg, 0.54 mmol, 6 eq.) according to the general procedure for aminopyridinemethanols (APMs) preparation. The residue was purified by flash chromatography (AcOEt/MeOH/NH₄OH 8:1:1) to afford 40 mg of 1h as a yellow oil; Yield: 80%; The NMR ($^1$H and $^{13}$C), IR spectra, and HRMS were identical to those of 1g; $[\alpha]_D^{20}$: −12.6° (c 0.1; MeOH); Chiral HPLC 98% ee, Chiralpak IB column, heptane/i-PrOH/EDA, 99:1:0.1; flow: 1 mL/min, tr(R)=40.1 min, tr(S)=37.8 min.

(S)-2-(((S)-1-Methoxy-3-phenylpropan-2-yl)amino)-1-(2-(trifluoromethyl)-6-(4-(trifluoromethyl)phenyl) pyridin-4-yl)ethanol (1i)

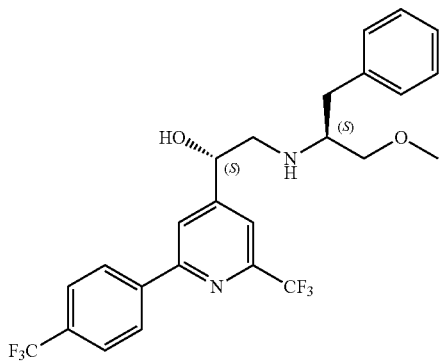

The compound 1i was obtained from 2a (30.0 mg, 0.09 mmol, 1 eq.) and (S)-1-methoxy-3-phenylpropan-2-amine 23 (74 mg, 0.45 mmol, 5 eq.) according to the general procedure for aminopyridinemethanols (APMs) preparation. The residue was purified by flash chromatography (DCM/MeOH 99:1) to afford 36 mg of 1i as a colorless oil. Yield: 80%; NMR $^1$H (400 MHz, CD₃OD): δ 2.68-2.75 (m, 2H), 2.88 [AB(ABX), J=12.4 Hz, J=8.1 Hz, J=3.9 Hz, 2H], 3.00-3.07 (m, 1H), 3.26-3.38 (m, 5H), 4.88 [X(ABX), J=8.1 Hz, J=3.9 Hz, 1H], 7.11-7.27 (m, 5H), 7.73 (s, 1H), 7.80 (d, J=8.3 Hz, 2H), 8.10 (s, 1H), 8.28 (d, J=8.2 Hz, 2H) ppm; NMR $^{13}$C (100 MHz, CD₃OD): δ38.9, 55.1, 59.2, 59.7, 72.0, 75.3, 118.2 (q, J=2.7 Hz), 122.0, 123.1 (q, J=273.7 Hz), 125.7 (q, J=271.3 Hz), 126.8 (q, J=3.8 Hz), 127.5, 128.8, 129.6, 130.2, 132.5 (q, J=32.4 Hz), 140.1, 142.7, 149.3 (q, J=34.4 Hz), 157.3, 158.1 ppm; IR $\sqrt{}_{max}$: 2899, 1323, 1122 cm⁻¹; HRMS calcd. for $C_{25}H_{25}F_6N_2O_2$ (M+H)⁺ 499.1820, found 499.1824; $[\alpha]_D^{20}$: +17.7° (c 0.1; MeOH); Chiral HPLC 99% ed, Chiralpak IA column, heptane/i-PrOH, 95:5; flow: 1 mL/min, tr(S,S)=21.4 min, tr(R,S)=26.1 min.

(R)-2-(((S)-1-Methoxy-3-phenylpropan-2-yl)amino)-1-(2-(trifluoromethyl)-6-(4-(trifluoromethyl)phenyl) pyridin-4-yl)ethanol (1j)

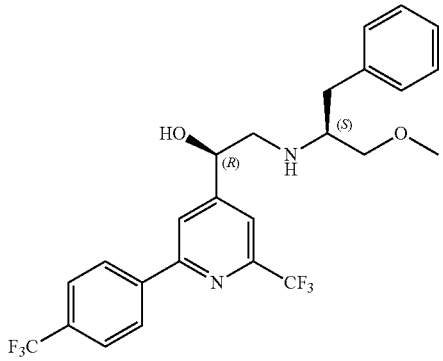

The compound 1j was obtained from 2b (30.0 mg, 0.09 mmol, 1 eq.) and (S)-1-methoxy-3-phenylpropan-2-amine 23 (74 mg, 0.45 mmol, 5 eq.) according to the general procedure for aminopyridinemethanols (APMs) preparation. The residue was purified by flash chromatography (DCM/MeOH 99:1) to afford 32 mg of 1j as a colorless oil. Yield: 71%; NMR $^1$H (400 MHz, CDCl₃): δ 2.65-2.82 (m, 2H), 2.83 [AB(ABX), J=12.7 Hz, J=8.9 Hz, J=3.5 Hz, 2H], 2.91-3.00 (m, 1H), 3.29 (s, 3H), 3.31 [AB(ABX), J=9.6 Hz, J=5.6 Hz, J=4.0 Hz, 2H], 4.67 [X(ABX), J=8.9 Hz, J=3.5 Hz, 1H], 7.09-7.15 (m, 2H), 7.16-7.18 (m, 1H), 7.21-7.28 (m, 2H), 7.53 (s, 1H), 7.65 (d, J=8.3 HZ, 2H), 7.86 (s, 1H), 8.09 (d, J=8.2 Hz, 2H) ppm; NMR $^{13}$C (100 MHz, CDCl₃): δ 38.4, 53.9, 59.07, 59.12, 70.2, 73.7, 116.6 (q, J=2.4 Hz), 120.1, 124.0 (q, J=272.6 Hz), 124.2 (q, J=274.5 Hz), 125.7 (q, J=3.8 Hz), 126.7, 127.5, 128.7, 129.2, 131.5 (q, J=32.5 Hz), 138.3, 141.1, 148.5 (q, J=34.5 Hz), 154.6, 156.3 ppm; IR $\sqrt{}_{max}$: 2899, 1323, 1122 cm⁻¹; HRMS calcd. for $C_{25}H_{25}F_6N_2O_2$ (M+H)⁺ 499.1820, found 499.1823; $[\alpha]_D^{20}$: −47.1° (c 0.1; MeOH); Chiral HPLC 98% de, Chiralpak IA column, heptane/i-PrOH, 95:5, flow: 1 mL/min, tr(S,S)= 21.6 min, tr(R,S)=25.5 min.

(S)-2-((2-Aminoethyl)aminomethylferrocenyl)-1-(2-(trifluoromethyl)-6-(4(trifluoromethyl) phenyl)pyridin-4-yl)ethanol (1k)

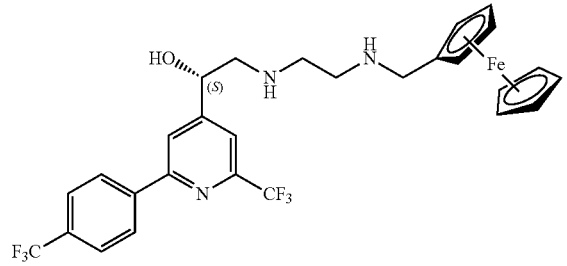

To a solution, under argon, of 67 mg (0.17 mmol, 1 eq.) of (S)-2-((2-aminoethyl)amino)-1-(2-(trifluoromethyl)-6-(4-(trifluoromethyl)phenyl)pyridin-4-yl)ethanol 24a in 3 mL of anhydrous methanol were added 36 mg (0.17 mmol, 1 eq.) of ferrocenecarboxaldehyde. The mixture was stirred for 3.5 h at 25° C. and then 10 mg (0.27 mmol, 1.6 eq.) of NaBH₄ were added. The solution was stirred at 25° C. for 15 h before being diluted with an excess of MeOH and concentrated in vacuo. The residue was purified directly by flash chromatography (DCM/MeOH 9:1 and 4:1) to afford 30 mg of 1k as a brown solid. Yield: 30%; m.p. 85° C.; NMR $^1$H (400 MHz, CDCl₃): δ 2.57-3.03 (m, 6H), 3.64 (s, 2H), 3.98-4.28 (m, 9H), 4.78-4.91 (m, 1H), 7.65 (s, 1H), 7.70 (d, J=8.2 Hz, 2H), 8.00 (s, 1H), 8.17 (d, J=8.2 Hz, 2H) ppm; NMR $^{13}$C (100 MHz, CDCl₃): δ 6.1, 46.3, 47.7, 56.1, 68.4, 68.5, 68.8, 68.91, 68.93, 69.7, 70.8, 116.7, 120.3, 121.4 (q, J=272.3 Hz), 124.2 (q, J=275.7 Hz), 125.7, 127.6, 131.5 (q, J=32.6 Hz), 141.0, 148.3 (q, J=34.9 Hz), 154.9, 156.2 ppm; IR $\sqrt{}_{max}$: 2919, 2849, 1654, 1610, 1323, 1120 cm$^{-1}$; HRMS calcd. for C₂₈H₂₈F₆FeN₃O (M+H)⁺ 592.1486, found 592.1469; $[\alpha]_D^{20}$: +16.0° (c 0.1; MeOH); Chiral HPLC 98% ee, Chiralpak IB column, heptane/i-PrOH/EDA, 99:1:0.1, flow: 1 mL/min, tr(R)=47.2 min, tr(S)=53.6 min.

(R)-2-((2-Aminoethyl)aminomethylferrocenyl)-1-(2-(trifluoromethyl)-6-(4(trifluoromethyl) phenyl)pyridin-4-yl)ethanol (1l)

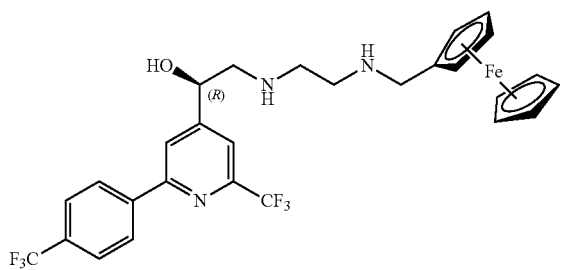

The compound 1l was obtained from 29 mg (0.07 mmol, 1 eq.) of 24b according to the same procedure as 1k to afford 7 mg of 1l as a brown solid; Yield: 17%; The NMR ($^1$H and $^{13}$C), IR spectra and HRMS were identical to those of 1k; $[\alpha]_D^{20}$: −15.8° (c 0.1; MeOH); Chiral HPLC 98% ee, Chiralpak IB column, heptane/i-PrOH/EDA, 99:1:0.1, flow: 1 mL/min, tr(R)=47.2 min, tr(S)=53.6 min.

(S)-2-((3-(4-benzhydrylpiperazin-1-yl)propyl)amino)-1-(2-(trifluoromethyl)-6-(4-(trifluoromethyl)phenyl)pyridin-4-yl)ethanol hydrochloride (1m.HCl)

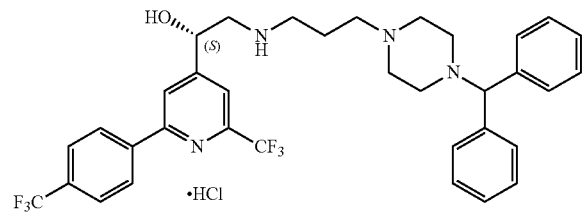

The compound 1m.HCl was obtained from 2a (50.0 mg, 0.15 mmol, 1 eq.) and 29 (232 mg, 0.75 mmol, 5 eq.) according to the general procedure for aminopyridinemethanols (APMs) preparation. The residue was purified by flash chromatography (AcOEt/MeOH/NH₄OH 8:0.5:0.5). The isolated compound was treated with 2 mL of HCl (4.0 M in dioxane). The mixture was concentrated in vacuo to afford 56 mg of 1m.HCl as a white solid. Yield: 55%; NMR $^1$H (400 MHz, CD₃OD): δ 2.25-2.38 (m, 2H), 3.22-3.35 (m, 3H), 3.41-3.46 (m, 2H), 3.51-3.60 (m, 5H), 3.76-3.89 (m, 4H), 5.30 (dd, J=10.1, 2.8 Hz, 1H), 5.42-5.55 (m, 1H), 7.37-7.41 (m, 2H), 7.41-7.50 (m, 4H), 7.81-7.83 (m, 4H), 7.83-7.84 (m, 2H), 7.94 (s, 1H), 8.36-8.38 (m, 2H), 8.38 (s, 1H) ppm; NMR $^{13}$C (100 MHz, CD₃OD): δ 21.8, 45.9, 49.8, 50.2, 54.0, 54.5, 68.8, 77.1, 118.2 (q, J=2.7 Hz), 122.2, 122.9 (q, J=271.4 Hz), 123.0 (q, J=273.7 Hz), 126.9 (q, J=3.8 Hz), 128.9, 129.6, 130.5, 130.7, 132.7 (q, J=32.4 Hz), 142.4, 149.8 (q, J=34.7 Hz), 155.3, 157.8 ppm; IR $\sqrt{}_{max}$: 3355, 1323, 1123 cm$^{-1}$; HRMS calcd. for C₃₅H₃₇N₄F₆O (M+H)⁺ 643.2872, found 643.2891; $[\alpha]_D^{20}$: +24.7° (c 0.1; MeOH); Chiral HPLC 98% ee, Chiralpak IB column, heptane/i-PrOH/EDA, 99:1:0.1, flow: 1 mL/min, tr(R)=39.1 min, tr(S)=59.0 min.

(R)-2-((3-(4-benzhydrylpiperazin-1-yl)propyl)amino)-1-(2-(trifluoromethyl)-6-(4-(trifluoromethyl)phenyl)pyridin-4-yl)ethanol hydrochloride (1n.HCl)

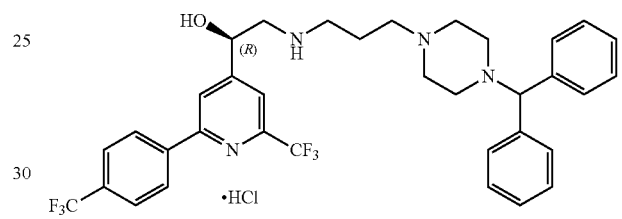

The compound 1n.HCl was obtained from 2b (24.0 mg, 0.07 mmol, 1 eq.) and 29 (111 mg, 0.36 mmol, 5 eq.) according to the general procedure for aminopyridinemethanols (APMs) preparation. The residue was purified by flash chromatography (AcOEt/MeOH/NH₄OH 8:0.5:0.5). The isolated compound was treated with 2 mL of HCl (4.0 M in dioxane). The mixture was concentrated in vacuo to afford 32 mg of 1n.HCl as a white solid. Yield: 65%; The NMR ($^1$H and $^{13}$C), IR spectra, HRMS and m.p. were identical to those of 1m.HCl; $[\alpha]_D^{20}$: −24.2° (c 0.1; MeOH); Chiral HPLC 96% ee, Chiralpak IB column, heptane/i-PrOH/EDA, 99:1:0.1, flow: 1 mL/min, tr(R)=39.1 min, tr(S)=59.0 min.

(S)-2-((4,4,4-trifluorobutyl)amino)-1-(2-(trifluoromethyl)-6-(4-(trifluoromethyl)phenyl)pyridin-4-yl)ethan-1-ol (1o)

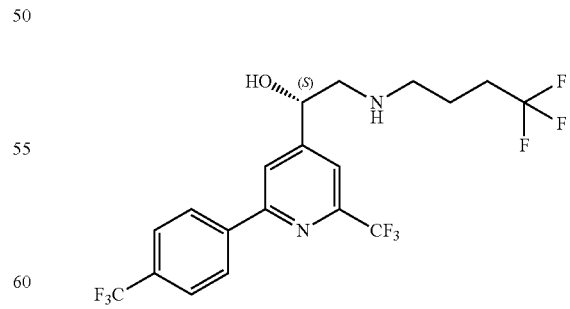

The compound 1o was obtained from 2a (175.0 mg, 0.53 mmol, 1 eq.) and 4,4,4-trifluorobutylamine (0.20 g, 1.58 mmol, 3 eq.) according to the general procedure for aminopyridinemethanols (APMs) preparation. The residue was purified by flash chromatography (DCM) to afford 187 mg of 1o as a white solid. Yield: 77%. m.p. 115.5-117.5° C. IR $v_{max}$ 3318, 3070, 2951, 2923, 2729, 1609, 1441, 1376, 1329, 1257, 1128, 1060, 1016, 841, 794 cm$^{-1}$. $^1$H NMR (400 MHz; CDCl$_3$) $\delta_H$ 8.19 (2H, d, J=8.1 Hz), 8.00 (1H, s), 7.74 (2H, d, J=8.2 Hz), 7.67 (1H, m), 4.89 (1H, dd, J=9.2, 3.6 Hz), 3.10 (1H, dd, J=12.3, 3.6 Hz), 2.83 (2H, m), 2.75 (1H, dd, J=12.4, 9.1 Hz), 2.19 (2H, m), 1.83 (2H, m). $^{13}$C NMR (100 MHz; CDCl$_3$) $\delta_C$ 156.7, 154.5, 149.0 (q, J=35 Hz), 141.1, 131.8 (q, J=33 Hz), 127.7, 127.1 (q, J=276 Hz), 126.0 (q, J=4 Hz), 121.6 (q, J=275 Hz), 121.4 (q, J=277 Hz), 120.2, 116.7, 70.0, 56.2, 48.1, 31.6 (q, J=29 Hz), 22.6 (q, J=2 Hz). HRMS (ESI$^+$): calcd for C$_{19}$H$_{17}$F$_9$N$_2$O [(M+H)$^+$]: 461.1275; Found: 461.1281. [α]$_D^{22}$: +20.5° (c 0.1; MeOH). Chiral HPLC 99% ee, Chiralpak IB column, heptane/i-PrOH/EDA, 99:01:0.1, flow 1 mL/min, tr(R)=36.7 min, tr(S)=42.5 min.

(R)-2-((4,4,4-trifluorobutyl)amino)-1-(2-(trifluoromethyl)-6-(4-(trifluoromethyl)phenyl)pyridin-4-yl)ethan-1-ol (1p)

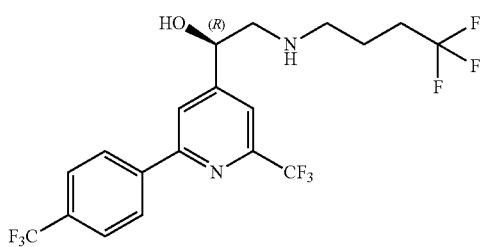

The compound 1p was obtained from 2b (175.0 mg, 0.53 mmol, 1 eq.) and 4,4,4-trifluorobutylamine (0.20 g, 1.58 mmol, 3 eq.) according to the general procedure for aminopyridinemethanols (APMs) preparation. The residue was purified by flash chromatography (DCM) to afford 145 mg of 1p as a white solid. Yield: 60%. The NMR ($^1$H and $^{13}$C), IR spectra, HRMS and m.p. were identical to those of 1o; [α]$_D^{22}$: -18.6° (c 0.1; MeOH). Chiral HPLC 98% ee, Chiralpak IB column, heptane/i-PrOH/EDA, 99/01/0.1, flow 1 mL/min, tr(R)=37.0 min, tr(S)=45.0 min.

(S)-2-((6-fluorohexyl)amino)-1-(2-(trifluoromethyl)-6-(4-(trifluoromethyl)phenyl)pyridine-4-yl)ethan-1-ol (1q)

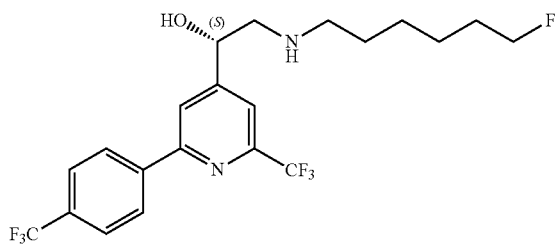

The compound 1q was obtained from 2a (51 mg, 0.153 mmol, 1 eq.) and amine C (60 mg, 0.38 mmol, 2.5 eq.) according to the general procedure for aminopyridinemethanols (APMs) preparation with the addition of N,N-diisopropylethylamine (67 µL, 0.38 mmol, 2.5 eq.). The crude mixture was washed with aqueous NaHCO$_3$ (1M) and extracted with dichloromethane. The organic layer was dried over Na$_2$SO$_4$, filtered and concentrated in vacuo. The residue was purified by flash chromatography (DCM to DCM/MeOH 98/2) to afford 32.7 mg of 1q as an amorphous white solid. Yield: 47%. IR $v_{max}$ 2933, 2863, 1325, 1200, 1164, 1114, 1064, 1012, 844 cm$^{-1}$. $^1$H NMR (400 MHz; CDCl$_3$) $\delta_H$ 8.19 (2H, d, J=8.0 Hz), 8.01 (1H, s), 7.74 (2H, d, J=8.3 Hz), 7.67 (1H, s), 4.90 (1H, dd, J=9.4, 3.6 Hz), 4.44 (2H, dt, J=47.3, 6.0 Hz), 3.10 (1H, dd, J=12.3, 3.6 Hz), 2.94 (2H, s), 2.68-2.80 (3H, m), 1.77-1.64 (2H, m), 1.62-1.55 (2H, m), 1.36-1.48 (4H, m). $^{13}$C NMR (100 MHz; CDCl$_3$) $\delta_C$ 156.6, 154.8, 149.2 (q, J=34.7 Hz), 141.2, 131.7 (q, J=32.6 Hz), 127.7, 125.9 (q, J=3.8 Hz), 124.2 (q, J=272.2 Hz), 121.6 (q, J=274.5 Hz), 120.2, 116.8 (q, J=2.8 Hz), 84.1 (d, J=164.3 Hz, C$_{24}$), 69.7, 56.2, 49.3, 30.4 (d, J=19.6 Hz), 29.6, 26.8, 25.2 (d, J=5.1 Hz). HRMS (ESI$^+$): calcd for C$_{21}$H$_{24}$F$_7$N$_2$O [(M+H)$^+$]: 453.1777; Found: 453.1776. [α]$_D^{22}$: +19.9° (c 0.1; MeOH). Chiral HPLC 98% ee, Chiralpak IB column, heptane/i-PrOH/EDA, 98/02/0.1, flow 1 mL/min, tr(R)=16.5 min, tr(S)=18.9 min.

(R)-2-((6-fluorohexyl)amino-1-(2-(trifluoromethyl)-6-(4-(trifluoromethyl)phenyl)pyridine-4-yl)ethan-1-ol (1r)

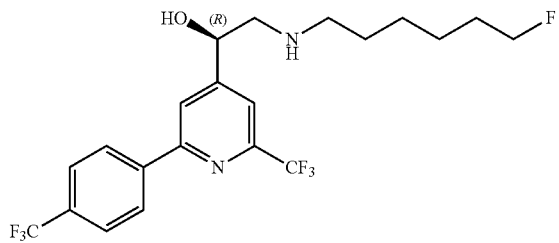

The compound 1r was obtained from 2b (59.0 mg, 0.177 mmol, 1 eq.) and amine C hydrochloride salt (69 mg, 0.44 mmol, 2.5 eq.) according to the general procedure for aminopyridinemethanols (APMs) preparation with the addition of N,N-diisopropylethylamine (77 µL, 0.44 mmol, 2.5 eq). The crude mixture was washed with aqueous NaHCO$_3$ (1M) and extracted with dichloromethane. The organic layer was dried over Na$_2$SO$_4$, filtered and concentrated in vacuo. The residue was purified by flash chromatography (DCM to DCM/MeOH 98/2) to afford 40.6 mg of 1r as an amorphous white solid. Yield: 51%. The NMR ($^1$H and $^{13}$C), IR spectra and HRMS were identical to those of 1q. [α]$_D^{22}$: -20.3° (c 0.1; MeOH). Chiral HPLC 98% ee, Chiralpak IB column, heptane/i-PrOH/EDA, 98/02/0.1, flow 1 mL/min, tr(R)=16.4 min, tr(S)=19.2 min.

(S)-2-((2-((di(pyridine-2-yl))methyl)amino)ethyl)amino)-1-(2-(trifluoromethyl)-6-(4-(trifluoromethyl)phenyl)-4-yl)ethan-1-ol trifluoroacetic acid salt (1s.TFA)

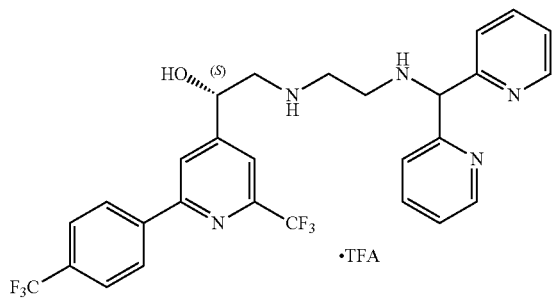

The compound 1s was obtained from 2a (175 mg, 0.53 mmol, 1 eq.) and N¹-(di(pyridin-2-yl)methyl)ethane-1,2-diamine B (300 mg, 1.31 mmol, 2.5 eq.) according to the general procedure for aminopyridinemethanols (APMs) preparation. The residue was purified by semi preparative HPLC (JUPILER 4u Proteo 90A 250×21.2 mm; MeCN/H$_2$O/TFA 30/70/0.1 to 80/20/0.1) to afford 132.4 mg of 1s.TFA as a yellow oil. Yield: 32%. IR $v_{max}$ 3364, 3088, 2862, 2503, 1666, 1325, 1178, 1124, 1064, 841, 801, 722 cm$^{-1}$. $^1$H NMR (400 MHz; CD$_3$OD) $\delta_H$ 8.67 (2H, d, J=4.9 Hz), 8.34 (2H, d, J=8.2 Hz), 8.30 (1H, s), 7.94-7.89 (2H, m), 7.91 (1H, s), 7.83 (2H, d, J=8.2 Hz), 7.58 (2H, d, J=7.8 Hz), 7.45 (2H, dd, J=7.5, 4.7 Hz), 5.89 (1H, s), 5.29 (1H, dd, J=10.0, 3.1 Hz), 3.63-3.58 (2H, m), 3.56 (1H, dd, J=12.6, 3.3 Hz), 3.48 (2H, t, J=6.5 Hz), 3.34-3.29 (1H, m). $^{13}$C NMR (100 MHz; CD$_3$OD) $\delta_C$ 162.5 (q, J=37.7 Hz), 157.8, 155.2, 154.9, 150.5, 149.7 (q, J=34.6 Hz), 142.4, 139.8, 132.7 (q, J=32.6 Hz), 128.8, 126.9 (q, J=4.0 Hz), 125.61, 125.57 (q, J=271.3 Hz), 124.8, 122.9 (q, J=273.8 Hz), 122.0, 118.1 (q, J=2.7 Hz), 117.8 (q, J=290.0 Hz), 68.9, 66.8, 54.3, 45.4, 44.5. HRMS (ESI$^+$): calcd for C$_{28}$H$_{26}$F$_6$N$_5$O [(M+H)+]: 562.2042; Found: 562.2043. [α]$_D^{22}$: +21.0° (c 0.1; MeOH). Chiral HPLC 98% ee, Chiralpak IG column, heptane/i-PrOH/EDA, 80/20/0.1, flow 1 mL/min, tr(R)=19.7 min, tr(S)=27.2 min.

(R)-2-((2-((di(pyridine-2-yl))methyl)amino)ethyl)aminol)-1-(2-(trifluoromethyl)-6-(4-(trifluoromethyl)phenyl)pyridin-4-yl)ethan-1-ol trifluoroacetic acid salt (1t.TFA)

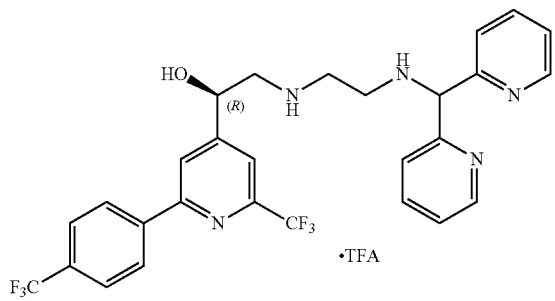

The compound it was obtained from 2b (175 mg, 0.53 mmol, 1 eq.) and N¹-(di(pyridin-2-yl)methyl)ethane-1,2-diamine B (300 mg, 1.31 mmol, 2.5 eq.) according to the general procedure for aminopyridinemethanols (APMs) preparation. The residue was purified by semi preparative HPLC (JUPILER 4u Proteo 90A 250×21.2 mm; MeCN/H$_2$O/TFA 30/70/0.1 to 80/20/0.1) to afford 243.5 mg of 1t.TFA as a yellow oil. Yield: 59%. The NMR ($^1$H and $^{13}$C), IR spectra and HRMS were identical to those of 1s.TFA; [α]$_D^{22}$: −20.0° (c 0.1; MeOH). Chiral HPLC 98% ee, Chiralpak IB column, heptane/i-PrOH/EDA, 80/20/0.1, flow 1 mL/min, tr(R)=18.9 min, tr(S)=27.3 min.

(S)-2-(((S)-1-(cyclopropylmethoxy)-3-phenylpropan-2-yl)amino)-1-(2-(trifluoromethyl)-6-(4-(trifluoromethyl)phenyl)pyridin-4-yl)ethan-1-ol (1u)

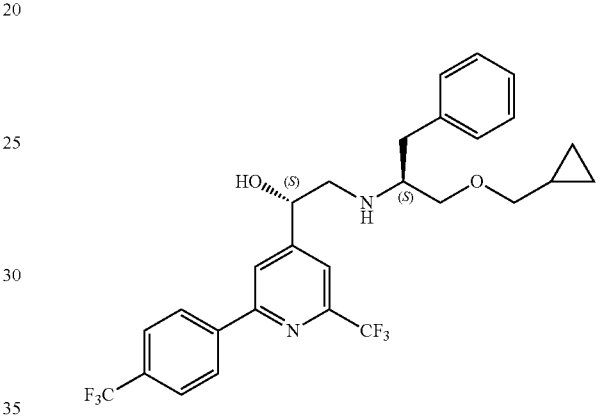

The compound 1u was obtained from 2a (175 mg, 0.53 mmol, 1 eq.) and (S)-1-(cyclopropylmethoxy)-3-phenylpropan-2-amine A (300 mg, 1.58 mmol, 3.0 eq.) according to the general procedure for aminopyridinemethanols (APMs) preparation. The residue was purified by flash chromatography (DCM/MeOH/NH$_{3(aq)}$ 98/1/1) to afford 184 mg of 1u as a white solid. Yield: 65%. m.p. 77.5-78.5° C. IR $v_{max}$ 3322, 3300, 3081, 2934, 2869, 1609, 1437, 1322, 1260, 1168, 1133, 1122, 1084, 1063, 1015, 850, 834, 739, 698 cm$^{-1}$. $^1$H NMR (400 MHz; CDCl$_3$) $\delta_H$ 8.18 (2H, d, J=8.1 Hz), 7.92 (1H, s), 7.74 (2H, d, J=8.2 Hz), 7.60 (1H, s), 7.31-7.27 (2H, m), 7.26-7.22 (1H, m), 7.21-7.17 (2H, m), 4.73 (1H, dd, J=8.9, 3.7 Hz), 3.47 (1H, dd, J=9.5, 4.0 Hz), 3.33 (1H, dd, J=9.5, 6.4 Hz), 3.34-3.25 (2H, m), 3.09 (1H, dd, J=12.6, 3.7 Hz), 3.05-3.00 (1H, m), 2.80-2.71 (2H, m), 2.59 (1H, dd, J=12.6, 9.0 Hz), 1.11-1.01 (1H, m), 0.57-0.53 (2H, m), 0.23-0.19 (2H, m). $^{13}$C NMR (100 MHz; CDCl$_3$) $\delta_C$ 156.5, 155.0, 148.6 (q, J=35 Hz), 141.3, 138.6, 131.7 (q, J=33 Hz), 129.4, 128.7, 127.7, 126.7, 125.9 (q, J=3.6 Hz), 124.2 (q, J=271 Hz), 121.7 (q, J=275 Hz), 120.2, 116.8 (q, J=2 Hz), 76.2, 72.2, 70.6, 59.0, 54.3, 38.8, 10.7, 3.20, 3.17. HRMS (ESI$^+$): calcd for C$_{28}$H$_{29}$F$_6$N$_2$O$_2$ [(M+H)$^+$]: 539.2133; Found: 539.2136. [α]$_D^{22}$: +26.0° (c 0.1; MeOH). Chiral HPLC 99% de, Chiralpak IA column, heptane/i-PrOH, 90/10, flow 1 mL/min, tr(S,S)=11.3 min, tr(R,S)=20.6 min.

(R)-2-(((S)-1-(cyclopropylmethoxy)-3-phenylpropan-2-yl)amino)-1-(2-(trifluoromethyl)-6-(4-(trifluoromethyl)phenyl)pyridin-4-yl)ethan-1-ol (1v)

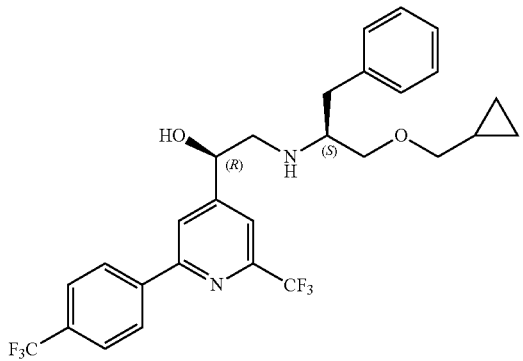

The compound 1v was obtained from 2b (175 mg, 0.53 mmol, 1 eq.) and (S)-1-(cyclopropylmethoxy)-3-phenylpropan-2-amine A (300 mg, 1.58 mmol, 3.0 eq.) according to the general procedure for aminopyridinemethanols (APMs) preparation. The residue was purified by flash chromatography (DCM/MeOH/NH$_{3(aq)}$ 98/1/1) to afford 135 mg of 1v as a white solid. Yield: 80%. m.p. 81.5-82.5° C. IR vu. 3303, 3085, 3027, 2926, 2866, 2818, 1609, 1441, 1322, 1260, 1168, 1120, 1085, 1060, 1016, 844, 791, 751, 704 cm$^{-1}$. $^1$H NMR (400 MHz; CDCl$_3$) $\delta_H$ 8.17 (2H, d, J=8.1 Hz), 7.93 (1H, s), 7.74 (2H, d, J=8.1 Hz), 7.61 (1H, s), 7.34-7.29 (2H, m), 7.26-7.21 (1H, m), 7.21-7.19 (2H, m), 4.71 (1H, dd, J=8.7, 3.6 Hz), 3.50 (1H, dd, J=9.5, 4.1 Hz), 3.38 (1H, dd, J=9.5, 5.7 Hz), 3.32-3.25 (2H, m), 3.11 (1H, dd, J=12.7, 3.7 Hz), 3.08-3.02 (1H, m), 2.84 (1H, dd, J=13.6, 6.5 Hz), 2.75 (1H, dd, J=13.6, 7.7 Hz), 2.69 (1H, dd, J=12.8, 8.8 Hz), 1.09-0.99 (1H, m), 0.55-0.50 (2H, m), 0.21-0.17 (2H, m). $^{13}$C NMR (100 MHz; CDCl$_3$) $\delta_C$ 156.5, 155.0, 148.6 (q, J=34 Hz), 141.3, 138.7, 131.7 (q, J=32 Hz), 129.4, 128.8, 127.7, 126.8, 126.0 (CH, J=4 Hz), 124.2 (q, J=272 Hz), 121.6 (q, J=277 Hz), 120.3, 116.8 (q, J=2 Hz), 76.1, 71.9, 70.6, 59.2, 54.1, 38.8, 10.6, 3.16, 3.13. HRMS (ESI$^+$): calcd for C$_{28}$H$_{29}$F$_6$N$_2$O$_2$ [(M+H)$^+$]: 539.2133; Found: 539.2147. [α]$_D^{22}$: −23.7° (c 0.1; MeOH). Chiral HPLC 99% de, Chiralpak IA column, heptane/i-PrOH, 90/10, flow 1 mL/min, tr(S,S)=11.3 min, tr(R,S)=20.3 min. 3.3.2. Compounds 30 of Formulae IIa and IIb

(S)-2-(Butylamino)-1-(2-(trifluoromethyl)-6-(4-(trifluoromethyl)phenyl)pyridin-3-yl)ethanol (30a)

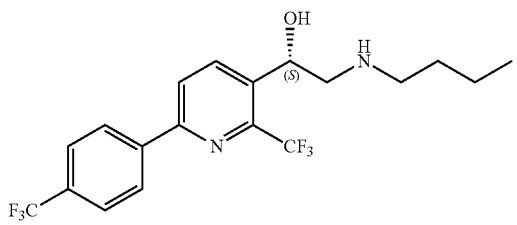

The compound 30a was obtained from 31a (50.0 mg, 0.15 mmol, 1 eq.) and n-butylamine (0.07 mL, 0.75 mmol, 5 eq.) according to the general procedure for aminopyridinemethanols (APMs) preparation. The residue was purified by flash chromatography (DCM/MeOH 99:1) to afford 51 mg of 30a as a white solid. Yield: 84%; m.p. 109° C.; NMR $^1$H (400 MHz, CD$_3$OD): δ 0.96 (t, J=7.3 Hz, 3H), 1.34-1.45 (m, 2H), 1.47-1.59 (m, 2H), 2.56-2.83 (m, 4H), 5.24-5.34 (m, 1H), 7.80 (d, J=8.3 Hz, 2H), 8.24 (d, J=8.3 Hz, 1H), 8.32 (d, J=8.3 Hz, 2H), 8.36 (d, J=8.3 Hz, 1H) ppm; NMR $^{13}$C (100 MHz, CD$_3$OD): δ14.3, 21.5, 32.7, 49.8, 57.7, 67.2 (q, J=2.8 Hz), 123.7 (q, J=275.2 Hz), 124.7, 125.6 (q, J=271.3 Hz), 126.8 (q, J=3.7 Hz), 128.5, 132.4 (q, J=32.2 Hz), 139.4, 139.7, 142.4, 144.7 (q, J=33.3 Hz), 155.0 ppm; IR $\sqrt{}_{max}$: 2963, 2736, 1325, 1109 cm$^{-1}$; HRMS calcd. for C$_{19}$H$_{21}$F$_6$N$_2$O (M+Na)$^+$ 407.1558, found 407.1561; [α]$_D^{20}$: +34.6° (c 0.1; MeOH); Chiral HPLC 99% ee, Chiralpak IB column, heptane/i-PrOH/EDA, 99:1:0.1, flow 1 mL/min, tr(S)=23.7 min, tr(R)=28.5 min.

(R)-2-(Butylamino)-1-(2-(trifluoromethyl-(4-(trifluoromethyl)phenyl)pyridin-3-yl)ethanol (30b)

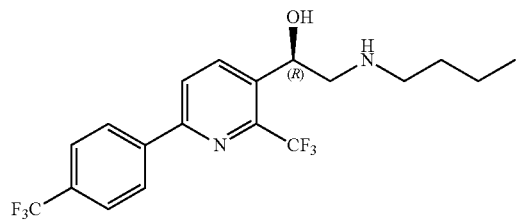

The compound 30b was obtained from 31b (50.0 mg, 0.15 mmol, 1 eq.) and n-butylamine (0.07 mL, 0.75 mmol, 5 eq.) according to the general procedure for aminopyridinemethanols (APMs) preparation. The residue was purified by flash chromatography (DCM/MeOH 99:1) to afford 56 mg of 30b as a white solid. Yield: 92%; The NMR ($^1$H and $^{13}$C), IR spectra, HRMS and m.p. were identical to those of 30a; [α]$_D^{20}$: −34.3° (c 0.1; MeOH); Chiral HPLC 96% ee, Chiralpak IB column, heptane/i-PrOH/EDA, 99:1:0.1, flow 1 mL/min, tr(S)=23.7 min, tr(R)=28.5 min.

(S)-2-(Pentylamino)-1-(2-(trifluoromethyl)-6-(4-(trifluoromethyl)phenyl)pyridin-3-yl)ethanol (30c)

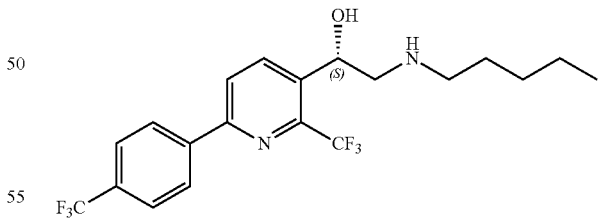

The compound 30c was obtained from 31a (50.0 mg, 0.15 mmol, 1 eq.) and n-pentylamine (0.09 mL, 0.75 mmol, 5 eq.) according to the general procedure for aminopyridinemethanols (APMs) preparation. The residue was purified by flash chromatography (DCM/MeOH 99:1) to afford 42 mg of 30c as a white solid. Yield: 67%; m.p. 94° C.; NMR $^1$H (400 MHz, CD$_3$OD): δ 0.92 (t, J=7.0 Hz, 3H), 1.28-1.43 (m, 4H), 1.49-1.59 (m, 2H), 2.55-2.73 (m, 2H), 2.73-2.81 (m, 2H), 5.29 (dd, J=5.3, 4.6 Hz, 1H), 7.80 (d, J=8.3 Hz, 2H), 8.24 (d, J=8.4 Hz, 1H), 8.32 (d, J=8.3 Hz, 2H), 8.36 (d, J=8.4 Hz, 1H) ppm; NMR $^{13}$C (100 MHz, CD$_3$OD): δ14.4, 23.7, 30.3, 30.7, 50.1, 57.8, 67.2 (q, J=2.8 Hz), 123.7 (q, J=275.1 Hz), 124.8, 125.7 (q, J=271.3 Hz), 126.9 (q, J=3.8 Hz), 128.6, 132.5 (q, J=32.3 Hz), 139.5, 139.7, 142.4, 144.8 (q, J=33.4 Hz), 155.1 ppm; IR $\nu_{max}$: 2928, 2730, 1324, 1109 cm$^{-1}$; HRMS calcd. for C$_{20}$H$_{23}$F$_6$N$_2$O (M+Na)$^+$ 421.1715, found 421.1719; [α]$_D^{20}$: +35.7° (c 0.1; MeOH); Chiral HPLC 99% ee, Chiralpak IB column, heptane/i-PrOH/EDA, 99:1:0.1, flow 1 mL/min, tr(S)=22.4 min, tr(R)=26.0 min.

(R)-2-(Pentylamino)-1-(2-(trifluoromethyl)-6-(4-(trifluoromethyl)phenyl)pyridin-3-yl)ethanol (30d)

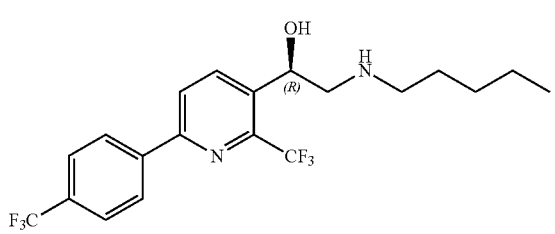

The compound 30d was obtained from 31b (50.0 mg, 0.15 mmol, 1 eq.) and n-pentylamine (0.09 mL, 0.75 mmol, 5 eq.) according to the general procedure for aminopyridinemethanols (APMs) preparation. The residue was purified by flash chromatography (DCM/MeOH 99:1) to afford 51 mg of 30d as a white solid. Yield: 81%; The NMR ($^1$H and $^{13}$C), IR spectra, HRMS and m.p. were identical to those of 30c; [α]$_D^{20}$: −36.2° (c 0.1; MeOH); Chiral HPLC 96% ee, Chiralpak IB column, heptane/i-PrOH/EDA, 99:1:0.1, flow 1 mL/min, tr(S)=22.4 min, tr(R)=26.0 min.

(S)-2-(Hexylamino)-1-(2-(trifluoromethyl)-6-(4-(trifluoromethyl)phenyl)pyridin-3-yl)ethanol (30e)

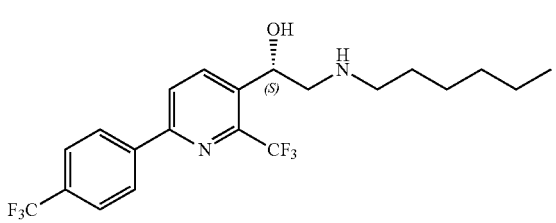

The compound 30e was obtained from 31a (50.0 mg, 0.15 mmol, 1 eq.) and n-hexylamine (0.10 mL, 0.75 mmol, 5 eq.) according to the general procedure for aminopyridinemethanols (APMs) preparation. The residue was purified by flash chromatography (DCM/MeOH 99:1) to afford 52 mg of 30e as a white solid. Yield: 80%; m.p. 103° C.; NMR $^1$H (400 MHz, CD$_3$OD): δ 0.85-0.97 (m, 3H), 1.28-1.43 (m, 6H), 1.49-1.61 (m, 2H), 2.59-2.76 (m, 2H), 2.74-2.82 (m, 2H), 5.30 (dd, J=6.7 Hz, J=2.2 Hz, 1H), 7.80 (d, J=8.3 Hz, 2H), 8.24 (d, J=8.4 Hz, 1H), 8.32 (d, J=8.3 Hz, 2H), 8.37 (d, J=8.4 Hz, 1H) ppm; NMR $^{13}$C (100 MHz, CD$_3$OD): δ 14.4, 23.7, 28.1, 30.4, 32.9, 50.1, 57.6, 67.1 (q, J=2.8 Hz), 123.7 (q, J=275.0 Hz), 124.8, 125.7 (q, J=271.3 Hz), 126.9 (q, J=3.8 Hz), 128.6, 132.5 (q, J=32.3 Hz), 139.4, 139.7, 142.4, 144.8 (q, J=33.4 Hz), 155.1 ppm; IR $\nu_{max}$: 2850, 2732, 1324, 1109 cm$^{-1}$; HRMS calcd. for C$_{21}$H$_{25}$F$_6$N$_2$O (M+H)$^+$ 435.1871, found 435.1876; [α]$_D^{22}$: +42.3° (c 0.1; MeOH); Chiral HPLC 99% ee, Chiralpak IB column, heptane/i-PrOH/EDA, 99:1:0.1, flow 1 mL/min, tr(S)=22.0 min, tr(R)=25.3 min.

(R)-2-(Hexylamino)-1-(2-(trifluoromethyl)-6-(4-(trifluoromethyl)phenyl)pyridin-3-yl)ethanol (30f)

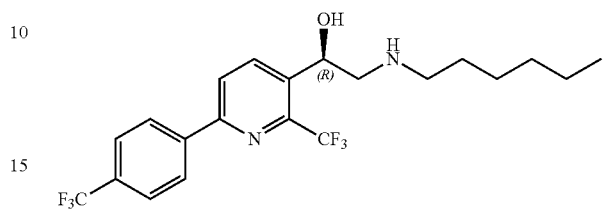

The compound 30f was obtained from 31b (50.0 mg, 0.15 mmol, 1 eq.) and n-hexylamine (0.10 mL, 0.75 mmol, 5 eq.) according to the general procedure for aminopyridinemethanols (APMs) preparation. The residue was purified by flash chromatography (DCM/MeOH 99:1) to afford 52 mg of 30f as a white solid. Yield: 80%; The NMR ($^1$H and $^{13}$C), IR spectra, HRMS and m.p. were identical to those of 30e; [α]$_D^{20}$: −43.3° (c 0.1; MeOH); Chiral HPLC 99% ee, Chiralpak IB column, heptane/i-PrOH/EDA, 99:1:0.1, flow 1 mL/min, tr(S)=22.0 min, tr(R)=25.3 min.

(S)-2-(Heptylamino)-1-(2-(trifluoromethyl)-6-(4-(trifluoromethyl)phenyl)pyridin-3-yl)ethanol (302)

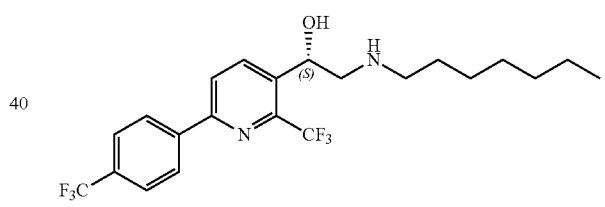

The compound 30g was obtained from 31a (50.0 mg, 0.15 mmol, 1 eq.) and n-heptylamine (0.12 mL, 0.75 mmol, 5 eq.) according to the general procedure for aminopyridinemethanols (APMs) preparation. The residue was purified by flash chromatography (DCM/MeOH 99:1) to afford 55 mg of 30g as a white solid. Yield: 82%; m.p. 93° C.; NMR $^1$H (400 MHz, CD$_3$OD): δ 0.88-0.92 (m, 3H), 1.28-1.35 (m, 8H), 1.51-1.56 (m, 2H), 2.57-2.75 (m, 2H), 2.75-2.80 (m, 2H), 5.29 (dd, J=6.6 Hz, J=4.4 Hz, 1H), 7.80 (d, J=8.3 Hz, 2H), 8.24 (d, 0.1=8.4 Hz, 1H), 8.32 (d, J=8.3 Hz, 2H), 8.36 (d, J=8.4 Hz, 1H) ppm; NMR $^{13}$C (100 MHz, CD$_3$OD): δ14.4, 23.7, 28.4, 30.4, 30.5, 33.0, 21.5, 32.7, 50.2, 57.7, 67.2 (q, J=2.8 Hz), 123.7 (q, J=275.0 Hz), 124.8, 125.7 (q, J=271.3 Hz), 126.9 (q, J=3.8 Hz), 128.6, 132.5 (q, J=32.3 Hz), 139.5, 139.7, 142.4, 144.8 (q, J=33.4 Hz), 155.1 ppm; IR $\nu_{max}$: 2926, 2742, 1324, 1109 cm$^{-1}$; HRMS calcd. For C$_{22}$H$_{27}$F$_6$N$_2$O (M+H)$^+$ 449.2028, found 449.2030; [α]$_D^{20}$: +39.6° (c 0.1; MeOH); Chiral HPLC 99% ee, Chiralpak IB column, heptane/i-PrOH/EDA, 99:1:0.1, flow 1 mL/min, tr(S)=20.1 min, tr(R)=24.5 min.

(R)-2-(Heptylamino)-1-(2-(trifluoromethyl)-6-(4-(trifluoromethyl)phenyl)pyridin-3-yl) ethanol (30h)

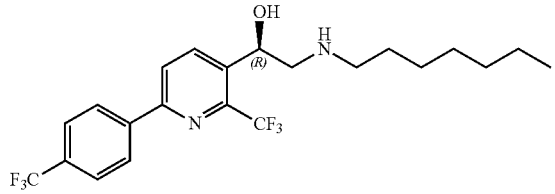

The compound 30h was obtained from 31b (50.0 mg, 0.15 mmol, 1 eq.) and n-heptylamine (0.12 mL, 0.75 mmol, 5 eq.) according to the general procedure for aminopyridinemethanols (APMs) preparation. The residue was purified by flash chromatography (DCM/MeOH 99:1) to afford 60 mg of 30h as a white solid; Yield: 90%; The NMR ($^1$H and $^{13}$C), IR spectra, HRMS and m.p. were identical to those of 30g; $[\alpha]_D^{20}$: −40.3° (c 0.1; MeOH); Chiral HPLC 99% ee, Chiralpak IB column, heptane/i-PrOH/EDA, 99:1:0.1, flow 1 mL/min, tr(S)=22.4 min, tr(R)=26.0 min.

(S)-2-((2-(Benzhydrylamino)ethyl)amino)-1-(2-(trifluoromethyl)-6-(4-(trifluoromethyl)phenyl)pyridin-3-yl)ethanol (30i)

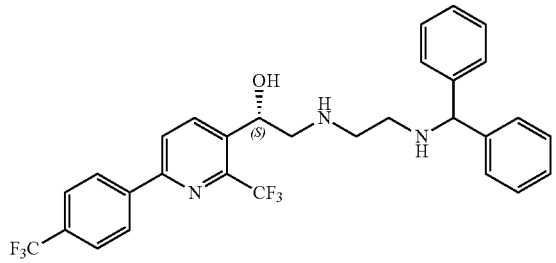

The compound 30i was obtained from 31a (30.0 mg, 0.09 mmol, 1 eq.) and N-benzhydrylethane-1,2-diamine 19 (102 mg, 0.45 mmol, 5 eq.) according to the general procedure for aminopyridinemethanols (APMs) preparation. The residue was purified by flash chromatography (DCM/MeOH 99:1) to afford 40 mg of 30i as a white solid. Yield: 80%; m.p. 93° C.; NMR $^1$H (400 MHz, CD$_3$OD): δ 2.71-2.81 (m, 3H), 2.79 [AB(ABX), J=12.5 Hz, J=9.5 Hz, J=2.9 Hz, 2H), 2.81-2.92 (m, 1H), 3.14 (Sb, 3H), 4.83 (s, 1H), 5.14-5.19 (m, 1H), 7.20-7.24 (m, 2H), 7.29-7.32 (m, 4H), 7.35-7.40 (m, 4H), 7.74 (d, J=8.2 Hz, 2H), 7.95 (d, J=8.3 Hz, 1H), 8.18 (d, J=8.2 Hz, 2H), 8.30 (d, J=8.3 Hz, 1H) ppm; NMR $^{13}$C (100 MHz, CD$_3$OD): δ 47.3, 48.7, 56.3, 66.0 (q, J=2.7 Hz), 67.5, 122.1 (q, J=275.8 Hz), 123.1, 124.0 (q, J=272.2 Hz), 125.8 (q, J=3.7 Hz), 127.16, 127.18, 127.2, 127.3, 128.6, 131.4 (q, J=32.6 Hz), 136.7, 137.9, 140.8, 143.7, 144.1 (q, J=33.6 Hz), 153.9 ppm; IR $\nu_{max}$: 2846, 2718, 1322, 1111 cm$^{-1}$; HRMS calcd. for C$_{30}$H$_{28}$F$_6$N$_3$O (M+H)$^+$ 560.2137, found 568.2144; $[\alpha]_D^{20}$: +33.0° (c 0.1; MeOH); Chiral HPLC 99% ee, Chiralpak IB column, heptane/i-PrOH; 98:2; flow 1 mL/min, tr(R)=62.3 min, (S)=74.0 min.

(R)-2-((2-(Benzhydrylamino)ethyl)amino)-1-(2-(trifluoromethyl)-6-(4-(trifluoromethyl)phenyl)pyridin-3-yl)ethanol (30j)

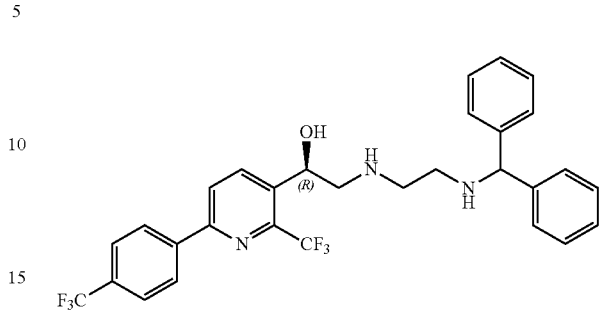

The compound 30j was obtained from 31b (50.0 mg, 0.15 mmol, 1 eq.) and N-benzhydrylethane-1,2-diamine 19 (170 mg, 0.75 mmol, 5 eq.) according to the general procedure for aminopyridinemethanols (APMs) preparation. The residue was purified by flash chromatography (DCM/MeOH 99:1) to afford 73 mg of 30j as a white solid. Yield: 87%; The NMR ($^1$H and $^{13}$C), IR spectra, HRMS and m.p. were identical to those of 30j; $[\alpha]_D^{20}$: −33.1° (c 0.1; MeOH); Chiral HPLC 99% ee, Chiralpak IB column, heptane/i-PrOH, 98:2; flow 1 mL/min, tr(R)=62.3 min, tr(S)=74.0 min; $[\alpha]_D^{20}$: +33.0° (c 0.1; MeOH).

(S)-2-(((S)-1-methoxy-3-phenylpropan-2-yl)amino)-1-(2-(trifluoromethyl)-6-(4-(trifluoromethyl)phenyl)pyridin-3-yl)ethanol (30k)

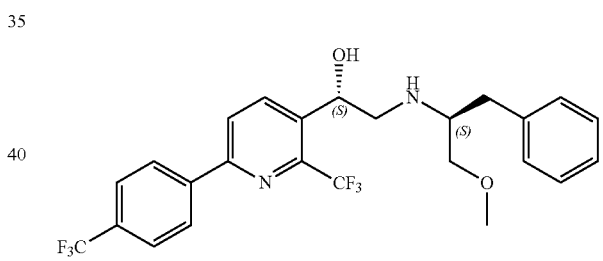

The compound 30k was obtained from 31a (30.0 mg, 0.09 mmol, 1 eq.) and 23 (74.0 mg, 0.45 mmol, 5 eq.) according to the general procedure for aminopyridinemethanols (APMs) preparation. The residue was purified by flash chromatography (DCM/MeOH 99:1) to afford 31.0 mg of 30k as a white solid. Yield: 69%; m.p. 99° C.; NMR $^1$H (400 MHz, CDCl$_3$): δ 2.70-2.83 (m, 2H), 2.81 [AB(ABX), J=12.7 Hz, J=9.4 Hz, J=3.1 Hz, 2H], 2.97-3.05 (m, 1H), 3.34 [AB(ABX), J=9.4 Hz, J=6.0, J=4.1 Hz, 2H], 3.38 (s, 3H), 5.09 [X(ABX), J=9.4 Hz, J=3.1 Hz, 2H], 7.19-7.21 (m, 2H), 7.23-7.25 (m, 1H), 7.30-7.35 (m, 2H), 7.74 (d, J=8.3 Hz, 2H), 7.94 (d, J=8.3 Hz, 1H), 8.17 (d, J=8.3 Hz, 2H), 8.23 (d, J=8.3 Hz, 1H) ppm; NMR $^{13}$C (100 MHz, CDCl$_3$): δ 38.3, 54.4, 58.6, 59.0, 66.3 (q, J=2.7 Hz), 74.2, 122.1 (q, J=275.6 Hz), 123.1, 124.0 (q, J=272.2 Hz), 125.8 (q, J=3.8 Hz), 126.4, 127.2, 128.5, 129.3, 131.4 (q, J=32.6 Hz), 136.6, 137.8, 138.5, 140.9, 144.1 (q, J=33.6 Hz), 153.8 ppm; IR $\nu_{max}$: 3087, 2895, 1322, 1110 cm$^{-1}$; HRMS calcd. for C$_{25}$H$_{25}$F$_6$N$_2$O$_2$ (M+H)$^+$ 499.1820, found 499.1817; $[\alpha]_D^{20}$: +29.5° (c 0.1; MeOH); Chiral HPLC 99% ee, Chiralpak IA column, heptane/i-PrOH, 95:5; flow 1 mL/min, tr(R,S)=15.1 min, tr(S,S)=18.3 min.

(R)-2-(((S)-1-methoxy-3-phenylpropan-2-yl)amino)-1-(2-(trifluoromethyl)-6-(4-(trifluoromethyl)phenyl)pyridin-3-yl)ethanol (30l)

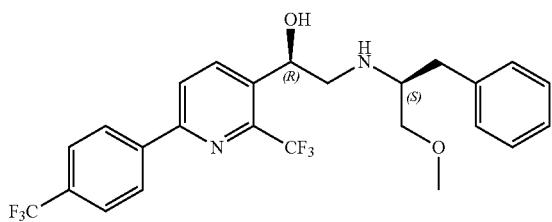

The compound 30l was obtained from 31b (30.0 mg, 0.09 mmol, 1 eq.) and 23 (74.0 mg, 0.45 mmol, 5 eq.) according to the general procedure for aminopyridinemethanols (APMs) preparation. The residue was purified by flash chromatography (DCM/MeOH 99:1) to afford 36.0 mg of 30l as a white solid. Yield: 80%; m.p. 99° C.; NMR $^1$H (400 MHz, CDCl$_3$): δ 2.79 [AB(ABX), J=13.6 Hz, J=7.5 Hz, J=6.6 Hz, 2H], 2.82 [AB(ABX), J=12.8 Hz, J=9.2 Hz, J=3.1 Hz, 2H], 2.97-3.03 (m, 1H), 3.37 [AB(ABX), J=9.5, J=5.3 Hz, J=4.2 Hz, 2H], 3.37 (s, 3H), 4.99 [X(ABX), J=9.2 Hz, J=3.1 Hz, 2H], 7.18-7.24 (m, 2H), 7.24-7.26 (m, 1H), 7.30-7.35 (m, 2H), 7.73 (d, J=8.3 Hz, 2H), 7.94 (d, J=8.3 Hz, 1H), 8.16 (d, J=8.2 Hz, 2H), 8.23 (d, J=8.3 Hz, 1H) ppm; NMR $^{13}$C (100 MHz, CDCl$_3$): δ 38.6, 54.2, 58.8, 59.0, 66.4 (q, J=2.7 Hz), 73.7, 122.1 (q, J=275.8 Hz), 123.0, 124.0 (q, J=272.2 Hz), 125.8 (q, J=3.8 Hz), 126.5, 127.2, 128.5, 129.2, 131.4 (q, J=32.6 Hz), 136.6, 137.8, 138.7, 144.1 (q, J=33.5 Hz), 153.8 ppm; IR $\nu_{max}$: 3087, 2895, 1322, 1110 cm$^{-1}$; HRMS calcd. for C$_{25}$H$_{25}$F$_6$N$_2$O$_2$ (M+H)$^+$ 499.1820, found 499.1823; [α]$_D^{20}$: −34.7° (c 0.1; MeOH); Chiral HPLC 98% ee, Chiralpak IA column, heptane/i-PrOH, 95:5; flow 1 mL/min, tr(R,S)=15.1 min, tr(S,S)=18.3 min.

(S)-2-((2-Aminoethyl)aminomethyl)ferrocenyl)-1-(2-(trifluoromethyl)-6-(4-(trifluoromethyl)phenyl)pyridin-3-yl)ethanol (30m)

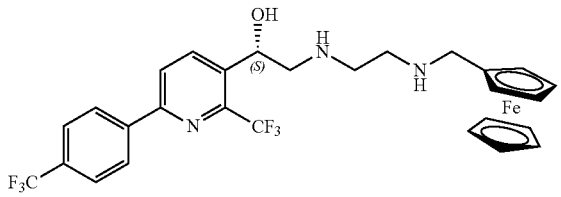

To a solution, under argon, of 90.0 mg (0.23 mmol, 1 eq.) of 45a in 4 mL of anhydrous MeOH were added 49.0 mg (0.23 mmol, 1 eq.) of ferrocenecarboxaldehyde. The solution was stirred for 4 h at 25° C. before to add 14.0 mg (0.37 mmol, 1.6 eq.) of NaBH$_4$. The mixture was stirred at 25° C. for 15 h before being diluted with an excess of MeOH. The solution was concentrated in vacuo and the residue directly purified by flash chromatography (AcOEt/MeOH/NH$_4$OH 8:0.5:0.5) to afford 48.0 mg of 30m as a brown solid. Yield: 35%; m. p. 59° C.; NMR $^1$H (400 MHz, CD$_3$OD): δ 2.54-2.65 (m, 1H), 2.68-2.88 (m, 4H), 2.88-3.03 (m, 1H), 3.52 (s, 2H), 4.07-4.17 (m, 9H), 5.16-5.22 (m, 1H), 7.72 (d, J=8.3 Hz, 2H), 7.93 (d, J=8.3 Hz, 1H), 8.16 (d, J=8.3 Hz, 2H), 8.28 (d, J=8.3 Hz, 1H) ppm; NMR $^{13}$C (100 MHz, CD$_3$OD): δ 48.3, 48.7, 48.8, 56.8, 66.3, 67.9, 68.4, 68.5, 86.0, 122.1 (q, J=276.4 Hz), 123.0, 124.0 (q, J=272.2 Hz), 125.7 (q, J=3.1 Hz), 127.2, 131.3126.9 (q, J=32.2 Hz), 137.2, 138.0, 140.8, 143.9 (q, J=33.5 Hz), 153.7 ppm; IR $\nu_{max}$: 3244, 2937, 1665, 1322, 1112 cm$^{-1}$; HRMS calcd. for C$_{28}$H$_{28}$F$_6$FeN$_3$O (M+H)$^+$ 592.1486, found 592.1506; [α]$_D^{20}$: +26.7° (c 0.1; MeOH); Chiral HPLC 82% ee, Chiralpak ID column, heptane/EtOH/EDA, 95:5:0.1, flow 1 mL/min, tr(R)=11.4 min, tr(R)=12.8 min.

(R)-2-((2-Aminoethyl)aminomethylferrocenyl)-1-(2-(trifluoromethyl)-6-(4-(trifluoromethyl)phenyl)pyridin-3-yl)ethanol (30n)

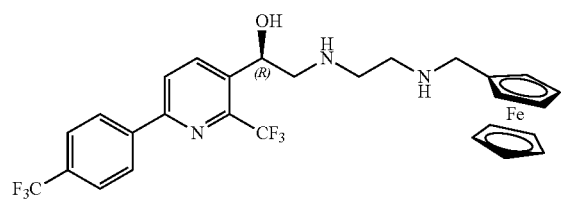

The compound 30n was obtained from 45b (71.0 mg, 0.18 mmol) according to the same procedure as 30m. 28.0 mg of 30n were obtained as a brown solid. Yield: 26%; The NMR ($^1$H and $^{13}$C), IR spectra, HRMS and m.p. were identical to those of 30m; Chiral HPLC 96% ee, Chiralpak ID column, heptane/EtOH/EDA, 95:5:0.1, flow 1 mL/min, tr(R)=11.4 min, tr(R)=12.8 min; [α]$_D^{20}$: −27.1° (c 0.1; MeOH).

(S)-2-((3-(4-Benzhydrylpiperazin-1-yl)propyl)amino)-1-(2-(trifluoromethyl)-6-(4-(trifluoromethyl)phenylpyridin-3-yl)ethanol (30o)

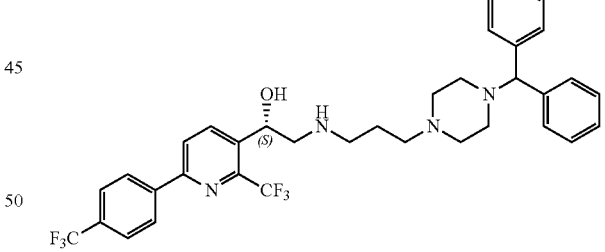

The compound 30o was obtained from 31a (30.0 mg, 0.09 mmol, 1 eq.) and 29 (139 mg, 0.45 mmol, 5 eq.) according to the general procedure for aminopyridinemethanols (APMs) preparation. The residue was purified by flash chromatography (AcOEt/MeOH/NH$_4$OH 8:0.5:0.5) to afford 27.0 mg of 30o as a white solid. Yield: 48%; m.p. 125° C.; NMR $^1$H (400 MHz, CDCl$_3$): δ 1.63-1.74 (m, 2H), 2.23-2.46 (m, 9H), 2.64-2.72 (m, 2H), 2.72-2.84 (m, 2H), 2.77 [AB(ABX), J=12.5 Hz, J=9.5 Hz, J=2.9 Hz, 2H], 4.17 (s, 1H), 5.12-5.21 (m, 1H), 7.13-7.19 (m, 2H), 7.19-7.26 (m, 4H), 7.37-7.39 (m, 4H), 7.72 (d, J=8.3 Hz, 2H), 7.95 (d, J=8.3 Hz, 1H), 8.16 (d, J=8.3 Hz, 2H), 8.29 (d, J=8.3 Hz, 1H) ppm; NMR $^{13}$C (100 MHz, CDCl$_3$): δ 26.3, 47.7, 51.7, 53.5, 56.5, 56.7, 65.8 (q, J=2.7 Hz), 76.2, 122.0 (q, J=275.7

Hz), 123.1, 124.0 (q, J=272.1 Hz), 125.8 (q, J=3.8 Hz), 126.8, 127.2, 127.8, 128.4, 131.3 (q, J=32.5 Hz), 136.9, 137.9, 140.8, 142.7, 144.0 (J=33.4 Hz), 153.8; IR $v_{max}$: 2943, 1323, 1116 cm$^{-1}$; HRMS calcd. for $C_{35}H_{37}F_6N_4O$ (M+H)$^+$ 643.2872, found 643.2884; [α]$_D^{20}$: +16.1° (c 0.1; MeOH); Chiral HPLC 99% ee, Chiralpak IB column, heptane/i-PrOH/EDA, 99:1:0.1, flow 1 mL/min, tr(S)=41.1 min, tr(R)=47.8 min.

(R)-2-((3-(4-Benzhydrylpiperazin-1-yl)propyl)amino)-1-(2-(trifluoromethyl)-6-(4-(trifluoromethyl)phenyl)pyridin-3-yl)ethanol (30p)

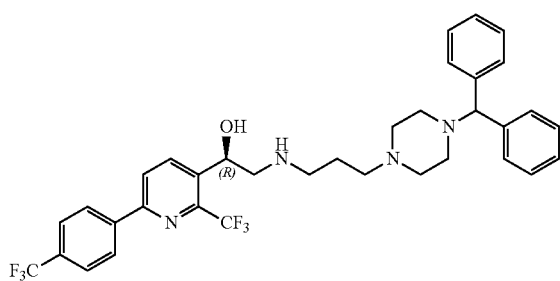

The compound 30p was obtained from 31b (30.0 mg, 0.09 mmol, 1 eq.) and 29 (139 mg, 0.45 mmol, 5 eq.) according to the general procedure for aminopyridinemethanols (APMs) preparation. The residue was purified by flash chromatography (AcOEt/MeOH/NH$_4$OH 8:0.5:0.5) to afford 39.0 mg of 30p as a white solid. Yield: 67%; The NMR ($^1$H and $^{13}$C), IR spectra, HRMS and m.p. were identical to those of 30o; [α]$_D^{20}$: −15.8° (c 0.1; MeOH); Chiral HPLC 98% ee, Chiralpak IB column, heptane/i-PrOH/EDA, 99:1:0.1, flow 1 mL/min, tr(S)=41.1 min, tr(R)=47.8 min.

(S)-2-((4,4,4-trifluorobutylamino)-1-(2-(trifluoromethyl)-6-(4-(trifluoromethyl)phenyl)pyridin-3-yl)ethan-1-ol (30q)

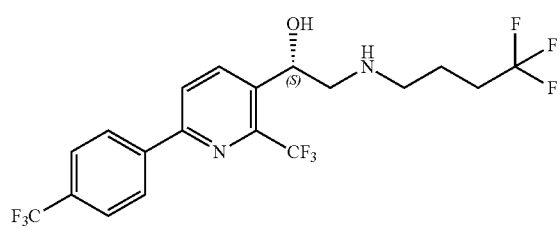

The compound 30q was obtained from 31a (175.0 mg, 0.53 mmol, 1 eq.) and 4,4,4-trifluorobutylamine (0.20 g, 1.58 mmol, 3 eq.) according to the general procedure for aminopyridinemethanols (APMs) preparation. The residue was purified by flash chromatography (DCM/MeOH 99/01) to afford 189 mg of 30q as a white solid. Yield: 78%. m.p. 110.5-111.5° C. IR $v_{max}$ 3293, 2945, 2858, 2668, 1325, 1246, 1207, 1160, 1117, 1066, 1012, 833 cm$^{-1}$. $^1$H NMR (400 MHz; CDCl$_3$) δ$_H$ 8.31 (1H, d, J=8.3 Hz), 8.18 (1H, d, J=8.0 Hz), 7.99 (1H, d, J=8.3 Hz), 7.75 (m, 2H), 5.21 (1H, d, J=9.5 Hz), 3.05 (1H, dd, J=12.6, 3.0 Hz), 2.87 (1H, d, J=12.0, 7.1 Hz), 2.78 (1H, d, J=11.9, 7.0 Hz), 2.64 (1H, dd, J=12.5, 9.6 Hz), 2.21 (2H, m), 1.84 (2H, m). $^{13}$C NMR (100 MHz; CDCl$_3$) δ$_C$ 154.4, 144.4 (q, J=34 Hz), 140.9, 138.0, 136.1, 131.7 (q, J=33 Hz), 127.4, 127.1 (q, J=276 Hz), 126.0 (q, J=4 Hz), 123.4, 122.2 (q, J=276 Hz), 121.5 (q, J=258 Hz), 66.0, 56.4, 47.9, 31.6 (q, J=29 Hz), 22.4. HRMS (ESI$^+$): calcd for $C_{19}H_{17}F_9N_2O$ [(M+H)$^+$]: 461.1275; Found: 461.1282. [α]$_D^{22}$: +25.5° (c 0.1; MeOH). Chiral HPLC 98% ee, Chiralpak IB column, heptane/i-PrOH/EDA, 95/05/0.1, flow 1 mL/min, tr(S)=11.8 min, tr(R)=14.9 min.

(R)-2-((4,4,4-trifluorobutyl)amino)-1-(2-(trifluoromethyl)-6-(4-(trifluoromethyl)phenyl)pyridin-3-yl)ethan-1-ol (30r)

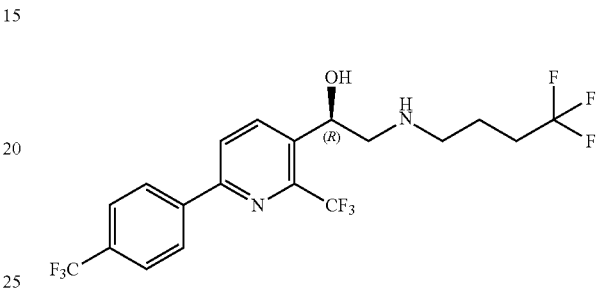

The compound 30r was obtained from 31b (175.0 mg, 0.53 mmol, 1 eq.) and 4,4,4-trifluorobutylamine (0.20 g, 1.58 mmol, 3 eq.) according to the general procedure for aminopyridinemethanols (APMs) preparation. The residue was purified by flash chromatography (DCM/MeOH 99/01) to afford 186 mg of 30r as a white solid. Yield: 77%. The NMR ($^1$H and $^{13}$C), IR spectra, HRMS and m.p. were identical to those of 30q; [α]$_D^{22}$: −26.4° (c 0.1; MeOH). Chiral HPLC 98% ee, Chiralpak IB column, heptane/i-PrOH/EDA, 95/05/0.1, flow 1 mL/min, tr(S)=11.6 min, tr(R)=14.5 min.

(S)-2-((6-fluorohexyl)amino-1-(2-(trifluoromethyl)-6-(4-(trifluoromethyl)phenyl)pyridine-3-yl)ethan-1-ol (30s)

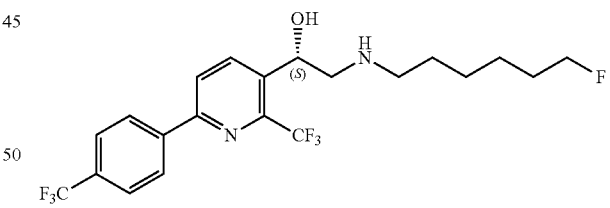

The compound 30s was obtained from 31a (154 mg, 0.46 mmol, 1 eq.) and amine C hydrochloride salt (210 mg, 1.35 mmol, 3.0 eq.) according to the general procedure for aminopyridinemethanols (APMs) preparation with the addition of N,N-diisopropylethylamine (0.2 mL, 1.16 mmol, 2.5 eq.). The crude mixture was washed with aqueous NaHCO$_3$ (1M) and extracted with dichloromethane. The organic layer was dried over Na$_2$SO$_4$, filtered and concentrated in vacuo. The residue was purified by flash chromatography (DCM to DCM/MeOH 98/2) to afford 136 mg of is as an amorphous white solid. Yield: 65%. IR $v_{max}$ 2927, 2852, 1325, 1159, 1106, 1065, 1044, 835 cm$^{-1}$. $^1$H NMR (400 MHz; CDCl$_3$) δ$_H$ 8.31 (1H, d, J=8.3 Hz), 8.18 (2H, d, J=8.2 Hz), 7.98 (1H, d, J=8.3 Hz), 7.74 (2H, d, J=8.3 Hz), 5.13 (1H, d, J=9.5), 4.46 (2H, dt, J=47.3, 6.1 Hz), 3.03 (1H, dd, J=12.4, 3.3 Hz), 2.76 (1H, dt, J=11.7, 7.1 Hz), 2.66 (1H, dt, J=11.7, 7.0 Hz), 2.55 (1H, dd, J=12.4, 9.6 Hz), 2.04 (2H, s), 1.78-1.65 (2H, m), 1.58-1.51 (2H, m), 1.49-1.37 (4H, m). $^{13}$C NMR (100 MHz; CDCl$_3$) $\delta_C$ 154.1, 144.4 (q, J=34 Hz), 141.0, 138.0, 136.8, 131.6 (q, J=33 Hz), 127.4, 126.0 (q, J=4 Hz), 124.2 (q, J=272 Hz), 123.3, 122.2 (q, J=276 Hz), 84.2 (d, J=164 Hz), 65.9, 56.7, 49.2, 30.5 (d, J=20 Hz), 30.0, 26.9, 25.3 (d, J=5 Hz). HRMS (ESI$^+$): calcd for C$_{21}$H$_{24}$F$_7$N$_2$O [(M+H)$^+$]: 453.1777; Found: 453.1783. [α]$_D^{22}$: +31.0° (c 0.1; MeOH). Chiral HPLC 98% ee, Chiralpak IB column, heptane/i-PrOH/EDA, 98/02/0.1, flow 1 mL/min, tr(S)=22.3 min, tr(R)=26.0 min.

(R)-2-((6-fluorohexyl)amino)-1-(2-(trifluoromethyl-6-(4-(trifluoromethyl)phenyl)pyridine-3-yl)ethan-1-ol (30t)

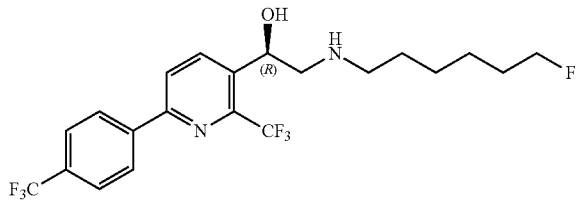

The compound 30t was obtained from 31b (150 mg, 0.45 mmol, 1 eq.) and amine C hydrochloride salt (210 mg, 1.35 mmol, 3.0 eq.) according to the general procedure for aminopyridinemethanols (APMs) preparation with the addition of N,N-diisopropylethylamine (0.24 mL, 1.35 mmol, 3.0 eq.). The crude mixture was washed with aqueous NaHCO$_3$ (1M) and extracted with dichloromethane. The organic layer was dried over Na$_2$SO$_4$, filtered and concentrated in vacuo. The residue was purified by flash chromatography (DCM to DCM/MeOH 98/2) to afford 86.5 mg of 30t as an amorphous white solid. Yield: 42%. The NMR ($^1$H and $^{13}$C), IR spectra and HRMS were identical to those of 30s. [α]$_D^{22}$: −34.0° (c 0.1; MeOH). Chiral HPLC 99% ee, Chiralpak IB column, heptane/i-PrOH/EDA, 98:02:0.1, flow 1 mL/min, tr(S)=22.6 min, tr(R)=25.4 min.

(S)-2-(((S)-1-(cyclopropylmethoxy)-3-phenylpropan-2-yl)amino)-1-(2-(trifluoromethyl)-6-(4-(trifluoromethyl)phenyl)pyridin-3-yl)ethan-1-ol (30u)

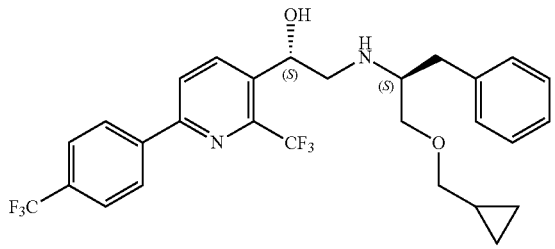

The compound 30u was obtained from 31a (175 mg, 0.53 mmol, 1 eq.) and (S)-1-(cyclopropylmethoxy)-3-phenylpropan-2-amine A (300 mg, 1.58 mmol, 3.0 eq.) according to the general procedure for aminopyridinemethanols (APMs) preparation. The residue was purified by flash chromatography (DCM/MeOH/NH$_{3(aq)}$ 98/1/1) to afford 291 mg of 30u as a colourless oil. Yield: 97%. IR $v_{max}$ 3077, 3027, 2923, 2862, 1462, 1426, 1322, 1173, 1116, 1069, 1050, 1017, 837, 740, 701 cm$^1$. $^1$H NMR (400 MHz; CDCl$_3$) $\delta_H$ 8.24 (1H, d, J=8.3 Hz), 8.17 (2H, d, J=7.9 Hz), 7.95 (1H, d, J=8.3 Hz), 7.74 (2H, d, J=8.0 Hz), 7.33-7.29 (2H, m), 7.25-7.19 (1H, m), 5.11 (1H, m), 3.46 (1H, dd, J=9.5, 4.1 Hz), 3.34 (1H, dd, J=9.5, 6.2 Hz), 3.33-3.26 (2H, m), 3.10 (1H, dd, J=12.8, 3.2 Hz), 3.07-3.01 (1H, m), 2.84-2.74 (2H, m), 2.51 (1H, dd, J=12.8, 9.4 Hz), 1.12-1.02 (1H, m), 0.57-0.52 (2H, m), 0.23-0.19 (2H, m). $^{13}$C NMR (100 MHz; CDCl$_3$) $\delta_C$ 154.0, 144.3 (q, J=33 Hz), 141.0, 138.7, 138.0, 136.8, 131.6 (q, J=33 Hz), 129.4, 128.7127.4, 126.6, 126.0 (q, J=4 Hz), 124.2 (q, J=272 Hz), 123.3, 122.3 (q, J=276 Hz), 76.1, 71.8, 66.3, 58.8, 54.5, 38.6, 10.6, 3.15. HRMS (ESI$^+$): calcd for C$_{28}$H$_{29}$F$_6$N$_2$O$_2$ [(M+H)$^+$]: 539.2133; Found: 539.2132. [α]$_D^{22}$: +19.2° (c 0.1; MeOH). Chiral HPLC 98% de, Chiralpak IA column, heptane/i-PrOH, 99/01, flow 1 mL/min, tr(R,S)=52.7 min, tr(S,S)=68.7 min.

(R)-2-(((S)-1-(cyclopropylmethoxy)-3-phenylpropan-2-yl)amino)-1-(2-(trifluoromethyl)-6-(4-(trifluoromethyl)phenyl)pyridin-3-yl)ethan-1-ol (30v)

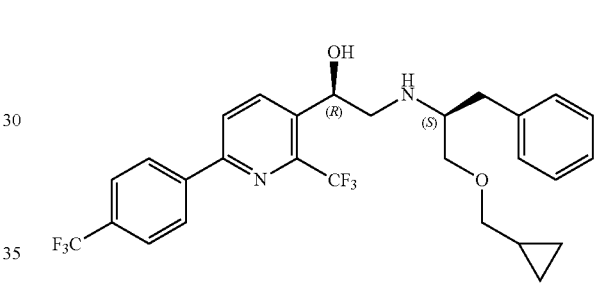

The compound 30v was obtained from 31b (175 mg, 0.53 mmol, 1 eq.) and (S)-1-(cyclopropylmethoxy)-3-phenylpropan-2-amine A (300 mg, 1.58 mmol, 3.0 eq.) according to the general procedure for aminopyridinemethanols (APMs) preparation. The residue was purified by flash chromatography (DCM/MeOH/NH$_{3(aq)}$ 98/1/1) to afford 270 mg of 30v as a white solid. Yield: 94%. m.p. 52-53° C. IR $v_{max}$ 3317, 3086, 3030, 2929, 2884, 2851, 1458, 1429, 1322, 1174, 1114, 1092, 1065, 1049, 841, 747, 701 cm$^1$. $^1$H NMR (400 MHz; CDCl$_3$) $\delta_H$ 8.25 (1H, d, J=8.3 Hz), 8.17 (2H, d, J=8.1 Hz), 7.95 (1H, d, J=8.3 Hz), 7.74 (2H, d, J=8.2 Hz), 7.34-7.30 (2H, m), 7.26-7.23 (1H, m), 7.22-7.20 (2H, m), 4.99 (1H, d, J=7.7 Hz), 3.48 (1H, dd, J=9.6, 4.2 Hz), 3.33 (1H, dd, J=9.5, 6.4 Hz), 3.33-3.25 (2H, m), 3.10 (1H, dd, J=12.9, 3.2 Hz), 3.07-3.01 (1H, m), 2.85-2.74 (2H, m), 2.59 (1H, dd, J=12.8, 9.2 Hz), 1.10-1.01 (1H, m), 0.56-0.51 (2H, m), 0.22-0.18 (2H, m). $^{13}$C NMR (100 MHz; CDCl$_3$) $\delta_C$ 156.5, 144.3 (q, J=34 Hz), 141.0, 138.9, 138.0, 136.8, 131.6 (q, J=32 Hz), 129.4, 128.7, 127.4, 126.6, 126.0 (q, J=3 Hz), 124.2 (q, J=272 Hz), 123.2, 122.2 (q, J=276 Hz), 76.1, 71.6, 66.7, 59.0, 54.3, 38.8, 10.6, 3.14, 3.13. HRMS (ESI$^+$): calcd for C$_{28}$H$_{29}$F$_6$N$_2$O$_2$ [(M+H)$^+$]: 539.2133; Found: 539.2136. [α]$_D^{22}$: −32.7° (c 0.1; MeOH). Chiral HPLC 98% de, Chiralpak IA column, heptane/i-PrOH, 99/01, flow 1 mL/min, tr(R,S)=52.7 min, tr(S,S)=70.8 min.

Biology Examples

Example 4. *Plasmodium falciparum* Susceptibility Assays 4.1. Method

The in vitro antiplasmodial activities were first tested over concentrations ranging from 39 nM to 40 µM and then, if the molecule efficacy warranted it, further checked over a concentration range of 1 nM to 1 µM. The reference strains used were culture-adapted *Plasmodium falciparum* 3D7 and W2. The former strain is susceptible to chloroquine but displays a decreased susceptibility to mefloquine, while the latter is resistant to chloroquine. Parasites were cultivated in RPMI medium (Sigma-Aldrich, Lyon, France) supplemented with 0.5% Albumax I (Life Technologies corporation, Paisley, United Kingdom), hypoxanthine (Sigma-Aldrich), gentamicin (Sigma-Aldrich), and human erythrocytes. They were incubated at 37° C. in a candle jar, as described previously (Desjardins R. E. et al., Antimicrob. Agents Chemother., 2004, 48, 1807-1810). The *P. falciparum* drug susceptibility test was carried out in 96-well flat bottom sterile plates under a final volume of 250 µL. After 48-h incubation with the drugs, quantities of DNA in treated and control cultures of parasites in human erythrocytes were compared according to the SYBR Green I (Sigma-Aldrich) fluorescence-based method (Bacon D. J. et al., Antimicrob. Agents Chemother., 2004, 48, 1807-1810).

Briefly, after incubation, plates were frozen at −20° C. until use. They were then left to thaw for 2 h at room temperature after which 100 µL of the homogenized culture were transferred to 96-well flat bottom sterile black plates (Nunc Inc.) already containing 100 µL of the SYBR Green I lysis buffer (2×SYBR Green, 20 mM Tris base pH 7.5, 5 mM EDTA, 0.008% w/v saponin, 0.08% w/v Triton X-100). A negative control, controls treated by solvents (DMSO and $H_2O$, typically), and positive controls (chloroquine and mefloquine) were added to each set of experiments. Plates were incubated for 1 h at room temperature and the SYBRGreen fluorescence was then read on a fluorescence plate reader (Tecan, Austria) using excitation and emission wavelengths of 485 and 535 nm, respectively. Concentrations inhibiting 50% of the parasite's growth (half maximal inhibitory concentration or $IC_{50}$ values) were then calculated from the obtained experimental results using a regression program available on line (Kaddouri H. et al., Antimicrob. Agents Chemother., 2006, 50, 3343-3349). A second round of susceptibility assays were performed on *P. falciparum* using a slightly different method described in the two following paragraphs:

In order to test the inhibitory effects on *P. falciparum*, two culture-adapted lines, 3D7 and W2 were used. While 3D7 is sensitive to chloroquine and displays a decreased susceptibility to mefloquine, W2 is resistant to chloroquine. Parasites were maintained in RPMI-1640 medium (Sigma-Aldrich, Lyon, France) supplemented with 0.5% AlbuMAX™ I (Life Technologies corporation, Paisley, United Kingdom), hypoxanthine (Sigma-Aldrich), gentamicin (Sigma-Aldrich), in the presence of human erythrocytes as described previously with some modifications (Trager W and Jensen J B, Science 20 Aug. 1976: Vol. 193, Issue 4254, pp. 673-675 DOI: 10.1126/science.781840). Parasites were incubated at 37° C. under conditions of 5% carbon oxygen.

*P. falciparum* 3D7 or W2 growth inhibition assays were performed using the SYBR Green I assay (Bacon et al; 2007) as previously described with some modifications. Briefly, in vitro cultured asynchronous *P. falciparum* 3D7 or W2 infected erythrocytes (0.5% parasitemia, 1% haematocrit) were seeded, in triplicate wells, in two biological replicates, into 96-well tissue culture plates containing vehicle control (DMSO, <0.5%), positive control (chloroquine, mefloquine and enpiroline) or test compound. Plates were incubated under standard *P. falciparum* culture conditions for 48 h and were then frozen at −20° C. Plates were thawed at room temperature prior to the addition of lysis buffer (20 mM Tris pH 7.5, 5 mM EDTA, 0.008% saponin, 0.08% Triton X-100 containing 0.2 µL/mL of 10,000×SYBR Green I nucleic gel stain dye). The lysates were incubated 30 min at room temperature, protected from light in 96-well flat bottom sterile black plates (Nunc Inc.) The fluorescence was read at an excitation wavelength of 485 nm and an emission wavelength of 535 nm using the microplate reader Infinite® M1000 (TECAN). All $IC_{50}$ values (50% or half maximal inhibitory concentration) were calculated using ICEstimator, a software available online, applying a nonlinear regression method and were determined over one to four independent experiments (mean values f SD) (Le Nagard H et al.; Comput Methods Programs Biomed. 2011 October; 104(1): 10-8. doi: 10.1016/j.cmpb.2010.08.003. Kaddouri H et al.; Antimicrobial Agents and Chemotherapy, 2006, 50: 3343-3349.)

4.2. Results

Antimalarial activities of compounds 1a-1n and 30a-30p obtained with to the first round of susceptibility assays are described in tables 6 and 7, respectively, in comparison with chloroquine and mefloquine.

Activities obtained after the second round of susceptibility assays for compounds 1o, 1p, 1q, 1r, 1u, 1v and their corresponding racemic mixtures and for compounds 30s, 30t, 30u, 30v and their corresponding racemic mixtures and are described in tables 6a and 7a respectively, in comparison with enpiroline.

Compounds 1a-1n possess $IC_{50}$ values in the range of 17.7 (compound 1e) to 125.8 nM (compound 1m) on 3D7 strain and 3.5 (compound 1f) to 86.9 nM (compound 1n) on W2 strain. The 4-aminopyridinemethanol 1e was the most active pyridine synthesized whatever the strain ($IC_{50}$=17.7 nM (3D7) and 5.6 nM (W2)). Compounds 1a-j were more active than the references chloroquine and mefloquine. In this series, the $IC_{50}$ ratio (R)/(S) is weak ranging from 0.45 to 3.07, according to the strain (see table 6).

Compounds 30a-30p have $IC_{50}$ values ranging from 32.9 (compound 30i) and 1379.7 nM (compound 30b) on 3D7 strain and 24.4 nM (compound 30c) and 550.6 (compound 30d) on W2 strain (see table 7). They are more active on the W2 strain than on the 3D7 strain. In this series, a difference of activity was observed between the two enantiomers. The (S)-enantiomers were, most often, more active that their (R)-counterpart whatever the plasmodial strain. For the compounds 30a-30n, the $IC_{50}$ ratio (R)/(S) on the 3D7 strain is ranging from 2.5 to 5.3. For the two enantiomer pairs 30c/30d and 30f/30e, the $IC_{50}$ ratio (R)/(S) is even higher than 19 on the W2 strain (see table 7).

Compounds 1o, 1p, 1q, 1r, 1n and 1v were tested according to the second round of susceptibility assays in comparison with chloroquine, mefloquine and enpiroline. They all showed $IC_{50}$s<50 nM, and are more active than chloroquine and very close to mefloquine and enpiroline $IC_{50}$s (Table 6a). In this series, $IC_{50}$ ratios (RY(S) are close to 1 and the $IC_{50}$ of racemic mixtures (S)+(R) (50:50) are also close to the $IC_{50}$ of each enantiomer.

Compounds 30s, 30t, 30a and 30v were tested according to the second round of susceptibility assays in comparison with chloroquine, mefloquine and enpiroline. In this series, a difference of activity was also observed between the two enantiomers. The (S)-enantiomers were, most often, more active that their (R)-counterpart. $IC_{50}$ of the racemic mixture (S)+(R) (50:50) was also determined (table 7a).

TABLE 6

In vitro antimalarial activity of 4-aminopyridinemethanols derivatives 1a-1n.

| Compound | Structure | Absolute configuration | IC$_{50}$ (nM)[a] Plasmodium falciparum | |
|---|---|---|---|---|
| | | | 3D7[b] | W2[c] |
| 1a | | (S) | 52.4 ± 1.7[d] | 8.6 ± 1.0[d] |
| 1b | | (R) | 41.8 ± 5.5[d] | 7.2 ± 0.5[d] |
| 1c | | (S) | 47.1 ± 13.2[d] | N.D.[e] |
| 1d | | (R) | 32.3 ± 2.0[d] | 8.3 ± 0.8[d] |
| 1e | | (S) | 17.7 ± 4.7[d] | 5.6 ± 0.3[d] |
| 1f | | (R) | 54.4 ± 3.2[d] | 3.5 ± 0.5[d] |
| 1g | | (S) | 22.4 ± 2.5[d] | 13.1 ± 1.0[d] |
| 1h | | (R) | 25.0 ± 2.4[d] | 5.9 ± 1.6[d] |
| 1i | | (S,S) | 28.3 ± 1.5[d] | 28.8 ± 3.8[d] |
| 1j | | (R,S) | 32.8 ± 2.9[d] | 14.4 ± 1.4[d] |

TABLE 6-continued

In vitro antimalarial activity of 4-aminopyridinemethanols derivatives 1a-1n.

| Compound | Structure | Absolute configu-ration | IC$_{50}$ (nM)$^a$ Plasmodium falciparum | |
|---|---|---|---|---|
| | | | 3D7$^b$ | W2$^c$ |
| 1k | | (S) | N.D. | N.D. |
| 1l | | (R) | N.D. | N.D. |
| 1m·HCl | | (S) | 125.8 ± 7.2$^d$ | 67.0 ± 9.3$^d$ |
| 1n·HCl | | (R) | 124.9 ± 20.7$^d$ | 86.9 ± 5.9$^d$ |
| CQ | Chloroquine | — | 75.9 ± 3.0$^d$ | 198.8 ± 27.0$^d$ |
| MQ | Mefloquine | — | 79.7 ± 8.5$^d$ | 31.8 ± 1.0$^d$ |

$^a$Results expressed as mean ± standard deviation.
$^b$P. falciparum strain susceptible to CQ and displays decreased susceptibility to MQ.
$^c$P. falciparum strain resistant to CQ and sensitive to MQ.
$^d$SYBR Green I in vitro test was used.
$^e$Not determined.

TABLE 6a

In vitro antimalarial activity of 4-aminopyridinemethanols derivatives pair of enantiomers 1o, 1p; 1q, 1r; 1u, 1v; and their corresponding racemic mixtures

| Compound | Structure | Absolute configu-ration | IC$_{50}$ (nM)$^{a,d,e}$ Plasmodium falciparum | |
|---|---|---|---|---|
| | | | 3D7$^b$ | W2$^c$ |
| 1o | | (S) | 39.29 ± 5.83 | N.D.$^f$ |
| 1p | | (R) | 43.04 ± 9.38 | N.D.$^f$ |
| 1o + 1p 50:50 | | racemic | 55.38$^g$ | N.D.$^f$ |
| 1q | | (S) | 31.35$^g$ | N.D.$^f$ |
| 1r | | (R) | 13.66$^g$ | N.D.$^f$ |
| 1q + 1r 50:50 | | racemic | 34.02$^g$ | N.D.$^f$ |

TABLE 6a-continued

In vitro antimalarial activity of 4-aminopyridinemethanols derivatives pair of
enantiomers 1o, 1p; 1q, 1r; 1u, 1v; and their corresponding racemic mixtures

| Compound | Structure | Absolute configuration | IC$_{50}$ (nM)$^{a,d,e}$ Plasmodium falciparum | |
|---|---|---|---|---|
| | | | 3D7$^b$ | W2$^c$ |
| 1u | | (S) | 9.31 ± 2.16 | N.D.$^f$ |
| 1v | | (R) | 6.88 ± 0.78 | N.D.$^f$ |
| 1u + 1v 50:50 | | racemic | N.D.$^f$ | N.D.$^f$ |
| CQ | Chloroquine | — | 63.48 ± 8.23 | N.D.$^f$ |
| MQ | Mefloquine | — | 32.27 ± 3.2 | N.D.$^f$ |
| | Enpiroline | — | 21.6 ± 1.43 | N.D.$^f$ |

$^a$Results expressed as mean ± standard deviation.
$^b$P. falciparum line susceptible to CQ and displays decreased susceptibility to MQ.
$^c$P. falciparum line resistant to CQ and susceptible to MQ.
$^d$SYBR Green I in vitro assay was used.
$^e$IC$_{50}$s were calculated using ICEstimator software.
$^f$Not determined.
$^g$One biological replicate has been done.

TABLE 7

In vitro antimalarial activity of 3-aminopyridinemethanols derivatives 30a-30p.

| Compound | Structure | Absolute configuration | IC$_{50}$ (nM)$^a$ Plasmodium falciparum | |
|---|---|---|---|---|
| | | | 3D7$^b$ | W2$^c$ |
| 30a | | (S) | 479.0 ± 38.2$^{d,e}$ | 131.7 ± 10.3$^{d,e}$ |
| 30b | | (R) | 1379.7 ± 992.8$^{d,e}$ | 522.8 ± 95.8$^{d,e}$ |
| 30c | | (S) | 232.2 ± 17.0$^{d,e}$ | 24.4 ± 6.2$^{d,e}$ |
| 30d | | (R) | 557.8 ± 50.4$^{d,e}$ | 550.6 ± 6$^{d,e}$ |
| 30e | | (S) | 170.1 ± 24.0$^{d,e}$ | 27.2 ± 9.3$^{d,e}$ |
| 30f | | (R) | 574.8 ± 117.2$^{d,e}$ | 522.6 ± 141.3$^{d,e}$ |

TABLE 7-continued

In vitro antimalarial activity of 3-aminopyridinemethanols derivatives 30a-30p.

| Compound | Structure | Absolute configuration | IC$_{50}$ (nM)$^a$ Plasmodium falciparum | |
|---|---|---|---|---|
| | | | 3D7$^b$ | W2$^c$ |
| 30g | | (S) | 97.0 ± 14.0$^{d,e}$ | 25.2 ± 1.2$^{d,e}$ |
| 30h | | (R) | 518.6 ± 63.3$^{d,e}$ | 31.7 ± 3.4$^{d,e}$ |
| 30i | | (S) | 32.9 ± 8.8$^{d,e}$ | 247.5 ± 36.0$^{d,e}$ |
| 30j | | (R) | 92.1 ± 30.3$^{d,e}$ | 171.2 ± 26.6$^{d,e}$ |
| 30k | | (S,S) | 65.3 ± 8.4$^{d,e}$ | 350.8 ± 50.7$^{d,e}$ |
| 30l | | (R,S) | 413.8 ± 135.2$^{d,e}$ | 257.6 ± 24.7$^{d,e}$ |

TABLE 7-continued

In vitro antimalarial activity of 3-aminopyridinemethanols derivatives 30a-30p.

| Compound | Structure | Absolute configuration | IC$_{50}$ (nM)$^a$ Plasmodium falciparum | |
|---|---|---|---|---|
| | | | 3D7$^b$ | W2$^c$ |
| 30m | (structure with OH, pyridine-CF$_3$, 4-CF$_3$-phenyl, NH-CH$_2$CH$_2$-NH-CH$_2$-ferrocene) | (S) | 228.7 ± 30.6$^{d,e}$ | 233.8 ± 20.0$^{d,e}$ |
| 30n | | (R) | 590.8 ± 45.4$^{d,e}$ | 256.6 ± 37.4$^{d,e}$ |
| 30o | (structure with OH, pyridine-CF$_3$, 4-CF$_3$-phenyl, NH-CH$_2$CH$_2$CH$_2$-piperazine-CH(Ph)$_2$) | (S) | 111.2 ± 8.3$^{d,e}$ | 211.9 ± 38.6$^{d,e}$ |
| 30p | | (R) | 84.9 ± 11.4$^{d,e}$ | 89.6 ± 14.4$^{d,e}$ |
| CQ | Chloroquine | — | 75.9 ± 3.0$^{d,e}$ | 198.8 ± 27.0$^{d,e}$ |
| MQ | Mefloquine | — | 79.7 ± 8.5$^{d,e}$ | 31.8 ± 1.0$^{d,e}$ |

$^a$Results expressed as mean ± standard deviation.
$^b$P. falciparum strain susceptible to CQ and displays decreased susceptibility to MQ.
$^c$P. falciparum strain resistant to CQ and sensitive to MQ.
$^d$SYBR Green I in vitro test was used.
$^e$IC$_{50}$s were calculated using IC$_{50}$ estimator software.

TABLE 7a

In vitro antimalarial activity of 3-aminopyridinemethanols derivatives pair of enantiomers 30s, 30t; 30u, 30v; and their corresponding racemic mixtures.

| Compound | Structure | Absolute configuration | IC$_{50}$ (nM)$^{a,d,e}$ Plasmodium falciparum | |
|---|---|---|---|---|
| | | | 3D7$^b$ | W2$^c$ |
| 30s | (structure with OH, pyridine-CF$_3$, 4-CF$_3$-phenyl, NH-(CH$_2$)$_n$-F) | (S) | 420.84 | 97.09 |
| 30t | | (R) | 1455.37 | 181.49 |
| 30s + 30t 50:50 | | racemic | 1223.47 | 195.49 |

TABLE 7a-continued

In vitro antimalarial activity of 3-aminopyridinemethanols derivatives pair of enantiomers 30s, 30t; 30u, 30v; and their corresponding racemic mixtures.

| Compound | Structure | Absolute configuration | IC$_{50}$ (nM)[a,d,e] Plasmodium falciparum | |
|---|---|---|---|---|
| | | | 3D7[b] | W2[c] |
| 30u | 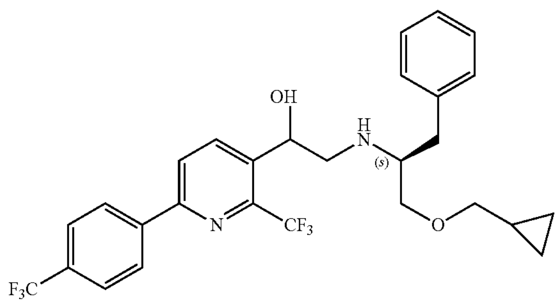 [SMILES: OC(CN[C@H](COCC1CC1)Cc1ccccc1)c1ccc(-c2ccc(C(F)(F)F)cc2)nc1C(F)(F)F] | (S) | 164.68±21.93 | N.D.[f] |
| 30v | | (R) | 896.34±56.73 | N.D.[f] |
| 30u + 30v 50:50 | | racemic | 292.61[g] | N.D.[f] |
| CQ | Chloroquine | — | 63.48 ± 8.23 | N.D.[f] |
| MQ | Mefloquine | — | 32.27 ± 3.2 | N.D.[f] |
| | Enpiroline | — | 21.6 ± 1.43 | N.D.[f] |

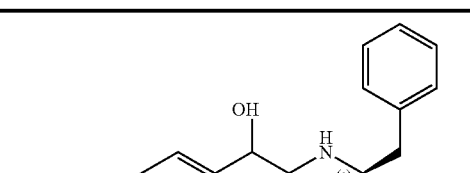

[a]Results expressed as mean ± standard deviation.
[b]P. falciparum line susceptible to CQ and displays decreased susceptibility to MQ.
[c]P. falciparum line resistant to CQ and susceptible to MQ.
[d]SYBR Green I in vitro assay was used.
[e]IC$_{50}$s were calculated using ICEstimator software.
[f]Not determined.
[g]One biological replicate has been done.

Example 5. Pharmacokinetic Profile

In order to predict the pharmacokinetics profiles of the 3- and 4-aminopyridinemethanols, some properties were calculated with the QikProp software (table 8). Globally, the lead compounds possess a good pharmacokinetic profile with values in the recommended standard.

TABLE 8

PK profiles calculated with QikProp.

| Compound | MM[a] | QPlogPo/w[b] | QPlogS[c] | QPlogHERG[d] | QPPcaco[e] | QPlogBB[f] |
|---|---|---|---|---|---|---|
| 30c, 30d | 420.40 | 4.88 | −5.52 | −6.61 | 1099.46 | 0.58 |
| 30g, 30h | 448.45 | 5.60 | −6.32 | −6.94 | 1099.50 | 0.43 |
| 1a, 1b | 420.40 | 5.05 | −5.72 | −6.63 | 656.44 | 0.24 |
| 1e, 1f | 448.45 | 5.78 | −6.53 | −6.95 | 656.42 | 0.08 |
| 1g, 1h | 559.55 | 6.60 | −7.09 | −10.02 | 146.50 | 0.36 |
| Chloroquine | 319.88 | 3.95 | −5.52 | −6.16 | 1239.61 | 0.32 |
| Enpiroline | 404.35 | 4.53 | −5.23 | −6.19 | 927.23 | 0.74 |
| Mefloquine | 378.32 | 3.88 | −4.62 | −6.03 | 1249.15 | 0.91 |
| Recommended values | 130-725 | −2.0-6.5 | −6.5-0.5 | Concern below −5 | <25 poor, >500 great | −3.0-1.2 |

[a]Molecular weight of the molecule.
[b]Predicted octanol/water partition coefficient.
[c]Predicted aqueous solubility, log S. S in mol dm$^{-3}$ is the concentration of the solute in a saturated solution that is in equilibrium with the crystalline solid.
[d]Predicted IC$_{50}$ value for blockage of HERG K+ channels.
[e]Predicted apparent Caco-2 cell permeability in nm/sec. Caco-2 cells are a model for the gut-blood barrier. QikProp predictions are for non-active transport.
[f]Predicted brain/blood partition coefficient.

Example 6. Toxicity: Cytotoxicity, Genotoxicity

6.1. In Vine Micronucleus Assays

6.1.1. Method a. Assay Protocol/Short-Term Exposure

All the assays were conducted in duplicate. The CHO-K$_1$ cells, suspended in McCoy's 5A medium, were transferred into Labteck wells at a concentration of 100,000 cells/mL, and incubated for 24 hours at 37° C. in CO$_2$ (5%).

When the test was performed without metabolic activation, the test substances were added into cell cultures at concentrations previously defined. A negative control containing culture medium, a solvent control containing 1% DMSO and a positive control containing 0.6 μg/mL of mitomycin C were added.

When the assay was performed in the presence of metabolic activation, S9 mix metabolizing mixture was added to cell cultures at a concentration of 10%. Then the test substances were added to the cell cultures at concentrations previously defined. A negative control containing culture medium, a solvent control containing 1% DMSO and a positive control containing 5 µg/mL of benzo-a-pyrene were added.

After 3 hours of incubation at 37° C. in $CO_2$ (5%), the culture medium was removed, the cells were rinsed with phosphate buffered saline (PBS), and then returned to culture in McCoy's 5A medium containing 3 sg/mL of cytochalasin B. After a 21-hour incubation period at 37° C., cells were rinsed with phosphate buffered saline (PBS), fixed with methanol and stained with 10% Giemsa for 20 minutes.

b. Assay Protocol/Long-Term Exposure

The protocol based on a long-term exposure was conducted when negative results were obtained with the short-term exposure assay. All the assays were conducted in duplicate. The CHO-$K_1$ cells, suspended in Mac Coy's 5A medium, were transferred into Labteck wells at a concentration of 100,000 cells/mL, and incubated for 24 hours at 37° C. in $CO_2$ (5%).

The test was performed without metabolic activation: the test substances were added into cell cultures at concentrations previously defined. A negative control containing culture medium, a solvent control containing 1% DMSO and a positive control containing 0.6 µg/mL of mitomycin C were added. After 24 hours of incubation at 37° C. in $CO_2$ (5%), the culture medium was removed, the cells were rinsed with phosphate buffered saline (PBS), and then returned in culture medium containing 3 sg/mL of cytochalasine B. After a 24-hour incubation period at 37° C., cells were rinsed with phosphate buffered saline (PBS), fixed with methanol and stained with 10% Giemsa for 20 minutes.

c. Analysis of Results

The analysis of results was performed under a microscope at ×1000 magnification. The antiproliferative activity of test substances was estimated by counting the number of binucleated cells relative to the number of mononucleated cells on a total of 500 cells for each dose (250 cells counted per well). The proliferation index (Cytokinesis Blocked Proliferative Index CBPI) was calculated using the following formula:

$$CPBI = \frac{2 \times BI + MONO}{500}$$

$BI$: number of binucleted cells $MONO$: number of mononucleated cells

The cytostasis index (CI %), i.e. the percentage of cell replication inhibition, was calculated using the following formula:

$$CI\% = 100 - \{100 \times (CBPI_{test\ material} - 1)/(CBPI_{solvent\ control} - 1)\}$$

After this step, only the doses inducing a decrease of less than 55±5% of CI % as compared to the negative control were taken into account for counting micronuclei.

The rates of micronuclei were evaluated for the presence of independent nuclear core entities in 1000 binucleated cells per well, which corresponds to 2000 cells examined by test substance dose. Micronuclei were identified as small nuclei well differentiated from cell nucleus, stained in the same manner and having a diameter less than one third of that of the cell nucleus.

Micronuclei rates obtained for different doses of test substances were compared to the negative control by a $\chi 2$ test. The assay was considered positive if:

A dose-response relationship was obtained between the rate of micronuclei and the doses tested, At least one of these doses induced a statistically significant increase ($P<0.05$) in the number of micronucleated cells as compared to the negative control.

6.1.2. Results a. Solubility of Test Substances

Examination of cell culture wells at the end of incubation period by inverted microscope was used to check the absence of precipitate or emulsion in cell cultures treated with the test substances.

b. Validity of the Experiments

CBPI values in control cultures showed adequate viability and growth. The rate of micronucleated cells in the control cultures (negative controls and positive controls) was consistent with historical values of the laboratory:

CBPI between 1.78 and 1.86

Micronucleated cell rates between 8 and 14% in the negative controls

Micronucleated cell rates between 25 and 35% in the mitomycin C control

Micronucleated cell rates between 20 and 30% in the benzo-a-pyrene control c. Results of the Short-Term Exposure Assay Results observed for the micronucleus assay with and without metabolic activation (S9 mix) for compounds of the invention (S)-1i, (S)-30c and (S)-1a are summarized in the following tables.

TABLE 9

| | Results observed for (S)-1i. | | | | | | | |
|---|---|---|---|---|---|---|---|---|
| | Proliferation index | | | | Micronucleated cell rates ‰ | | | |
| | BI | MONO | CBPI | CI % | MNC1 | MNC2 | MNC-M | P |
| Test without S9 mix | | | | | | | | |
| Control | 464 | 36 | 1.92 | 0 | 10 | 11 | 10.5 ± 0.7 | — |
| Solvent control | 460 | 40 | 1.92 | 0 | 9 | 10 | 9.5 ± 0.7 | — |
| Mitomycin C control | 452 | 48 | 1.91 | 1 | 28 | 32 | 30 ± 2.8 | <0.001 |
| (µM)          10 | 438 | 62 | 1.88 | 4 | 10 | 12 | 11 ± 1.4 | >0.05 NS |
|               50 | 347 | 153 | 1.69 | 25 | 11 | 9 | 10 ± 1.4 | >0.05 NS |
|              100 | 212 | 288 | 1.42 | 54 | 12 | 14 | 11 ± 1.4 | >0.05 NS |
|              500 | TOXIC | TOXIC | TOXIC | TOXIC | — | — | — | |
| Test with S9 mix | | | | | | | | |
| Control | 481 | 19 | 1.96 | 0 | 10 | 11 | 10.5 ± 0.7 | — |
| Solvent control | 485 | 15 | 1.97 | 0 | 9 | 10 | 9.5 ± 0.7 | — |

TABLE 9-continued

Results observed for (S)-1i.

|  | | Proliferation index | | | Micronucleated cell rates ‰ | | | |
|---|---|---|---|---|---|---|---|---|
|  | | BI | MONO | CBPI | CI % | MNC1 | MNC2 | MNC-M | P |
| Benzo-a-pyrene control | | 475 | 25 | 1.95 | 2 | 28 | 25 | 26.5 ± 2.12 | <0.001 |
| (µM) | 10 | 443 | 57 | 1.89 | 8 | 9 | 11 | 10 ± 1.4 | >0.05 NS |
|  | 50 | 388 | 112 | 1.76 | 21 | 10 | 12 | 11 ± 1.4 | >0.05 NS |
|  | 100 | 236 | 264 | 1.47 | 51 | 11 | 9 | 10 ± 1.4 | >0.05 NS |
|  | 500 | TOXIC | TOXIC | TOXIC | TOXIC | — | — | — | — |

BI: Binucleated cells
MONO: Mononucleated cells
CBPI: Cytokinesis-Blocked Proliferative Index
CI %: Cytostasis index expressed in percentage as compared to the control
MNC1, MNC-2: Micronucleated cell rates
MNC-M: Means of the micronucleated cell rates
P: probability of the chi-squared test (p < 0.05: significant difference as compared to the control culture)
NS: non-significant difference as compared to the control culture

TABLE 10

Results observed for (S)-30c.

|  | | Proliferation index | | | | Micronucleated cell rates ‰ | | | |
|---|---|---|---|---|---|---|---|---|---|
|  | | BI | MONO | CBPI | CBPI % | MNC1 | MNC2 | MNC-M | P |
| Test without S9 mix | | | | | | | | | |
| Control | | 464 | 36 | 1.92 | 0 | 10 | 11 | 10.5 ± 0.7 | — |
| Solvent control | | 460 | 40 | 1.92 | 0 | 9 | 10 | 9.5 ± 0.7 | — |
| Mitomycin C control | | 452 | 48 | 1.91 | 1 | 28 | 32 | 30 ± 2.8 | <0.001 |
| (µM) | 10 | 448 | 52 | 1.90 | 2 | 8 | 9 | 8.5 ± 0.7 | >0.05 NS |
|  | 50 | 384 | 116 | 1.76 | 18 | 11 | 12 | 11.5 ± 0.7 | >0.05 NS |
|  | 100 | 211 | 289 | 1.43 | 51 | 12 | 15 | 13.5 ± 2.1 | >0.05 NS |
|  | 500 | TOXIC | TOXIC | TOXIC | TOXIC | — | — | — | — |
| Test with S9 mix | | | | | | | | | |
| Control | | 481 | 19 | 1.96 | 0 | 10 | 11 | 10.5 ± 0.7 | — |
| Solvent control | | 485 | 15 | 1.97 | 0 | 9 | 10 | 9.5 ± 0.7 | — |
| Benzo-a-pyrene control | | 475 | 25 | 1.95 | 2 | 28 | 25 | 26.5 ± 2.12 | <0.001 |
| (µM) | 10 | 473 | 27 | 1.94 | 3 | 9 | 12 | 9.5 ± 0.7 | >0.05 NS |
|  | 50 | 452 | 48 | 1.91 | 6 | 10 | 11 | 10 ± 1.4 | >0.05 NS |
|  | 100 | 267 | 233 | 1.53 | 44 | 9 | 9 | 11 ± 1.4 | >0.05 NS |
|  | 500 | TOXIC | TOXIC | TOXIC | TOXIC | — | — | — | — |

BI: Binucleated cells
MONO: Mononucleated cells
CBPI: Cytokinesis-Blocked Proliferative Index
CI %: Cytostasis index expressed in percentage as compared to the control
MNC1, MNC-2: Micronucleated cell rates
MNC-M: Means of the micronucleated cell rates
P: probability of the chi-squared test (p < 0.05: significant difference as compared to the control culture)
NS: non-significant difference as compared to the control culture

TABLE 11

Results observed for (S)-1a.

|  | | Proliferation index | | | | Micronucleated cell rates ‰ | | | |
|---|---|---|---|---|---|---|---|---|---|
|  | | BI | MONO | CBPI | CBPI % | MNC1 | MNC2 | MNC-M | P |
| Test without S9 mix | | | | | | | | | |
| Control | | 464 | 36 | 1.92 | 0 | 10 | 11 | 10.5 ± 0.7 | — |
| Solvent control | | 460 | 40 | 1.92 | 0 | 9 | 10 | 9.5 ± 0.7 | — |
| Mitomycin C control | | 452 | 48 | 1.91 | 1 | 28 | 32 | 30 ± 2.8 | <0.001 |
| (µM) | 10 | 446 | 54 | 1.89 | 3 | 10 | 12 | 9.5 ± 0.7 | >0.05 NS |
|  | 50 | 394 | 106 | 1.78 | 16 | 9 | 13 | 10 ± 1.4 | >0.05 NS |

TABLE 11-continued

Results observed for (S)-1a

|  | | Proliferation index | | | | Micronucleated cell rates ‰ | | | |
| --- | --- | --- | --- | --- | --- | --- | --- | --- | --- |
|  | | BI | MONO | CBPI | CBPI % | MNC1 | MNC2 | MNC-M | P |
|  | 100 | 229 | 271 | 1.46 | 52 | 11 | 11 | 11 ± 1.4 | >0.05 NS |
|  | 500 | TOXIC | TOXIC | TOXIC | TOXIC | — | — | — | — |
| Test with S9 mix | | | | | | | | | |
| Control | | 481 | 19 | 1.96 | 0 | 10 | 11 | 10.5 ± 0.7 | — |
| Solvent control | | 485 | 15 | 1.97 | 0 | 9 | 10 | 9.5 ± 0.7 | — |
| Benzo-a-pyrene control | | 475 | 25 | 1.95 | 2 | 28 | 25 | 26.5 ± 2.12 | <0.001 |
| (µM) | 10 | 462 | 38 | 1.93 | 4 | 11 | 8 | 9.5 ± 0.7 | >0.05 NS |
|  | 50 | 443 | 57 | 1.88 | 9 | 10 | 12 | 10 ± 1.4 | >0.05 NS |
|  | 100 | 267 | 233 | 1.53 | 44 | 8 | 14 | 11 ± 1.4 | >0.05 NS |
|  | 500 | TOXIC | TOXIC | TOXIC | TOXIC | — | — | — | — |

BI: Binucleated cells
MONO: Mononucleated cells
CBPI: Cytokinesis-Blocked Proliferative Index
CI %: Cytostasis index expressed in percentage as compared to the control
MNC1, MNC-2: Micronucleated cell rates
MNC-M: Means of the micronucleated cell rates
P: probability of the chi-squared test (p < 0.05: significant difference as compared to the control culture)
NS: non-significant difference as compared to the control culture d. Results of the Long-Term Exposure Assay Results observed for the micronucleus assay without metabolic activation (S9 mix) for compounds of the invention (S)-1i, (S)-30c and (S)-1a are summarized in the following tables:

TABLE 12

Results observed for (S)-1i.

|  | | Proliferation index | | | | Micronucleated cell rates ‰ | | | |
| --- | --- | --- | --- | --- | --- | --- | --- | --- | --- |
| Test without S9 mix | | BI | MONO | CBPI | CI % | MNC1 | MNC2 | MNC-M | P |
| Control | | 463 | 37 | 1.92 | 0 | 10 | 11 | 10.5 ± 0.7 | — |
| Solvent control | | 455 | 45 | 1.91 | 0 | 9 | 10 | 9.5 ± 0.7 | — |
| Mitomycin C control | | 448 | 52 | 1.89 | 3 | 28 | 32 | 30 ± 2.8 | <0.001 |
| (µM) | 5 | 402 | 98 | 1.81 | 13 | 9 | 11 | 10 ± 1.4 | >0.05 NS |
|  | 10 | 308 | 192 | 1.62 | 34 | 10 | 12 | 11 ± 1.4 | >0.05 NS |
|  | 50 | 214 | 286 | 1.42 | 57 | 11 | 9 | 10 ± 1.4 | >0.05 NS |
|  | 100 | TOXIC | TOXIC | TOXIC | TOXIC | — | — | — | — |

BI: Binucleated cells
MONO: Mononucleated cells
CBPI: Cytokinesis-Blocked Proliferative Index
CI %: Cytostasis index expressed in percentage as compared to the control
MNC1, MNC-2: Micronucleated cell rates
MNC-M: Means of the micronucleated cell rates
P: probability of the chi-squared test (p < 0.05: significant difference as compared to the control culture)
NS: non-significant difference as compared to the control culture

TABLE 13

Results observed for (S)-30c.

|  | | Proliferation index | | | | Micronucleated cell rates ‰ | | | |
| --- | --- | --- | --- | --- | --- | --- | --- | --- | --- |
| Test without S9 mix | | BI | MONO | CBPI | CI % | MNC1 | MNC2 | MNC-M | P |
| Control | | 463 | 37 | 1.92 | 0 | 10 | 11 | 10.5 ± 0.7 | — |
| Solvent control | | 455 | 45 | 1.91 | 0 | 9 | 10 | 9.5 ± 0.7 | — |
| Mitomycin C control | | 448 | 52 | 1.89 | 3 | 28 | 32 | 30 ± 2.8 | <0.001 |
| (µM) | 5 | 432 | 68 | 1.86 | 5 | 8 | 12 | 10 ± 2.8 | >0.05 NS |
|  | 10 | 331 | 169 | 1.66 | 27 | 9 | 11 | 10 ± 1.4 | >0.05 NS |

TABLE 13-continued

Results observed for (S)-30c.

| Test without S9 mix | Proliferation index | | | | Micronucleated cell rates ‰ | | | |
|---|---|---|---|---|---|---|---|---|
| | BI | MONO | CBPI | CI % | MNC1 | MNC2 | MNC-M | P |
| 50 | 218 | 282 | 1.42 | 52 | 10 | 12 | 11 ± 1.4 | >0.05 NS |
| 100 | TOXIC | TOXIC | TOXIC | TOXIC | — | — | — | — |

BI: Binucleated cells
MONO: Mononucleated cells
CBPI: Cytokinesis-Blocked Proliferative Index
CI %: Cytostasis index expressed in percentage as compared to the control
MNC1, MNC-2: Micronucleated cell rates
MNC-M: Means of the micronucleated cell rates
P: probability of the chi-squared test (p < 0.05: significant difference as compared to the control culture)
NS: non-significant difference as compared to the control culture

TABLE 14

Results observed for (S)-1a.

| Test without S9 mix | Proliferation index | | | | Micronucleated cell rates ‰ | | | |
|---|---|---|---|---|---|---|---|---|
| | BI | MONO | CBPI | CI % | MNC1 | MNC2 | MNC-M | P |
| Control | 463 | 37 | 1.92 | 0 | 10 | 11 | 10.5 ± 0.7 | — |
| Solvent control | 455 | 45 | 1.91 | 0 | 9 | 10 | 9.5 ± 0.7 | — |
| Mitomycin C control | 448 | 52 | 1.89 | 3 | 28 | 32 | 30 ± 2.8 | <0.001 |
| (µM) 5 | 417 | 83 | 1.83 | 8 | 10 | 9 | 9.5 ± 0.7 | >0.05 NS |
| 10 | 323 | 177 | 1.64 | 29 | 9 | 11 | 10 ± 1.4 | >0.05 NS |
| 50 | 226 | 274 | 1.46 | 52 | 10 | 12 | 11 ± 1.4 | >0.05 NS |
| 100 | TOXIC | TOXIC | TOXIC | TOXIC | — | — | — | — |

BI: Binucleated cells
MONO: Mononucleated cells
CBPI: Cytokinesis-Blocked Proliferative Index
CI %: Cytostasis index expressed in percentage as compared to the control
MNC1, MNC-2: Micronucleated cell rates
MNC-M: Means of the micronucleated cell rates
P: probability of the chi-squared test (p < 0.05: significant difference as compared to the control culture)
NS: non-significant difference as compared to the control culture

6.13. Conclusion

The compounds of the invention (S)-1i, (S)-30c and (S)-1a gave negative results in the in vitro micronucleus assay conducted according to the OECD guideline No 487. They are devoid of clastogenic and/or aneugenic activities in the experimental conditions described in this guideline.

6.2. Bacterial Reverse Mutation Assay (Ames Test)

6.2.1. Chemicals

All reagents were handled and used in sterile conditions.
Nutrient Broth No. 2 and agar (Oxoid France, France).
Ampicillin and tetracyclin solutions (Sigma-Aldrich, France).
Histidin and biotin and all the reagents for culture media and salt solutions were from Sigma-Aldrich, France).
Positive controls: sodium azide, mitomycin C, benzo[a]pyrene (BaP), 2-methoxy-6-chloro-9-(3-(2-chloroethyl)aminopropylamino)acridine (ICR 191), 2,4,7-trinitrofluorenone (TNFone), (Sigma-Aldrich: stock solutions 1 mg/mL in DMSO, storage at −80° C.).
Liver homogenate used for metabolic activation (S9): S9 was prepared from male Sprague-Dawley rats treated with Aroclor 1254 (500 mg/kg body weight).

6.2.2. Salmonella Strains

Five strains of *S. typhimurium* were used. They included four strains with GC base pairs at the primary reversion site, which have been shown to be reliable and reproducibly responsive between laboratories: TA1535, TA97a, TA98, and TA100. An additional strain has been chosen to detect cross-linking mutagens, hydrazines and oxidative agents: TA102, which have an AT base pair at the primary reversion site. *Salmonella* tester strains were gifts from Prof. B. N. Ames (Berkeley, Calif., USA). They were stored at −80° C. and regularly checked for genetic markers.

TABLE 15

Genetic characteristics of the Ames tester strains.

| Strains | His Mutations | LPS[a] | repair[b] | pKM101[c] | Revertants[d] |
|---|---|---|---|---|---|
| TA 1535 | hisG46 [g] | rfa | ΔuvrB | — | 5-40 |
| TA 97a | hisO1242 [e] hisD6610 | rfa | ΔuvrB | +R | 90-280 |

TABLE 15-continued

Genetic characteristics of the Ames tester strains.

| Strains | His Mutations | LPS[a] | repair[b] | pKM101[c] | Revertants[d] |
|---|---|---|---|---|---|
| TA 98 | hisD3052 [f] | rfa | ΔuvrB | +R | 15-60 |
| TA 100 | HisG46 [g] | rfa | ΔuvrB | +R | 100-240 |
| TA 102 | hisG428 [h] sur pAQ1 | rfa | + | +R | 240-500 |

[a] rfa mutation (deep rough): this mutation modifies the structure of the cell wall and allows the passage of large molecules.
[b] Deletion of the uvrB gene, this mutation decreases the efficacy of the nucleotide excision repair system and thus increases repair by the mutagenic SOS pathway.
[c] pKM101 Plasmid: carry mucA et mucB genes that increase the sensitivity of the strains to mutagens by the amplifying the activity of SOS repair system (Witkin, 1976). This plasmid also includes a gene for ampicillin resistance.
[d] Number of spontaneous revertants/plate (cumulated historical values since 1983).
[e] Frameshift his6610: mutation which was incorporated by the his01242 mutation and corresponded to the addition of one cytosine. The site of this mutation is constituted by a run of six G-C close to a second repetitive run of G-C-C-G. The tester strain TA 97a detects frameshift mutations by addition of base pairs (exp: ICR-191, acridine orange).
[f] Frameshift hisD3052 mutation is due to the loss of one base pair near a run of a repetitive series of 8 G-C. The tester strain TA 98 detects frameshift mutagens by loss of base pairs (exp: benzo[a]pyrene, 2-aminoanthracene).
[g] The hisG46 mutation is a GC ⇒ AT transition corresponding to the substitution of the proline codon by the leucine codon. The tester strain TA 100 can detect base pair (point) mutations (exp: NaN₃; metronidazole).
[h] The hisG428 is an ochre mutation of the hisG gene in the region of the histidine operator, G, D and part of the C genes. The hisG428 was introduced in the pAQ1 plasmid. Another mutation hisΔ(G)8476 in the genome, insures that his reversion is possible through the hisG428 mutation. The strain TA 102 includes 20-60 copies of pAQ1. This plasmid contains also a tetracycline resistance gene. The tester strain TA102 can detect oxidative types of mutagens (exp: $H_2O_2$) and a variety of mutagens that are not detected or are poorly detected by the other tester strains (exp: bleomycin, mitomycin C).

6.2.3. Assay Protocol

Few crystals of the frozen working strains were taken with a sterile pipette, and seeded in 10 mL of nutrient broth (NB No 2, Oxoid). Strains were grown overnight at 37° C. with shaking in Nutrient Broth No. 2, with ampicillin (25 μg/mL) for TA1535, TA97a, TA98, and TA 100, or ampicillin (25 μg/mL) plus tetracyclin (2 μg/mL) for TA 102. At the end of the incubation period, 0.1 mL of each overnight culture was mixed to 0.1 mL S9 Mix or 0.1 mL phosphate-buffered saline (PBS, pH 7.4) in 5 mL plastic tubes and various volumes of the tested samples were added to the mixtures. Each experiment included triplicate plates of four tested doses. A solvent (DMSO, 10 μL) control was added to determine the spontaneous frequency of revertants (quadruple plates). Five positive controls were also included to ensure the performance of the tester strains and the S9 Mix. After a 60 min pre-incubation period at 37° C., 2 mL of melted top agar, complemented with 40 μg/mL histidine and 48.8 μg/mL biotin mix, was added to each tube and the contents were poured immediately onto Vogel-Bonner minimal agar plates. After hardening, the plates were incubated at 37° C. for 48 hours.

6.2.4. Analysis of Results

At the end of the incubation period, revertants were counted with a laser colony counter equipped with a bacterial enumeration program (Spiral System Instrument Inc., Bethesda, Md., USA).

The Dunnett test was performed to determine a significant difference between the mean number of induced revertants and the mean number of spontaneous revertants. The assay was considered positive if:

a dose-response relationship was obtained between the rate revertants and the doses, at least one of these doses induced a statistically significant increase ($P<0.05$) in the number of revertants as compared to the negative control.

6.2.5. Results a. Solubility of Test Substances

Examination of plates at the end of incubation period was used to check the absence of precipitate or emulsion.

b. Validity of the Experiments

Values in negative and positive control plates were consistent with the historical data obtained in the laboratory.

c. Results of the Assay

Results observed for the bacterial reverse mutation assay for compounds of the invention (S)-1i, (S)-30c and (S)-1a are presented in the following tables. Due to the strong toxicity of the compounds, a 1/10 dilution gradient was applied.

TABLE 16

Results observed for (S)-1i.

| | | Number of revertants by plate (Means ± SD) | | | | |
|---|---|---|---|---|---|---|
| | | TA1535 | TA97a | TA98 | TA100 | TA102 |
| Test without S9 mix | | | | | | |
| Control | | 24 ± 6 | 141 ± 8 | 33 ± 3 | 189 ± 5 | 402 ± 17 |
| Solvent control | | 25 ± 8 | 143 ± 3 | 25 ± 3 | 179 ± 7 | 365 ± 13 |
| Positive controls | ICR 191 | NT | 2511 ± 122*** | NT | NT | NT |
| | TNFone | NT | NT | 525 ± 33*** | NT | NT |
| | NaN₃ | 68 ± 10*** | NT | NT | 290 ± 14*** | NT |
| | MitC | NT | NT | NT | NT | 1412 ± 69*** |
| (μg/plate) | 0.4 | 22 ± 4$^{NS}$ | 153 ± 5$^{NS}$ | 32 ± 3$^{NS}$ | 200 ± 7$^{NS}$ | 332 ± 19$^{NS}$ |
| | 0.6 | 29 ± 6$^{NS}$ | 163 ± 4$^{NS}$ | 33 ± 3$^{NS}$ | 199 ± 10$^{NS}$ | 293 ± 4$^{NS}$ |
| | 0.8 | 28 ± 5$^{NS}$ | 164 ± 5$^{NS}$ | 33 ± 3$^{NS}$ | 209 ± 17$^{NS}$ | 328 ± 14$^{NS}$ |
| | 1 | 20 ± 4$^{NS}$ | 144 ± 11$^{NS}$ | 34 ± 7$^{NS}$ | 205 ± 21$^{NS}$ | 347 ± 11$^{NS}$ |
| Test with S9 mix | | | | | | |
| Control | | 25 ± 8 | 145 ± 12 | 29 ± 8 | 197 ± 6 | 384 ± 18 |
| Solvent control | | 28 ± 8 | 139 ± 6 | 32 ± 4 | 184 ± 9 | 395 ± 15 |
| Positive control (BAP) | | 519 ± 9*** | 1081 ± 51*** | 658 ± 51*** | 810 ± 11*** | 719 ± 44*** |
| (μg/plate) | 0.4 | 23 ± 6$^{NS}$ | 132 ± 11$^{NS}$ | 24 ± 2$^{NS}$ | 191 ± 11$^{NS}$ | 351 ± 6$^{NS}$ |
| | 0.6 | 29 ± 4$^{NS}$ | 137 ± 2$^{NS}$ | 18 ± 3$^{NS}$ | 173 ± 10$^{NS}$ | 355 ± 16$^{NS}$ |
| | 0.8 | 27 ± 5$^{NS}$ | 127 ± 9$^{NS}$ | 17 ± 1$^{NS}$ | 182 ± 10$^{NS}$ | 376 ± 10$^{NS}$ |
| | 1 | 29 ± 9$^{NS}$ | 124 ± 4$^{NS}$ | 20 ± 2$^{NS}$ | 174 ± 10$^{NS}$ | 362 ± 4$^{NS}$ |

NT: not tested.
$^{NS}$No significant difference as compared to the control by the Dunnett test.
***$P < 0.001$

TABLE 17

Results observed for (S)-30c.

Number of revertants by plate (Means ± SD)

| | | TA1535 | TA97a | TA98 | TA100 | TA102 |
|---|---|---|---|---|---|---|
| Test without S9 mix | | | | | | |
| Control | | 24 ± 6 | 141 ± 8 | 33 ± 3 | 189 ± 5 | 402 ± 17 |
| Solvent control | | 25 ± 8 | 143 ± 3 | 25 ± 3 | 179 ± 7 | 365 ± 13 |
| Positive controls | ICR 191 | NT | 2511 ± 122*** | NT | NT | NT |
| | TNFone | NT | NT | 525 ± 33*** | NT | NT |
| | $NaN_3$ | 68 ± 10*** | NT | NT | 290 ± 14*** | NT |
| | MitC | NT | NT | NT | NT | 1412 ± 69*** |
| (µg/plate) | 0.4 | 26 ± 3$^{NS}$ | 148 ± 8$^{NS}$ | 35 ± 3$^{NS}$ | 197 ± 6$^{NS}$ | 298 ± 21$^{NS}$ |
| | 0.6 | 25 ± 4$^{NS}$ | 155 ± 6$^{NS}$ | 33 ± 2$^{NS}$ | 201 ± 9$^{NS}$ | 319 ± 14$^{NS}$ |
| | 0.8 | 28 ± 8$^{NS}$ | 159 ± 8$^{NS}$ | 34 ± 5$^{NS}$ | 211 ± 12$^{NS}$ | 331 ± 17$^{NS}$ |
| | 1 | 25 ± 6$^{NS}$ | 138 ± 8$^{NS}$ | 32 ± 6$^{NS}$ | 206 ± 14$^{NS}$ | 339 ± 12$^{NS}$ |
| Test with S9 mix | | | | | | |
| Control | | 25 ± 8 | 145 ± 12 | 29 ± 8 | 197 ± 6 | 384 ± 18 |
| Solvent control | | 28 ± 8 | 139 ± 6 | 32 ± 4 | 184 ± 9 | 395 ± 15 |
| Positive control (BAP) | | 519 ± 9*** | 1081 ± 51*** | 658 ± 51*** | 810 ± 11*** | 719 ± 44*** |
| (µg/plate) | 0.4 | 22 ± 5$^{NS}$ | 128 ± 10$^{NS}$ | 34 ± 6$^{NS}$ | 202 ± 8$^{NS}$ | 346 ± 8$^{NS}$ |
| | 0.6 | 26 ± 6$^{NS}$ | 134 ± 8$^{NS}$ | 38 ± 5$^{NS}$ | 183 ± 12$^{NS}$ | 349 ± 12$^{NS}$ |
| | 0.8 | 25 ± 8$^{NS}$ | 137 ± 11$^{NS}$ | 28 ± 4$^{NS}$ | 178 ± 11$^{NS}$ | 368 ± 11$^{NS}$ |
| | 1 | 26 ± 7$^{NS}$ | 125 ± 8$^{NS}$ | 26 ± 6$^{NS}$ | 168 ± 12$^{NS}$ | 359 ± 6$^{NS}$ |

NT: not tested.
$^{NS}$No significant difference as compared to the control by the Dunnett test.
***P < 0.001

TABLE 18

Results observed for (S)-1a.

Number of revertants by plate (Means ± SD)

| | | TA1535 | TA97a | TA98 | TA100 | TA102 |
|---|---|---|---|---|---|---|
| Test without S9 mix | | | | | | |
| Control | | 24 ± 6 | 141 ± 8 | 33 ± 3 | 189 ± 5 | 402 ± 17 |
| Solvent control | | 25 ± 8 | 143 ± 3 | 25 ± 3 | 179 ± 7 | 365 ± 13 |
| Positive controls | ICR 191 | NT | 2511 ± 122 | NT | NT | NT |
| | TNFone | NT | NT | 525 ± 33*** | NT | NT |
| | $NaN_3$ | 68 ± 10*** | NT | NT | 290 ± 14*** | NT |
| | MitC | NT | NT | NT | NT | 1412 ± 69*** |
| (µg/plate) | 0.4 | 25 ± 6$^{NS}$ | 161 ± 8$^{NS}$ | 30 ± 4$^{NS}$ | 189 ± 8 | 319 ± 12$^{NS}$ |
| | 0.6 | 30 ± 5$^{NS}$ | 155 ± 6$^{NS}$ | 28 ± 8$^{NS}$ | 192 ± 9$^{NS}$ | 308 ± 10$^{NS}$ |
| | 0.8 | 31 ± 4$^{NS}$ | 159 ± 8$^{NS}$ | 31 ± 6$^{NS}$ | 215 ± 13$^{NS}$ | 325 ± 13$^{NS}$ |
| | 1 | 26 ± 6$^{NS}$ | 154 ± 9$^{NS}$ | 24 ± 5$^{NS}$ | 196 ± 14$^{NS}$ | 318 ± 10$^{NS}$ |
| Test without S9 mix | | | | | | |
| Control | | 25 ± 8 | 145 ± 12 | 29 ± 8 | 197 ± 6 | 384 ± 18 |
| Solvent control | | 28 ± 8 | 139 ± 6 | 32 ± 4 | 184 ± 9 | 395 ± 15 |
| Positive control (BAP) | | 519 ± 9*** | 1081 ± 51*** | 658 ± 51*** | 810 ± 11*** | 719 ± 44*** |
| (µg/plate) | 0.4 | 29 ± 8$^{NS}$ | 128 ± 8$^{NS}$ | 28 ± 3$^{NS}$ | 185 ± 8 | 387 ± 8$^{NS}$ |
| | 0.6 | 29 ± 9$^{NS}$ | 133 ± 4$^{NS}$ | 25 ± 5$^{NS}$ | 183 ± 7$^{NS}$ | 395 ± 9$^{NS}$ |
| | 0.8 | 32 ± 8$^{NS}$ | 147 ± 10$^{NS}$ | 31 ± 6$^{NS}$ | 172 ± 6$^{NS}$ | 379 ± 8$^{NS}$ |
| | 1 | 27 ± 4$^{NS}$ | 151 ± 6$^{NS}$ | 25 ± 3$^{NS}$ | 177 ± 4$^{NS}$ | 378 ± 5$^{NS}$ |

NT: not tested.
$^{NS}$No significant difference as ompared to the control by the Dunnett test.
***P < 0.001

6.2.6. Conclusion

No significant increase in revertant rates was observed for all the tested doses, either in the absence or presence of the metabolizing mixture. This result indicates that none of the compounds of the invention (S)-1i, (S)-30c and (S)-1a exerted mutagenic activity in *Salmonella* strains, and none of the compounds of the invention (S)-1i, (S)-30c and (S)-1a produced metabolites with mutagenic effects.

The invention claimed is:

1. A compound of formula I:

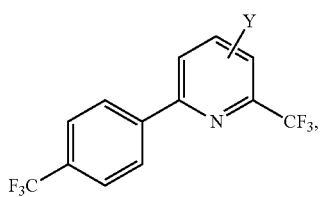

I or a pharmaceutically acceptable salt or solvate thereof, wherein:

Y is formulae i or ii:

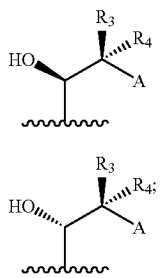

A is $NR^1R^2$ wherein:
  $R^1$ and $R^2$ are independently selected from the group consisting of:
    a hydrogen atom;
    a straight C1-C9 alkyl or haloalkyl group;
    a straight or branched C1-C9 heteroalkyl group containing one or two heteroatoms, said group being optionally substituted by one or two groups independently selected from aryl, heteroaryl, cycloalkyl and metallocene;
    a group of following formula:

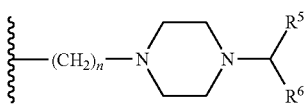

wherein n is an integer from 1 to 4 and $R^5$ and $R^6$ are independently aryl or heteroaryl groups,
    a substituted or unsubstituted C3-C7 cycloalkyl group; and
    an aryl group;
    with the proviso that $R^1$ and $R^2$ are not both a hydrogen atom;
  $R^3$ and $R^4$ are independently selected from the group consisting of a hydrogen atom and a C1-C9 alkyl group optionally containing a heteroatom, said group being optionally substituted by an aryl group or a cycloalkyl group; and
  wherein the symbol

means that Y may be located at any free position of the pyridine ring;
  with the proviso that the compound of Formula I is not one, more or all of the following,
    2-(butylamino)-1-(2-(trifluoromethyl)-6-(4-(trifluoromethyl)phenyl)pyridin-4-yl)ethan-1-ol;
    2-(dibutylamino)-1-(2-(trifluoromethyl)-6-(4-(trifluoromethyl)phenyl)pyridin-4-yl)ethan-1-ol;
    2-(pentan-3-ylamino)-1-(2-(trifluoromethyl)-6-(4-(trifluoromethyl)phenyl)pyridin-4-yl)ethan-1-ol;
    2-(di(pentan-3-yl)amino)-1-(2-trifluoromethyl)-6-(4-(trifluoromethyl)phenyl)pyridin-4-yl)ethan-1-ol; and
    2-(heptan-4-ylamino)-1-(2-(trifluoromethyl)-6-(4-(trifluoromethyl)phenyl)pyridin-4-ylethan-1-ol.

2. The compound according to claim 1, wherein $R^3$ and $R^4$ are hydrogen atoms.

3. The compound according to claim 1, wherein $R^2$ is a hydrogen atom.

4. The compound according to claim 1, wherein $R^1$ is selected from n-butyl, n-pentyl, n-hexyl, n-heptyl, 4,4,4-trifluoro-n-butyl, 6-fluoro-n-hexyl, 2-(benzhydrylamino)ethyl, 2-((di(pyridin-2-yl)methyl)amino)ethyl, (S)-1-methoxy-3-phenylpropan-2-yl, (S)-1-(cyclopropylmethoxy)-3-phenylpropan-2-yl, 2-(ferrocenylamino)ethyl, or 3-(4-benzhydrylpiperazin-1-yl)propyl and $R^2$ is a hydrogen atom.

5. The compound according to claim 1, having formula II:

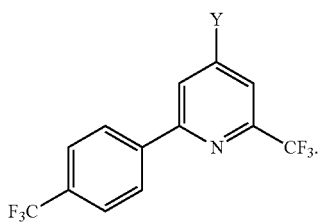

II

6. The compound according to claim 5, having formula IIa:

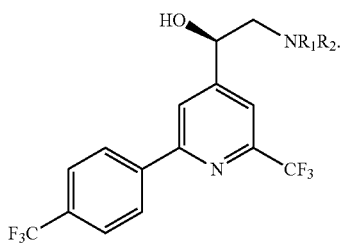

IIa

7. The compound according to claim 5, having formula IIb:

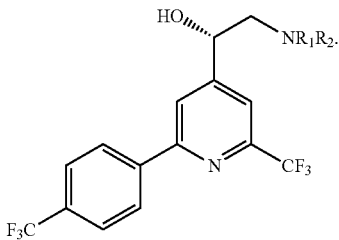

IIb

8. The compound according to claim 5, wherein R¹ is selected from 4,4,4-trifluoro-n-butyl, 6-fluoro-n-hexyl, 2-(benzhydrylamino)ethyl, 2-((di(pyridin-2-yl)methyl)amino)ethyl, (S)-1-methoxy-3-phenylpropan-2-yl, 2-(ferrocenylamino)ethyl, 3-(4-benzhydrylpiperazin-1-yl)propyl, and (S)-1-(cyclopropylmethoxy)-3-phenylpropan-2-yl, and R² is a hydrogen atom.

9. The compound according to claim 1, having formula III:

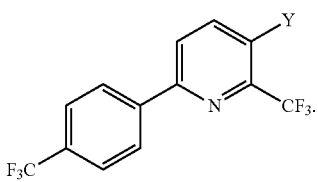

III

10. The compound according to claim 9, having formula IIIa:

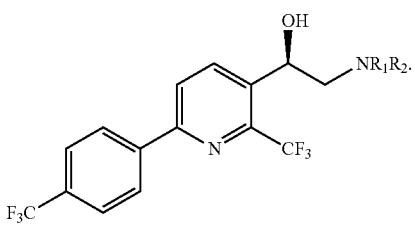

IIIa

11. The compound according to claim 9, having formula IIIb:

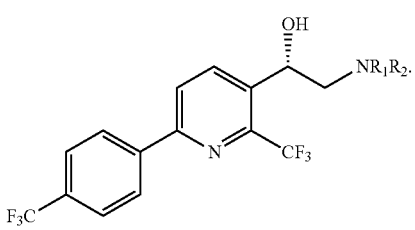

IIIb

12. The compound according to claim 1, selected from the group consisting of:
(S)-2-(n-pentylamino)-1-(2-(trifluoromethyl)-6-(4-(trifluoromethyl)phenyl)pyridin-4-yl)ethanol;
(R)-2-(n-pentylamino)-1-(2-(trifluoromethyl)-6-(4-(trifluoromethyl)phenyl)pyridin-4-yl)ethanol;
(S)-2-(n-hexylamino)-1-(2-(trifluoromethyl)-6-(4-(trifluoromethyl)phenyl)pyridin-4-yl)ethanol;
(R)-2-(n-hexylamino)-1-(2-(trifluoromethyl)-6-(4-(trifluoromethyl)phenyl)pyridin-4-yl)ethanol;
(S)-2-(n-heptylamino)-1-(2-(trifluoromethyl)-6-(4-(trifluoromethyl)phenyl)pyridin-4-yl)ethanol;
(R)-2-(n-heptylamino)-1-(2-(trifluoromethyl)-6-(4-(trifluoromethyl)phenyl)pyridin-4-yl)ethanol;
(S)-2-((2-(benzhydrylamino)ethyl)amino)-1-(2-(trifluoromethyl)-6-(4-(trifluoromethyl)phenyl)pyridin-4-yl)ethanol;
(R)-2-((2-(benzhydrylamino)ethyl)amino)-1-(2-(trifluoromethyl)-6-(4-(trifluoromethyl)phenyl)pyridin-4-yl)ethanol;
(S)-2-(((S)-1-methoxy-3-phenylpropan-2-yl)amino)-1-(2-(trifluoromethyl)-6-(4-(trifluoromethyl)phenyl)pyridin-4-yl)ethanol;
(R)-2-(((S)-1-methoxy-3-phenylpropan-2-yl)amino)-1-(2-(trifluoromethyl)-6-(4-(trifluoromethyl)phenyl)pyridin-4-yl)ethanol;
(S)-2-((2-(ferrocenylmethylamino)ethyl)amino)-1-(2-(trifluoromethyl)-6-(4-(trifluoromethyl)phenyl)pyridin-4-yl)ethanol;
(R)-2-((2-(ferrocenylmethylamino)ethyl)amino)-1-(2-(trifluoromethyl)-6-(4-(trifluoromethyl)phenyl)pyridin-4-yl)ethanol;
(S)-2-((3-(4-benzhydrylpiperazin-1-yl)propyl)amino)-1-(2-(trifluoromethyl)-6-(4-(trifluoromethyl)phenyl)pyridin-4-yl)ethanol;
(R)-2-((3-(4-benzhydrylpiperazin-1-yl)propyl)amino)-1-(2-(trifluoromethyl)-6-(4-(trifluoromethyl)phenyl)pyridin-4-yl)ethanol;
(S)-2-((4,4,4-trifluorobutyl)amino)-1-(2-(trifluoromethyl)-6-(4-(trifluoromethyl)phenyl)pyridin-4-yl)ethan-1-ol;
(R)-2-((4,4,4-trifluorobutyl)amino)-1-(2-(trifluoromethyl)-6-(4-(trifluoromethyl)phenyl)pyridin-4-yl)ethan-1-ol;
(S)-2-((6-fluorohexyl)amino)-1-(2-(trifluoromethyl)-6-(4-(trifluoromethyl)phenyl)pyridine-4-yl)ethan-1-ol;
(R)-2-((6-fluorohexyl)amino)-1-(2-(trifluoromethyl)-6-(4-(trifluoromethyl)phenyl)pyridine-4-yl)ethan-1-ol;
(S)-2-((2-((di(pyridine-2-yl)methyl)amino)ethyl)amino)-1-(2-(trifluoromethyl)-6-(4-(trifluoro methyl)phenyl)pyridin-4-yl)ethan-1-ol trifluoroacetic acid salt;
(R)-2-((2-((di(pyridine-2-yl)methyl)amino)ethyl)amino)-1-(2-(trifluoromethyl)-6-(4-(trifluoro methyl)phenyl)pyridin-4-yl)ethan-1-ol trifluoroacetic acid salt;
(S)-2-(((S)-1-(cyclopropylmethoxy)-3-phenylpropan-2-yl)amino)-1-(2-(trifluoromethyl)-6-(4-(trifluoromethyl)phenyl)pyridin-4-yl)ethan-1-ol;
(R)-2-(((S)-1-(cyclopropylmethoxy)-3-phenylpropan-2-yl)amino)-1-(2-(trifluoromethyl)-6-(4-(trifluoromethyl)phenyl)pyridin-4-yl)ethan-1-ol;
(S)-2-(n-butylamino)-1-(2-(trifluoromethyl)-6-(4-(trifluoromethyl)phenyl)pyridin-3-yl)ethanol;
(R)-2-(n-butylamino)-1-(2-(trifluoromethyl)-6-(4-(trifluoromethyl)phenyl)pyridin-3-yl)ethanol;
(S)-2-(n-pentylamino)-1-(2-(trifluoromethyl)-6-(4-(trifluoromethyl)phenyl)pyridin-3-yl)ethanol;
(R)-2-(n-pentylamino)-1-(2-(trifluoromethyl)-6-(4-(trifluoromethyl)phenyl)pyridin-3-yl)ethanol;
(S)-2-(n-hexylamino)-1-(2-(trifluoromethyl)-6-(4-(trifluoromethyl)phenyl)pyridin-3-yl)ethanol;

(R)-2-(n-hexylamino)-1-(2-(trifluoromethyl)-6-(4-(trifluoromethyl)phenyl)pyridin-3-yl)ethanol;
(S)-2-(n-heptylamino)-1-(2-(trifluoromethyl)-6-(4-(trifluoromethyl)phenyl)pyridin-3-yl)ethanol;
(R)-2-(n-heptylamino)-1-(2-(trifluoromethyl)-6-(4-(trifluoromethyl)phenyl)pyridin-3-yl)ethanol;
(S)-2-((2-(benzhydrylamino)ethyl)amino)-1-(2-(trifluoromethyl)-6-(4-(trifluoromethyl)phenyl)pyridin-3-yl)ethanol;
(R)-2-((2-(benzhydrylamino)ethyl)amino)-1-(2-(trifluoromethyl)-6-(4-(trifluoromethyl)phenyl)pyridin-3-yl)ethanol;
(S)-2-(((S)-1-methoxy-3-phenylpropan-2-yl)amino)-1-(2-(trifluoromethyl)-6-(4-(trifluoromethyl)phenyl)pyridin-3-yl)ethanol;
(R)-2-(((S)-1-methoxy-3-phenylpropan-2-yl)amino)-1-(2-(trifluoromethyl)-6-(4-(trifluoromethyl)phenyl)pyridin-3-yl)ethanol;
(S)-2-((2-(ferrocenylmethylamino)ethyl)amino)-1-(2-(trifluoromethyl)-6-(4(trifluoromethyl) phenyl)pyridin-3-yl)ethanol;
(R)-2-((2-(ferrocenylmethylamino)ethyl)amino)-1-(2-(trifluoromethyl)-6-(4(trifluoromethyl) phenyl)pyridin-3-yl)ethanol;
(S)-2-((3-(4-benzhydrylpiperazin-1-yl)propyl)amino)-1-(2-(trifluoromethyl)-6-(4-(trifluoromethyl)phenyl)pyridin-3-yl)ethanol;
(R)-2-((3-(4-benzhydrylpiperazin-1-yl)propyl)amino)-1-(2-(trifluoromethyl)-6-(4-(trifluoromethyl)phenyl)pyridin-3-yl)ethanol;
(S)-2-((4,4,4-trifluorobutyl)amino)-1-(2-(trifluoromethyl)-6-(4-(trifluoromethyl)phenyl)pyridin-3-yl)ethan-1-ol;
(R)-2-((4,4,4-trifluorobutyl)amino)-1-(2-(trifluoromethyl)-6-(4-(trifluoromethyl)phenyl)pyridin-3-yl)ethan-1-ol;
(S)-2-((6-fluorohexyl)amino)-1-(2-(trifluoromethyl)-6-(4-(trifluoromethyl)phenyl)pyridine-3-yl)ethan-1-ol;
(R)-2-((6-fluorohexyl)amino)-1-(2-(trifluoromethyl)-6-(4-(trifluoromethyl)phenyl)pyridine-3-yl)ethan-1-ol;
(S)-2-(((S)-1-(cyclopropylmethoxy)-3-phenylpropan-2-yl)amino)-1-(2-(trifluoromethyl)-6-(4-(trifluoromethyl)phenyl)pyridin-3-yl)ethan-1-ol; and
(R)-2-(((S)-1-(cyclopropylmethoxy)-3-phenylpropan-2-yl)amino)-1-(2-(trifluoromethyl)-6-(4-(trifluoromethyl)phenyl)pyridin-3-yl)ethan-1-ol,
or a pharmaceutically acceptable salt or solvate thereof.

13. A pharmaceutical composition, comprising a compound according to claim 1, or a pharmaceutically acceptable salt or solvate thereof, and at least one pharmaceutically acceptable carrier, diluent, excipient and/or adjuvant.

14. A method of treating and/or preventing malaria, comprising the step of administering to a patient of an effective amount of a compound according to claim 1, or a pharmaceutically acceptable salt or solvate thereof.

15. A process for providing a compound according to claim 1, comprising the following steps in the following order:
   preparation of 2-(trifluoromethyl)-6-(4-(trifluoromethyl)phenyl)-vinylpyridine;
   addition of an asymmetric dihydroxylation catalyst to said 2-(trifluoromethyl)-6-(4-(trifluoromethyl)phenyl)-vinylpyridine to obtain (R)- or (S)-1-(2-(trifluoromethyl)-6-(4-(trifluoromethyl)phenyl)pyridinyl) ethane-1,2-diol;
   preparation of (R)- or (S)-(oxiran-2-yl)-2-(trifluoromethyl)-6-(4-(trifluoromethyl)phenyl)pyridinestarting from said (R)- or (S)-1-(2-(trifluoromethyl)-6-(4-(trifluoromethyl)phenyl)pyridinyl) ethane-1,2-diol respectively; and
   addition of an amine to said (R)- or (S)-(oxiran-2-yl)-2-(trifluoromethyl)-6-(4-(trifluoromethyl)phenyl)pyridine.

16. The process according to claim 15, wherein said asymmetric dihydroxylation catalyst is one of AD-mix α and AD-mix β.

17. The process according to claim 15, wherein $K_2OsO_2(OH)_4$ is further added to prepare said (R)- or (S)-1-(2-(trifluoromethyl)-6-(4-(trifluoromethyl)phenyl)pyridinyl) ethane-1,2-diol.

\* \* \* \* \*